(12) United States Patent
Gibbs et al.

(10) Patent No.: US 11,492,359 B2
(45) Date of Patent: Nov. 8, 2022

(54) NEAR-INFRARED NERVE-SPARING FLUOROPHORES

(71) Applicant: OREGON HEALTH & SCIENCE UNIVERSITY, Portland, OR (US)

(72) Inventors: Summer L. Gibbs, Westlinn, OR (US); Lei G. Wang, Portland, OR (US); Connor W. Barth, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 17/263,863

(22) PCT Filed: Jul. 26, 2019

(86) PCT No.: PCT/US2019/043739
§ 371 (c)(1),
(2) Date: Jan. 27, 2021

(87) PCT Pub. No.: WO2020/023911
PCT Pub. Date: Jan. 30, 2020

(65) Prior Publication Data
US 2021/0317137 A1    Oct. 14, 2021

Related U.S. Application Data

(60) Provisional application No. 62/711,465, filed on Jul. 27, 2018.

(51) Int. Cl.
*C07D 498/22* (2006.01)
*C07D 498/16* (2006.01)
*A61K 49/00* (2006.01)

(52) U.S. Cl.
CPC ........ *C07D 498/16* (2013.01); *A61K 49/0028* (2013.01)

(58) Field of Classification Search
CPC .. C07D 498/22; C07D 498/14; A61K 31/538; A61K 31/5383
USPC ...................... 544/99, 102; 514/229.5, 229.8
See application file for complete search history.

(56) References Cited

FOREIGN PATENT DOCUMENTS

| CH | 619476 | * 12/1978 | ............. C09B 19/00 |
|---|---|---|---|
| CN | 1699685 A | 11/2005 | |
| WO | WO2009120416 A1 | 10/2009 | |
| WO | WO2015066296 A1 | 5/2015 | |
| WO | WO2018115154 A1 | 6/2018 | |

OTHER PUBLICATIONS

Hintersteiner, et al., Nature Biotechnology (2005), 23(5), 577-583. (Year: 2005).*
Barth & Gibbs, "Direct Administration of Nerve-Specific Contrast to Improve Nerve Sparing Radical Prostatectomy," Theranostics, vol. 7, No. 3, 2017, pp. 573-593.
Barth & Gibbs, "Visualizing Oxazine 4 nerve-specific fluorescence ex vivo in frozen tissue sections," Proceedings SPIE International Society for Optical Engineering, vol. 9696, 2016, 11 pages.
Belov, et al., "Rhodamine spiroamides for multicolor single-molecule switching fluorescent nanoscopy," Chemistry—A European Journal, vol. 15, No. 41, 2009, pp. 10762-10776.
Gibbs, et al., "Structure-Activity Relationship of Nerve-Highlighting Fluorophores," Plos One, vol. 8, No. 9, 2013, 12 pages.
Klapars & Buchwald, "Copper-Catalyzed Halogen Exchange in Aryl Halides: An Aromatic Finkelstein Reaction," Journal of the American Chemical Society, vol. 124, No. 50, 2002, pp. 14844-14845.
Maiti & Buchwald, "Orthogonal Cu- and Pd-Based Catalyst Systems for the O- and N-Arylation of Aminophenols," Journal of the American Chemical Society, vol. 131, No. 47, 2009, pp. 17423-17429.
Ge, et al., "Discovery of Novel Benzo[a]phenoxazine SSJ-183 as a Drug Candidate for Malaria," ASC Medicinal Chemistry Letters, vol. 1, No. 7, 2010, pp. 360-364.
PubChem CID 11559988 Create Date: Oct. 26, 2006, p. 2 Fig., retrieved from <<https://pubchem.ncbi.nlm.nih.gov/compound/11559988>>.
PubChem CID 13358647 Create Date: Aug. 2, 2007, p. 2 Fig., retrieved from <<https://pubchem.ncbi.nlm.nih.gov/compound/13358647>>.
Takasu, et al., "Synthesis and Antimalarial Property of Orally Active Phenoxazinium Salts," Journal of Medicinal Chemistry, vol. 50, No. 10, 2007, pp. 2281-2284.
Tougan, et al., "In vitro and in vivo characterization of anti-malarial acyl phenoxazine derivatives prepared from basic blue 3," Malaria Journal, vol. 18, No. 237, 2019, 12 pages.
Cohen, et al, "Changes in axon flourescence during activity: Molecular probes of membrane potential", Dec. 1974Journal of Membrane Biology, vol. 19, No. 1, pp. 1-36.
Venner, et al, "Lasing properties of novel near-infrared laser dyes", Apr. 2005, Algorithms and Technologies for Multispectral, Hyperspectral and Ultraspectral Imagery, vol. 5707, pp. 227-236.

* cited by examiner

*Primary Examiner* — Jeffrey H Murray
(74) *Attorney, Agent, or Firm* — Lee & Hayes, P.C.

(57) ABSTRACT

The compounds provided herein are phenoxazines that can be used as far red to near-infrared nerve-sparing fluorescent compounds in medical procedures.

16 Claims, 26 Drawing Sheets

NEAR-INFRARED NERVE-SPARING FLUOROPHORES

CROSS REFERENCE TO RELATED APPLICATIONS

This is the U.S. National Phase of PCT/US2019/043739, filed Jul. 26, 2019, which claims priority to and the benefit of the earlier filing of U.S. Provisional Application No. 62/711,465, filed on Jul. 27, 2018, which is incorporated by reference herein in its entirety.

GOVERNMENTAL RIGHTS

This invention was made with government support under Grant No. 1R01EB021362-01A1 awarded by the National Institutes of Health/National Institute of Biomedical Imaging and Bioengineering. The government has certain rights in the invention.

This invention concerns far red to near-infrared nerve-sparing fluorescent compounds, compositions comprising them, and methods of their use in medical procedures.

BACKGROUND OF THE INVENTION

Accidental nerve transection or injury is a major morbidity associated with many surgical interventions, resulting in persistent postsurgical numbness, chronic pain, and/or paralysis. Nerve sparing can be a difficult task due to patient-patient variability and the difficulty of nerve visualization in the operating room. Currently, nerve detection in the operating room is largely completed through electromyographical monitoring, palpation or direct visualization under white light. Fluorescence image-guided surgery to aid in the precise visualization of vital nerve structures in real time could greatly improve patient outcomes. However, no clinically approved nerve-specific contrast agent exists. Contrast agents that fall within the near-infrared (NIR) window (650-900 nm) are particularly attractive for fluorescence image-guided surgery because absorbance, scatter and autofluorescence are all at local minima, making tissue light penetration maximal in this range. To date, a NIR nerve-specific fluorophore does not exist, where Oxazine 4 has the longest emission wavelength (635 nm maximum) among the nerve-specific fluorophores that have been reported to highlight peripheral nerves. This is a particularly challenging problem because nerve-specific contrast agents must have a relatively low molecular weight in order to cross the blood-nerve barrier. Complicating this requirement is the fact that NIR fluorophores must have a sufficient number of double bonds to reach NIR wavelengths, by definition increasing their molecular weight. There remains a need for NIR nerve-specific contrast agents that improve nerve visualization for diagnostic procedures and use during fluorescence image-guided surgery. There remains a need for new agents for identifying tissues, particularly nerve tissues.

SUMMARY OF THE INVENTION

Provided are fluorophore compounds of Formula I:

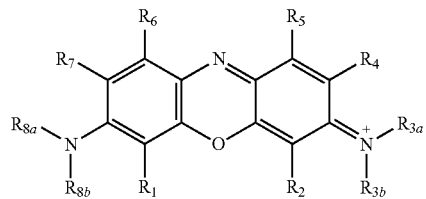

Formula I wherein:

$R_1$ and $R_2$ are each independently selected from hydrogen and $C_1$-$C_4$ alkyl;

$R_{3a}$ and $R_{3b}$ are independently selected from hydrogen and $C_1$-$C_4$ alkyl, with the proviso that at least one of $R_{3a}$ and $R_{3b}$ is not hydrogen; or $R_{3a}$ and $R_{3b}$ together with the nitrogen atom to which they are bound form a 5- or 6-membered nitrogen-containing ring;

or $R_{3b}$ is selected from hydrogen and $C_1$-$C_4$ alkyl, and $R_{3a}$ together with the nitrogen to which it is bound and $R_4$ forms a fused 5-membered or 6-membered ring, the 5-membered or 6-membered ring having one nitrogen heteroatom, two nitrogen heteroatoms, or one nitrogen heteroatom and one oxygen heteroatom, wherein each nitrogen heteroatom is optionally substituted by a $C_1$-$C_4$ alkyl substituent;

or $R_{3a}$, the nitrogen to which it is bound, and $R_4$ form a fused 6-membered, nitrogen-containing ring and $R_{3b}$, the nitrogen to which it is bound, and $R_2$ together form a fused 6-membered, nitrogen-containing ring;

$R_4$ and $R_7$ are each independently selected from hydrogen, halogen, or $C_1$-$C_4$ alkyl;

$R_5$ and $R_6$ are each independently selected from hydrogen or $C_1$-$C_4$ alkyl;

$R_{8a}$ and $R_{8b}$ are independently selected from hydrogen and $C_1$-$C_4$ alkyl, with the proviso that at least one of $R_{8a}$ and $R_{8b}$ is not hydrogen; or $R_{8a}$ and $R_{8b}$ together with the nitrogen to which they are bound form a 5- or 6-membered nitrogen-containing ring optionally substituted by 1, 2, 3, or 4 $C_1$-$C_4$ alkyl substituents;

or $R_{8b}$ is selected from hydrogen and $C_1$-$C_4$ alkyl, and $R_{8a}$ together with the nitrogen to which it is bound and $R_7$ forms a fused 6-membered ring having one nitrogen heteroatom, two nitrogen heteroatoms, or one nitrogen heteroatom and one oxygen heteroatom, wherein each nitrogen heteroatom is optionally substituted by 1, 2, 3, or 4 $C_1$-$C_4$ alkyl substituents;

or $R_{8a}$, the nitrogen to which it is bound, and $R_7$ form a fused 6-membered, nitrogen-containing ring and $R_{8b}$, the nitrogen to which it is bound, and $R_1$ together form a fused 6-membered, nitrogen-containing ring.

Also provided is a compound of Formula I, as defined above, with the proviso that the compounds of Formula I do not include N3,N3,N7,N7-tetraethyl-10H-phenoxazine-3,7-diamine; N3,N7-diethyl-10H-phenoxazine-3,7-diamine; N3,N3,N7,N7-tetramethyl-10H-phenoxazine-3,7-diamine; and N7,N7-diethyl-N3,N3,2-trimethyl-10H-phenoxazine-3,7-diamine.

Also provided are pharmaceutically useful compositions comprising a pharmaceutically acceptable carrier and one or more compounds of Formula I, above, wherein:

$R_1$ and $R_2$ are each independently selected from hydrogen and $C_1$-$C_4$ alkyl;

$R_{3a}$ and $R_{3b}$ are independently selected from hydrogen and $C_1$-$C_4$ alkyl, with the proviso that at least one of $R_{3a}$ and $R_{3b}$ is not hydrogen; or $R_{3a}$ and $R_{3b}$ together with the nitrogen atom to which they are bound form a 5- or 6-membered nitrogen-containing ring;

or $R_{3b}$ is selected from hydrogen and $C_1$-$C_4$ alkyl, and $R_{3a}$ together with the nitrogen to which it is bound and $R_4$ forms a fused 6-membered ring having one nitrogen heteroatom, two nitrogen heteroatoms, or one nitrogen heteroatom and one oxygen heteroatom, wherein each nitrogen heteroatom is optionally substituted by a $C_1$-$C_4$ alkyl substituent;

or $R_{3a}$, the nitrogen to which it is bound, and $R_4$ form a fused 6-membered, nitrogen-containing ring and $R_{3b}$, the nitrogen to which it is bound, and $R_2$ together form a fused 6-membered, nitrogen-containing ring;

$R_4$ and $R_7$ are each independently selected from hydrogen, halogen, or $C_1$-$C_4$ alkyl;

$R_5$ and $R_6$ are each independently selected from hydrogen or $C_1$-$C_4$ alkyl; and $R_{8a}$ and $R_{8b}$ are independently selected from hydrogen and $C_1$-$C_4$ alkyl, with the proviso that at least one of $R_{8a}$ and $R_{8b}$ is not hydrogen; or $R_{8a}$ and $R_{8b}$ together with the nitrogen to which they are bound form a 5- or 6-membered nitrogen-containing ring optionally substituted by 1, 2, 3, or 4 $C_1$-$C_4$ alkyl substituents;

or $R_{8b}$ is selected from hydrogen and $C_1$-$C_4$ alkyl, and $R_{8a}$ together with the nitrogen to which it is bound and $R_7$ forms a fused 5-membered or 6-membered ring, the 5-membered or 6-membered ring having one nitrogen heteroatom, two nitrogen heteroatoms, or one nitrogen heteroatom and one oxygen heteroatom, wherein each nitrogen heteroatom is optionally substituted by 1, 2, 3, or 4 $C_1$-$C_4$ alkyl substituents;

or $R_{8a}$, the nitrogen to which it is bound, and $R_7$ form a fused 6-membered, nitrogen-containing ring and $R_{8b}$, the nitrogen to which it is bound, and $R_1$ together form a fused 6-membered, nitrogen-containing ring.

DETAILED DESCRIPTION OF THE INVENTION

Figure 1A:
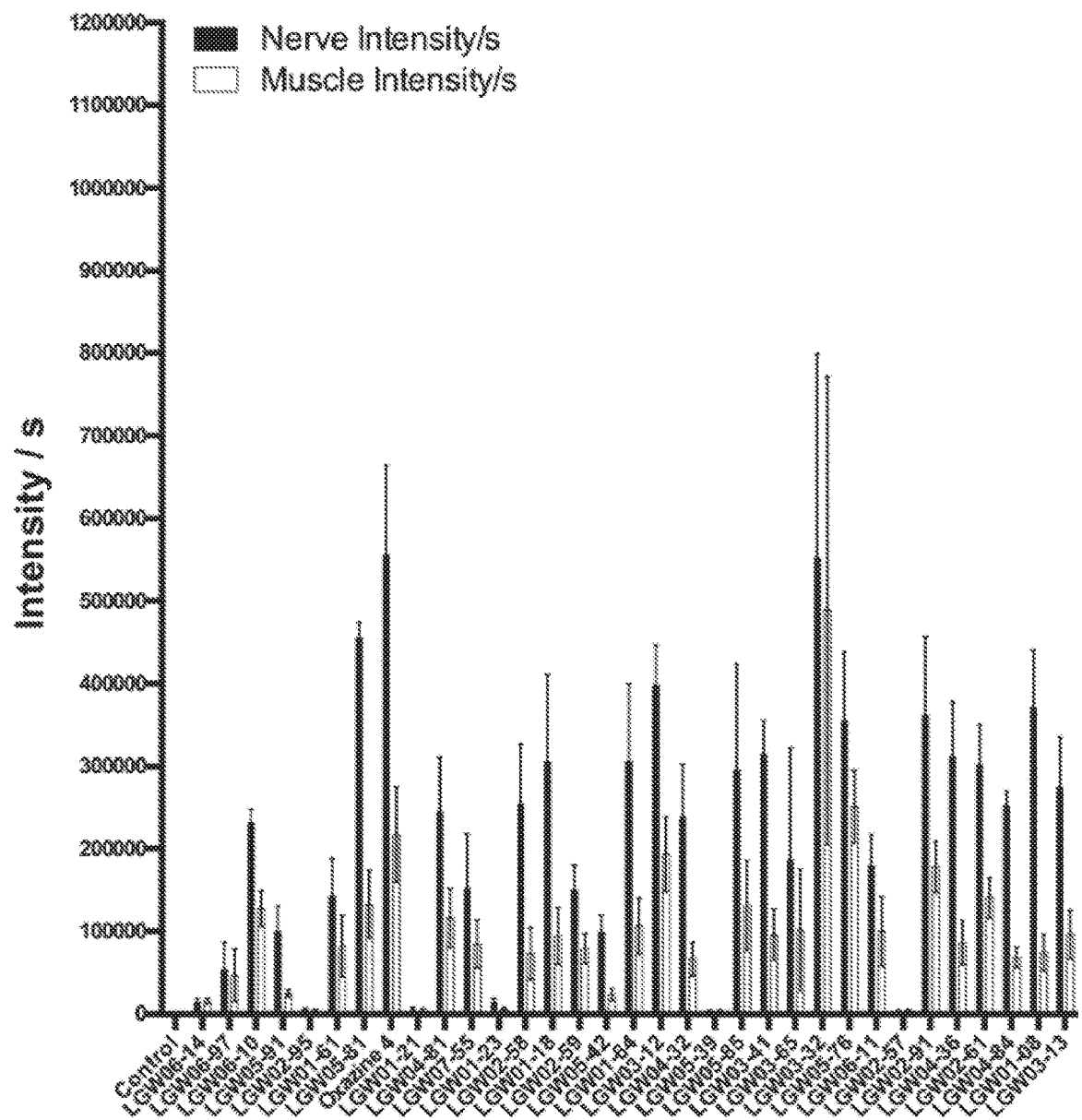
FIGS. 1A and 1B represent the fluorescent intensity of nerve, muscle and adipose tissues following direct/topical administration screening using the compounds herein.
Figure 1A:
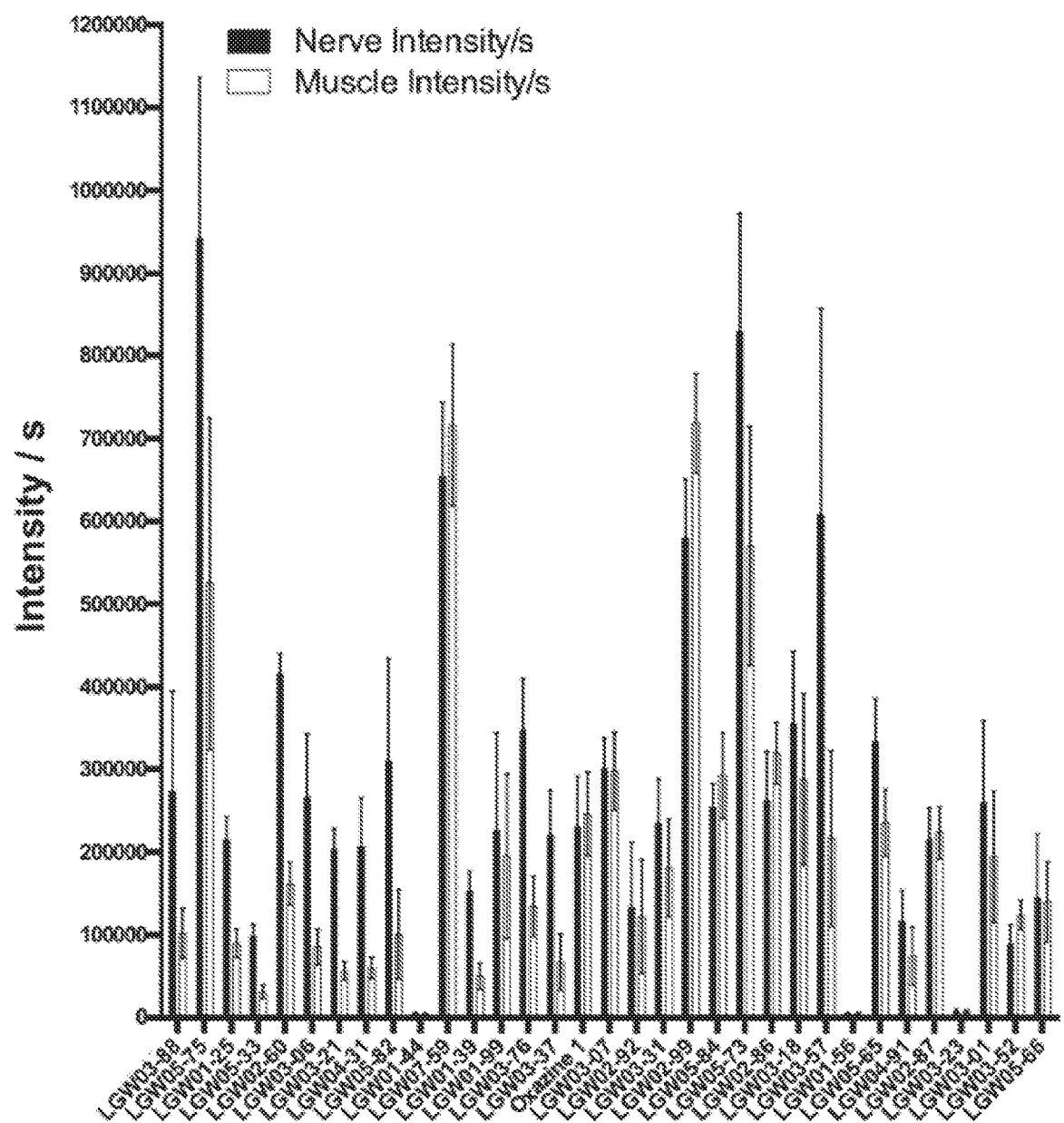

Also provided are compounds of Formula I:

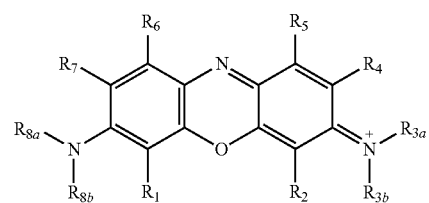

Formula I wherein:

$R_1$ and $R_2$ are each independently selected from hydrogen and methyl;

$R_{3a}$ and $R_{3b}$ are independently selected from hydrogen and $C_1$-$C_4$ alkyl, with the proviso that at least one of $R_{3a}$ and $R_{3b}$ is not hydrogen; or $R_{3a}$ and $R_{3b}$ together with the nitrogen atom to which they are bound form a 5- or 6-membered nitrogen-containing ring;

or $R_{3b}$ is selected from hydrogen and $C_1$-$C_2$ alkyl, and $R_{3a}$ together with the nitrogen to which it is bound and $R_4$ forms a fused 6-membered ring having one nitrogen heteroatom, two nitrogen heteroatoms, or one nitrogen heteroatom and one oxygen heteroatom, wherein each nitrogen heteroatom is optionally substituted by a $C_1$-$C_2$ alkyl substituent;

$R_4$, $R_5$, $R_6$, and $R_7$ are each independently selected from hydrogen or $C_1$-$C_2$ alkyl;

$R_{8a}$ and $R_{8b}$ are independently selected from hydrogen and $C_1$-$C_2$ alkyl, with the proviso that at least one of $R_{8a}$ and $R_{8b}$ is not hydrogen; or $R_{8a}$ and $R_{8b}$ together with the nitrogen to which they are bound form a 5- or 6-membered nitrogen-containing ring optionally substituted by 1, 2, 3, or 4 $C_1$-$C_2$ alkyl substituents;

or $R_{8b}$ is selected from hydrogen and $C_1$-$C_2$ alkyl, and $R_{8a}$ together the nitrogen to which it is bound and $R_7$ forms a fused 6-membered ring having one nitrogen heteroatom, two nitrogen heteroatoms, or one nitrogen heteroatom and one oxygen heteroatom, wherein each nitrogen heteroatom is optionally substituted by 1, 2, 3, or 4 $C_1$-$C_2$ alkyl substituents;

or $R_{8a}$, the nitrogen to which it is bound, and $R_7$ together form a fused 6-membered, nitrogen-containing ring and $R_{8b}$, the nitrogen to which it is bound, and $R_1$ together form a fused 6-membered, nitrogen-containing ring.

Provided is another group of compounds of Formula (I), as defined above, wherein $R_1$ and $R_2$ are each hydrogen and all other variables are as defined above.

Also provided another group of compounds of Formula (I), as defined above, wherein $R_1$ is methyl, $R_2$ is hydrogen, and all other variables are as defined above.

Also provided are compounds of Formula I:

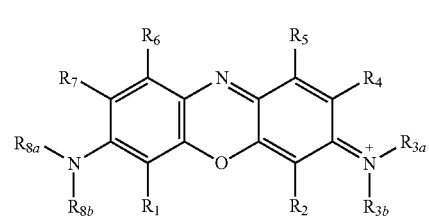

Formula I wherein:

$R_1$, $R_2$, $R_4$, $R_5$, $R_6$, and $R_7$ are each independently hydrogen or $C_1$-$C_4$ alkyl;

$R_{3a}$ and $R_{3b}$ are each independently hydrogen or $C_1$-$C_4$ alkyl, with the proviso that at least one of $R_{3a}$ and $R_{3b}$ is not hydrogen, or $R_{3a}$ and $R_{3b}$ together with the nitrogen atom to which they are bound form a 5- or 6-membered nitrogen containing ring; and $R_{8a}$ and $R_{8b}$ are each independently hydrogen or $C_1$-$C_4$ alkyl, with the proviso that at least one of $R_{8a}$ and $R_{8b}$ are not hydrogen, or $R_{8a}$ and $R_{8b}$ together with the nitrogen atom to which they are bound form a 5- or 6-membered nitrogen containing ring.

Another embodiment provides compounds of Formula I wherein:

$R_1$, $R_2$, $R_4$, $R_5$, $R_6$, and $R_7$ are each independently hydrogen or $C_1$-$C_4$ alkyl;

$R_{3a}$ and $R_{3b}$ are each independently hydrogen or $C_1$-$C_4$ alkyl, with the proviso that at least one of $R_{3a}$ and $R_{3b}$ is not hydrogen; and $R_{8a}$ and $R_{8b}$ together with the nitrogen atom to which they are bound form a 5- or 6-membered nitrogen containing ring.

Further provided are compounds selected individually from Formula I(a), Formula I(b), Formula I(c), Formula I(d), Formula I(e), and Formula I(f):

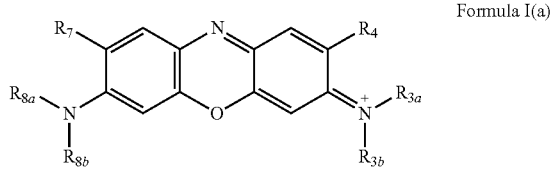

Formula I(a)

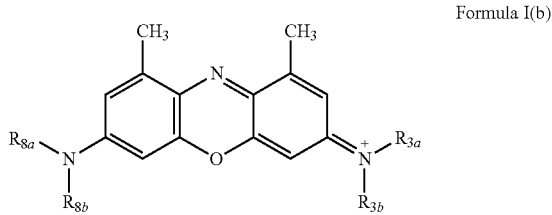

Formula I(b)

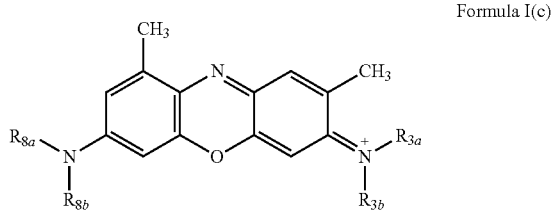

Formula I(c)

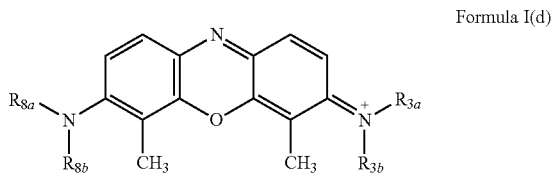

Formula I(d)

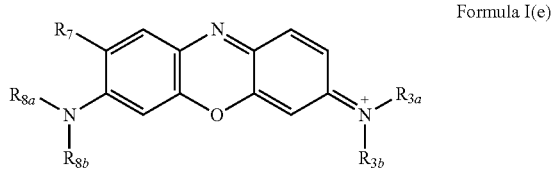

Formula I(e)

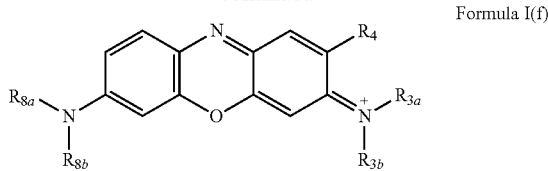

Formula I(f)

Wherein:

$R_4$ and $R_7$ in each instance are independently selected from halogen and $CH_3$;

$R_{3a}$ and $R_{3b}$ in each instance are independently selected from hydrogen and $C_1$-$C_4$ alkyl, with the proviso that at least one of $R_{3a}$ and $R_{3b}$ is not hydrogen; or $R_{3a}$ and $R_{3b}$ together with the nitrogen atom to which they are bound form a 5- or 6-membered nitrogen-containing ring;

or $R_{3b}$ is selected from hydrogen and $C_1$-$C_4$ alkyl, and $R_{3a}$ together with the nitrogen to which it is bound and $R_4$ forms a fused 6-membered ring having one nitrogen heteroatom, two nitrogen heteroatoms, or one nitrogen heteroatom and one oxygen heteroatom, wherein each nitrogen heteroatom is optionally substituted by a $C_1$-$C_4$ alkyl substituent;

or $R_{3a}$, the nitrogen to which it is bound, and $R_4$ form a fused 6-membered, nitrogen-containing ring and $R_{3b}$, the nitrogen to which it is bound, and $R_2$ together form a fused 6-membered, nitrogen-containing ring;

$R_{8a}$ and $R_{8b}$ in each instance are independently selected from hydrogen and $C_1$-$C_4$ alkyl, with the proviso that at least one of $R_{8a}$ and $R_{8b}$ is not hydrogen; or $R_{8a}$ and $R_{8b}$ together with the nitrogen to which they are bound form a 5- or 6-membered nitrogen-containing ring optionally substituted by 1, 2, 3, or 4 $C_1$-$C_4$ alkyl substituents;

or $R_{8b}$ is selected from hydrogen and $C_1$-$C_4$ alkyl, and $R_{8a}$ together with the nitrogen to which it is bound and $R_7$ forms a fused 6-membered ring having one nitrogen heteroatom, two nitrogen heteroatoms, or one nitrogen heteroatom and one oxygen heteroatom, wherein each nitrogen heteroatom is optionally substituted by 1, 2, 3, or 4 $C_1$-$C_4$ alkyl substituents; and or $R_{8a}$, the nitrogen to which it is bound, and $R_7$ form a fused 6-membered, nitrogen-containing ring and $R_{8b}$, the nitrogen to which it is bound, and $R_1$ together form a fused 6-membered, nitrogen-containing ring.

Further provided are compounds selected individually from Formula I(a), Formula I(b), Formula I(c), Formula I(d), Formula I(e), and Formula I(f) wherein $R_4$ and $R_7$ are in each instance independently selected from $CH_3$, F, and Cl; and each of $R_{3a}$, $R_{3b}$, $R_{8a}$, and $R_{8b}$ are as defined above.

Further provided are compounds selected individually from Formula I(a), Formula I(b), Formula I(c), Formula I(d), Formula I(e), and Formula I(f) wherein $R_4$ and $R_7$ are in each instance independently selected from $CH_3$, F, and Cl; and each of $R_{3a}$, $R_{3b}$, $R_{8a}$, and $R_{8b}$ is, independently, H or $C_1$-$C_4$ alkyl, with the proviso that at least one of $R_{3a}$, $R_{3b}$, $R_{8a}$, and $R_{8b}$ is $C_1$-$C_4$ alkyl.

Further provided are compounds selected individually from Formula I(a), Formula I(b), Formula I(c), Formula I(d), Formula I(e), and Formula I(f) wherein $R_4$ and $R_7$ are in each instance independently selected from $CH_3$, F, and Cl; and each of $R_{3a}$, $R_{3b}$, $R_{8a}$, and $R_{8b}$ are each, independently, H or $C_1$-$C_4$ alkyl, with the proviso that at least two of $R_{3a}$, $R_{3b}$, $R_{8a}$, and $R_{8b}$ are $C_1$-$C_4$ alkyl.

Further provided are compounds selected individually from Formula I(a), Formula I(b), Formula I(c), Formula I(d), Formula I(e), and Formula I(f) wherein $R_4$ and $R_7$ are in each instance independently selected from $CH_3$, F, and Cl; and each of $R_{3a}$, $R_{3b}$, $R_{8a}$, and $R_{8b}$ are each, independently, H or $C_1$-$C_4$ alkyl, with the proviso that at least three of $R_{3a}$, $R_{3b}$, $R_{8a}$, and $R_{8b}$ are $C_1$-$C_4$ alkyl.

Additionally, provided are compounds of Formula I(a):

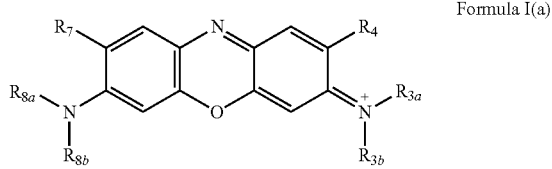

Formula I(a)

wherein $R_4$ and $R_7$ are independently selected from $CH_3$ and halogen; and each of $R_{3a}$, $R_{3b}$, $R_{8a}$, and $R_{8b}$ are independently selected from hydrogen and $C_1$-$C_4$ alkyl.

Also provided are compounds of Formula I(a) wherein $R_4$ and $R_7$ are independently selected from $CH_3$, Cl, and F; and each of $R_{3a}$, $R_{3b}$, $R_{8a}$, and $R_{8b}$ are independently selected from hydrogen and $C_1$-$C_4$ alkyl.

Also provided are compounds of Formula I(a) wherein $R_4$ and $R_7$ are each $CH_3$; and each of $R_{3a}$, $R_{3b}$, $R_{8a}$, and $R_{8b}$ are independently selected from hydrogen and $C_1$-$C_4$ alkyl.

Also provided are compounds of Formula I(a) wherein $R_4$ and $R_7$ are each $CH_3$; and each of $R_{3a}$, $R_{3b}$, $R_{8a}$, and $R_{8b}$ are independently selected from hydrogen and $C_1$-$C_4$ alkyl; with the proviso that at least one of $R_{3a}$ and $R_{3b}$ is not hydrogen and at least one of $R_{8a}$ and $R_{8b}$ is not hydrogen.

Also provided are compounds of Formula I(a) wherein $R_4$ and $R_7$ are each Cl; and each of $R_{3a}$, $R_{3b}$, $R_{8a}$, and $R_{8b}$ are independently selected from hydrogen and $C_1$-$C_4$ alkyl; with the proviso that at least one of $R_{3a}$ and $R_{3b}$ is not hydrogen and at least one of $R_{8a}$ and $R_{8b}$ is not hydrogen.

Also provided are compounds of Formula I(a) wherein $R_4$ and $R_7$ are each F; and each of $R_{3a}$, $R_{3b}$, $R_{8a}$, and $R_{8b}$ are independently selected from hydrogen and $C_1$-$C_4$ alkyl; with the proviso that at least one of $R_{3a}$ and $R_{3b}$ is not hydrogen and at least one of $R_{8a}$ and $R_{8b}$ is not hydrogen.

Also provided are compounds of Formula I(a) wherein $R_4$ is $CH_3$; $R_7$ is F; and each of $R_{3a}$, $R_{3b}$, $R_{8a}$, and $R_{8b}$ are independently selected from hydrogen and $C_1$-$C_4$ alkyl; with the proviso that at least one of $R_{3a}$ and $R_{3b}$ is not hydrogen and at least one of $R_{8a}$ and $R_{8b}$ is not hydrogen.

Also provided are compounds of Formula I(a) wherein $R_4$ is $CH_3$; $R_7$ is Cl; and each of $R_{3a}$, $R_{3b}$, $R_{8a}$, and $R_{8b}$ are independently selected from hydrogen and $C_1$-$C_4$ alkyl; with the proviso that at least one of $R_{3a}$ and $R_{3b}$ is not hydrogen and at least one of $R_{8a}$ and $R_{8b}$ is not hydrogen.

Provided are compounds of Formula I(e):

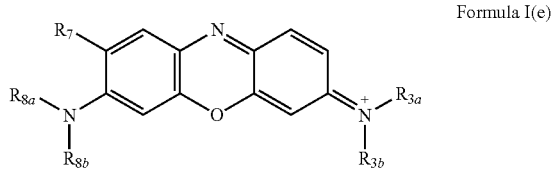

Formula I(e)

wherein $R_7$ is $CH_3$; and each of $R_{3a}$, $R_{3b}$, $R_{8a}$, and $R_{8b}$ are independently selected from hydrogen and $C_1$-$C_4$ alkyl; with the proviso that at least one of $R_{3a}$, $R_{3b}$, $R_{8a}$, and $R_{8b}$ is not hydrogen.

Also provided are compounds of Formula I(e), wherein $R_7$ is $CH_3$; and each of $R_{3a}$, $R_{3b}$, $R_{8a}$, and $R_{8b}$ are independently selected from hydrogen and $C_1$-$C_3$ alkyl; with the proviso that at least one of $R_{3a}$ and $R_{3b}$ is not hydrogen and at least one of $R_{8a}$ and $R_{8b}$ is not hydrogen.

Also provided are compounds of Formula I(e), wherein $R_7$ is $CH_3$; and each of $R_{3a}$, $R_{3b}$, $R_{8a}$, and $R_{8b}$ are independently selected from hydrogen and $C_1$-$C_2$ alkyl; with the proviso that at least one of $R_{3a}$ and $R_{3b}$ is not hydrogen and at least one of $R_{8a}$ and $R_{8b}$ is not hydrogen.

Also provided are compounds of Formula I(e), wherein $R_7$ is $CH_3$; and each of $R_{3a}$, $R_{3b}$, $R_{8a}$, and $R_{8b}$ are independently selected from hydrogen and ethyl; with the proviso that at least one of $R_{3a}$ and $R_{3b}$ is not hydrogen and at least one of $R_{8a}$ and $R_{8b}$ is not hydrogen.

Provided are compounds of Formula I(f):

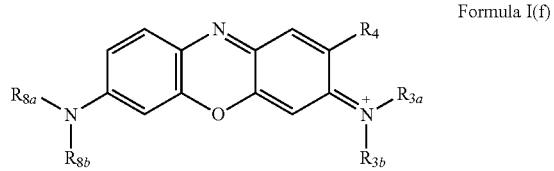

Formula I(f)

wherein $R_4$ is selected from $CH_3$ and hydrogen; $R_{8a}$ and $R_{8b}$ together with the nitrogen to which they are bound form a 5- or 6-membered nitrogen-containing ring; and of $R_{3a}$ and $R_{3b}$ are independently selected from hydrogen and $C_1$-$C_4$ alkyl; or $R_{3a}$ and $R_{3b}$ together with the nitrogen to which they are bound form a 5- or 6-membered nitrogen-containing ring.

Provided are additional compounds of Formula I(f) wherein $R_4$ is $CH_3$; $R_{8a}$ and $R_{8b}$ together with the nitrogen to which they are bound form a 5- or 6-membered nitrogen-containing ring; and of $R_{3a}$ and $R_{3b}$ are independently selected from hydrogen and $C_1$-$C_4$ alkyl; or $R_{3a}$ and $R_{3b}$ together with the nitrogen to which they are bound form a 5- or 6-membered nitrogen-containing ring.

Provided are additional compounds of Formula I(f) wherein $R_4$ is H; $R_{8a}$ and $R_{8b}$ together with the nitrogen to which they are bound form a 5- or 6-membered nitrogen-containing ring; and of $R_{3a}$ and $R_{3b}$ are independently selected from hydrogen and $C_1$-$C_4$ alkyl; or $R_{3a}$ and $R_{3b}$ together with the nitrogen to which they are bound form a 5- or 6-membered nitrogen-containing ring.

Further provided are compounds of Formula I(g):

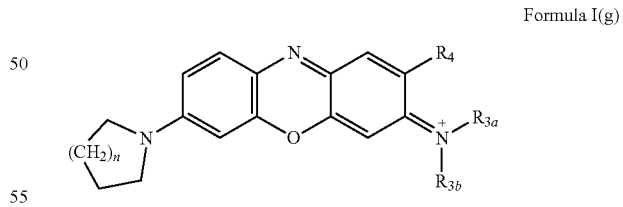

Formula I(g)

wherein:
$R_{3a}$ and $R_{3b}$ are independently selected from hydrogen and $C_1$-$C_4$ alkyl; with the proviso that at least one of $R_{3a}$ and $R_{3b}$ is $C_1$-$C_4$ alkyl; or $R_{3a}$ and $R_{3b}$ together with the nitrogen to which they are bound form a 5- or 6-membered nitrogen-containing ring;
$R_4$ is selected from hydrogen and $CH_3$; and
n is an integer selected from 1 and 2.

It is understood in the description above that n=1 indicates the presence of a pyrrolidinyl ring and n=2 indicates a piperidinyl ring.

Further provided are compounds of Formula I(g), wherein $R_{3a}$ and $R_{3b}$ are independently selected from hydrogen and $C_1$-$C_3$ alkyl; with the proviso that at least one of $R_{3a}$ and $R_{3b}$ is $C_1$-$C_3$ alkyl; or $R_{3a}$ and $R_{3b}$ together with the nitrogen to which they are bound form a 5- or 6-membered nitrogen-containing ring; $R_4$ is selected from hydrogen and $CH_3$; and n is an integer selected from 1 and 2.

Further provided are compounds of Formula I(g), wherein $R_{3a}$ and $R_{3b}$ are independently selected from hydrogen and $C_1$-$C_2$ alkyl; with the proviso that at least one of $R_{3a}$ and $R_{3b}$ is $C_1$-$C_2$ alkyl; or $R_{3a}$ and $R_{3b}$ together with the nitrogen to which they are bound form a 5- or 6-membered nitrogen-containing ring; $R_4$ is selected from hydrogen and $CH_3$; and n is an integer selected from 1 and 2.

Further provided are compounds of Formula I(g), wherein $R_{3a}$ and $R_{3b}$ are independently selected from hydrogen and $C_1$-$C_2$ alkyl; with the proviso that at least one of $R_{3a}$ and $R_{3b}$ is $C_1$-$C_2$ alkyl; or $R_{3a}$ and $R_{3b}$ together with the nitrogen to which they are bound form a 5- or 6-membered nitrogen-containing ring; $R_4$ is selected from hydrogen and $CH_3$; and n is 1.

Further provided are compounds of Formula I(g), wherein $R_{3a}$ and $R_{3b}$ are independently selected from hydrogen and $C_1$-$C_2$ alkyl; with the proviso that at least one of $R_{3a}$ and $R_{3b}$ is $C_1$-$C_2$ alkyl; or $R_{3a}$ and $R_{3b}$ together with the nitrogen to which they are bound form a 5- or 6-membered nitrogen-containing ring; $R_4$ is selected from hydrogen and $CH_3$; and n is 2.

Further provided are compounds of Formula I(g), wherein $R_{3a}$ and $R_{3b}$ together with the nitrogen to which they are bound form a 5- or 6-membered nitrogen-containing ring; $R_4$ is selected from hydrogen and $CH_3$; and n is an integer selected from 1 and 2.

Further provided are compounds of Formula I(g), wherein $R_{3a}$ and $R_{3b}$ together with the nitrogen to which they are bound form a 5- or 6-membered nitrogen-containing ring; $R_4$ is $CH_3$; and n is an integer selected from 1 and 2.

Further provided are compounds of Formula I(g), wherein $R_{3a}$ and $R_{3b}$ together with the nitrogen to which they are bound form a 5- or 6-membered nitrogen-containing ring; $R_4$ is H; and n is an integer selected from 1 and 2.

Also provided are compounds of Formula II:

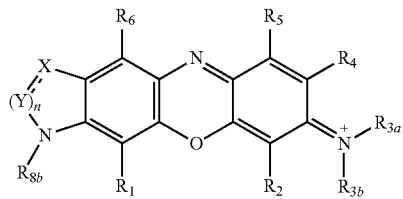

Formula II wherein:

$R_1$, $R_2$, $R_4$, $R_5$, and $R_6$ are each independently selected from hydrogen or $C_1$-$C_4$ alkyl;

X is selected from the group of —C(H)—, —CH$_2$—, —CH($C_1$-$C_4$ alkyl)-, —C($C_1$-$C_4$ alkyl)-, —N(H)—, —N($C_1$-$C_4$ alkyl)-, and —O—;

Y is selected from —CH$_2$—, —CH$_2$—CH$_2$—, —CH$_2$—CH—, —CH($C_1$-$C_4$ alkyl)-CH$_2$—, —C($C_1$-$C_4$ alkyl)$_2$-CH$_2$—, —CH($C_1$-$C_4$ alkyl)-CH—, and —C($C_1$-$C_4$ alkyl)$_2$-CH—;

the dashed line (---) represents an optional double bond that exists when X is selected from —C(H)— or —C($C_1$-$C_4$ alkyl)- and Y is selected from —CH$_2$—CH—, —CH($C_1$-$C_4$ alkyl)-CH—, and —C($C_1$-$C_4$ alkyl)$_2$-CH—;

$R_{3a}$ and $R_{3b}$ are each independently hydrogen or $C_1$-$C_4$ alkyl, with the proviso that at least one of $R_{3a}$ and $R_{3b}$ is not hydrogen, or $R_{3a}$ and $R_{3b}$ together with the nitrogen atom to which they are bound form a 5- or 6-membered nitrogen containing ring; and $R_{8b}$ is selected from hydrogen and $C_1$-$C_4$ alkyl.

A further embodiment provides compounds of Formula II, above, wherein:

$R_1$, $R_2$, $R_4$, $R_5$, and $R_6$ are each independently selected from hydrogen and $C_1$-$C_4$ alkyl;

X is selected from the group of —C(H)—, —CH$_2$—, —CH($C_1$-$C_4$ alkyl)-, —C($C_1$-$C_4$ alkyl)-, —N(H)—, —N($C_1$-$C_4$ alkyl)-, and —O—;

Y is selected from —CH$_2$—, —CH$_2$—CH$_2$—, —CH$_2$—CH—, —CH($C_1$-$C_4$ alkyl)-CH$_2$—, and —C($C_1$-$C_4$ alkyl)$_2$-CH$_2$—;

the dashed line (---) represents and optional double bond when X is —C(H)— or —C($C_1$-$C_4$ alkyl)- and Y is selected from —CH$_2$—CH—, —CH($C_1$-$C_4$ alkyl)-CH—, and —C($C_1$-$C_4$ alkyl)$_2$-CH—;

$R_{3a}$ and $R_{3b}$ are each independently hydrogen or $C_1$-$C_4$ alkyl, with the proviso that at least one of $R_{3a}$ and $R_{3b}$ is not hydrogen; and $R_{8b}$ is selected from hydrogen and $C_1$-$C_4$ alkyl.

Further provided are compounds of Formula III:

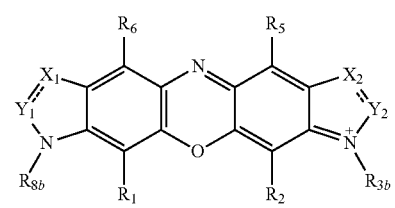

Formula III $R_1$, $R_2$, $R_5$, and $R_6$ are each independently selected from hydrogen and $C_1$-$C_4$ alkyl;

$X_1$ and $X_2$ are selected from —CH—, —CH$_2$—, —C($C_1$-$C_4$ alkyl)-, —N(H)—, —N($C_1$-$C_4$ alkyl)-, and —O—;

$Y_1$ and $Y_2$ are independently selected from —CH—, —CH$_2$—, —CH$_2$—CH$_2$—, —CH$_2$—CH—, —CH($C_1$-$C_4$ alkyl)-CH$_2$—, —C($C_1$-$C_4$ alkyl)$_2$-CH$_2$—, —CH($C_1$-$C_4$ alkyl)-CH—, and —C($C_1$-$C_4$ alkyl)$_2$-CH—;

the dashed line (---) in each instance represents and optional double bond when $X^1$ or $X_2$ is —C(H)— or —C($C_1$-$C_4$ alkyl)- and $Y_1$ or $Y_2$ is selected from —CH—, —CH$_2$—CH—, —CH($C_1$-$C_4$ alkyl)-CH—, and —C($C_1$-$C_4$ alkyl)$_2$-CH—; and $R_{3b}$ and $R_{8b}$ are each independently selected from hydrogen and $C_1$-$C_4$ alkyl.

Also provided are compounds of Formula IV:

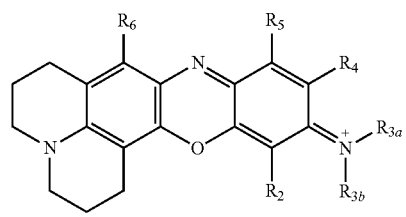

Formula IV wherein:

$R_2$, $R_4$, $R_5$, and $R_6$ are each independently selected from hydrogen and $C_1$-$C_4$ alkyl; and $R_{3a}$ and $R_{3b}$ are each independently hydrogen or $C_1$-$C_4$ alkyl, with the proviso that at least one of $R_{3a}$ and $R_{3b}$ is not hydrogen, or $R_{3a}$ and $R_{3b}$ together with the nitrogen atom to which they are bound form a 5- or 6-membered nitrogen containing ring.

Also provided is a compound of the Formula V:

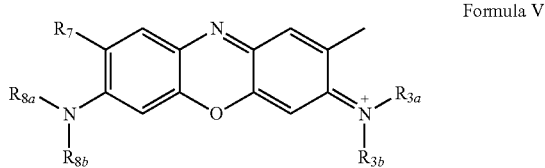

Formula V wherein:

$R_{3a}$ is $C_1$-$C_4$ alkyl;

$R_{3b}$ is selected from H and $C_1$-$C_4$ alkyl; and a) $R_7$ is hydrogen; and $R_{8a}$ and $R_{8b}$, along with the nitrogen atom to which they are bound, form a 5-membered saturated ring containing one nitrogen heteroatom or a 6-membered saturated ring containing one nitrogen heteroatom; or b) $R_7$ and $R_{8a}$, along with the nitrogen atom to which $R_{8a}$ is bound, form a 6-membered saturated or partially unsaturated ring containing one nitrogen heteroatom, the ring being optionally substituted by 1, 2, 3, or 4 $C_1$-$C_4$ alkyl substituents; and $R_{8b}$ is selected from H and $C_1$-$C_4$ alkyl.

Also provided is a compound of Formula V, above, wherein:

$R_{3a}$ is $C_1$-$C_3$ alkyl;

$R_{3b}$ is selected from H and $C_1$-$C_3$ alkyl; and a) $R_7$ is hydrogen; and $R_{8a}$ and $R_{8b}$, along with the nitrogen atom to which they are bound, form a 5-membered saturated ring containing one nitrogen heteroatom or a 6-membered saturated ring containing one nitrogen heteroatom; or b) $R_7$ and $R_{8a}$, along with the nitrogen atom to which $R_{8a}$ is bound, form a 6-membered saturated or partially unsaturated ring containing one nitrogen heteroatom the ring being optionally substituted by 1, 2, 3, or 4 $C_1$-$C_4$ alkyl substituents; and $R_{8b}$ is selected from H and $C_1$-$C_3$ alkyl.

Also provided is a compound of Formula V, above, wherein:

$R_{3a}$ is $C_1$-$C_3$ alkyl;

$R_{3b}$ is H; and a) $R_7$ is hydrogen; and $R_{8a}$ and $R_{8b}$, along with the nitrogen atom to which they are bound, form a 5-membered saturated ring containing one nitrogen heteroatom or a 6-membered saturated ring containing one nitrogen heteroatom; or b) $R_7$ and $R_{8a}$, along with the nitrogen atom to which $R_{8a}$ is bound, form a 6-membered saturated or partially unsaturated ring containing one nitrogen heteroatom the ring being optionally substituted by 1, 2, 3, or 4 $C_1$-$C_2$ alkyl substituents; and $R_{8b}$ is selected from H and $C_1$-$C_3$ alkyl.

Also provided is a compound of Formula V, above, wherein:

$R_{3a}$ is $C_1$-$C_3$ alkyl;

$R_{3b}$ is H; and a) $R_7$ is hydrogen; and $R_{8a}$ and $R_{8b}$, along with the nitrogen atom to which they are bound, form a 6-membered saturated ring containing one nitrogen heteroatom; or b) $R_7$ and $R_{8a}$, along with the nitrogen atom to which $R_{8a}$ is bound, form a 6-membered saturated or partially unsaturated ring containing one nitrogen heteroatom the ring being optionally substituted by 1, 2, 3, or 4 $C_1$-$C_2$ alkyl substituents; and $R_{8b}$ is selected from H and $C_1$-$C_3$ alkyl.

Also provided is a compound of Formula V, above, wherein:

$R_{3a}$ is ethyl;

$R_{3b}$ is H; and a) $R_7$ is hydrogen; and $R_{8a}$ and $R_{8b}$, along with the nitrogen atom to which they are bound, form a 6-membered saturated ring containing one nitrogen heteroatom; or b) $R_7$ and $R_{8a}$, along with the nitrogen atom to which $R_{8a}$ is bound, form a 6-membered saturated or partially unsaturated ring containing one nitrogen heteroatom the ring being optionally substituted by 1, 2, 3, or 4 methyl substituents; and $R_{8b}$ is selected from H and $C_1$-$C_3$ alkyl.

Also provided is a compound of Formula V, above, wherein:

$R_{3a}$ is ethyl;

$R_{3b}$ is H; and a) $R_7$ is hydrogen; and $R_{8a}$ and $R_{8b}$, along with the nitrogen atom to which they are bound, form a 6-membered saturated ring containing one nitrogen heteroatom; or b) $R_7$ and $R_{8a}$, along with the nitrogen atom to which $R_{8a}$ is bound, form a 6-membered saturated or partially unsaturated ring containing one nitrogen heteroatom the ring being optionally substituted by 1, 2, 3, or 4 methyl substituents; and $R_{8b}$ is selected from H and $C_1$-$C_2$ alkyl.

Also provided is a compound of the Formula VI:

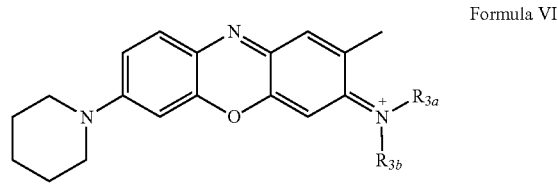

Formula VI wherein $R_{3a}$ is $C_1$-$C_4$ alkyl; and $R_{3b}$ is selected from H and $C_1$-$C_4$ alkyl.

Further provided is a compound of Formula VI, wherein $R_{3a}$ is $C_1$-$C_3$ alkyl; and $R_{3b}$ is selected from H and $C_1$-$C_3$ alkyl.

Also provided is a compound of Formula VI, wherein $R_{3a}$ is $C_1$-$C_3$ alkyl; and $R_{3b}$ is H.

Also provided is a compound of the Formula VII:

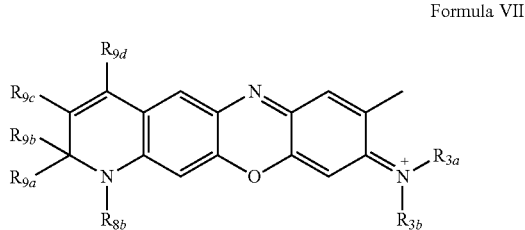

Formula VII wherein $R_{3a}$ is $C_1$-$C_4$ alkyl; $R_{3b}$ is selected from H and $C_1$-$C_4$ alkyl; $R_{8b}$ is selected from H and $C_1$-$C_4$ alkyl; and each of $R_{9a}$, $R_{9b}$, $R_{9c}$, and $R_{9d}$ are independently selected from H and methyl.

Also provided is a compound of the Formula VII, wherein $R_{3a}$ is $C_1$-$C_4$ alkyl; $R_{3b}$ is selected from H and $C_1$-$C_4$ alkyl; $R_{8b}$ is selected from H and $C_1$-$C_4$ alkyl; and each of $R_{9a}$, $R_{9b}$, $R_{9e}$, and $R_{9a}$ are independently selected from H and methyl, with the proviso that at least one of $R_{9a}$, $R_{9b}$, $R_{9e}$, and $R_{9a}$ is methyl.

Also provided is a compound of the Formula VII, wherein $R_{3a}$ is $C_1$-$C_4$ alkyl; $R_{3b}$ is selected from H and $C_1$-$C_4$ alkyl; $R_{8b}$ is $C_1$-$C_4$ alkyl; and each of $R_{9a}$, $R_{9b}$, $R_{9e}$, and $R_{9a}$ are independently selected from H and methyl, with the proviso that at least one of $R_{9a}$, $R_{9b}$, $R_{9e}$, and $R_{9a}$ is methyl.

Also provided is a compound of the Formula VII, wherein $R_{3a}$ is $C_1$-$C_4$ alkyl; $R_{3b}$ is selected from H and $C_1$-$C_4$ alkyl; $R_{8b}$ is selected from H and $C_1$-$C_4$ alkyl; and each of $R_{9a}$, $R_{9b}$, $R_{9e}$, and $R_{9a}$ are independently selected from H and methyl, with the proviso that at least two of $R_{9a}$, $R_{9b}$, $R_{9e}$, and $R_{9a}$ are methyl.

Also provided is a compound of the Formula VII, wherein $R_{3a}$ is $C_1$-$C_4$ alkyl; $R_{3b}$ is selected from H and $C_1$-$C_4$ alkyl; $R_{8b}$ is $C_1$-$C_4$ alkyl; and each of $R_{9a}$, $R_{9b}$, $R_{9e}$, and $R_{9a}$ are independently selected from H and methyl, with the proviso that at least two of $R_{9a}$, $R_{9b}$, $R_{9e}$, and $R_{9a}$ are methyl.

Also provided is a compound of the Formula VII, wherein $R_{3a}$ is $C_1$-$C_4$ alkyl; $R_{3b}$ is selected from H and $C_1$-$C_4$ alkyl; $R_{8b}$ is selected from H and $C_1$-$C_4$ alkyl; and each of $R_{9a}$, $R_{9b}$, $R_{9e}$, and $R_{9a}$ are independently selected from H and methyl, with the proviso that at least three of $R_{9a}$, $R_{9b}$, $R_{9e}$, and $R_{9a}$ are methyl.

Also provided is a compound of the Formula VII, wherein $R_{3a}$ is $C_1$-$C_4$ alkyl; $R_{3b}$ is selected from H and $C_1$-$C_4$ alkyl; $R_{8b}$ is $C_1$-$C_4$ alkyl; and each of $R_{9a}$, $R_{9b}$, $R_{9e}$, and $R_{9a}$ are independently selected from H and methyl, with the proviso that at least three of $R_{9a}$, $R_{9b}$, $R_{9c}$, and $R_{9a}$ are methyl.

Also provided is a compound of the Formula VII, wherein $R_{3a}$ is $C_1$-$C_3$ alkyl; $R_{3b}$ is selected from H and $C_1$-$C_4$ alkyl; $R_{8b}$ is selected from H and $C_1$-$C_3$ alkyl; and each of $R_{9a}$, $R_{9b}$, $R_{9e}$, and $R_{9a}$ are independently selected from H and methyl, with the proviso that at least one of $R_{9a}$, $R_{9b}$, $R_{9e}$, and $R_{9a}$ is methyl.

Also provided is a compound of the Formula VII, wherein $R_{3a}$ is $C_1$-$C_3$ alkyl; $R_{3b}$ is selected from H and $C_1$-$C_4$ alkyl; $R_{8b}$ is $C_1$-$C_3$ alkyl; and each of $R_{9a}$, $R_{9b}$, $R_{9e}$, and $R_{9a}$ are independently selected from H and methyl, with the proviso that at least one of $R_{9a}$, $R_{9b}$, $R_{9e}$, and $R_{9a}$ is methyl.

Also provided is a compound of the Formula VII, wherein $R_{3a}$ is $C_1$-$C_3$ alkyl; $R_{3b}$ is selected from H and $C_1$-$C_4$ alkyl; $R_{8b}$ is selected from H and $C_1$-$C_3$ alkyl; and each of $R_{9a}$, $R_{9b}$, $R_{9e}$, and $R_{9a}$ are independently selected from H and methyl, with the proviso that at least two of $R_{9a}$, $R_{9b}$, $R_{9e}$, and $R_{9a}$ are methyl.

Also provided is a compound of the Formula VII, wherein $R_{3a}$ is $C_1$-$C_3$ alkyl; $R_{3b}$ is selected from H and $C_1$-$C_4$ alkyl; $R_{8b}$ is $C_1$-$C_3$ alkyl; and each of $R_{9a}$, $R_{9b}$, $R_{9e}$, and $R_{9a}$ are independently selected from H and methyl, with the proviso that at least two of $R_{9a}$, $R_{9b}$, $R_{9e}$, and $R_{9a}$ are methyl.

Also provided is a compound of the Formula VII, wherein $R_{3a}$ is $C_1$-$C_3$ alkyl; $R_{3b}$ is selected from H and $C_1$-$C_4$ alkyl; $R_{8b}$ is selected from H and $C_1$-$C_3$ alkyl; and each of $R_{9a}$, $R_{9b}$, $R_{9e}$, and $R_{9a}$ are independently selected from H and methyl, with the proviso that at least three of $R_{9a}$, $R_{9b}$, $R_{9e}$, and $R_{9a}$ are methyl.

Also provided is a compound of the Formula VII, wherein $R_{3a}$ is $C_1$-$C_3$ alkyl; $R_{3b}$ is selected from H and $C_1$-$C_4$ alkyl; $R_{8b}$ is $C_1$-$C_3$ alkyl; and each of $R_{9a}$, $R_{9b}$, $R_{9e}$, and $R_{9a}$ are independently selected from H and methyl, with the proviso that at least three of $R_{9a}$, $R_{9b}$, $R_{9c}$, and $R_{9a}$ are methyl.

Also provided is a compound of the Formula VII, wherein $R_{3a}$ is $C_1$-$C_2$ alkyl; $R_{3b}$ is selected from H and $C_1$-$C_4$ alkyl; $R_{8b}$ is selected from H and $C_1$-$C_2$ alkyl; and each of $R_{9a}$, $R_{9b}$, $R_{9e}$, and $R_{9a}$ are independently selected from H and methyl, with the proviso that at least one of $R_{9a}$, $R_{9b}$, $R_{9e}$, and $R_{9a}$ is methyl.

Also provided is a compound of the Formula VII, wherein $R_{3a}$ is $C_1$-$C_2$ alkyl; $R_{3b}$ is selected from H and $C_1$-$C_4$ alkyl; $R_{8b}$ is $C_1$-$C_2$ alkyl; and each of $R_{9a}$, $R_{9b}$, $R_{9e}$, and $R_{9a}$ are independently selected from H and methyl, with the proviso that at least one of $R_{9a}$, $R_{9b}$, $R_{9e}$, and $R_{9a}$ is methyl.

Also provided is a compound of the Formula VII, wherein $R_{3a}$ is $C_1$-$C_2$ alkyl; $R_{3b}$ is selected from H and $C_1$-$C_4$ alkyl; $R_{8b}$ is selected from H and $C_1$-$C_2$ alkyl; and each of $R_{9a}$, $R_{9b}$, $R_{9e}$, and $R_{9a}$ are independently selected from H and methyl, with the proviso that at least two of $R_{9a}$, $R_{9b}$, $R_{9e}$, and $R_{9a}$ are methyl.

Also provided is a compound of the Formula VII, wherein $R_{3a}$ is $C_1$-$C_2$ alkyl; $R_{3b}$ is selected from H and $C_1$-$C_4$ alkyl; $R_{8b}$ is $C_1$-$C_2$ alkyl; and each of $R_{9a}$, $R_{9b}$, $R_{9e}$, and $R_{9a}$ are independently selected from H and methyl, with the proviso that at least two of $R_{9a}$, $R_{9b}$, $R_{9e}$, and $R_{9a}$ are methyl.

Also provided is a compound of the Formula VII, wherein $R_{3a}$ is $C_1$-$C_2$ alkyl; $R_{3b}$ is selected from H and $C_1$-$C_4$ alkyl; $R_{8b}$ is selected from H and $C_1$-$C_2$ alkyl; and each of $R_{9a}$, $R_{9b}$, $R_{9e}$, and $R_{9a}$ are independently selected from H and methyl, with the proviso that at least three of $R_{9a}$, $R_{9b}$, $R_{9e}$, and $R_{9a}$ are methyl.

Also provided is a compound of the Formula VII, wherein $R_{3a}$ is $C_1$-$C_2$ alkyl; $R_{3b}$ is selected from H and $C_1$-$C_4$ alkyl; $R_{8b}$ is $C_1$-$C_2$ alkyl; and each of $R_{9a}$, $R_{9b}$, $R_{9e}$, and $R_{9a}$ are independently selected from H and methyl, with the proviso that at least three of $R_{9a}$, $R_{9b}$, $R_{9c}$, and $R_{9a}$ are methyl.

Also provided is a compound of Formula VIII:

Formula VIII wherein $R_{3a}$ is $C_1$-$C_4$ alkyl; $R_{3b}$ is selected from H and $C_1$-$C_4$ alkyl; $R_{8b}$ is selected from H and $C_1$-$C_4$ alkyl.

Also provided is a compound of Formula VIII, wherein $R_{3a}$ is $C_1$-$C_4$ alkyl; $R_{3b}$ is selected from H and $C_1$-$C_4$ alkyl; and $R_{8b}$ is $C_1$-$C_4$ alkyl.

Also provided is a compound of Formula VIII, wherein $R_{3a}$ is $C_1$-$C_4$ alkyl; $R_{3b}$ is selected from H and $C_1$-$C_4$ alkyl; and $R_{8b}$ is H.

Also provided is a compound of Formula VIII, wherein $R_{3a}$ is $C_1$-$C_3$ alkyl; $R_{3b}$ is selected from H and $C_1$-$C_3$ alkyl; and $R_{8b}$ is $C_1$-$C_3$ alkyl.

Also provided is a compound of Formula VIII, wherein $R_{3a}$ is $C_1$-$C_3$ alkyl; $R_{3b}$ is selected from H and $C_1$-$C_3$ alkyl; and $R_{8b}$ is H.

Also provided is a compound of Formula VIII, wherein $R_{3a}$ is $C_1$-$C_2$ alkyl; $R_{3b}$ is selected from H and $C_1$-$C_2$ alkyl; and $R_{8b}$ is $C_1$-$C_2$ alkyl.

Also provided is a compound of Formula VIII, wherein $R_{3a}$ is $C_1$-$C_2$ alkyl; $R_{3b}$ is selected from H and $C_1$-$C_2$ alkyl; and $R_{8b}$ is H.

Also provided is a compound of Formula VIII, wherein $R_{3a}$ is $C_1$-$C_4$ alkyl; $R_{3b}$ is H; and $R_{8b}$ is $C_1$-$C_4$ alkyl.

Also provided is a compound of Formula VIII, wherein $R_{3a}$ is $C_1$-$C_3$ alkyl; $R_{3b}$ is H; and $R_{8b}$ is H.

Also provided is a compound of Formula VIII, wherein $R_{3a}$ is $C_1$-$C_3$ alkyl; $R_{3b}$ is H; and $R_{8b}$ is $C_1$-$C_3$ alkyl.

Also provided is a compound of Formula VIII, wherein $R_{3a}$ is $C_1$-$C_3$ alkyl; $R_{3b}$ is H; and $R_{8b}$ is H.

Also provided is a compound of Formula VIII, wherein $R_{3a}$ is $C_1$-$C_2$ alkyl; $R_{3b}$ is H; and $R_{8b}$ is $C_1$-$C_2$ alkyl.

Also provided is a compound of Formula VIII, wherein $R_{3a}$ is $C_1$-$C_2$ alkyl; $R_{3b}$ is H; and $R_{8b}$ is H.

Also provided herein are pharmaceutical or medical compositions comprising one or more fluorophore compound(s) described herein and a pharmaceutically or medically acceptable carrier or excipient. In some embodiments the composition is intended for direct/topical administration.

Suitable pharmaceutically-acceptable nonaqueous solvents that may be used as carriers or excipients with the present compounds include the following (as well as mixtures thereof): alcohols (these include, for example, s-glycerol formal, b-glycerol formal, 1,3-butyleneglycol; aliphatic or aromatic alcohols such as methanol, ethanol, propanol, isopropanol, butanol, t-butanol, hexanol, octanol, amylene hydrate, benzyl alcohol, glycerin (glycerol), glycol, hexylene, glycol, tetrahydrofuranyl alcohol, cetyl alcohol, and stearyl alcohol); fatty acid esters of fatty alcohols (polyalkylene glycols, such as polypropylene glycol and polyethylene glycol), sorbitan, sucrose, and cholesterol; amides such as dimethylacetamide (DMA), benzyl benzoate DMA, dimethylformamide, N-hydroxyethyl-lactamide N,N-dimethylacetamide-amides, 2-pyrrolidinone, l-methyl-2-pyrrolidinone, and polyvinylpyrrolidone); acetate esters, such as monoacetin, diacetin, and triacetin; aliphatic and aromatic esters, such as ethyl caprylate or octanoate, alkyl oleate, benzyl benzoate, or benzyl acetate; dimethylsulfoxide (DMSO); esters of glycerin (e.g., mono, di, and tri-glyceryl citrates and tartrates), ethyl benzoate, ethyl acetate, ethyl carbonate, ethyl lactate, ethyl oleate, fatty acid esters of sorbitan, glyceryl monostearate, glyceride esters (e.g., mono, di, or tri-glycerides), fatty acid esters (e.g., isopropyl myristrate), fatty acid derived PEG esters (e.g., PEG-hydroxy oleate and PEG-hydroxy stearate), N-methyl pyrrolidinone, pluronic 60, polyoxyethylene sorbitol oleic polyesters (e.g., Poly(ethoxylated)$_{30\text{-}60}$ sorbitol poly(oleate)$_{2\text{-}4}$, poly(oxyethylene)$_{15\text{-}20}$ monooleate, poly(oxyethylene)$_{15\text{-}20}$ mono 12-hydroxystearate, and poly(oxyethylene)15-20mono ricinoleate), polyoxyethylene sorbitan esters (e.g., polyoxyethylene-sorbitan monooleate, polyoxyethylene-sorbitan monopalmitate, polyoxyethylene-sorbitan monolaurate, polyoxyethylene-sorbitan monostearate, and POLYSORBATEs 20, 40, 60, and 80, polyvinylpyrrolidone, alkyleneoxy modified fatty acid esters (e.g., polyoxyl 40 hydrogenated castor oil and polyoxyethylated castor oils, such as CREMOPHOR EL solution or CREMOPHOR RH 40 solution), saccharide fatty acid esters (i.e., the condensation product of a monosaccharide (e.g., pentoses, such as, ribose, ribulose, arabinose, xylose, lyxose, and xylulose; hexoses, such as glucose, fructose, galactose, mannose, and sorbose; trioses; tetroses; heptoses; and octoses), disaccharide (e.g. sucrose, maltose, lactose, and trehalose), oligosaccharide, or a mixture thereof with one or more $C_4$-$C_{22}$ fatty acids (e.g., saturated fatty acids, such as caprylic acid, capric acid, lauric acid, myristic acid, palmitic acid, and stearic acid; and unsaturated fatty acids, such as palmitoleic acid, oleic acid, elaidic acid, erucic acid, and linoleic acid), and steroidal esters); ethers such as diethyl ether, tetrahydrofuran, dimethyl isosorbide, diethylene glycol monoethyl ether), and glycofurol (tetrahydrofurfuranyl alcohol polyethylene glycol ether); ketones such as acetone, methyl ethyl ketone, methyl isobutyl ketone; hydrocarbons such as benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO); and tetramethylene sulfoxide; oils such as mineral oils, vegetable oils, glycerides, animal oils, oleic oils, alkyl, alkenyl, or aryl halides, monoethanolamine; petroleum benzin; trolamine; omega-3 polyunsaturated fatty acids such as alpha-linolenic acid, eicosapentaenoic acid, docosapentaenoic acid, or docosahexaenoic acid); polyglycol ester of 12-hydroxy stearic acid and polyethylene glycol (SOLUTOL HS-15, from BASF, Ludwigshafen, Germany); polyoxyethylene glycerol; sodium laurate; sodium oleate; and sorbitan monooleate. Other pharmaceutically acceptable solvents for use in the invention are well known to those of ordinary skill in the art.

Additional components can cryoprotective agents; agents for preventing reprecipitation of the dithienopyrrole compound or salt surface; active, wetting, or emulsifying agents (e.g., lecithin, polysorbate-80, TWEEN 80, pluronic 60, and polyoxyethylene stearate); preservatives (e.g., ethyl-p-hydroxybenzoate); microbial preservatives (e.g., benzyl alcohol, phenol, m-cresol, chlorobutanol, sorbic acid, thimerosal, and paraben); agents for adjusting pH or buffering agents (e.g., acids, bases, sodium acetate, sorbitan monolaurate, etc.); agents for adjusting osmolarity (e.g., glycerin); and diluents (e.g., water, saline, electrolyte solutions, etc.).

One embodiment provides a composition comprising at least one fluorescent compound as described herein, such as a compound of Formula I, and dimethyl sulfoxide (DMSO).

Definitions

The terms "administer," "administering", "administration," and the like, as used herein, refer to methods used to enable delivery of agents or compositions disclosed herein to the desired site of action, such as a site to be medically imaged. These methods include, but are not limited to parenteral injection (e.g., intravenous, subcutaneous, intraperitoneal, intramuscular, intravascular, intrathecal, intravitreal, infusion, or local). In some embodiments the administration is topical. Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The terms "effective amount" or "medically effective amount" or like terms refers to an amount of a compound or composition as described herein to cover a target area sufficiently to complete binding to one or more nerves such that they may be identified through relevant imaging techniques, particularly far red to near-infrared imaging techniques.

The term "imaging" herein refers to the use of fluorescent compounds in conventional medical imaging techniques including, but not limited to, those related to fluorescence image-guided surgery (including minimally invasive laparoscopy or endoscopy techniques), computer-assisted surgery or surgical navigation, radiosurgery or radiation therapy, interventional radiology, fluorescence microscopy, and laser-confocal microscopy. These techniques may include near infrared wavelengths from about 650 nm to 900 nm.

The term "label" refers to a molecule that facilitates the visualization and/or detection of a targeting molecule disclosed herein. In some embodiments, the label is a fluorescent moiety.

As used herein, the term "neuron" means an electrically excitable cell that processes and transmits information by electrical and chemical signaling. Neurons possess a cell body (i.e., the soma), dendrites, and an axon. Neurons are electrically excitable, maintaining voltage gradients across their membranes by ion pumps, which combine with ion channels embedded in the membrane to generate intracellular-versus-extracellular concentration differences of ions (e.g., sodium, potassium, chloride, and calcium). A neuron may or may not include a myelin sheath. The term "neuron" is intended to include any tissues (e.g., the sinoatrial node or atrioventricular node) or structures associated therewith (e.g., neuromuscular junctions).

The term "nerve" means a bundle of neural axons. Within a nerve, each axon is surrounded by a layer of connective tissue called the endoneurium. The axons are bundled together into groups called fascicles, and each fascicle is wrapped in a layer of connective tissue called the perineurium. The entire nerve is wrapped in a layer of connective tissue called the epineurium. The term "nerve" is intended to include any tissues (e.g., the sinoatrial node or the atriventricular node) or structures associated therewith (e.g., neuromuscular junctions).

The terms "patient," "individual," and "subject" are used interchangeably. As used herein, they mean any mammal. In some embodiments, the mammal is a human. In some embodiments, the mammal is a non-human, including farm animals (cattle, hogs, horses, goats, sheep, etc.), companion animals (dogs, cats, etc.), and research animals (mice and rats).

The term "pharmaceutically acceptable" as used herein, refers to a material that does not abrogate the biological activity or properties of the agents described herein, such as binding to a desired target, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "fluorescence guided surgery (FGS)" refers to a surgery aided by medical imaging techniques capable of detecting fluorescently labeled structures or tissues.

As used herein, the terms "robotic surgery", "robot-assisted surgery", or "computer-assisted surgery" refer to surgical techniques involving robotic systems that control the movement of medical instruments to conduct a surgical procedure with precise, flexible, and/or minimally invasive actions designed to limit the amount of surgical trauma, blood loss, pain, scarring, and post-surgical patient recovery time and/or complications, such as infection at the surgical area. Examples of robotic surgery include those conducted using the da Vinci Surgical System (Intuitive Surgical, Sunnyvale, Calif., USA) approved by the U.S. Food and Drug Administration in 2000. Specific examples include the FLARE (Curadel Marlborough, Mass.), Fluobeam (Fluoptics, Grenoble, France), Photodynamic eye (Hamamatsu Photonics, Hamamatsu, Japan), HyperEye Medical System (Mizuho Medical Company, Tokyo, Japan), SPY fluorescence imaging system (Stryker Endoscopy, San Jose, Calif.), Image 1S Camera System (Karl Storz, Tuttlingen, Germany), and Firefly on the da Vinci Surgical System (Intuitive Surgical, Inc., Sunnyvale, Calif.). FGS systems operate almost exclusively at near infrared (NIR) wavelengths (650-900 nm), where tissue chromophore absorbance, autofluorescence and scattering are all at local minima, allowing for tissue visualization at up to centimeter depths.

The terms "surgery" or "surgical method" as used herein, refers to any method used to manipulate, change, or cause an effect by a physical intervention. These methods include, but are not limited to open surgery, endoscopic surgery, laparoscopic surgery, minimally invasive surgery, robotic surgery, any procedures that may affect any neuron or nerve, such as placement of retractors during spinal surgery, electrically conducting cardiac tissue or nerve ablation, epidural injection, intrathecal injections, neuron or nerve blocks, implantation of devices such as neuron or nerve stimulators and implantation of pumps. These methods may also include biopsy or other invasive techniques for the collection of cell or tissue samples, such as for diagnostic purposes.

As used herein, the term "targeting molecule" refers to any agent (e.g., peptide, protein, nucleic acid polymer, aptamer, or small molecule) that associates with (e.g., binds to) a target of interest. The target of interest may be a nerve cell or an organ or tissue associated with one or more nerve cells or nerve structures. In some embodiments, the targeting molecule is any agent that associates with (e.g., binds to) a target comprising one or more neurons, nerves, or tissues or structures associated therewith, i.e. nerve tissues, nervous system tissues, nerve bundles, etc. It is understood that nerve and nerve-related targets include those associated with the brain and spinal cord of the central nervous system (CNS) and the nerves of the peripheral nervous system (PNS).

It is understood that the compounds and compositions herein may be administered to the cells, tissue, organ, or system of interest by "direct administration" or by "systemic administration." Direct administration to the cells, tissue, organ, or system of interest may be accomplished by any direct means, including spraying, irrigating, brushing, sponging, or wiping the relevant compound or composition to or on the desired location. In some embodiments, direct administration may be considered topical administration. Systemic administration may refer to general intravenous administration or administration to a blood vessel associated with the cells, tissue, organ, or system of interest.

Also provided herein are methods of imaging nervous tissue tumors (neoplasms), including Gliomas, such as bliomatosis cerbri, Oligoastrocytomas, Choroid plexus papillomas, Ependymomas, Astrocytomas (Pilocytic astrocytomas and Glioblastoma multiforme), Dysembryoplastic neuroepithelial tumors, Oligodendrogliomas, Medulloblastomas, and Primitive neuroectodermal tumors; Neuroepitheliomatous tumors, such as Ganglioneuromas, Neruoblastomas, Atypical teratoid rhabdoid tumors, Retinoblastomas, and Esthesio neuroblastomas; and Nerve Sheath Tumors, such as Neruofibromas (Neurofibrosarcomas and Neurofibromatosis), Schannomas, Neurinomas, Acoustic neuromas, and Neuromas.

Provided is a method of imaging a target area in a subject, the method comprising contacting the target area in the subject with a compound selected from those herein and detecting the compound in the target using fluorescence or near-infrared imaging.

Also provided is a method of imaging one or more nerves in a target area in a subject, the method comprising contacting the target area in the subject with a compound selected from those herein and detecting the compound in the target using fluorescence imaging.

Also provided is a method of minimizing nerve damage in a target area in a subject during a medical procedure, the method comprising the steps of:
a) contacting the target area in the subject with a compound selected from those herein;
b) detecting one or more nerves bound by the compound in the target area using fluorescence imaging; and
c) minimizing actions of the medical procedure that may damage one or more nerves detected.

The method above may be used to identify nerves and minimize damage to them that may be caused by a medical procedure, including traumatic, thermal, and radiological damage or that are caused by the application of therapeutic agents, anesthetics, or anesthesia in the target area.

In some embodiments, the medical procedure referenced in the method above is a surgical procedure. In other embodiments, the medical procedure is a biopsy procedure, a radiological procedure, or the application of anesthetic or anesthesia to the subject.

Also provided is the use of any compound disclosed herein in the preparation of a composition for use in imaging one or more nerves in a subject using from far red to near-infrared imaging.

Further provided is a kit comprising a container with a composition comprising a medically useful amount of a compound as described herein and a set of instructions for the use of the composition in a nerve imaging procedure.

General.

All reagents were purchased from Sigma Aldrich, Fisher Scientific, TCI, or Ark Pharm. Unless otherwise indicated, all commercially available starting materials were used directly without further purification. Analytical thin layer chromatography (TLC) was performed on Millipore ready-to-use plates with silica gel 60 (F254, 32-63 µm). Flash chromatography was performed on Sorbent Technologies silica gel for column chromatography or on a Biotage Isolera Flash System using SNAP Ultra cartridges. High-resolution mass spectra (HRMS) were measured on a ThermoElectron LTQ-Orbitrap high resolution mass spectrometer with a dedicated Accela HPLC system, or an Agilent 6244 time-of-flight LCMS with diode array detector VL+.

LCMS and Purity Characterization

Mass-to-charge ratio and purity of the Oxazine compounds were characterized on an Agilent 6244 time-of-flight tandem liquid chromatography mass spectroscopy (LCMS) with diode array detector VL+. Sample (10 µL) was injected into a C18 column (Poroshell 120, 4.6×50 mm, 2.7 micron), and eluted with a solvent system of A ($H_2O$, 0.1% FA) and B (MeCN, 01.% FA) at 0.4 mL/min, from A/B=90/10 to 5/95 over 10 min, maintained at A/B=5/95 for additional 5 min. Ions were detected in positive ion mode by setting the capillary voltage at 4 kV and gas temperature at 350° C. Purity was calculated through area under the curve analysis of the absorbance at 254 nm.

UV-Vis Absorption and Fluorescence Spectroscopy.

UV-Vis spectra were collected with a Cary 50 UV-Vis spectrophotometer at room temperature, using a 1-cm quartz cuvette. Fluorescence spectra were collected on a Cary Eclipse fluorescence spectrophotometer (Agilent Technologies). All absorbance spectra were reference corrected. Extinction coefficient was calculated from Beer's Law plots of absorbance versus concentration. Fluorescence spectra were corrected for the wavelength dependent response of the R928 photomultiplier tube using a manufacturer generated correction file. Relative quantum yields are reported as the average of multiple measurements using multiple references, including Oxazine 1, Oxazine 170, and Rhodamine 101.

Physicochemical Property Calculation.

Physicochemical partition coefficients (Log D) values at pH 7.4, number of hydrogen bond donors and acceptors, polar surface area, and the number of rotatable bonds were calculated using Marvin and JChem calculator plugins (ChemAxon, Budapest, Hungary).

Nerve-Specificity Screening using Direct/Topical Administration

Each compound was screened for its tissue-specificity using a previously published direct/topical administration strategy in murine brachial plexus and sciatic nerves.[1] Each compound from the Oxazine library was formulated in the previously utilized co-solvent formulation (10% DMSO, 5% Kolliphor, 65% serum and 20% phosphate buffered saline) at 125 µM. 100 µL of the formulated Oxazine were incubated on the exposed brachial plexus or sciatic nerve for 5 minutes. The fluorophore containing solution was removed and the area was irrigated with saline 18 times to remove any unbound fluorophore. Co-registered fluorescence and color images were collected of each stained area 30 minutes after Oxazine direct/topical administration using a custom built macroscopic imaging system with 620/60 nm excitation and 700/75 nm bandpass emission filters. Custom written MatLab code was used to analyze the tissue specific fluorescence where regions of interest were selected on the nerve, muscle and adipose tissue using the white light images. These regions of interest were then analyzed on the co-registered matched fluorescence images permitting assessment of the nerve to muscle and nerve to adipose ratios in blinded manner. The nerve, muscle and adipose intensity from this screening are shown in FIG. 1. The nerve to muscle and nerve to adipose ratios from this screening are shown in FIG. 2.

Nerve-Specificity Screening Using Systemic Administration

Each compound was screened for its tissue-specificity using a previously published systemic administration strategy in murine brachial plexus and sciatic nerves.[1] Each compound from the Oxazine library was formulated in the previously utilized co-solvent formulation (10% DMSO, 5% Kolliphor, 65% serum and 20% phosphate buffered saline) at 2 mM. 100 µL of the formulated Oxazine were administered intravenously 4 hours before exposing the brachial plexus and sciatic nerves. Co-registered fluorescence and color images were collected of each nerve site using a custom built macroscopic imaging system with 620/60 nm excitation and 700/75 nm bandpass emission filters. Custom written MatLab code was used to analyze the tissue specific fluorescence where regions of interest were selected on the nerve, muscle and adipose tissue using the white light images. These regions of interest were then analyzed on the co-registered matched fluorescence images permitting assessment of the nerve to muscle and nerve to adipose ratios in blinded manner. The nerve, muscle and adipose intensity from this screening are shown in FIG. 3. The nerve to muscle and nerve to adipose ratios from this screening are shown in FIG. 4.

Resonance Structures

It will be understood that the fluorescent compounds described herein may exist in any possible resonance form. For instance, the compounds depicted as Formula I:

Formula I

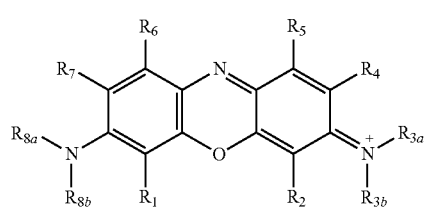

could be equally referred to using the structures:

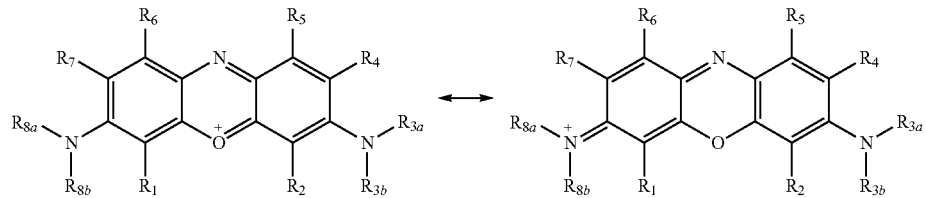

or by the structure:

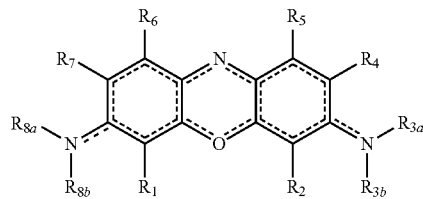

wherein, in each instance, the general listing of " ----- " indicates a single or a double bond as needed to satisfy valence requirements.

TABLE 1

LCMS and purity characterization for the Oxazine library

| ID | Retention Time (min) | Measured m/z | Calculated m/z | Mass Accuracy (ppm) | Purity |
| --- | --- | --- | --- | --- | --- |
| LGW01-08 | 7.74 | 310.1930 | 310.1914 | 5.16 | >99% |
| LGW01-18 | 7.02 | 282.1616 | 282.1601 | 5.32 | >99% |
| LGW01-21 | 6.61 | 268.1456 | 268.1444 | 4.48 | 99% |
| LGW01-23 | 8.77 | 324.2094 | 324.2070 | 7.40 | 96% |
| LGW01-25 | 7.41 | 296.1764 | 296.1757 | 2.36 | >99% |
| LGW01-39 | 6.34 | 268.1461 | 268.1444 | 6.34 | 98% |
| LGW01-44 | 8.51 | 334.1915 | 334.1914 | 0.30 | >99% |
| LGW01-56 | 8.71 | 348.2081 | 348.2070 | 3.16 | >99% |
| LGW01-61 | 8.65 | 268.1462 | 268.1444 | 6.71 | 98% |
| LGW01-64 | 8.68 | 324.2097 | 324.2070 | 8.33 | >99% |
| LGW01-99 | 8.17 | 334.1939 | 334.1914 | 7.48 | 97% |
| LGW02-57 | 7.51 | 296.1773 | 296.1757 | 5.40 | 97% |
| LGW02-58 | 7.68 | 296.1775 | 296.1757 | 6.08 | 97% |
| LGW02-59 | 8.09 | 296.1776 | 296.1757 | 6.42 | 96% |
| LGW02-60 | 7.99 | 310.1935 | 310.1914 | 6.77 | >99% |
| LGW02-61 | 8.29 | 310.1910 | 310.1914 | −1.29 | >99% |
| LGW02-86 | 8.41 | 348.2095 | 348.2070 | 7.18 | >99% |
| LGW02-87 | 8.67 | 372.2095 | 372.2070 | 6.72 | 97% |
| LGW02-91 | 8.04 | 322.1937 | 322.1914 | 7.14 | >99% |
| LGW02-92 | 8.35 | 336.2091 | 336.2070 | 6.25 | 93% |
| LGW02-95 | 8.22 | 296.1776 | 296.1757 | 6.42 | 97% |
| LGW02-99 | 8.47 | 348.2095 | 348.2070 | 7.18 | >99% |
| LGW03-01 | 9.77 | 372.2097 | 372.2070 | 7.25 | 98% |
| LGW03-06 | 7.74 | 308.1778 | 308.1757 | 6.81 | 98% |
| LGW03-07 | 7.81 | 322.1926 | 322.1914 | 3.72 | >99% |
| LGW03-12 | 7.31 | 294.1615 | 294.1601 | 4.76 | 97% |
| LGW03-13 | 7.64 | 308.1776 | 308.1757 | 6.17 | >99% |
| LGW03-18 | 8.39 | 336.2095 | 336.2070 | 7.44 | >99% |
| LGW03-21 | 8.19 | 322.1935 | 322.1914 | 6.52 | 97% |
| LGW03-23 | 8.62 | 338.2238 | 338.2227 | 3.25 | 98% |
| LGW03-31 | 7.77 | 320.1780 | 320.1757 | 7.18 | >99% |
| LGW03-32 | 7.09 | 292.1459 | 292.1444 | 5.13 | 99% |
| LGW03-37 | 7.20 | 310.1568 | 310.1550 | 5.80 | >99% |
| LGW03-41 | 6.81 | 296.1409 | 296.1394 | 5.07 | 96% |
| LGW03-52 | 9.31 | 376.2394 | 376.2383 | 2.92 | >99% |
| LGW03-57 | 9.29 | 362.2256 | 362.2227 | 8.01 | >99% |
| LGW03-65 | 6.24 | 296.1041 | 296.1030 | 3.71 | 99% |
| LGW03-76 | 7.29 | 296.1777 | 296.1757 | 6.75 | 97% |
| LGW03-88 | 7.23 | 294.1617 | 294.1601 | 5.44 | >99% |
| LGW04-31 | 8.51 | 324.2093 | 324.2070 | 7.09 | 99% |
| LGW04-32 | 8.21 | 310.1933 | 310.1914 | 6.13 | 98% |
| LGW04-36 | 6.97 | 282.1617 | 282.1601 | 5.67 | 99% |
| LGW04-81 | 7.15 | 282.1616 | 282.1601 | 5.32 | 99% |
| LGW04-84 | 7.51 | 296.1774 | 296.1757 | 5.74 | >99% |
| LGW04-91 | 8.55 | 348.2096 | 348.2070 | 7.47 | >99% |
| LGW05-33 | 7.93 | 330.1385 | 330.1368 | 5.15 | 94% |
| LGW05-39 | 7.65 | 336.0682 | 336.0665 | 5.06 | >99% |
| LGW05-42 | 7.71 | 316.1227 | 316.1211 | 5.06 | >99% |
| LGW05-65 | 7.85 | 338.1886 | 338.1863 | 6.80 | 98% |
| LGW05-66 | 10.62 | 428.2686 | 428.2696 | −2.33 | >99% |
| LGW05-73 | 7.41 | 352.1679 | 352.1656 | 6.53 | 94% |
| LGW05-75 | 7.52 | 324.1728 | 324.1707 | 6.48 | 97% |
| LGW05-76 | 7.62 | 308.1776 | 308.1757 | 6.17 | >99% |
| LGW05-81 | 7.07 | 300.1493 | 300.1507 | −4.66 | >99% |
| LGW05-82 | 7.51 | 314.1682 | 314.1663 | 6.05 | >99% |
| LGW05-84 | 7.99 | 322.1934 | 322.1914 | 6.21 | >99% |
| LGW05-85 | 6.81 | 280.1457 | 280.1444 | 4.64 | 97% |
| LGW05-91 | 6.69 | 304.1271 | 304.1256 | 4.93 | 93% |
| LGW06-10 | 6.69 | 268.1448 | 268.1444 | 1.49 | >99% |
| LGW06-11 | 7.12 | 282.1614 | 282.1601 | 4.61 | 97% |
| LGW06-14 | 6.01 | 240.1130 | 240.1131 | −0.42 | 98% |
| LGW06-97 | 6.19 | 254.1290 | 254.1288 | 0.79 | >99% |
| LGW07-55 | 6.09 | 264.1138 | 264.1131 | 2.65 | >99% |
| LGW07-59 | 7.75 | 320.1777 | 320.1757 | 6.25 | 96% |

TABLE 2

Spectroscopic and photochemical properties of the Oxazine library

| Compound ID | Max Abs (nm) | Max Ex (nm) | Max Em (nm) | Extinction coefficient ($M^{-1}$ $cm^{-1}$) | Quantum yield (%) | Brightness ($M^{-1}$ $cm^{-1}$) |
|---|---|---|---|---|---|---|
| OX-1 | 655 | 660 | 671 | 93211 | 7.40 | 6.90 |
| OX-4 | 618 | 620 | 634 | 77156 | 38.37 | 29.61 |
| LGW01-08 | 638 | 640 | 659 | 78650 | 5.68 | 4.47 |
| LGW01-18 | 617 | 620 | 636 | 60731 | 32.91 | 19.99 |
| LGW01-21 | 617 | 620 | 634 | 28745 | 30.12 | 8.66 |
| LGW01-23 | 645 | 620 | 635 | 62445 | 0.67 | 0.42 |
| LGW01-25 | 635 | 640 | 660 | 41771 | 3.31 | 1.38 |
| LGW01-39 | 648 | 650 | 667 | 76144 | 9.56 | 7.28 |
| LGW01-44 | 648 | 650 | 664 | 40124 | 21.63 | 8.68 |
| LGW01-56 | 664 | 670 | 684 | 38832 | 11.68 | 4.53 |
| LGW01-61 | 612 | 610 | 631 | 21783 | 40.27 | 8.77 |
| LGW01-64 | 620 | 620 | 638 | 50166 | 42.15 | 21.15 |
| LGW01-99 | 648 | 650 | 667 | 56046 | 10.14 | 5.68 |
| LGW02-57 | 635 | 635 | 653 | 56713 | 11.15 | 6.32 |
| LGW02-58 | 620 | 620 | 635 | 42685 | 25.26 | 10.78 |
| LGW02-59 | 611 | 615 | 636 | 41229 | 31.74 | 13.09 |
| LGW02-60 | 645 | 650 | 661 | 65369 | 8.98 | 5.87 |
| LGW02-61 | 630 | 635 | 658 | 68548 | 6.12 | 4.20 |
| LGW02-86 | 661 | 665 | 680 | 39472 | 13.18 | 5.20 |
| LGW02-87 | 678 | 680 | 690 | 59937 | 15.03 | 9.01 |
| LGW02-91 | 640 | 645 | 657 | 59971 | 23.58 | 14.14 |
| LGW02-92 | 656 | 660 | 673 | 43659 | 9.27 | 4.05 |
| LGW02-95 | 606 | 605 | 627 | 48653 | 32.50 | 15.81 |
| LGW02-99 | 640 | 665 | 675 | 59971 | 24.67 | 14.80 |
| LGW03-01 | 677 | 680 | 695 | 44453 | 17.27 | 7.68 |
| LGW03-06 | 640 | 640 | 661 | 35942 | 11.94 | 4.29 |
| LGW03-07 | 654 | 660 | 672 | 52356 | 9.28 | 4.86 |
| LGW03-12 | 624 | 630 | 638 | 40041 | 27.22 | 10.90 |
| LGW03-13 | 641 | 645 | 659 | 64045 | 6.49 | 4.16 |
| LGW03-18 | 661 | 665 | 680 | 66206 | 3.49 | 2.31 |
| LGW03-21 | 642 | 640 | 661 | 36049 | 2.25 | 0.81 |
| LGW03-23 | 664 | 645 | 690 | 23099 | 1.53 | 0.35 |
| LGW03-31 | 655 | 655 | 674 | 48226 | 15.78 | 7.61 |
| LGW03-32 | 631 | 630 | 644 | 45650 | 29.92 | 13.66 |
| LGW03-37 | 646 | 650 | 670 | 48849 | 4.34 | 2.12 |
| LGW03-41 | 607 | 625 | 641 | 19729 | 25.80 | 5.09 |
| LGW03-52 | 678 | 680 | 699 | 38039 | 6.82 | 2.59 |
| LGW03-57 | 661 | 665 | 680 | 54072 | 18.17 | 9.83 |
| LGW03-65 | 629 | 630 | 643 | 28067 | 27.39 | 7.69 |
| LGW03-76 | 654 | 655 | 669 | 66111 | 7.99 | 5.28 |
| LGW03-88 | 631 | 640 | 659 | 59737 | 6.22 | 3.71 |
| LGW04-31 | 641 | 640 | 661 | 59586 | 5.01 | 2.99 |
| LGW04-32 | 620 | 620 | 638 | 61084 | 39.77 | 24.29 |
| LGW04-36 | 636 | 635 | 657 | 60819 | 8.15 | 4.96 |
| LGW04-81 | 616 | 615 | 634 | 52291 | 39.47 | 20.64 |
| LGW04-84 | 637 | 640 | 658 | 50981 | 3.95 | 2.02 |
| LGW04-91 | 663 | 665 | 689 | 85597 | 2.77 | 2.37 |
| LGW05-33 | 638 | 640 | 660 | 36166 | 3.84 | 1.39 |
| LGW05-39 | 620 | 620 | 638 | 18223 | 34.29 | 6.25 |
| LGW05-42 | 612 | 615 | 636 | 41527 | 37.22 | 15.46 |
| LGW05-65 | 661 | 665 | 684 | 61535 | 7.85 | 4.83 |
| LGW05-66 | 701 | 710 | 718 | 34002 | 36.68 | 12.47 |
| LGW05-73 | 657 | 660 | 676 | 55570 | 32.95 | 18.31 |
| LGW05-75 | 638 | 640 | 659 | 57360 | 31.70 | 18.19 |
| LGW05-76 | 628 | 630 | 650 | 45449 | 32.68 | 14.85 |
| LGW05-81 | 611 | 610 | 632 | 58410 | 43.02 | 25.13 |
| LGW05-82 | 636 | 640 | 661 | 36833 | 2.70 | 1.00 |
| LGW05-84 | 643 | 650 | 675 | 46048 | 4.85 | 2.23 |
| LGW05-85 | 613 | 615 | 640 | 45382 | 41.05 | 18.63 |
| LGW05-91 | 606 | 610 | 626 | 16763 | 33.45 | 5.61 |
| LGW06-10 | 602 | 605 | 621 | 55807 | 26.54 | 14.81 |
| LGW06-11 | 628 | 625 | 650 | 31843 | 2.52 | 0.80 |
| LGW06-14 | 590 | 590 | 606 | 39303 | 37.61 | 14.78 |
| LGW06-97 | 599 | 600 | 617 | 38616 | 25.39 | 9.81 |
| LGW07-55 | 619 | 620 | 634 | 20163 | 28.25 | 5.70 |
| LGW07-59 | 649 | 655 | 665 | 51130 | 32.17 | 16.45 |

TABLE 3

Calculated physicochemical properties of the Oxazine library

| Compound ID | Molecular weight (g/mol) | LogD (pH 7.4) | Number of H bond donor/ acceptor | Polar surface area | Number of Rotatable bonds |
|---|---|---|---|---|---|
| OX-1 | 324.45 | 5.21 | 0/3 | 27.84 | 5 |
| OX-4 | 296.39 | 4.26 | 2/3 | 47.59 | 3 |
| LGW01-08 | 310.42 | 4.73 | 1/3 | 36.63 | 4 |
| LGW01-18 | 282.37 | 3.74 | 2/3 | 47.59 | 3 |
| LGW01-21 | 268.34 | 3.23 | 2/3 | 47.59 | 3 |
| LGW01-23 | 324.45 | 5.25 | 1/3 | 36.63 | 4 |
| LGW01-25 | 296.39 | 4.22 | 1/3 | 36.63 | 4 |
| LGW01-39 | 268.34 | 3.79 | 0/3 | 27.84 | 1 |
| LGW01-44 | 334.44 | 4.74 | 2/3 | 47.59 | 2 |
| LGW01-56 | 348.47 | 5.22 | 1/3 | 38.8 | 3 |
| LGW01-61 | 268.34 | 3.54 | 2/3 | 47.59 | 1 |
| LGW01-64 | 324.45 | 5.3 | 2/3 | 47.59 | 5 |
| LGW01-99 | 319.38 | 5.07 | 1/3 | 44.83 | 2 |
| LGW02-57 | 334.44 | 4.99 | 1/3 | 36.63 | 2 |
| LGW02-58 | 296.39 | 4.26 | 2/3 | 47.59 | 3 |
| LGW02-59 | 296.39 | 4.26 | 2/3 | 47.59 | 3 |
| LGW02-60 | 296.39 | 4.26 | 2/3 | 47.59 | 3 |
| LGW02-61 | 310.41 | 4.73 | 1/3 | 36.63 | 4 |
| LGW02-86 | 310.41 | 4.73 | 1/3 | 36.63 | 4 |
| LGW02-87 | 348.46 | 5.47 | 0/3 | 27.84 | 2 |
| LGW02-91 | 372.48 | 5.72 | 0/3 | 27.84 | 0 |
| LGW02-92 | 322.42 | 4.86 | 1/3 | 38.8 | 2 |
| LGW02-95 | 336.45 | 5.34 | 0/3 | 27.84 | 3 |
| LGW02-99 | 296.39 | 4.26 | 2/3 | 47.59 | 3 |
| LGW03-01 | 348.46 | 5.47 | 0/3 | 27.84 | 2 |
| LGW03-06 | 372.48 | 5.23 | 2/3 | 47.59 | 0 |
| LGW03-07 | 308.40 | 4.43 | 1/3 | 38.8 | 2 |
| LGW03-12 | 322.42 | 4.9 | 0/3 | 27.84 | 3 |
| LGW03-13 | 294.37 | 3.87 | 2/3 | 47.59 | 1 |
| LGW03-18 | 308.40 | 4.35 | 1/3 | 36.63 | 2 |
| LGW03-21 | 336.45 | 5.35 | 0/3 | 27.84 | 3 |
| LGW03-23 | 322.42 | 4.87 | 1/3 | 38.8 | 2 |
| LGW03-31 | 338.47 | 5.73 | 0/3 | 27.84 | 5 |
| LGW03-32 | 320.41 | 4.6 | 0/3 | 27.84 | 1 |
| LGW03-37 | 292.35 | 3.48 | 2/3 | 47.59 | 0 |
| LGW03-41 | 310.37 | 3.53 | 1/4 | 45.86 | 2 |
| LGW03-52 | 296.34 | 3.06 | 2/4 | 56.82 | 1 |
| LGW03-57 | 376.51 | 6.21 | 0/3 | 27.84 | 3 |
| LGW03-65 | 352.49 | 6.24 | 0/3 | 27.84 | 5 |
| LGW03-76 | 296.39 | 4.5 | 0/3 | 27.84 | 3 |
| LGW03-88 | 294.37 | 3.9 | 1/3 | 36.63 | 2 |
| LGW04-31 | 324.45 | 5.26 | 1/3 | 36.63 | 5 |
| LGW04-32 | 310.42 | 4.78 | 2/3 | 47.59 | 4 |
| LGW04-36 | 282.37 | 4.02 | 1/3 | 38.8 | 2 |
| LGW04-81 | 282.37 | 3.9 | 2/3 | 47.59 | 2 |
| LGW04-84 | 296.39 | 4.38 | 1/3 | 36.63 | 3 |
| LGW04-91 | 348.47 | 5.49 | 0/3 | 27.84 | 1 |
| LGW05-33 | 330.84 | 4.82 | 1/4 | 36.63 | 4 |
| LGW05-39 | 337.22 | 4.44 | 2/5 | 47.59 | 3 |
| LGW05-42 | 316.81 | 4.35 | 2/4 | 47.59 | 3 |
| LGW05-65 | 338.43 | 4.53 | 0/4 | 37.07 | 3 |
| LGW05-66 | 428.60 | 7.21 | 0/3 | 27.84 | 2 |
| LGW05-73 | 352.41 | 3.84 | 0/5 | 46.3 | 2 |
| LGW05-75 | 324.40 | 4.05 | 1/4 | 48.03 | 2 |
| LGW05-76 | 308.40 | 4.42 | 1/3 | 38.8 | 2 |
| LGW05-81 | 300.36 | 3.88 | 2/4 | 47.59 | 3 |
| LGW05-82 | 314.38 | 4.36 | 1/4 | 36.63 | 4 |
| LGW05-84 | 322.43 | 4.9 | 0/3 | 27.84 | 3 |
| LGW05-85 | 280.35 | 3.42 | 2/3 | 47.59 | 1 |
| LGW05-91 | 304.32 | 3.51 | 2/5 | 47.59 | 3 |
| LGW06-10 | 268.34 | 3.6 | 2/3 | 62.58 | 1 |
| LGW06-11 | 282.37 | 4.08 | 1/3 | 50.62 | 2 |
| LGW06-14 | 240.29 | 2.94 | 2/3 | 73.2 | 0 |
| LGW06-97 | 254.31 | 3.08 | 2/3 | 61.58 | 1 |
| LGW07-55 | 264.31 | 2.59 | 2/3 | 47.59 | 0 |
| LGW07-59 | 320.42 | 4.58 | 0/3 | 27.84 | 2 |

Figure 1B:
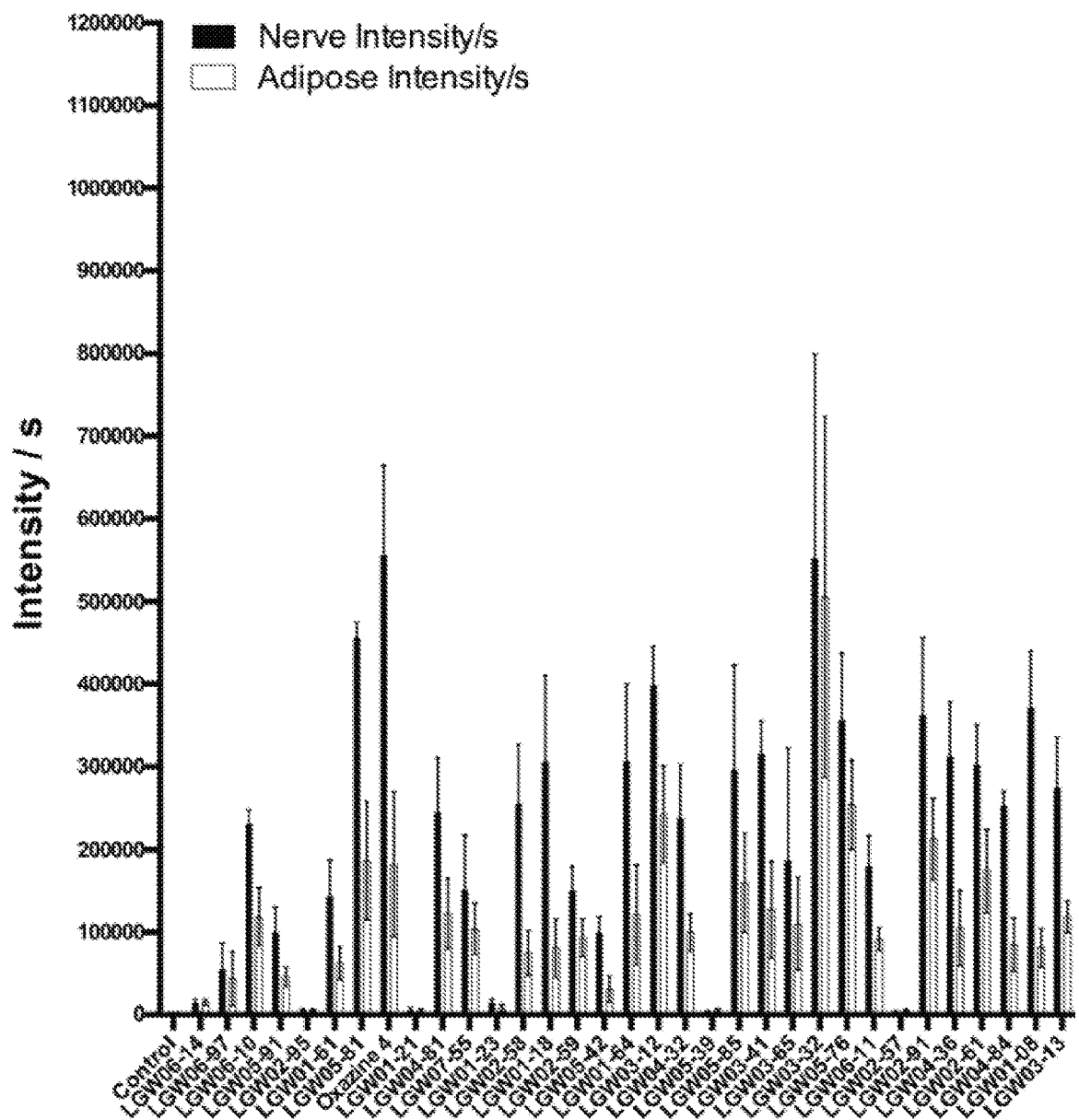
Figure 1B:
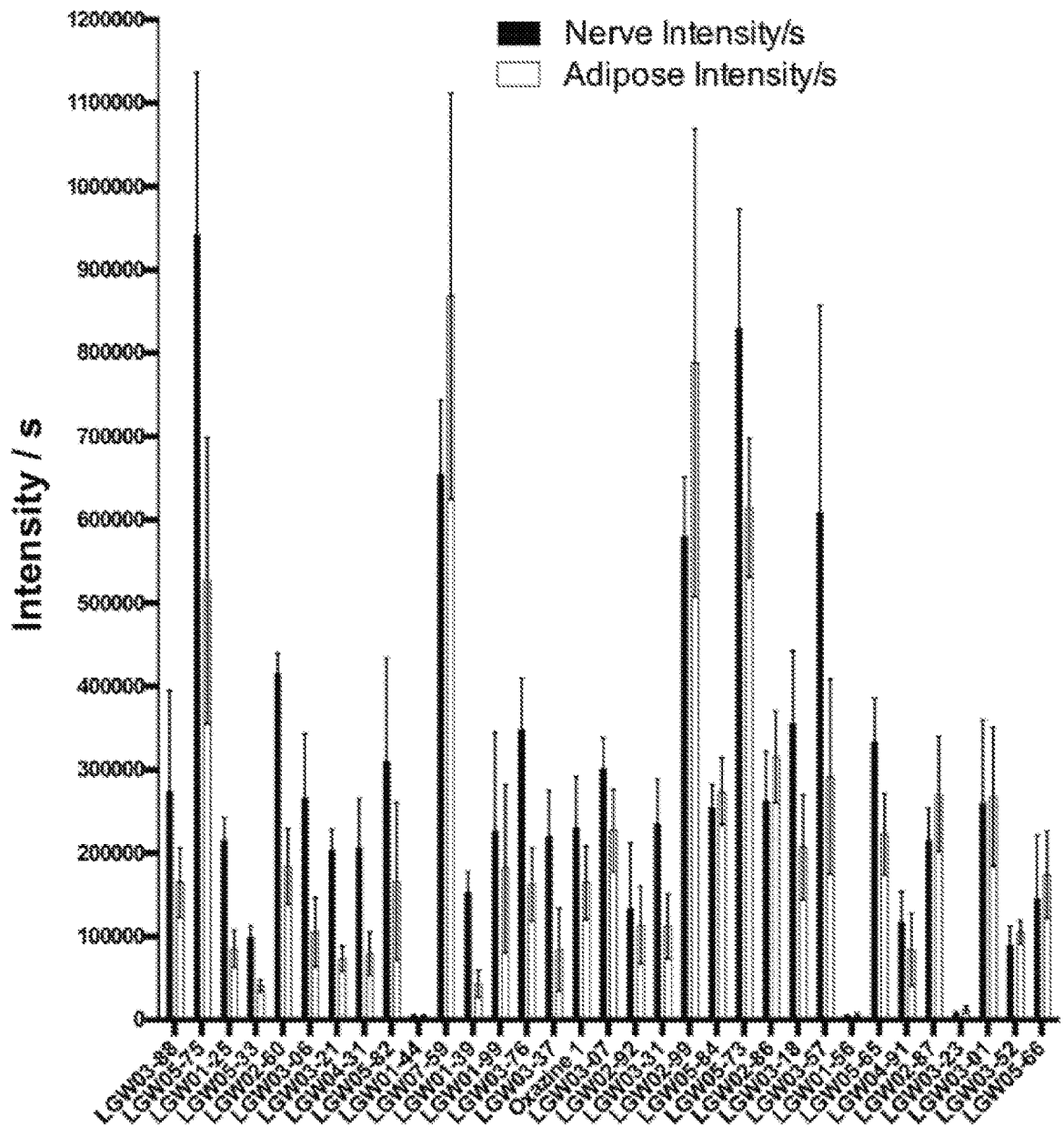

FIGS. 1A and 1B depict tissue specific intensity following oxazine library direct/topical administration. The compounds are organized by emission wavelength where the reddest compounds are shown on the right-hand side of the graph. Nerve and muscle tissue fluorescence intensity per second (1A) as well as nerve and adipose tissue fluorescence intensity per second (1B) are shown as the mean plus and minus the standard deviation.

Figure 2A:
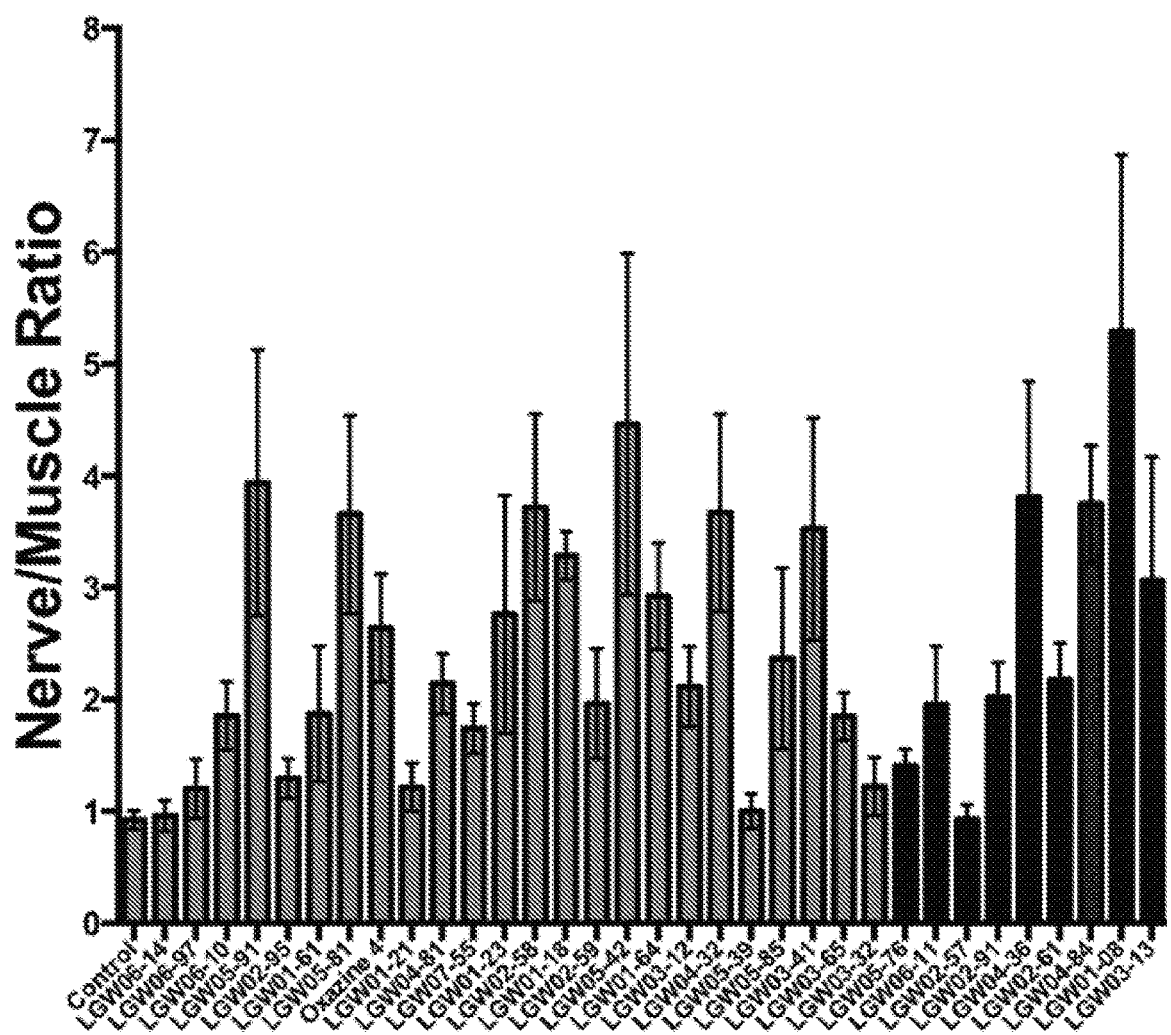
FIGS. 2A and 2B represent nerve to muscle and nerve to adipose ratios following direct/topical administration screening using compounds herein.
Figure 2A:
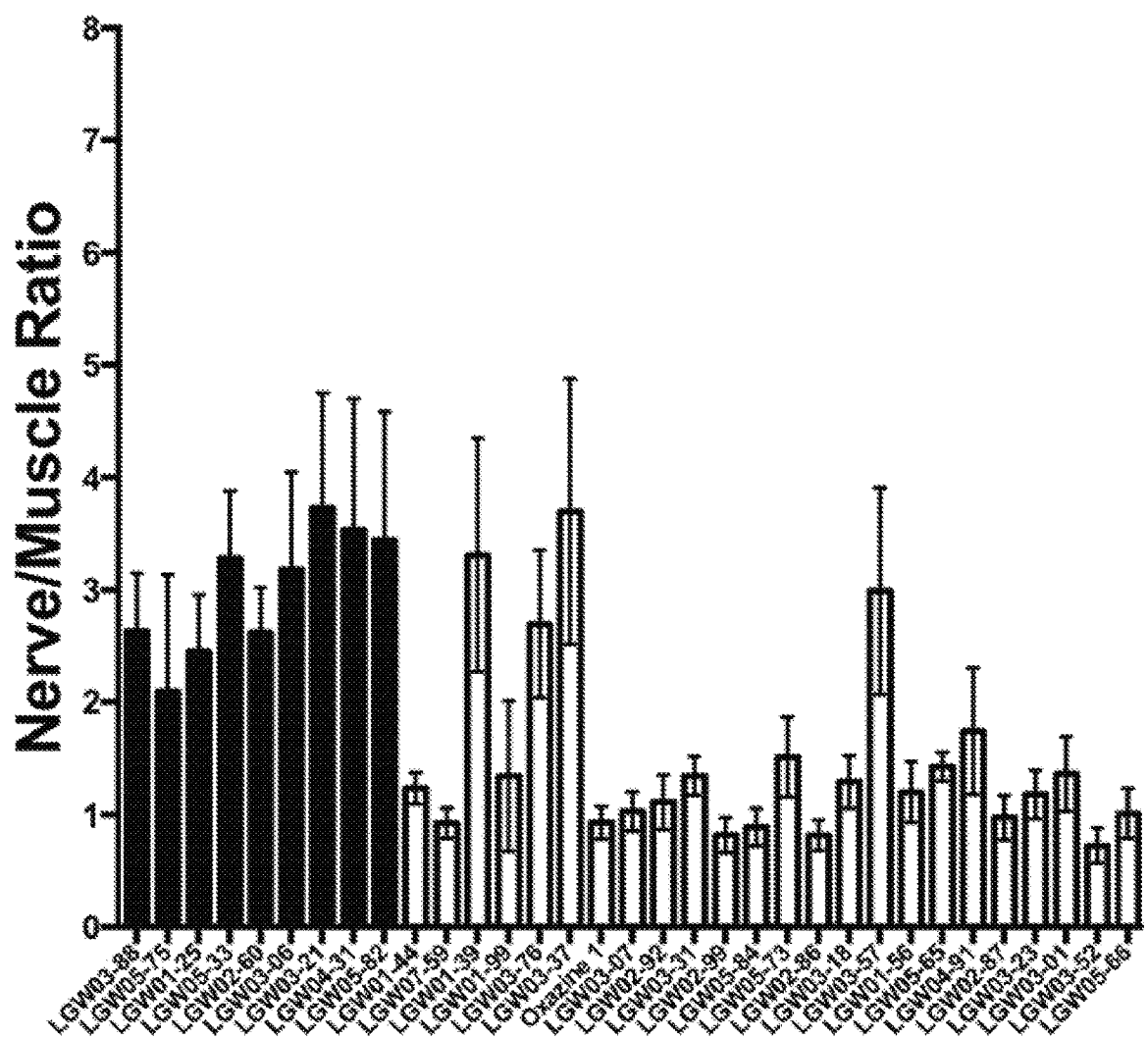
Figure 2B:
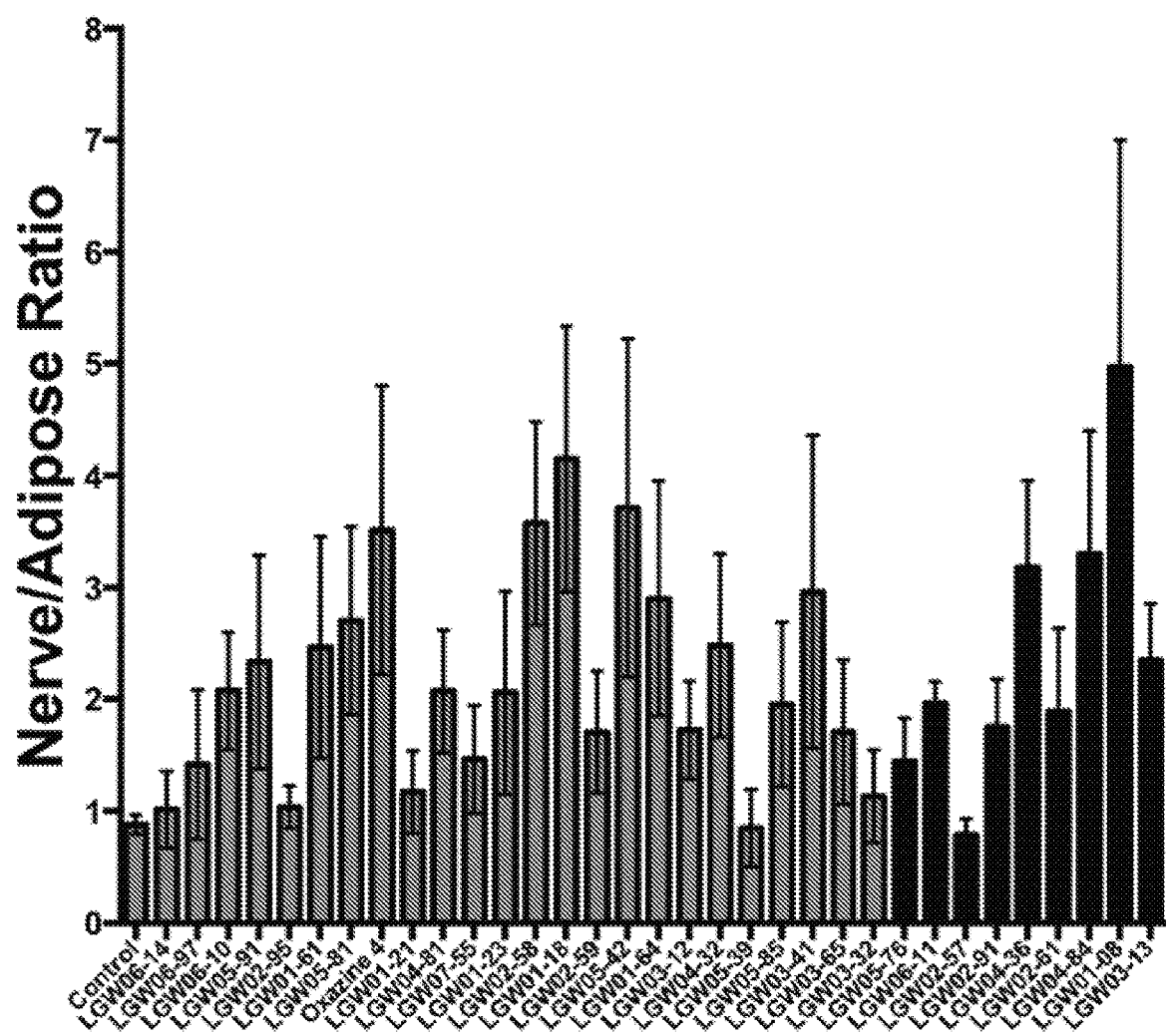
Figure 2B:
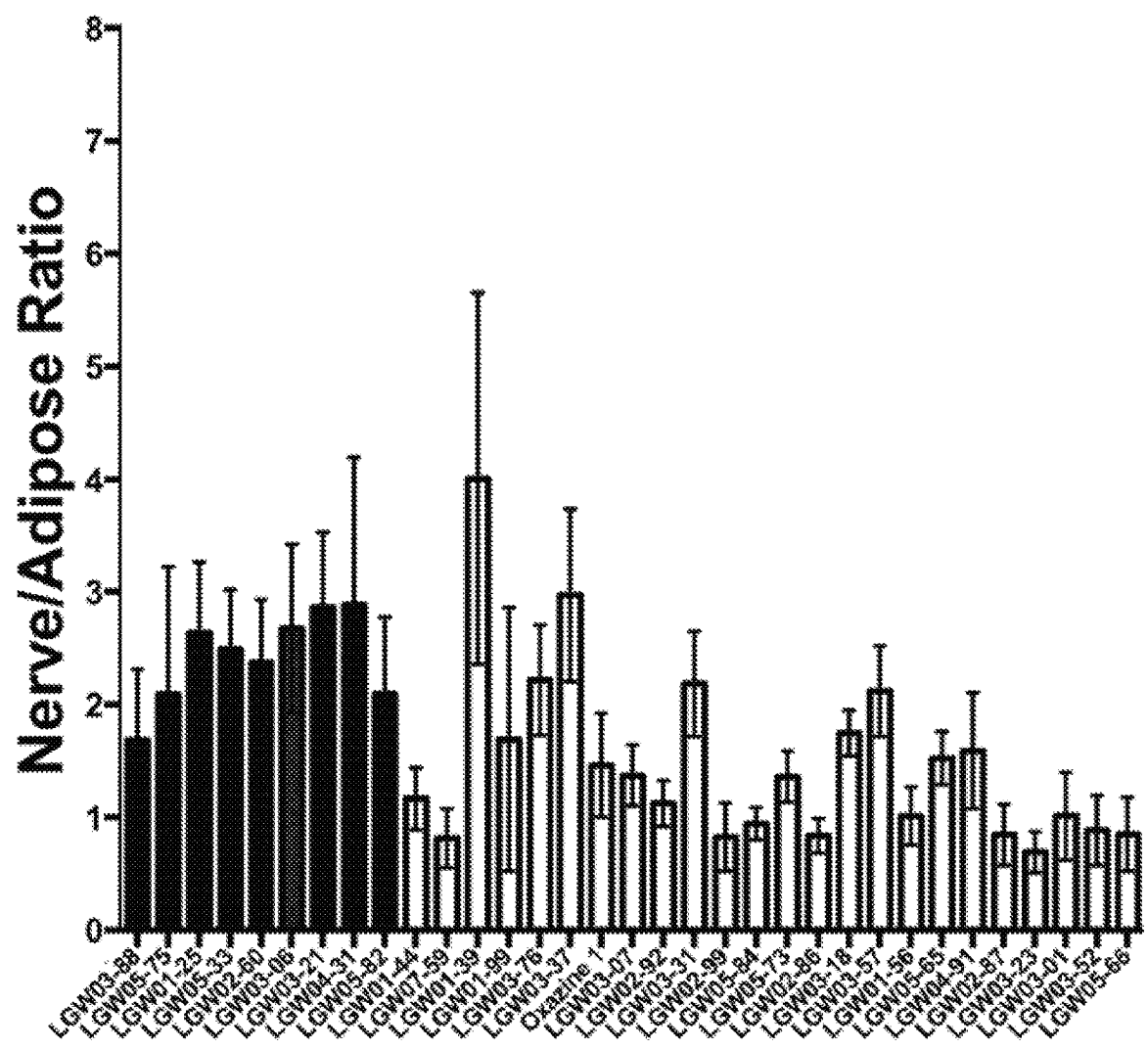

FIGS. 2A and 2B represent nerve to muscle and nerve to adipose ratios following direct/topical administration. The nerve to muscle and nerve to adipose ratios were calculated from the tissue-specific intensities following direct/topical administration. Compounds with excitation and emission below 650 nm and shown in gray. Compounds with emission above 650 nm are shown in black. Compounds with excitation and emission above 650 nm are shown in white. The nerve to muscle (2A) and nerve to adipose (2B) ratios are each displayed as the mean plus and minus the standard deviation.

Figure 3A:
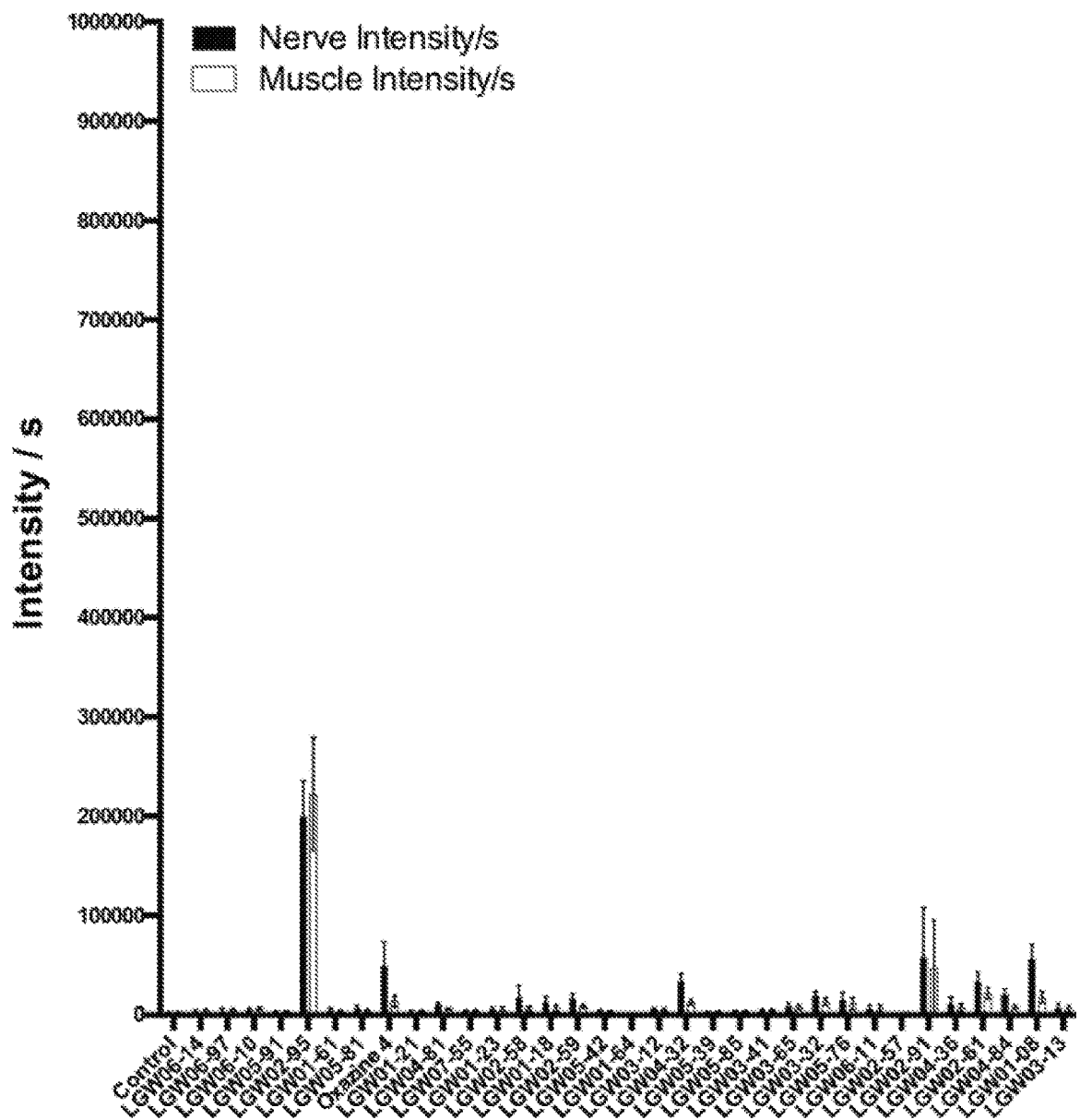
FIGS. 3A and 3B represent the fluorescent intensity of nerve, muscle and adipose tissues following systemic administration screening using the compounds herein.
Figure 3A:
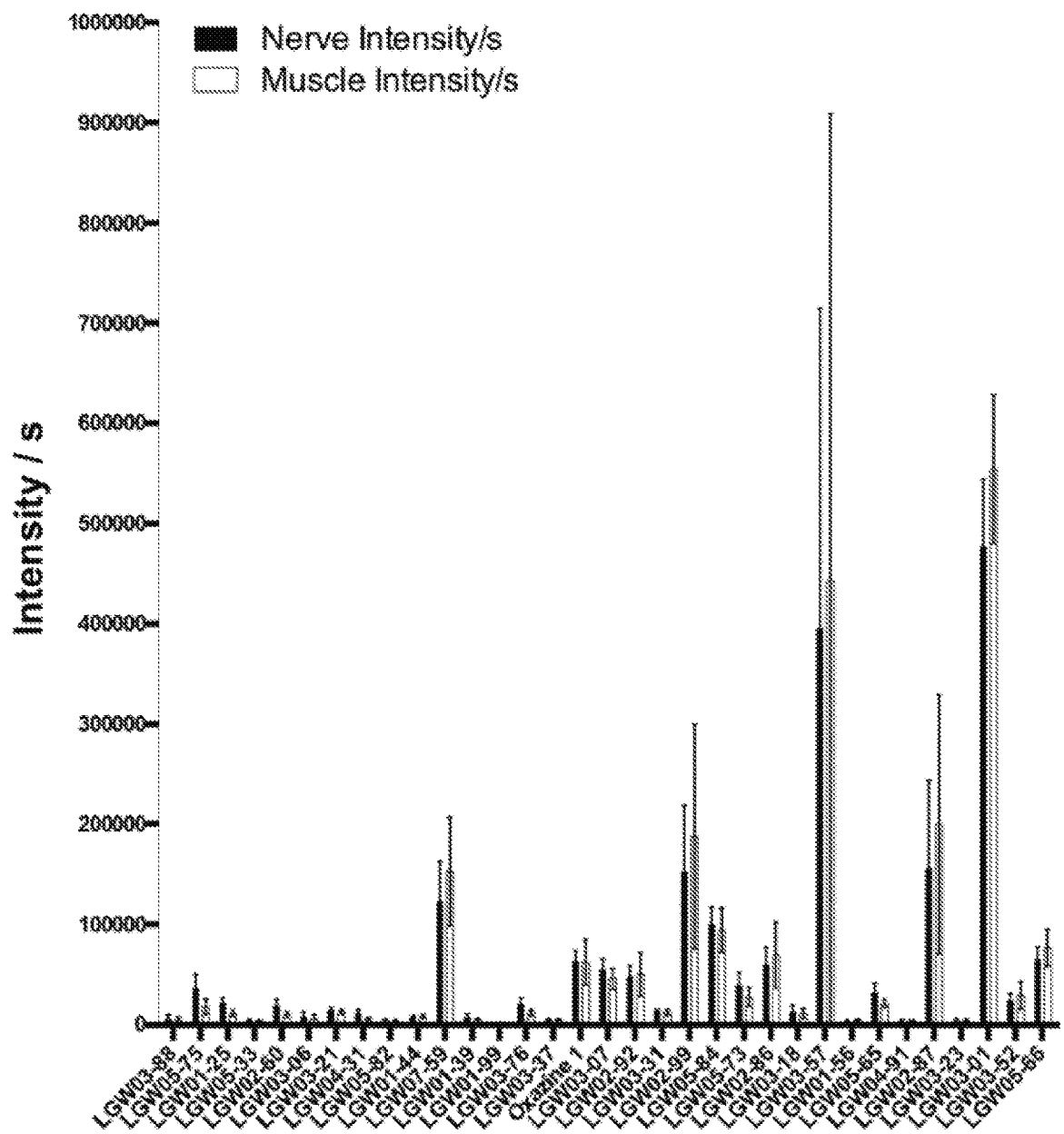
Figure 3B:
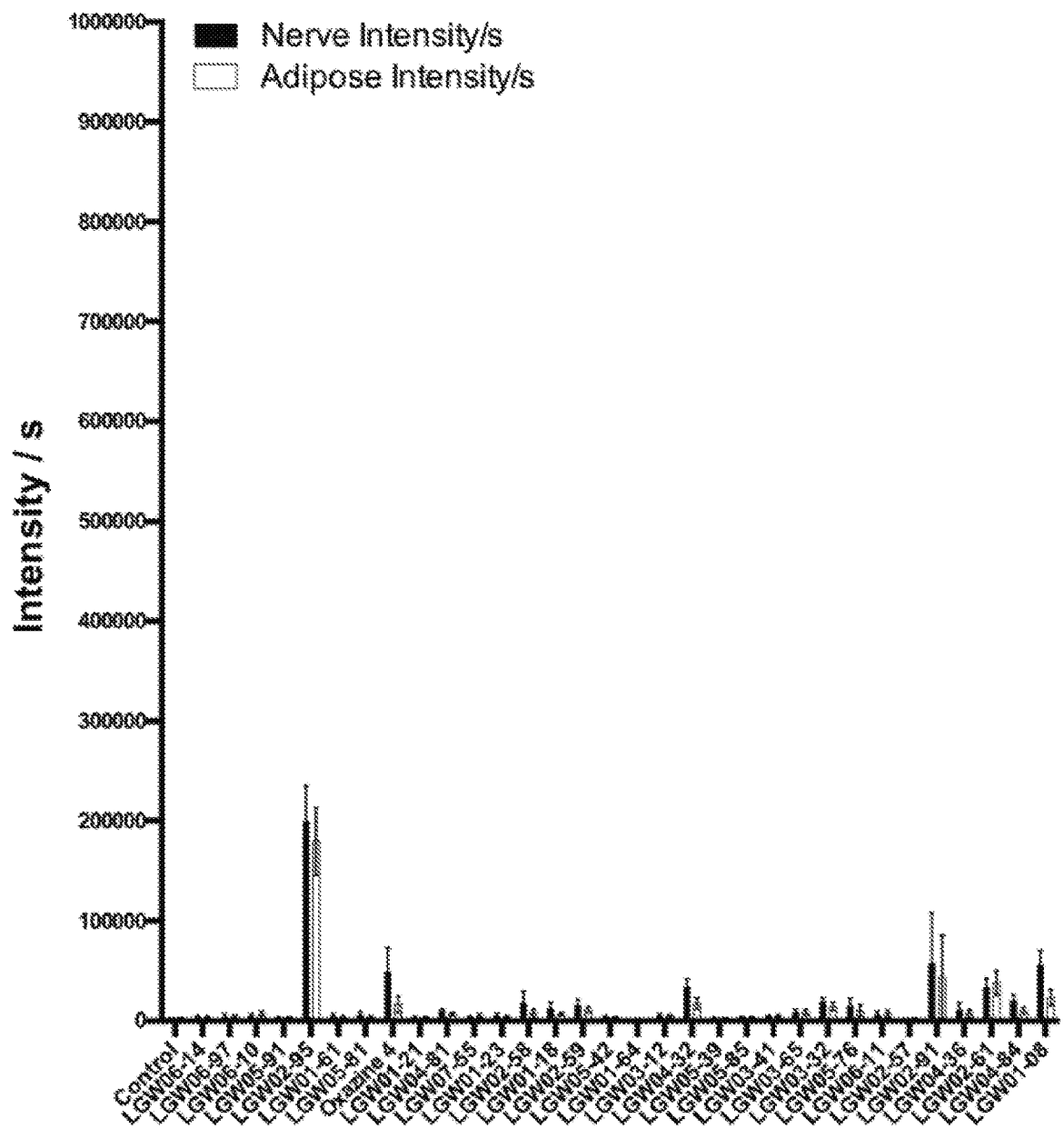
Figure 3B:
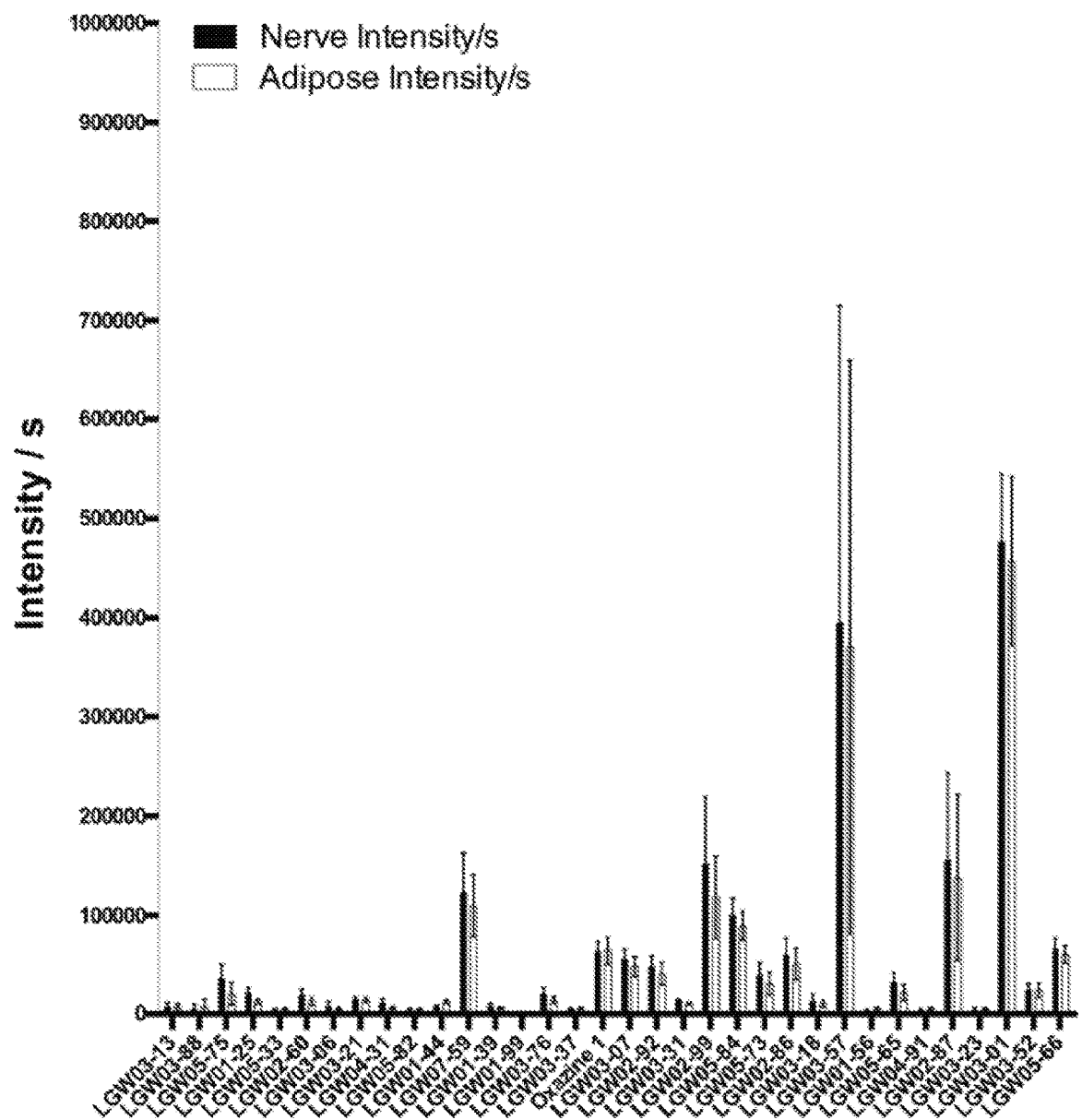

FIGS. 3A and 3B represent tissue-specific intensity following oxazine library systemic administration. Compounds are organized by emission wavelength where the reddest compounds are shown on the right-hand side of the graph. Nerve and muscle tissue fluorescence intensity per second (3A) as well as nerve and adipose tissue fluorescence intensity per second (3B) are shown as the mean plus and minus the standard deviation.

Figure 4A:
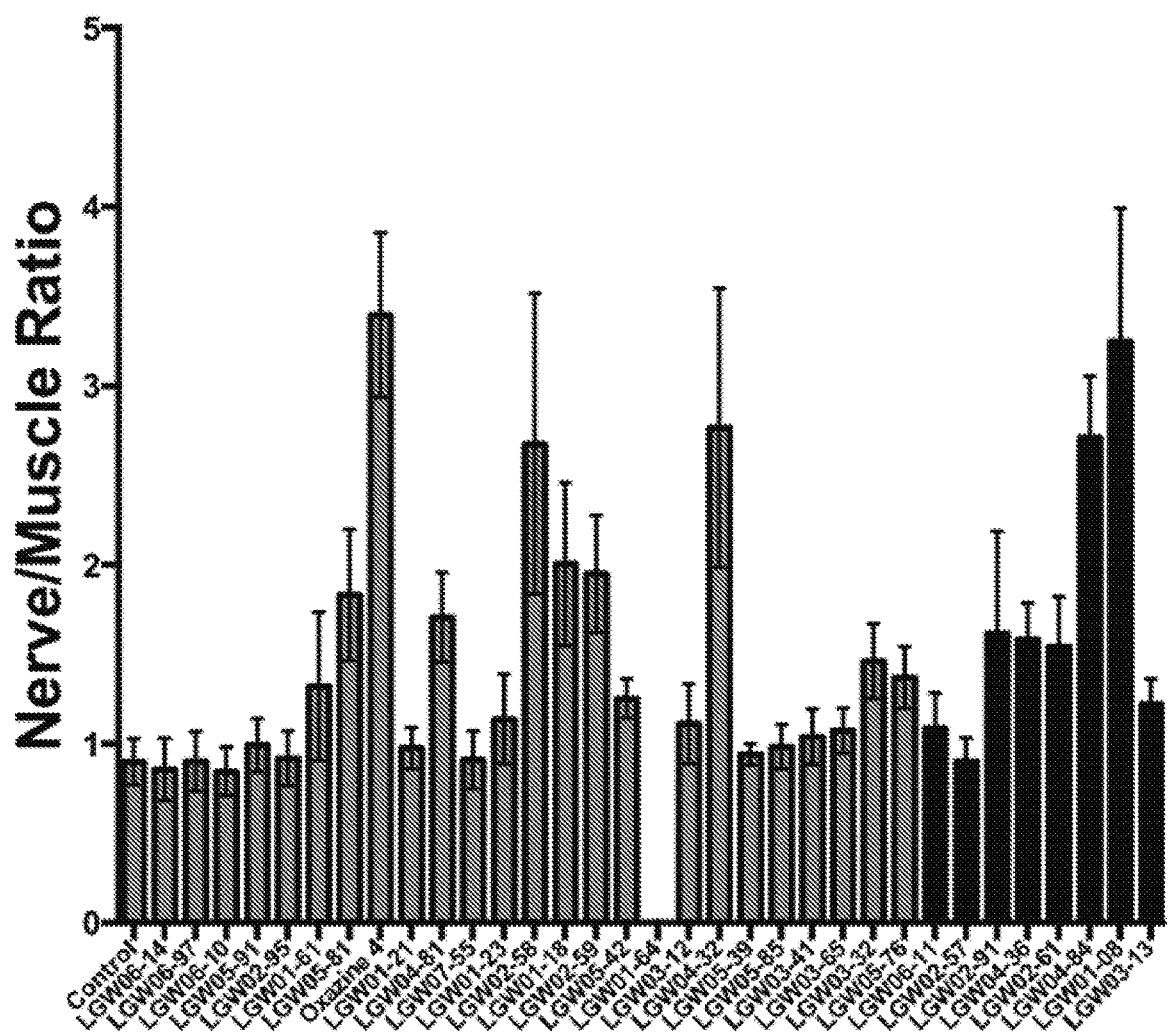
FIGS. 4A and 4B represent nerve to muscle and nerve to adipose ratios following direct/topical administration screening using compounds herein.
Figure 4A:
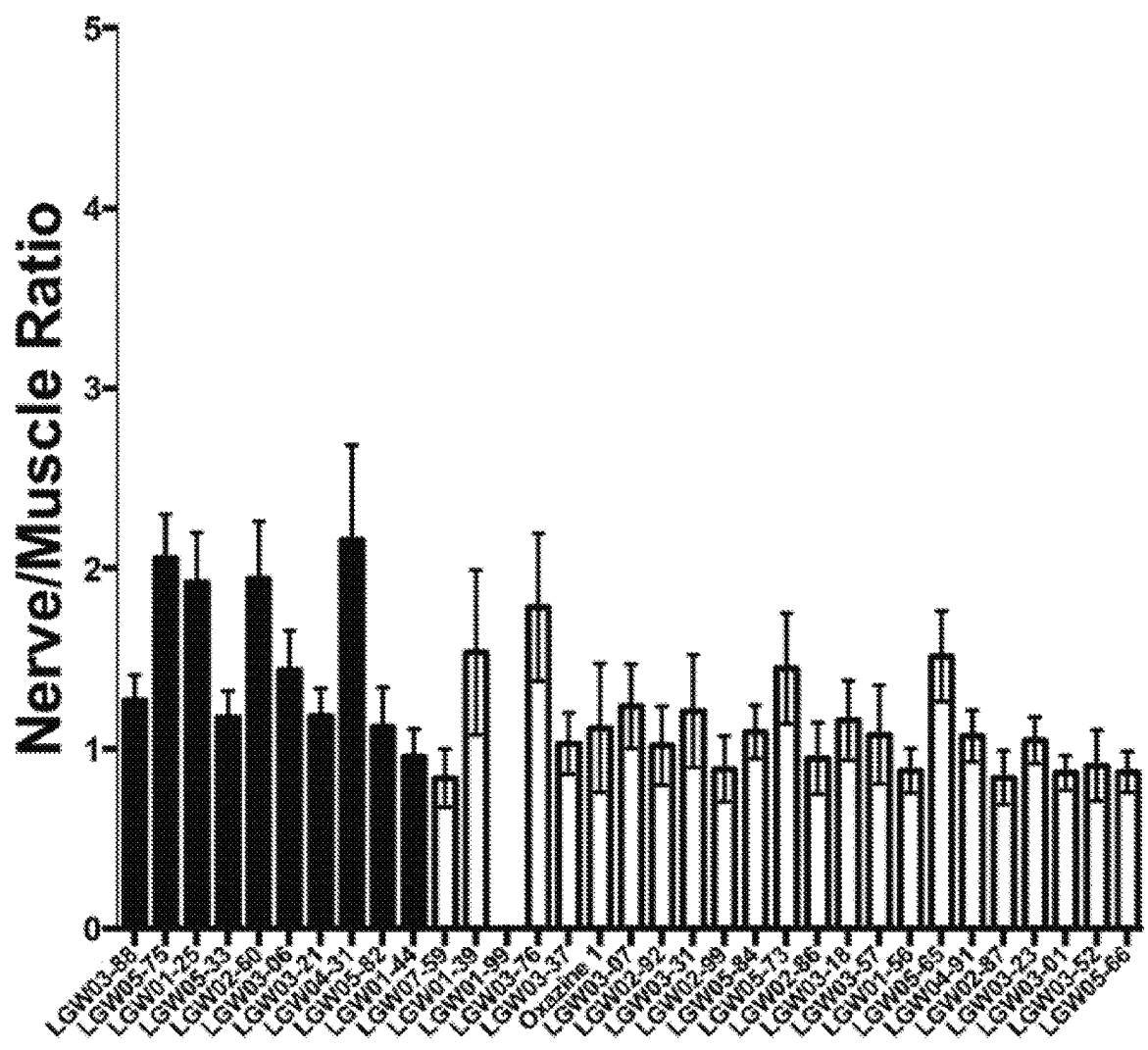
Figure 4B:
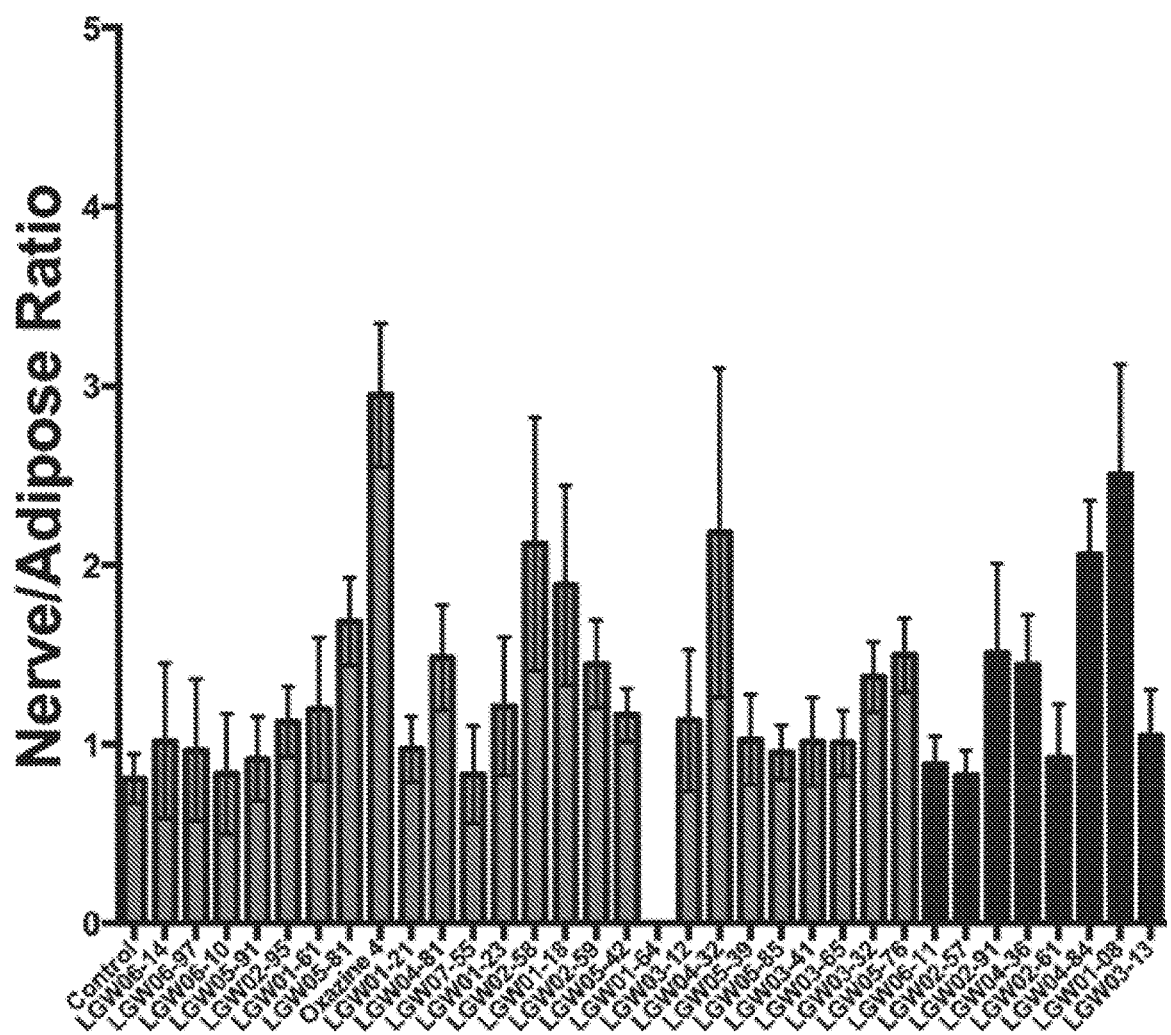
Figure 4B:
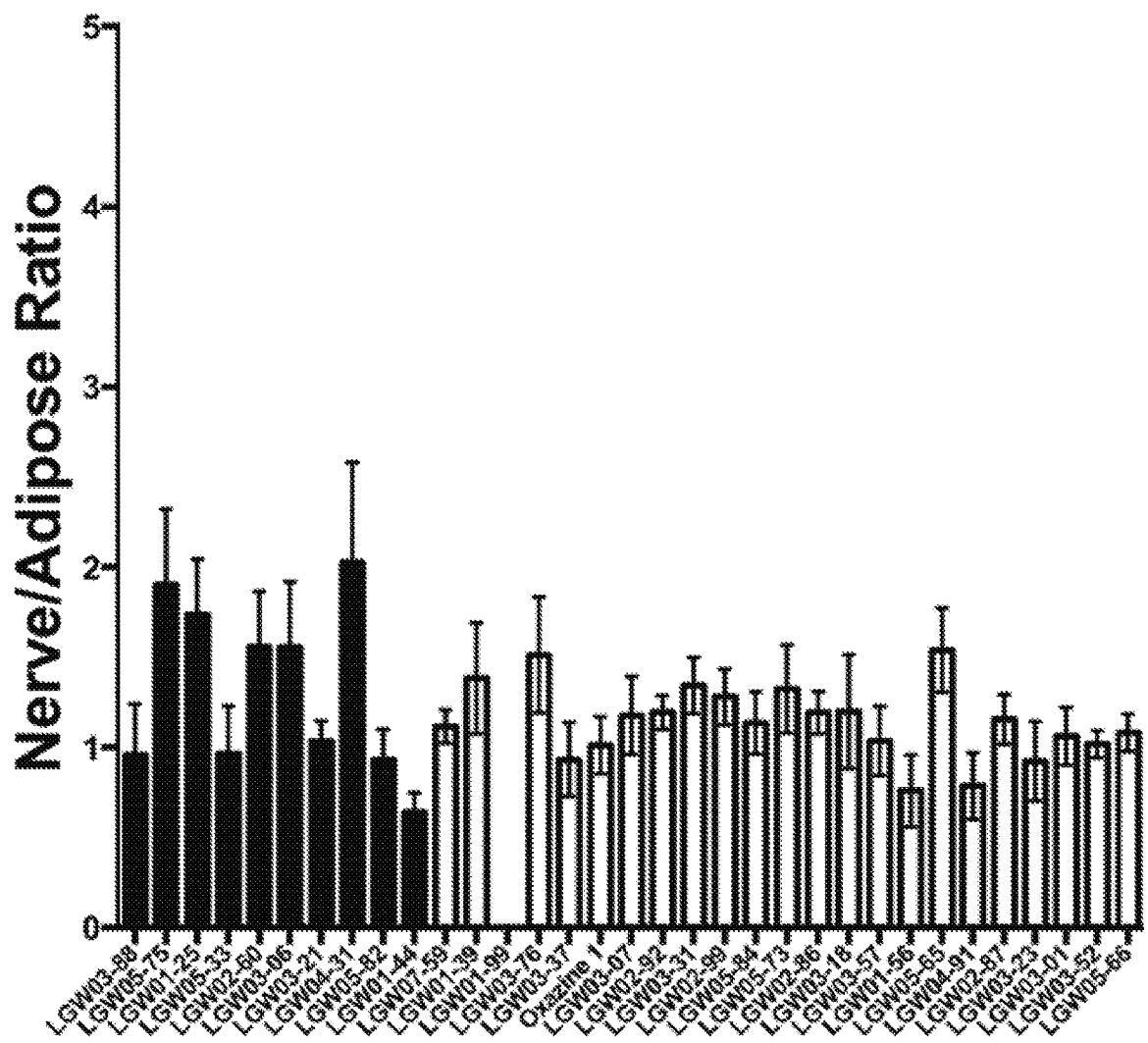

FIGS. 4A and 4B represent nerve to muscle and nerve to adipose ratios following systemic administration. The nerve to muscle and nerve to adipose ratios were calculated from the tissue-specific intensities following systemic administration. Compounds with excitation and emission below 650 nm and shown in gray. Compounds with emission above 650 nm are shown in black. Compounds with excitation and emission above 650 nm are shown in white. The nerve to muscle (4A) and nerve to adipose (4B) ratios are each displayed as the mean plus and minus the standard deviation.

Figure 5A:
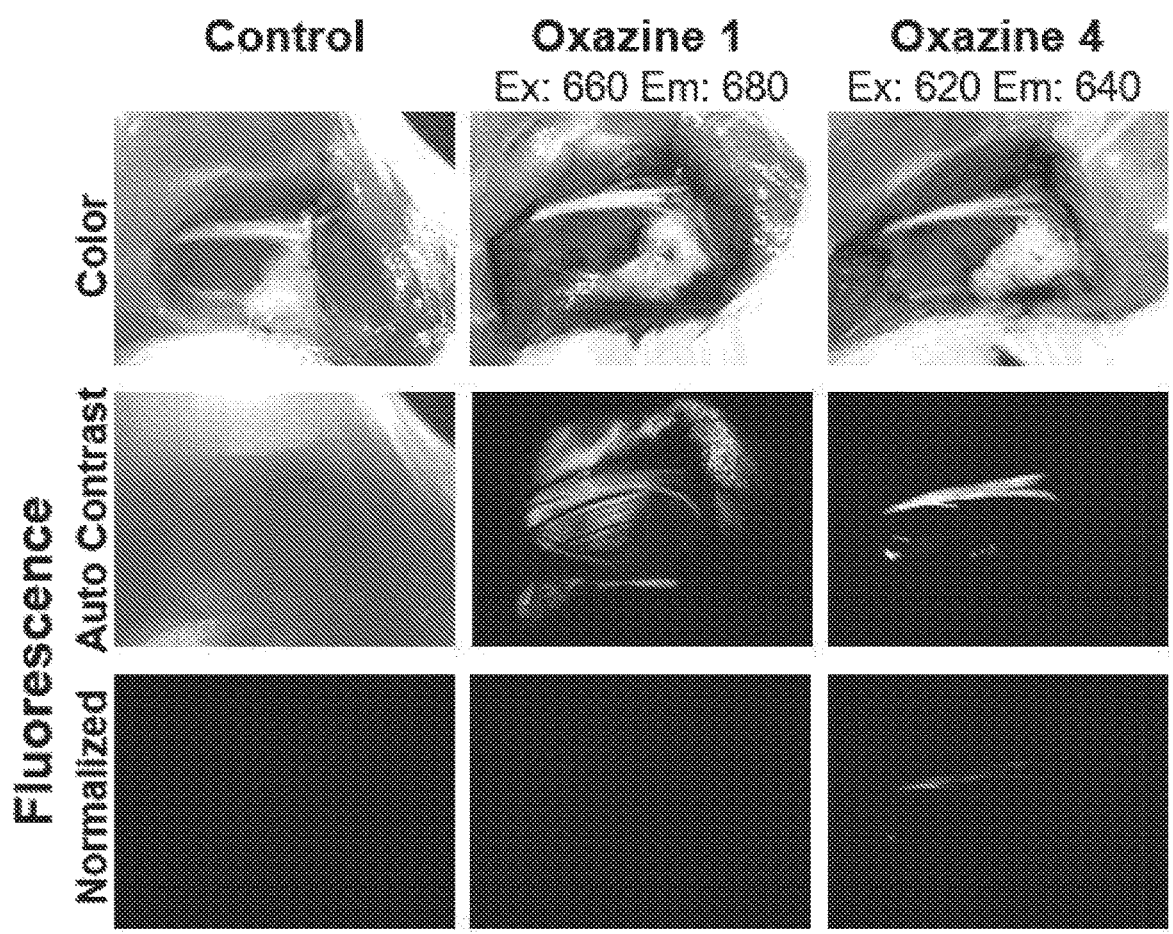
FIGS. 5A, 5B, and 5C depict oxazine derivative staining following direct/topical administration.
Figure 5B:
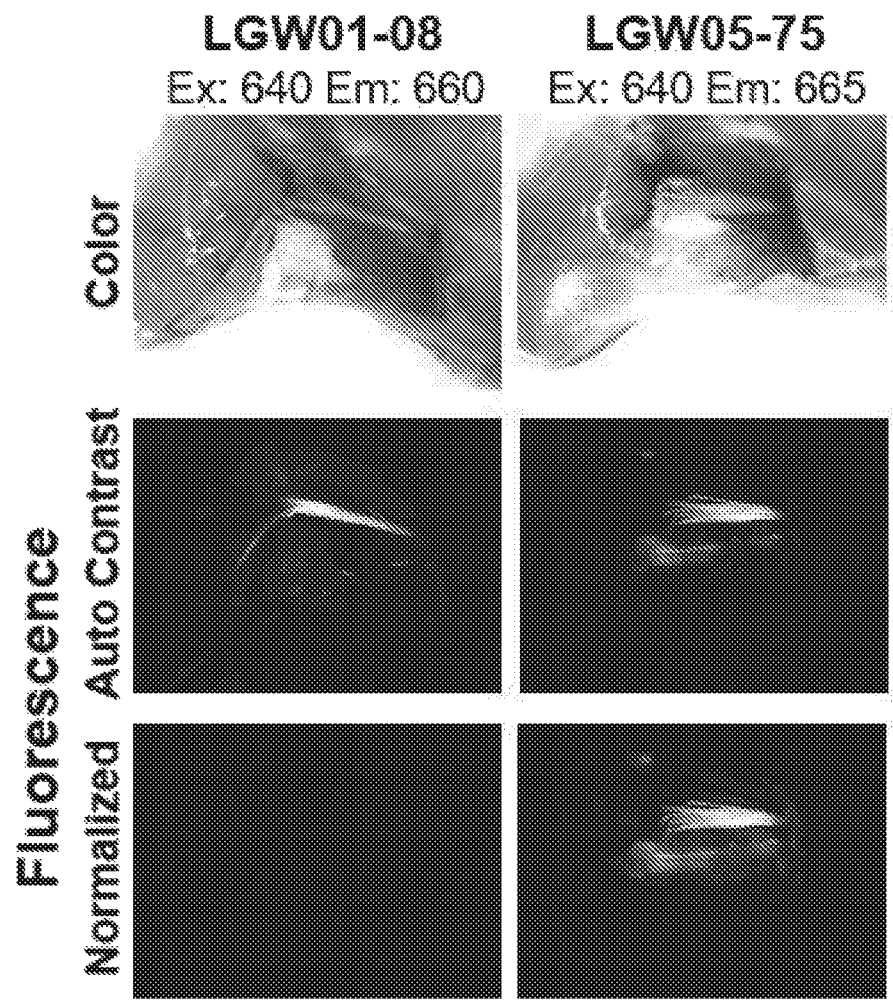
Figure 5C:
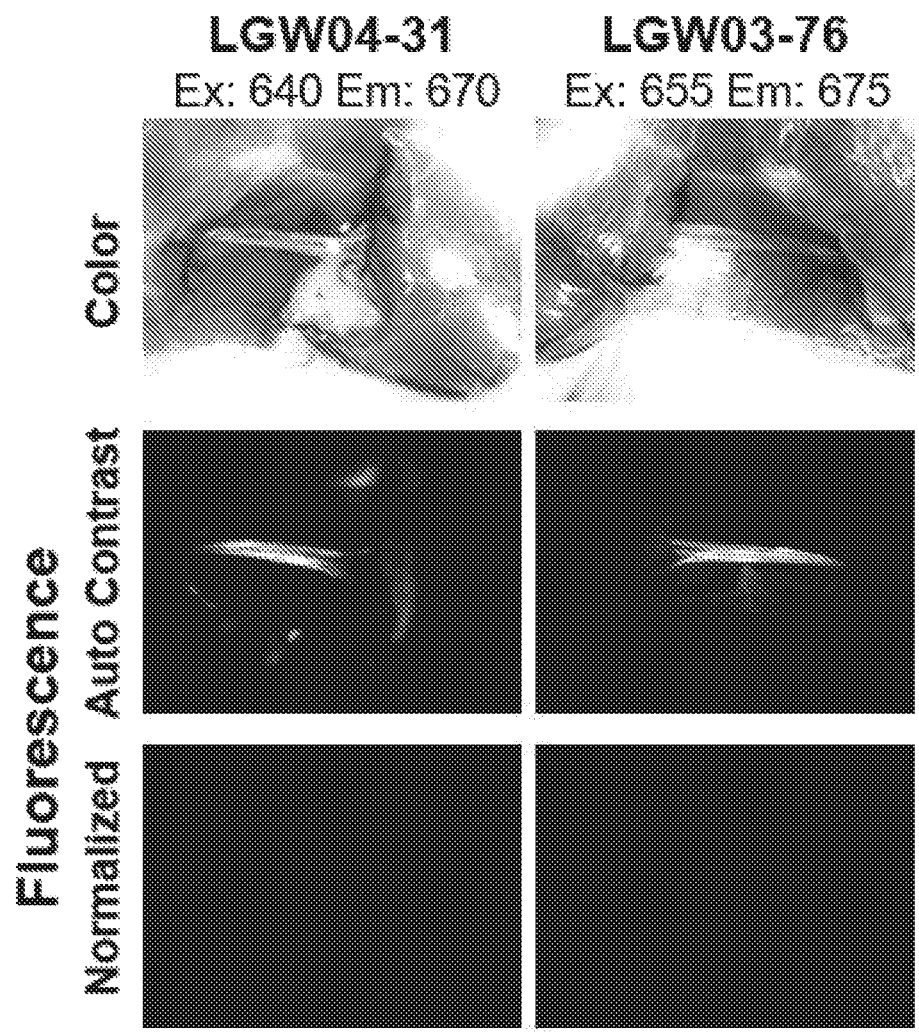

FIGS. 5A, 5B, and 5C depict images of oxazine derivative staining following direct/topical administration. Mouse sciatic nerves are shown following staining with Oxazine 1, Oxazine 4 and four representative nerve-specific derivatives from the Oxazine library. Images are shown with auto contrast as well as with the same normalization so that intensity can be compared across fluorophores. The control animal was stained with co-solvent not containing fluorophore to facilitate assessment of autofluorescence.

Figure 6A:
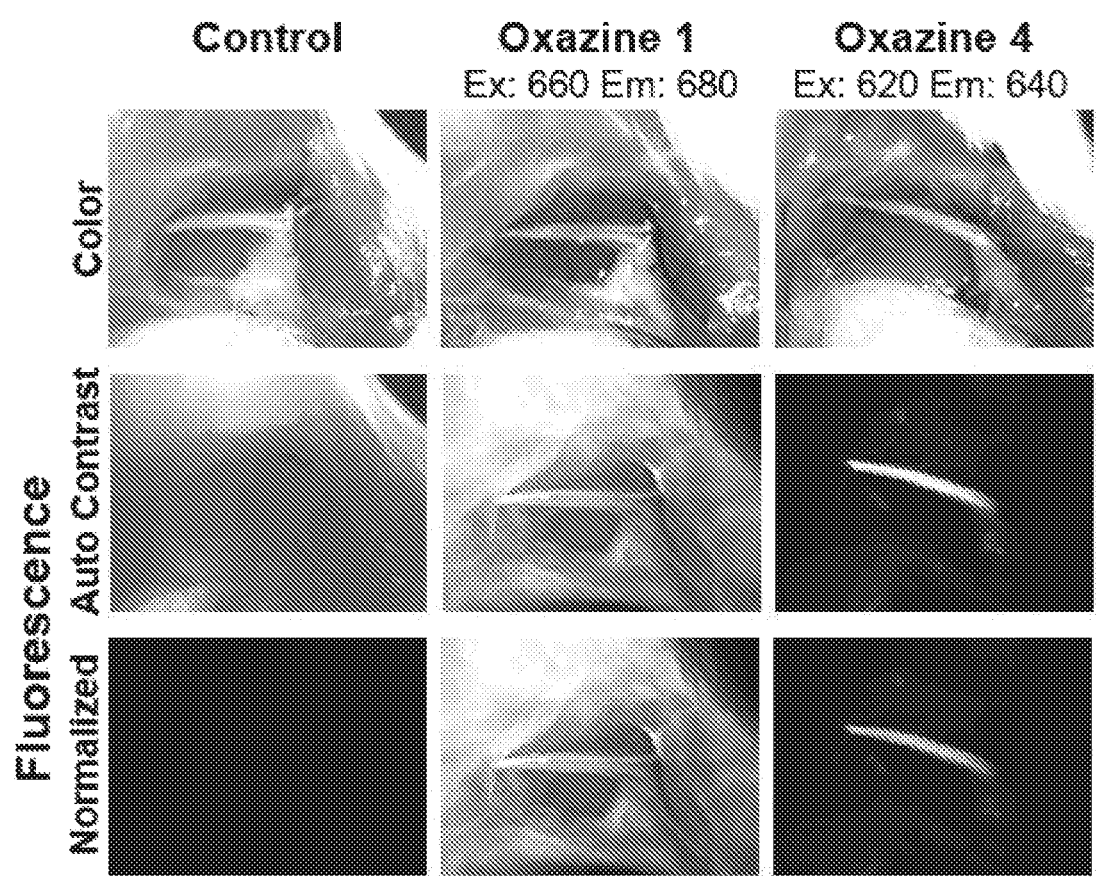
FIGS. 6A, 6B, and 6C depict oxazine derivative staining following direct/topical administration.
Figure 6B:
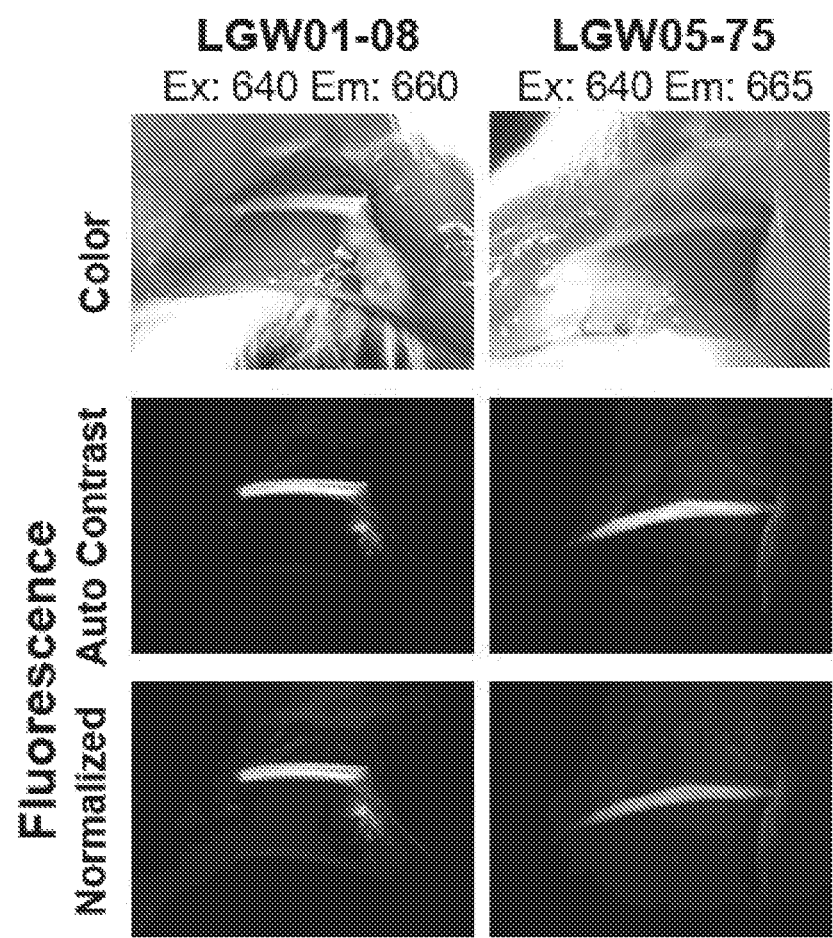
Figure 6C:
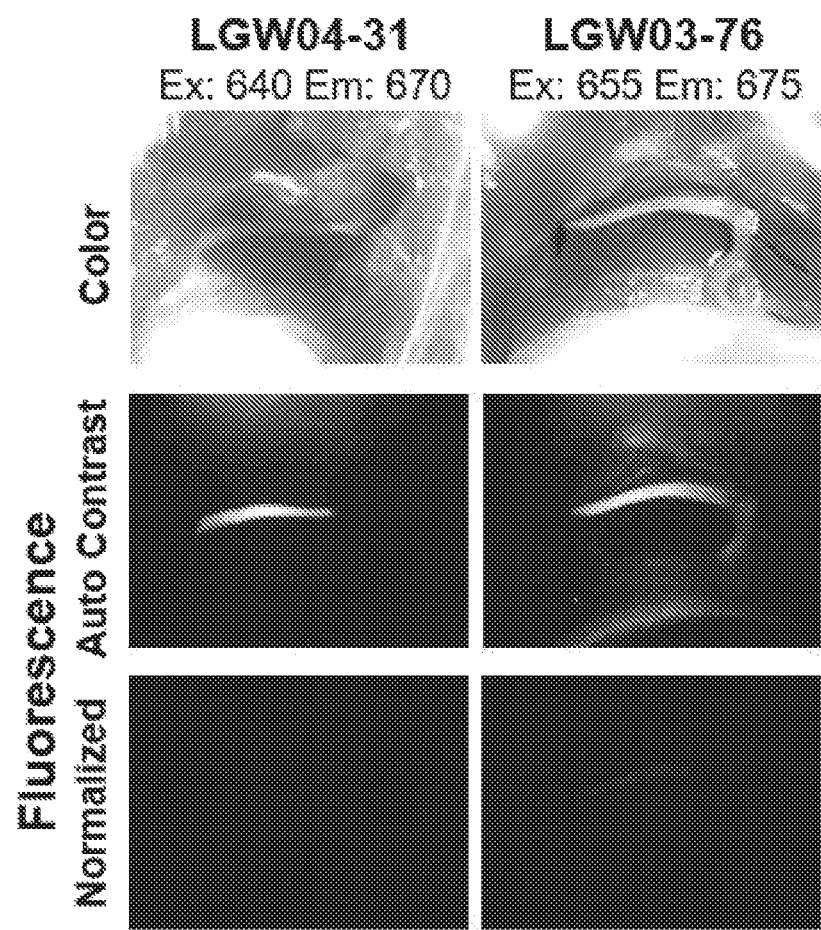

FIGS. 6A, 6B, and 6C also depict oxazine derivative staining following systemic administration. Mouse sciatic nerves are shown following staining with Oxazine 1, Oxazine 4 and four representative nerve-specific derivatives from the Oxazine library. Images are shown with auto contrast as well as with the same normalization so that intensity can be compared across fluorophores. The control animal was stained with co-solvent not containing fluorophore to facilitate assessment of autofluorescence.

Figure 7A:
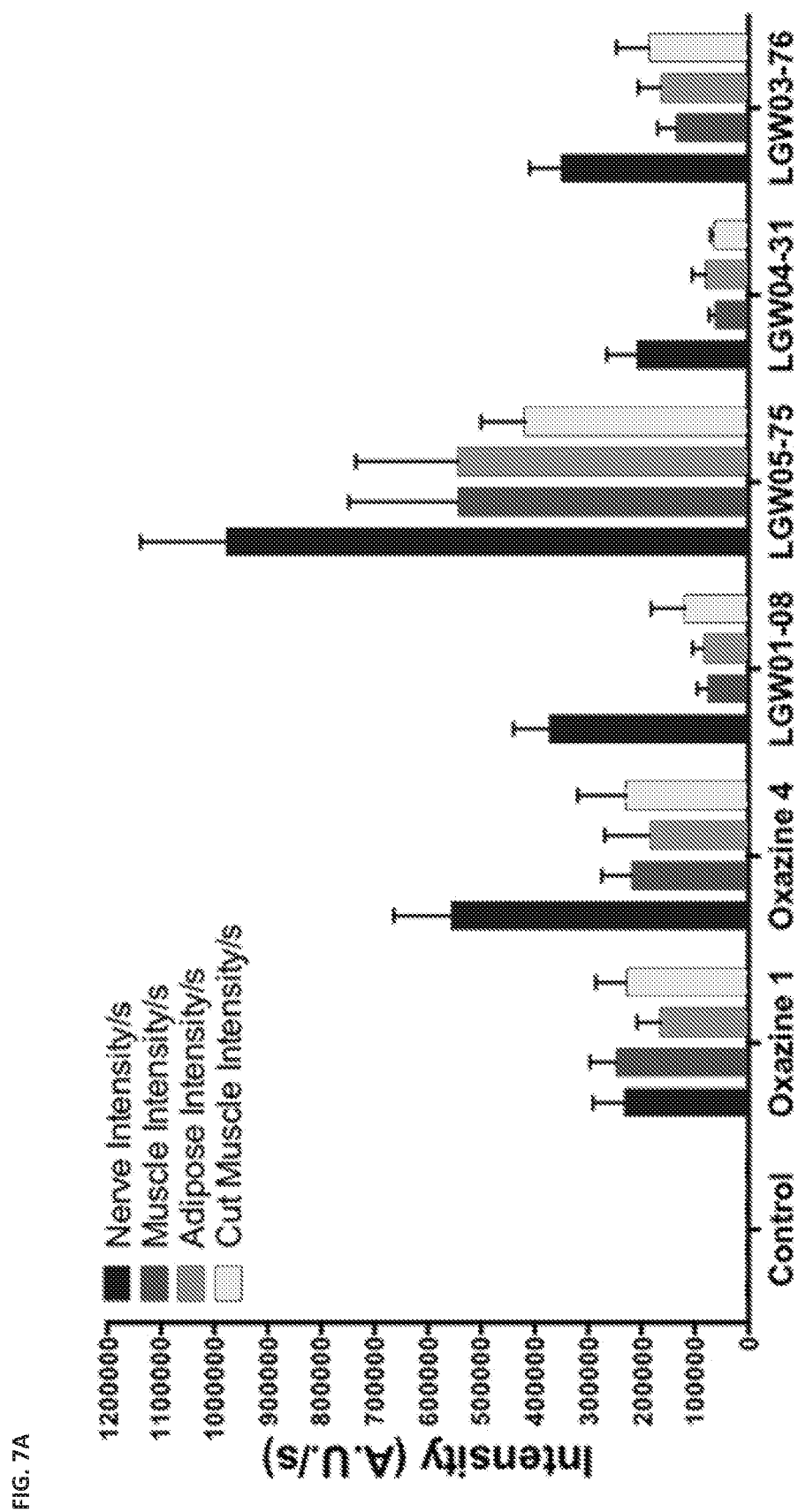
FIGS. 7A and 7B represent intensities following direct administration of oxazine derivative library NIR candidates.
Figure 7B:
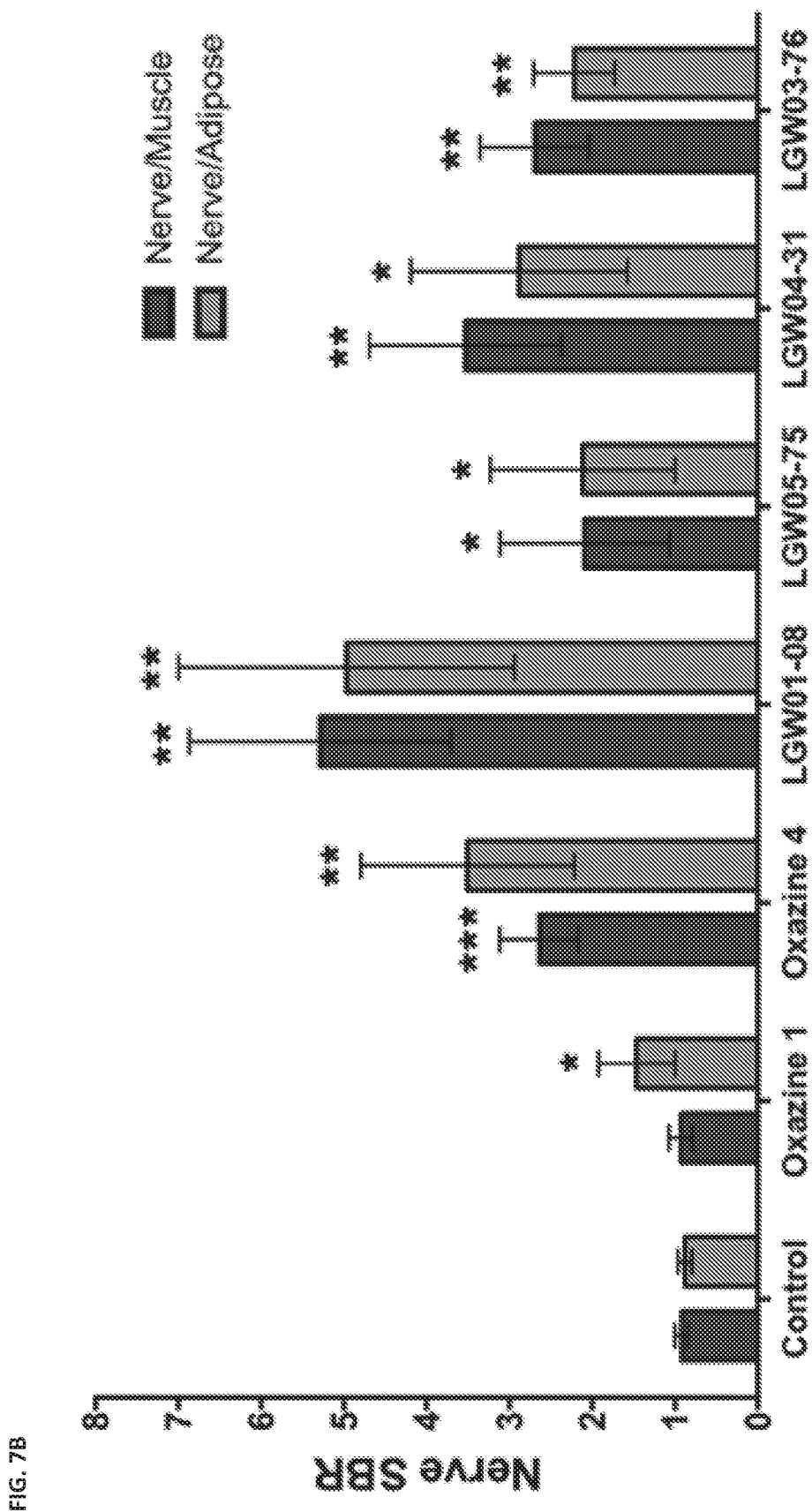

FIGS. 7A and 7B represent intensities following direct administration of oxazine derivative library NIR candidates. FIG. 7A represents quantified tissue intensities and 7B represents nerve SBRs for the NIR Oxazine derivatives LGW01-08, LGW05-75, LGW04-31 and LGW03-76 are shown compared to Oxazine 1, Oxazine 4 and an unstained control group following direct administration. All images are representative of data collected for n=6 nerve sites per fluorophore. Relevant tissue types are labeled in the control group color image to aid in visualization. Scale bars=3 mm. All quantified data is presented as mean+/−standard deviation. Ex=maximum excitation (nm), Em=maximum emission (nm). Data for each fluorophore was compared to the unstained control group to test for nerve SBR significance, where *=p value<0.05, =p value<0.01, *=p value<0.001, ****=p value<0.0001.

Figure 8A:
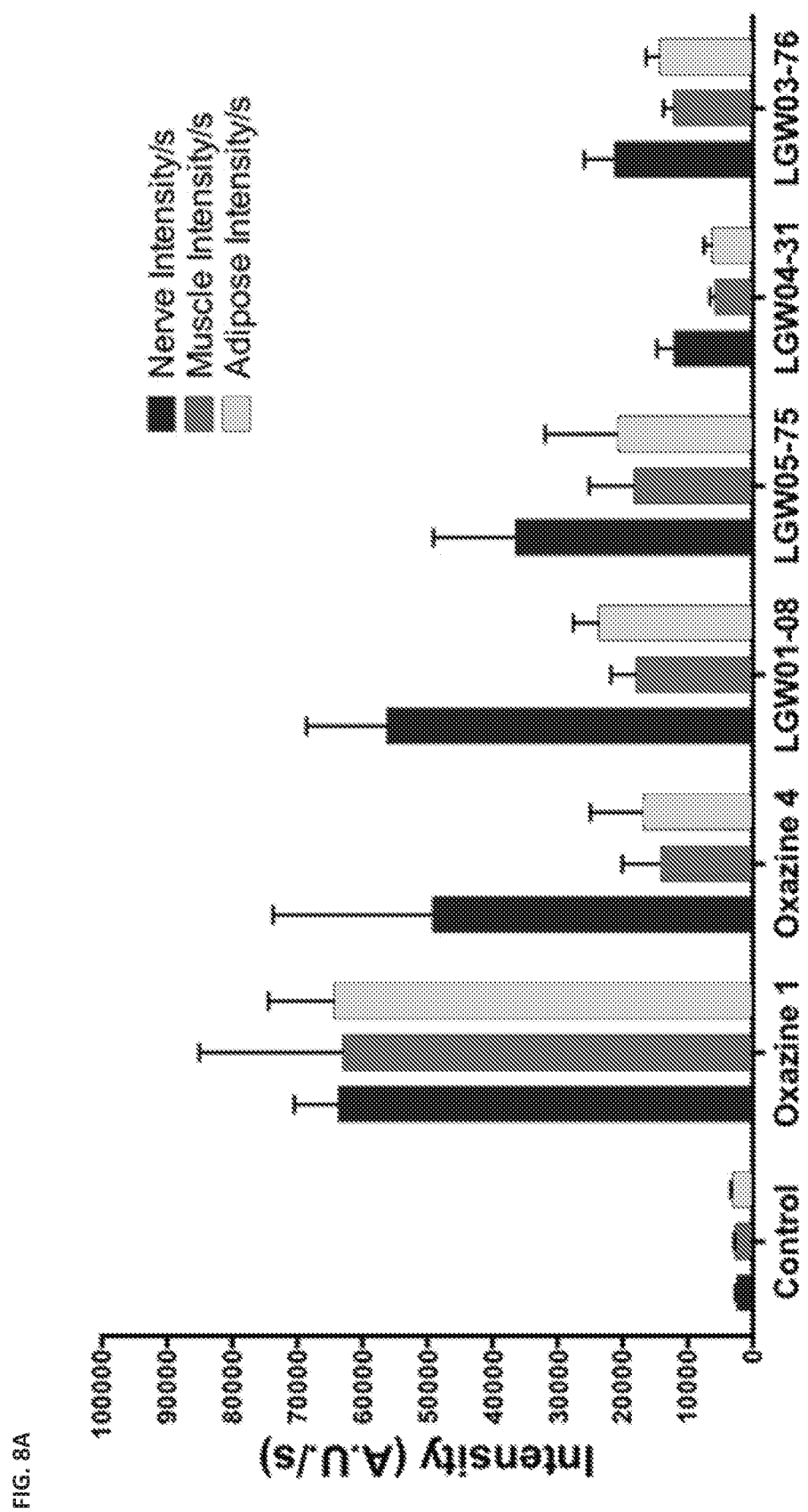
FIGS. 8A and 8B represent intensities following systemic administration of oxazine derivative library NIR candidates.
Figure 8B:
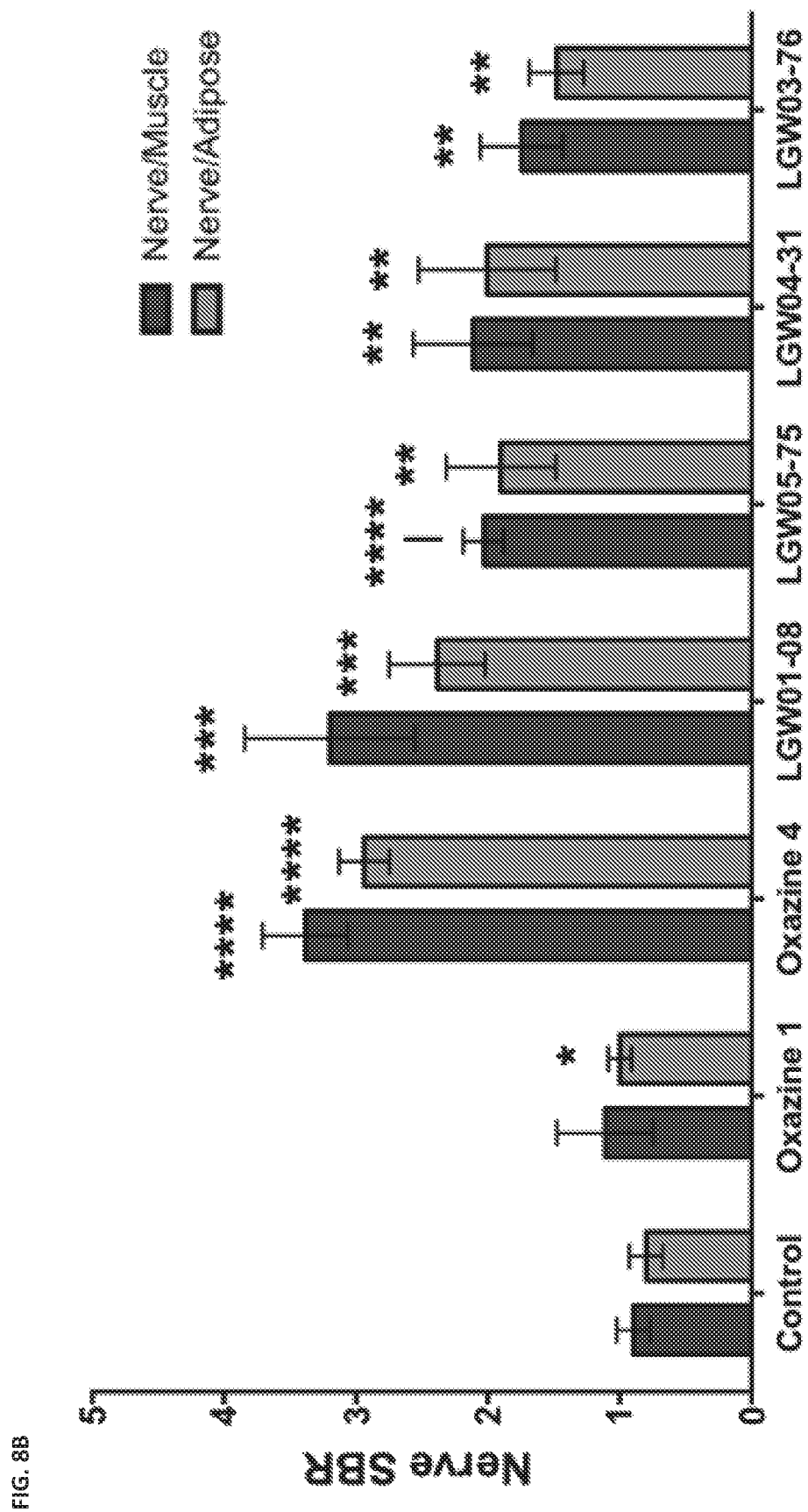

FIGS. 8A and 8B represent intensities following systemic administration of oxazine derivative library NIR candidates. FIG. 8A represents quantified tissue intensities and FIG. 8B represents nerve SBRs for the NIR Oxazine derivatives LGW01-08, LGW05-75, LGW04-31 and LGW03-76 are shown compared to Oxazine 1, Oxazine 4 and an uninjected control group following systemic administration. All images are representative of data collected for n=6 nerve sites per fluorophore. Relevant tissue types are labeled in the control group color image to aid in visualization. Scale bars=3 mm. All quantified data is presented as mean+/−standard deviation. Ex=maximum excitation (nm), Em=maximum emission (nm). Data for each fluorophore was compared to the uninjected control group to test for nerve SBR significance, where *=p value<0.05, =p value<0.01, *=p value<0.001, ****=p value<0.0001.

Oxazine Derivative Library Synthesis.

The key synthetic steps for library production involved direct nitrosation of aromatic amines by nitrous acid and subsequent condensation reactions. Hydrogen chloride (HCl) and sodium nitrite ($NaNO_2$) were used to favorably produce the para-nitroso anilines over the N-nitrosoamine. Subsequent condensation reactions of the para-nitroso-N-substituted anilines with the corresponding aromatic amines were carried out in a mixture of isopropanol:water (9:1) with perchloric acid ($HClO_4$) as the catalyst at 80° C. for 2-24 h. In general, relatively high overall yields were obtained for the majority of the Oxazine derivatives (up to 67%). However, in some cases, undesired self-condensation products resulted from the hydrolysis of the primary nitroso intermediates, followed by self-condensation reactions. In these cases, para-arylazo intermediates were prepared from the p-nitrophenyldiazonium salt and corresponding aromatic amines in acidified methanolic solution as an alternative synthetic route. Notably, preparation of diaryl ethers as electronically activated nucleophiles prior to synthesis of the para-arylazo intermediates offered a more efficient synthetic route with improved overall yields for some derivatives, where extremely low yields (<3%) were obtained when using the previously described synthetic sequence.

Chemical Synthesis

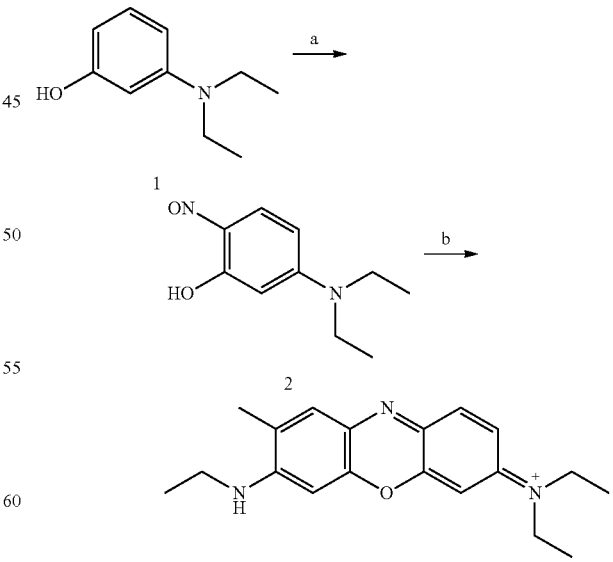

Scheme 1 Synthesis of LGW-01-08.

LGW-01-08

Reagents and conditions: a) 6M HCl, $NaNO_2$, 0° C.; b) Compund 6, $HClO_4$, 90% i-PrOH, 80° C.

5-(diethylamino)-2-nitrosophenol (2)

Compound 1 (10 g, 60.52 mmol) was dissolved in an ice-cold 6 M HCl solution (50 mL). To the solution above, $NaNO_2$ (4.26 g, 61.73 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 2 (9.67 g, 82%) as a yellow solid, which was used for the next step without further purification.

N-ethyl-N-(7-(ethylamino)-8-methyl-3H-phenoxazin-3-ylidene)ethanaminium (LGW-01-08)

Compound 6 (150 mg, 0.99 mmol) was dissolved in a solution of i-PrOH/$H_2O$ (9/1, 2 mL) at 80° C. for 30 min. A suspended solution of 2 (202 mg, 1.04 mmol) and $HClO_4$ (70%, 90 μL) in 90% i-PrOH (3 mL) was added into the solution above in 4 portions over 1 h. The resulting solution was stirred overnight. During which time, the color of the reaction mixture changed from light brown to green and finally dark blue. After which, the dark blue solution was evaporated under reduced pressure, and the residue was purified on a Biotage Isolera Flash System using SNAP Ultra cartridge with a mobile phase of $CHCl_3$ and MeOH containing 0.5% formic acid (gradient, 2-15% of MeOH in $CHCl_3$). The fractions containing product were pooled and evaporated, affording LGW-01-08 (254 mg, 72%) as a dark green solid.

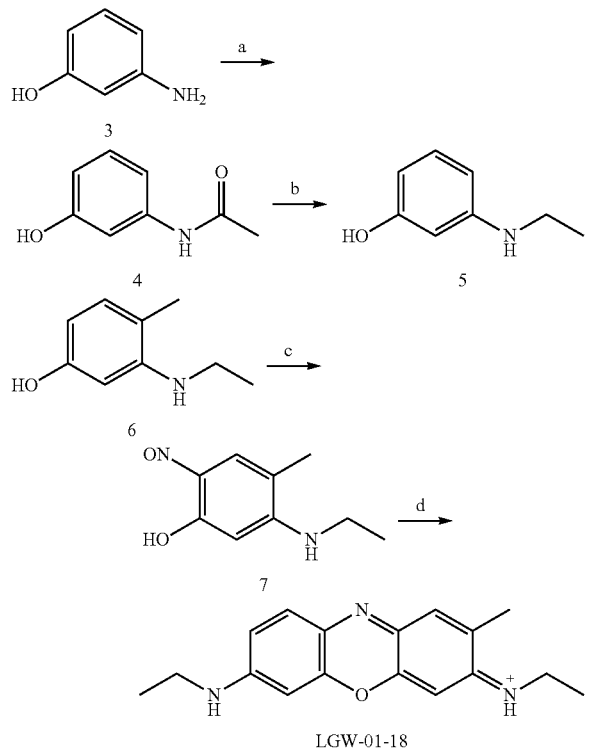

Scheme 2 Synthesis of LGW-01-18.

Reagents and conditions: a) $Ac_2O$, $H_2O$, 50° C. to rt; b) $BH_3$—THF, THF, 0° C. to rt; c) 6M HCl, $NaNO_2$, 0° C.; d) Compound 5, $HClO_4$, 90% i-PrOH, 80° C.

N-(3-hydroxyphenyl)acetamide (4)

Compound 3 (1 g, 9.16 mmol) was suspended in 10 mL DI water, to which Acetic anhydride (2.60 mL, 27.49 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford Compound 4 (1.19 g, 86%) as a light gray solid, which was used for the next step without further purification.

3-(ethylamino)phenol (5)

A solution of 4 (1 g, 6.62 mmol) in anhydrous THE (20 mL) was stirred in an ice bath under N2 for 30 mins. Borane tetrahydrofuran complex solution (1 M, 20 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel (25 g), using DCM/Hexane as eluent to obtain 5 (832 mg, 92%) as a black solid.

5-(ethylamino)-4-methyl-2-nitrosophenol (7)

Compound 6 (10 g, 66.13 mmol) was dissolved in an ice-cold 6 M HCl solution (50 mL). To the solution above, $NaNO_2$ (4.79 g, 69.44 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 7 (9.42 g, 79%) as a yellow solid, which was used for the next step without further purification.

(Z)—N-(7-(ethylamino)-2-methyl-3H-phenoxazin-3-ylidene)ethanaminium (LGW-01-18)

Compound 5 (150 mg, 1.09 mmol) was dissolved in a solution of i-PrOH/$H_2O$ (9/1, 2 mL) at 80° C. for 30 min. A suspended solution of 7 (207 mg, 1.15 mmol) and $HClO_4$ (70%, 99 μL) in 90% i-PrOH (3 mL) was added into the solution above in 4 portions over 1 h. The resulting solution was stirred overnight. During which time, the color of the reaction mixture changed from light brown to green and finally dark blue. After which, the dark blue solution was evaporated under reduced pressure, and the residue was purified on a Biotage Isolera Flash System using SNAP Ultra cartridge with a mobile phase of $CHCl_3$ and MeOH containing 0.5% formic acid (gradient, 2-15% of MeOH in $CHCl_3$). The fractions containing product were pooled and evaporated, affording LGW-01-18 (45 mg, 13%) as a dark green solid.

Scheme 3 Synthesis of LGW-01-21.

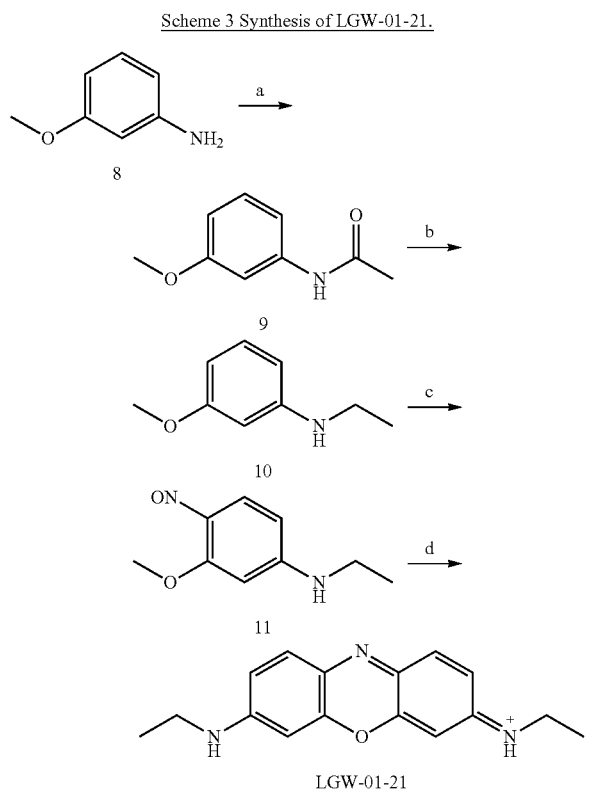

Reagents and conditions: a) Ac₂O, H₂O, 50° C. to rt; b) BH₃—THF, THF, 0° C. to rt; c) i) 2M HCl, NaNO₂, 0° C., ii) K₂CO₃, 0° C.; d) Compound 5, HClO₄, 90% i-PrOH, 80° C.

N-(3-methoxyphenyl)acetamide (9)

Compound 8 (0.91 mL, 8.12 mmol) was suspended in 10 mL DI water, to which Acetic anhydride (2.30 mL, 24.36 mmol) was added dropwise. The reaction mixture was placed in an ultrasonication bath for 1 min, then was stirred in a water bath (50° C.) for 10 min. The resulting clear solution was stirred overnight at rt. After which, the solution was diluted with 50 mL DI water, and solid $K_2CO_3$ was added until the pH value of the solution rose above 8. The white precipitate was collected via vacuum filtration and washed with small portions of DI water. The product was left in the funnel and air dried overnight to afford compound 9 (1.27 g, 95%) as a light gray solid, which was used for the next step without further purification.

N-ethyl-3-methoxyaniline (10)

A solution of 9 (1 g, 6.05 mmol) in anhydrous THF (18 mL) was stirred in an ice bath under N2 for 30 mins. Borane tetrahydrofuran complex solution (1 M, 18 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel (25 g), using DCM/Hexane as eluent to give 10 (878 mg, 96%) as a clear liquid.

N-ethyl-3-methoxy-4-nitrosoaniline (11)

Compound 10 (0.5 g, 3.31 mmol) was dissolved in an ice-cold 2 M HCl solution (10 mL). To the solution above, $NaNO_2$ (0.25 g, 3.64 mmol) was added portion wise over 1 h while maintaining the temperature of the solution below 5° C., such that no brown NOx vapors were observed. The reaction mixture was stirred for additional 2 h. The solution was carefully basified with solid $K_2CO_3$ until the pH value rose above 8. After which, the aqueous solution was extracted with DCM (3×50 mL). The combined organic layers were rinsed with brine and dried over anhydrous $Na_2SO_4$. The solvent was removed using a rotary evaporator to give 11 (0.534 g, 90%) as a light green oil, which was used for the next step without further purification.

(E)-N-(7-(ethylamino)-3H-phenoxazin-3-ylidene) ethanaminium (LGW-01-21)

Compound 5 (50 mg, 0.36 mmol) was dissolved in a solution of i-PrOH/$H_2O$ (9/1, 1 mL) at 80° C. for 30 min. A suspended solution of 11 (69 mg, 0.38 mmol) and $HClO_4$ (70%, 35 µL) in 90% i-PrOH (2 mL) was added into the solution above in 4 portions over 1 h. The resulting solution was stirred overnight. During which time, the color of the reaction mixture changed from light brown to green and finally dark blue. After which, the dark blue solution was evaporated under reduced pressure, and the residue was purified on a Biotage Isolera Flash System using SNAP Ultra cartridge with a mobile phase of $CHCl_3$ and MeOH containing 0.5% formic acid (gradient, 2-15% of MeOH in $CHCl_3$). The fractions containing product were pooled and evaporated, affording LGW-01-21 (9 mg, 8%) as a dark blue solid.

Scheme 4 Synthetic route to LGW-01-23.

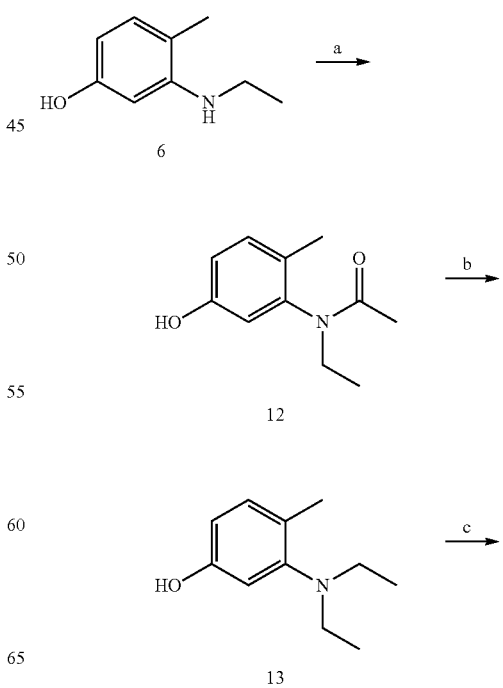

-continued

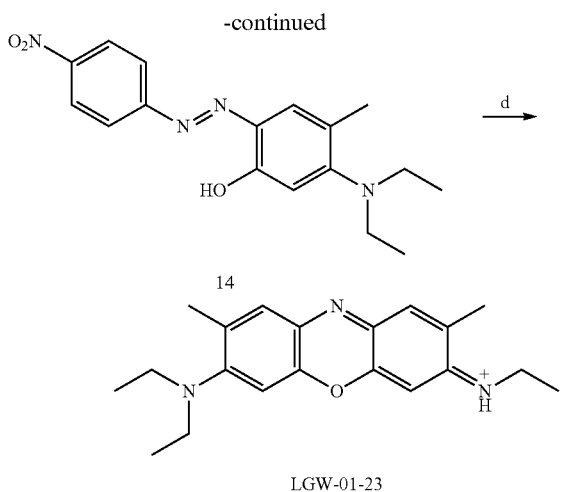

LGW-01-23

Reagents and conditions: a) Ac₂O, H₂O, 50° C. to rt; b) BH₃—THF, THF, 0° C. to rt; c) i) 2M HCl, p-nitrobenzenediazonium tetrafluoroborate, 0° C.; ii) K₂CO₃, 0° C.; d) Compound 6, HClO₄, 90% i-PrOH, 80° C.

N-ethyl-N-(5-hydroxy-2-methylphenyl)acetamide (12)

Compound 6 (1 g, 6.61 mmol) was suspended in 10 mL DI water, to which Acetic anhydride (1.9 mL, 19.84 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 12 (1.09 g, 85%) as a light gray solid, which was used for the next step without further purification.

3-(diethylamino)-4-methylphenol (13) A solution of 12 (1 g, 5.17 mmol) in anhydrous THF (16 mL) was stirred in an ice bath under N2 for 30 mins. Borane tetrahydrofuran complex solution (1 M, 16 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel (25 g), using DCM/Hexane as eluent to give 13 (872 mg, 94%).

(E)-5-(diethylamino)-4-methyl-2-((4-nitrophenyl)diazenyl)phenol (14)

Compound 13 (0.5 g, 2.79 mmol) was dissolved in 1 mL MeOH. The solution was chilled in an ice bath, then was treated with HCl (2 M, 10 mL). After 15 mins, p-nitrobenzenediazonium tetrafluoroborate (0.695 g, 2.93 mmol) was added to the solution above in 5 portions over 15 mins, then stirred at 0° C. for additional 1 h. During which time, the color of the reaction mixture changed from orange to dark red. After which, the solution was carefully basified with solid K₂CO₃ until pH value of the solution rose above 8. The deep red precipitate was collected via vacuum filtration and washed with small portions of DI water. The product was left in the funnel and air dried overnight to afford compound 14 (0.77 g, 84%), which was used for the next step without further purification.

(Z)—N-(7-(diethylamino)-2,8-dimethyl-3H-phenoxazin-3-ylidene)ethanaminium (LGW-01-23)

Compound 6 (50 mg, 0.33 mmol) was dissolved in a solution of i-PrOH/H₂O (9/1, 3 mL) at 80° C. for 30 min. Compound 14 (109 mg, 0.33 mmol) was added to the solution above in 5 portions over 15 mins. Then the reaction mixture was treated with HClO₄ (70%, 29 μL). The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-01-23 (10.23 mg, 10%) as a dark blue solid.

Scheme 5 Synthesis of LGW-01-25.

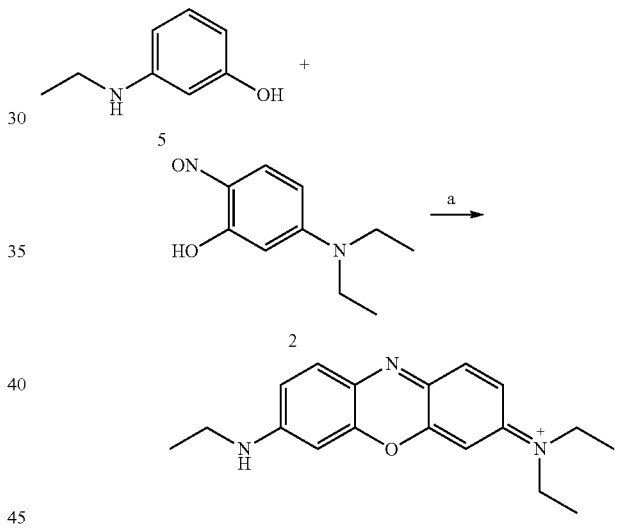

LGW-01-25

Reagents and conditions: a) HClO₄, 90% i-PrOH, 80° C.

N-ethyl-N-(7-(ethylamino)-3H-phenoxazin-3-ylidene)ethanaminium (LGW-01-25)

Compound 5 (50 mg, 0.36 mmol) was dissolved in a solution of i-PrOH/H₂O (9/1, 1 mL) at 80° C. for 30 min. A suspended solution of 2 (74 mg, 0.38 mmol) and HClO₄ (70%, 35 μL) in 90% i-PrOH (2 mL) was added into the solution above in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-01-25 (12 mg, 11%) as a dark blue solid.

Scheme 6 Synthetic route to LGW-01-39.

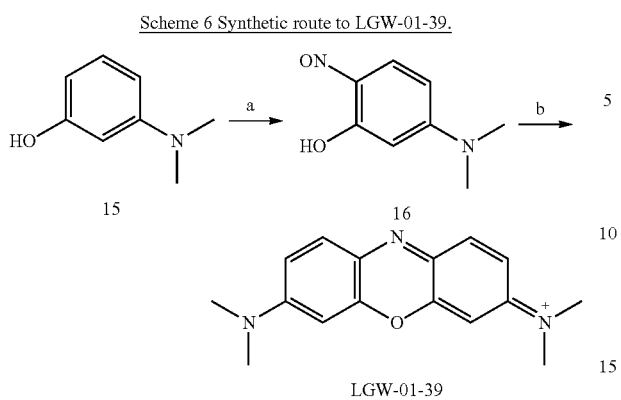

LGW-01-39

Reagents and conditions: a) 6M HCl, NaNO₂, 0° C.; b) Compound 15, HClO₄, 90% i-PrOH, 80° C.

5-(dimethylamino)-2-nitrosophenol (16)

Compound 15 (1 g, 7.29 mmol) was dissolved in an ice-cold 6 M HCl solution (5 mL). To the solution above, NaNO₂ (0.513 g, 7.44 mmol) was added portion wise over 1 h while maintaining the temperature of the solution below 5 C, such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 16 (1.01 g, 84%) as a yellow solid, which was used for the next step without further purification.

N-(7-(dimethylamino)-3H-phenoxazin-3-ylidene)-N-methylmethanaminium (LGW-01-39)

Compound 15 (50 mg, 0.36 mmol) was dissolved in a solution of i-PrOH/H₂O (9/1, 1 mL) at 80° C. for 30 min. A suspended solution of 16 (64 mg, 0.38 mmol) and HClO₄ (70%, 35 µL) in 90% i-PrOH (2 mL) was added into the solution above in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-01-39 (67 mg, 69%) as a dark blue solid.

Scheme 7 Synthetic route to LGW-01-44.

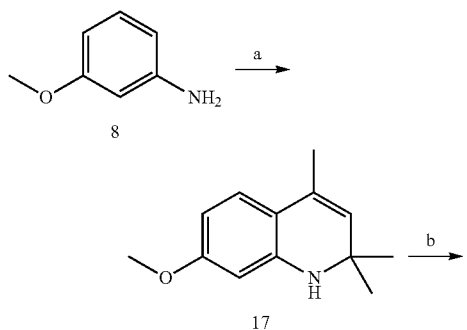

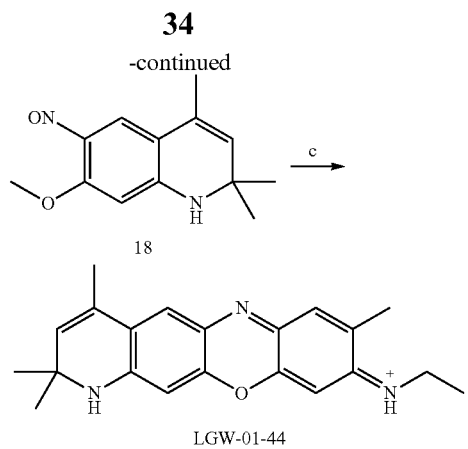

LGW-01-44

Reagents and conditions: a) Yb(OTf)₃, Acetone, rt; b) 2M HCl, NaNO₂, 0° C.; ii) K₂CO₃, 0° C.; c) Compound 6, HClO₄, 90% i-PrOH, 80° C.

7-methoxy-2,2,4-trimethyl-1,2-dihydroquinoline (17)

Compound 17 was synthesized using a modified protocol published by Belov Vladimir et al.[2] Compound 8 (9.09 mL, 81.2 mmol) was diluted in acetone (200 mL) under N2, to the solution above ytterbium(III) triflate (2.52 g, 4.06 mmol) was added. The resulting solution was stirred at rt for 24 h. After which, the reaction mixture was concentrated under reduced pressure. The residue was dissolved in EtOAc, which was washed with water, brine, and dried over anhydrous Na₂SO₄. The organic solvent was removed using rotary evaporator. The crude product was purified by flash column chromatography with silica gel (100 g), using EtOAc/Hexane as eluent to give compound 17 (13.50 g, 82%) as a pale yellow solid.

7-methoxy-2,2,4-trimethyl-6-nitroso-1,2-dihydroquinoline (18)

Compound 17 (1 g, 4.92 mmol) was dissolved in an ice-cold 2 M HCl solution (15 mL). To the solution above, NaNO₂ (0.37 g, 5.41 mmol) was added portion wise over 1 h while maintaining the temperature of the solution below 5° C., such that no brown NOx vapors were observed. The reaction mixture was stirred for additional 2 h. The solution was carefully basified with solid K₂CO₃ until pH value of the above solution rose above 8. After which, the precipitate was filtered through a Buchner funnel and washed with small portions of DI water. The product was left in the funnel and air dried overnight to afford compound 18 (1.04 g, 91%) as a yellow-brownish solid, which was used for the next step without further purification.

(Z)—N-(2,2,4,8-tetramethyl-1,2-dihydro-9H-pyrido[3,2-b]phenoxazin-9-ylidene)ethanaminium (LGW-01-44)

Compound 6 (50 mg, 0.33 mmol) was dissolved in a solution of i-PrOH/H₂O (9/1, 1 mL) at 80° C. for 30 min. A suspended solution of 18 (81 mg, 0.35 mmol) and HClO₄ (70%, 30 µL) in 90% i-PrOH (2 mL) was added into the solution above in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-01-44 (83 mg, 66%) as a dark blue solid.

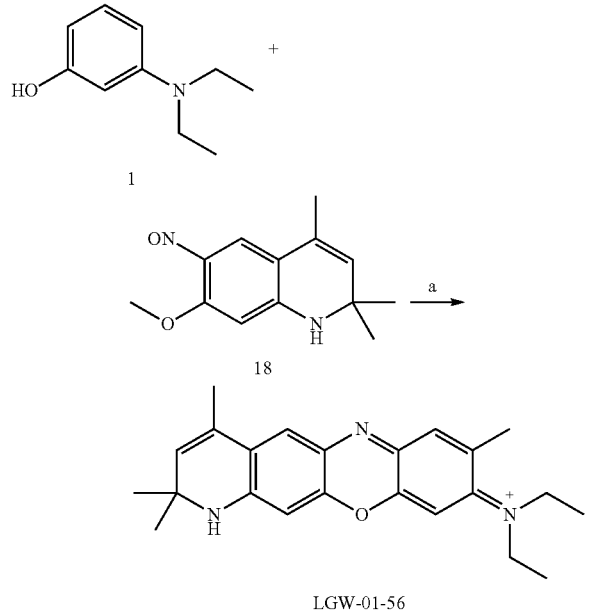

Scheme 8 Synthesis of LGW-01-56.

LGW-01-56

Reagents and conditions: a) HClO₄, 90% i-PrOH, 80° C.

N-ethyl-N-(2,2,4,8-tetramethyl-1,2-dihydro-9H-pyrido[3,2-b]phenoxazin-9-ylidene)ethanaminium (LGW-01-56)

Compound 1 (50 mg, 0.3 mmol) was dissolved in a solution of i-PrOH/H₂O (9/1, 1 mL) at 80° C. for 30 min. A suspended solution of 18 (74 mg, 0.32 mmol) and HClO₄ (70%, 30 μL) in 90% i-PrOH (2 mL) was added into the solution above in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-01-56 (69 mg, 58%) as a dark blue solid.

Scheme 9 Synthesis of LGW-01-61.

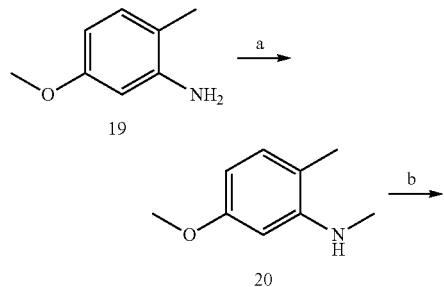

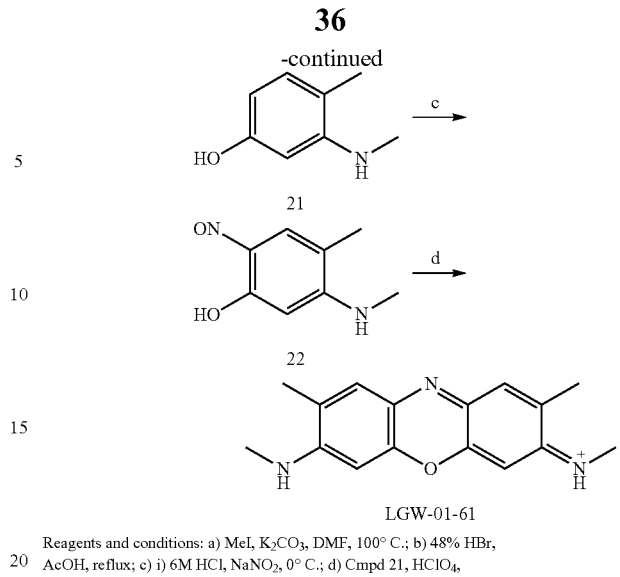

LGW-01-61

Reagents and conditions: a) MeI, K₂CO₃, DMF, 100° C.; b) 48% HBr, AcOH, reflux; c) i) 6M HCl, NaNO₂, 0° C.; d) Cmpd 21, HClO₄, 90% i-PrOH, 80° C.

5-methoxy-N,2-dimethylaniline (20)

To a suspension of compound 19 (2 g, 14.58 mmol) and K₂CO₃ (2.12 g, 15.31 mmol) in anhydrous DMF (10 mL) under N2, was added MeI (0.91 mL, 14.58 mmol) at rt. The reaction mixture was then heated up to 100° C. and stirred for additional 2 h. The solution was cooled down to rt and concentrated under reduced pressure. The crude product was diluted with DI water, and the resulting suspension was extracted with DCM (3×50 mL). The combined organic layers were rinsed with brine, dried over anhydrous Na₂SO₄. The solvent was removed using a rotary evaporator, and the residue was purified by flash column chromatography with silica gel (50 g), using EtOAc/Hexane as eluent to give compound 20 (1.41 g, 64%).

4-methyl-3-(methylamino)phenol (21)

Compound 20 (0.9 g, 5.95 mmol) was dissolved in glacial AcOH (9 mL) at rt after which aqueous HBr (48%, 9 mL) was added. The resulting solution was heated at 110° C. for 5 h before cooling. After which, the reaction mixture was diluted with 50 mL DI water, and the pH of the solution was adjusted to 5-6 with 2 M NaOH solution. The aqueous solution was extracted with DCM (3×50 mL). The combined organic layers were rinsed with brine, dried over anhydrous Na₂SO₄. The solvent was removed using a rotary evaporator and the residue was purified by flash column chromatography with silica gel (30 g), using EtOAc/Hexane as eluent to give compound 21 (478 mg, 59%).

4-methyl-5-(methylamino)-2-nitrosophenol (22)

Compound 21 (200 mg, 1.46 mmol) was dissolved in an ice-cold 6 M HCl solution (2 mL). To the solution above, NaNO₂ (106 mg, 1.53 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 22 (192 mg, 79%), which was used for the next step without further purification.

(Z)—N-(2,8-dimethyl-7-(methylamino)-3H-phenoxazin-3-ylidene)methanaminium (LGW-01-61)

Compound 21 (40 mg, 0.29 mmol) was dissolved in a solution of i-PrOH/H$_2$O (9/1, 1 mL) at 80° C. for 30 min. A suspended solution of 22 (51 mg, 0.31 mmol) and HClO$_4$ (70%, 30 μL) in 90% i-PrOH (2 mL) was added to the solution in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-01-61 (58 mg, 64%) as a dark blue solid.

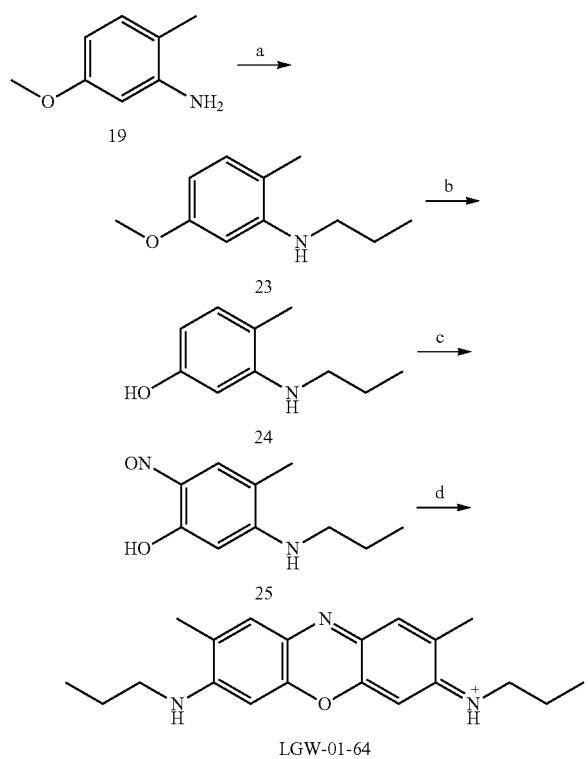

Scheme 10 Synthesis of LGW-01-64 a) 1-Iodopropane, K$_2$CO$_3$, DMF, 100° C.; b) 48% HBr, AcOH, reflux; c) i) 6 M HCl, NaNO$_2$, 0° C.; d) Compound 24, HClO$_4$, 90% i-PrOH, 80° C.

5-methoxy-2-methyl-N-propylaniline (23)

To a suspension of compound 19 (1 g, 5.58 mmol) and K$_2$CO$_3$ (2.12 g, 15.31 mmol) in anhydrous DMF (10 mL) under N2, was added 1-Iodopropane (1.42 mL, 14.58 mmol) at rt. The reaction mixture was then heated up to 100° C., and stirred for additional 2 h. The solution was cooled down to rt and concentrated under reduced pressure. The crude product was diluted with DI water, and the resulting suspension was extracted with DCM (3×50 mL). The combined organic layers were rinsed with brine and dried over anhydrous Na$_2$SO$_4$. The solvent was removed using a rotary evaporator, and the residue was purified by flash column chromatography with silica gel (50 g), using EtOAc/Hexane as eluent to give compound 23 (1.53 g, 59%).

4-methyl-3-(propylamino)phenol (24)

Compound 23 (1 g, 5.58 mmol) was dissolved in glacial AcOH (9 mL) at rt, aqueous HBr (48%, 9 mL) was added to the solution above. The resulting solution was heated at 110° C. for 5 h before cooling. After which the reaction mixture was diluted with 50 mL DI water, and the pH of the solution was adjusted to 5-6 with 2 M NaOH solution. The aqueous solution was extracted with DCM (3×50 mL). The combined organic layers were rinsed with brine, dried over anhydrous Na$_2$SO$_4$. The solvent was removed using a rotary evaporator and the residue was purified by flash column chromatography with silica gel (30 g), using EtOAc/Hexane as eluent to give compound 24 (518 mg, 56%) as brown oil.

4-methyl-2-nitroso-5-(propylamino)phenol (25)

Compound 24 (200 mg, 1.21 mmol) was dissolved in an ice-cold 6 M HCl solution (2 mL). To the solution above, NaNO$_2$ (88 mg, 1.27 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 25 (215 mg, 91%) as an orange solid, which was used for the next step without further purification.

(Z)—N-(2,8-dimethyl-7-(propylamino)-3H-phenoxazin-3-ylidene)propan-1-aminium (LGW-01-64)

Compound 24 (50 mg, 0.3 mmol) was dissolved in a solution of i-PrOH/H$_2$O (9/1, 1 mL) at 80° C. for 30 min. A suspended solution of 25 (62 mg, 0.31 mmol) and HClO$_4$ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-01-64 (72 mg, 65%) as a dark blue solid.

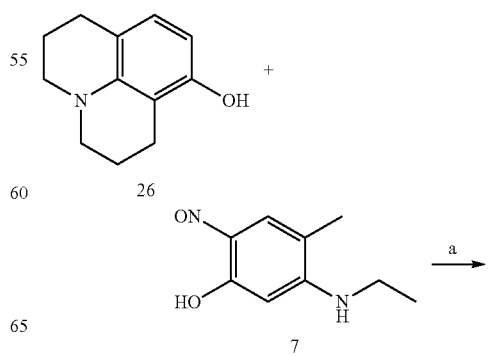

Scheme 11 Synthesis of LGW-01-99.

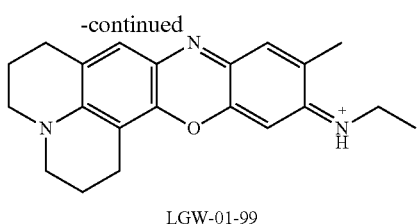

LGW-01-99

Reagents and conditions: a) HClO₄, 90% i-PrOH, 80° C.

(Z)—N-(11-methyl-2,3,6,7-tetrahydro-1H,5H,12H-quinolizino[1,9-bc]phenoxazin-12-ylidene)ethanaminium (LGW-01-99)

Compound 26 (50 mg, 0.26 mmol) was dissolved in a solution of i-PrOH/H₂O (9/1, 1 mL) at 80° C. for 30 min. A suspended solution of 7 (50 mg, 0.27 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-01-99 (33 mg, 33%) as a dark blue solid.

Scheme 12 Synthesis of LGW-02-57.

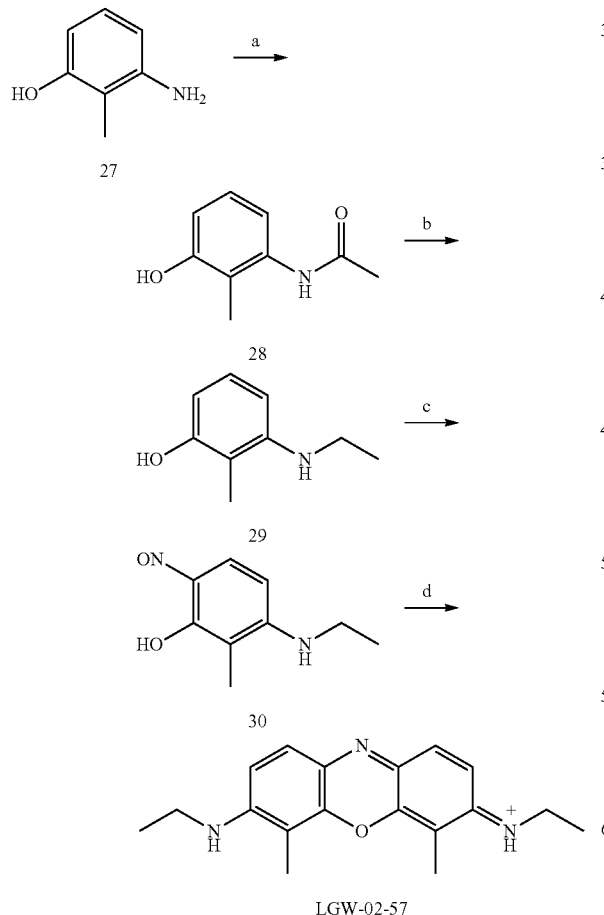

LGW-02-57

Reagents and conditions: a) Ac₂O, H₂O, 50° C. to rt; b) BH₃—THF, THF, 0° C. to rt; c) 6M HCl, NaNO₂, 0° C.; d) Compound 30, HClO₄, 90% i-PrOH, 80° C.

N-(3-hydroxy-2-methylphenyl)acetamide (28)

Compound 27 (2 g, 16.24 mmol) was suspended in 10 mL DI water, to which Acetic anhydride (4.61 mL, 48.72 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 28 (1.65 g, 62%) as a light gray solid, which was used for the next step without further purification.

3-(ethylamino)-2-methylphenol (29)

A solution of 28 (1.5 g, 9.08 mmol) in anhydrous THF (25 mL) was stirred in an ice bath under N2 for 30 mins. Borane tetrahydrofuran complex solution (1 M, 27 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel (25 g), using DCM/Hexane as eluent to obtain 29 (1.18 g, 86%) as brown oil.

3-(ethylamino)-2-methyl-6-nitrosophenol (30)

Compound 29 (300 mg, 1.98 mmol) was dissolved in an ice-cold 6 M HCl solution (2 mL). To the solution above, NaNO₂ (144 mg, 2.08 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 30 (257 mg, 72%) as a brown solid, which was used for the next step without further purification.

(E)-N-(7-(ethylamino)-4,6-dimethyl-3H-phenoxazin-3-ylidene)ethanaminium (LGW-02-57)

Compound 29 (50 mg, 0.33 mmol) was dissolved in a solution of i-PrOH/H₂O (9/1, 1 mL) at 80° C. for 30 min. A suspended solution of 30 (63 mg, 0.35 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-02-57 (8 mg, 7%) as a dark blue solid.

Scheme 13 Synthesis of LGW-02-58.

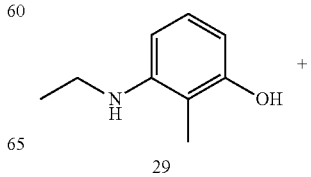

29

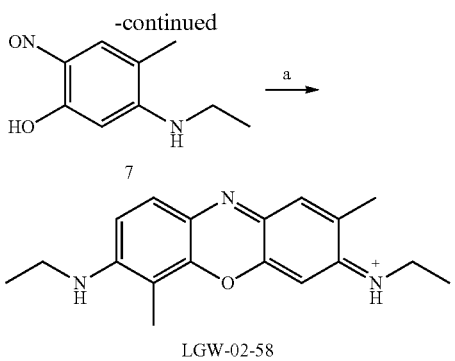

Reagents and conditions: a) HClO₄, 90% i-PrOH, 80° C.

(Z)—N-(7-(ethylamino)-2,6-dimethyl-3H-phenoxazin-3-ylidene)ethanaminium (LGW-02-58)

Compound 29 (50 mg, 0.33 mmol) was dissolved in a solution of i-PrOH/H₂O (9/1, 1 mL) at 80° C. for 30 min. A suspended solution of 7 (63 mg, 0.35 mmol) and HClO₄ (70%, 30 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-02-58 (72 mg, 73%) as a dark blue solid.

Scheme 14 Synthetic route to LGW-02-59.

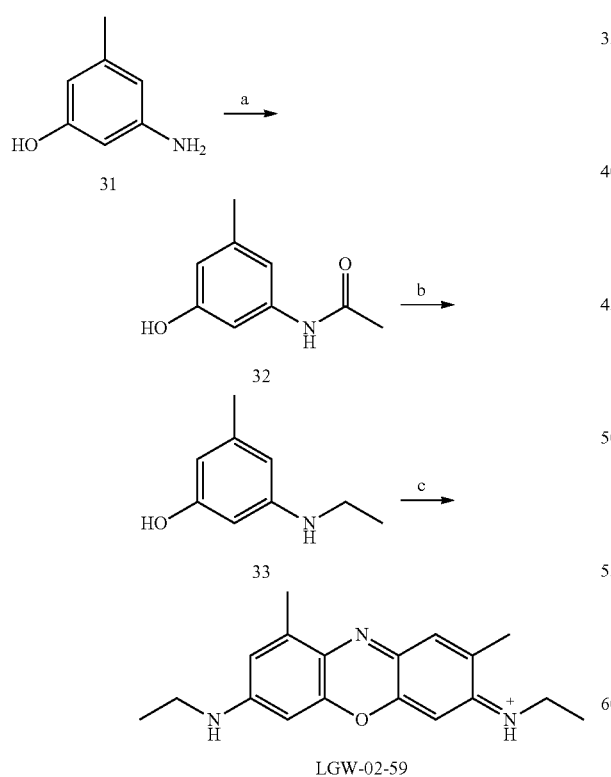

Reagents and conditions:
a) Ac₂O, H₂O, 50° C. to rt;
b) BH₃—THF, THF, 0° C. to rt;
c) Compound 7, HClO₄, 90% i-PrOH, 80° C.

N-(3-hydroxy-5-methylphenyl)acetamide (32)

Compound 31 (1 g, 8.12 mmol) was suspended in 10 mL DI water, to which Acetic anhydride (4.61 mL, 48.72 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 32 (1.28 g, 95%) as a light gray solid, which was used for the next step without further purification.

3-(ethylamino)-5-methylphenol (33)

A solution of 32 (1.2 g, 7.26 mmol) in anhydrous THF (22 mL) was stirred in an ice bath under N2 for 30 mins. Borane tetrahydrofuran complex solution (1 M, 22 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel (25 g), using DCM/Hexane as eluent to give 33 (1.04 g, 94%).

(Z)—N-(7-(ethylamino)-2,9-dimethyl-3H-phenoxazin-3-ylidene)ethanaminium (LGW-02-59)

Compound 33 (50 mg, 0.33 mmol) was dissolved in a solution of i-PrOH/H₂O (9/1, 1 mL) at 80° C. for 30 min. A suspended solution of 7 (63 mg, 0.35 mmol) and HClO₄ (70%, 30 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-02-59 (9 mg, 8%) as a dark blue solid.

Scheme 15 Synthetic route to LGW-02-60.

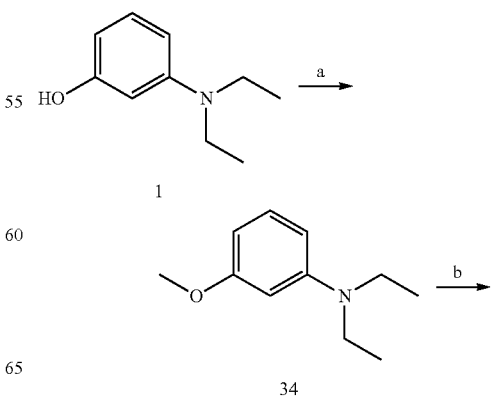

-continued

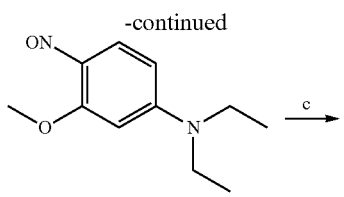

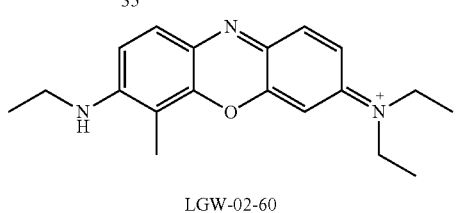

LGW-02-60

Reagents and conditions:
a) MeI, NaH, THF, 0° C. to rt;
b) 2M HCl, NaNO₂, 0° C.;
ii) K₂CO₃, 0° C.;
c) Compound 29, HClO₄, 90% i-PrOH, 80° C.

N,N-diethyl-3-methoxyaniline (34)

Compound 1 (5 g, 30.26 mmol) was dissolved in anhydrous THF (50 mL) under N2, and chilled in an ice bath for 30 mins. NaH (60%, 3.63 g, 90.78 mmol) was added to the solution in 3 portions over 10 mins while the temperature was maintained below 5° C. After 10 mins, MeI (7.54 mL, 121 mmol) was added into the reaction mixture in one portion. The resulting suspension was slowly warmed up to rt and stirred overnight. Upon completion of the reaction, DI water was added to the reaction mixture to destroy excess NaH. Organic solvent was removed under reduced pressure, and the residue was extracted with DCM (3×100 mL). The combined organic layers were rinsed with brine and dried over anhydrous Na₂SO₄. The solvent was removed using a rotary evaporator and the residue was purified by flash column chromatography with silica gel (100 g), using DCM/Hexane as eluent to give compound 34 (4.70 g, 88%) as clear oil.

N,N-diethyl-3-methoxy-4-nitrosoaniline (35)

Compound 34 (1.08 g, 6.02 mmol) was dissolved in an ice-cold 2 M HCl solution (15 mL). To the solution above, NaNO₂ (0.457 g, 6.63 mmol) was added portion wise over 1 h while maintaining the temperature of the solution below 5° C., such that no brown NOx vapors were observed. The reaction mixture was stirred for an additional 2 h. The solution was carefully basified with solid K₂CO₃ until pH value of the solution rose above 8. After which, the precipitate was filtered through a Buchner funnel and washed with small portions of DI water. The product was left in the funnel and air dried overnight to afford compound 35 (1.05 g, 84%) as a green solid, which was used for the next step without further purification.

N-ethyl-N-(7-(ethylamino)-6-methyl-3H-phenoxazin-3-ylidene)ethanaminium (LGW-02-60)

Compound 29 (50 mg, 0.33 mmol) was dissolved in a solution of i-PrOH/H₂O (9/1, 1 mL) at 80° C. for 30 min. A suspended solution of 35 (72 mg, 0.35 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-02-60 (95 mg, 81%) as a dark blue solid.

Scheme 16 Synthesis of LGW-02-61.

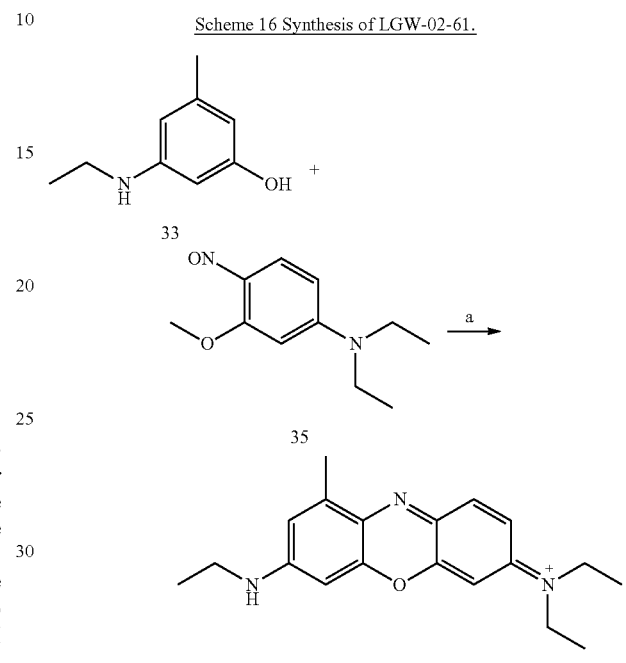

LGW-02-61

Reagents and conditions:
a) HClO₄, 90% i-PrOH, 80° C.

N-ethyl-N-(7-(ethylamino)-9-methyl-3H-phenoxazin-3-ylidene)ethanaminium (LGW-02-61)

Compound 33 (50 mg, 0.33 mmol) was dissolved in a solution of i-PrOH/H₂O (9/1, 1 mL) at 80° C. for 30 min. A suspended solution of 35 (72 mg, 0.35 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-02-61 (52 mg, 44%) as a dark blue solid.

Scheme 17 Synthesis of LGW-02-86.

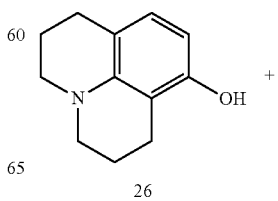

26

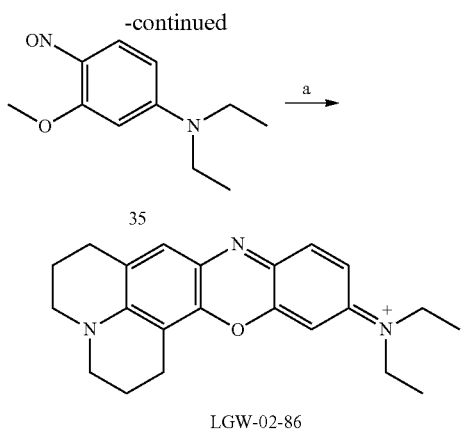

Reagents and conditions:
a) HClO₄, 90% i-PrOH, 80° C.

N-ethyl-N-(2,3,6,7-tetrahydro-1H,5H,12H-quinolizino[1,9-bc]phenoxazin-12-ylidene)ethanaminium (LGW-02-86)

Compound 26 (50 mg, 0.26 mmol) was dissolved in a solution of i-PrOH/H₂O (9/1, 1 mL) at 80° C. for 30 min. A suspended solution of 35 (58 mg, 0.28 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-02-86 (36 mg, 34%) as a dark blue solid.

(E)-9-((4-nitrophenyl)diazenyl)-2,3,6,7-tetrahydro-1H,5H-pyrido[3,2,1-ij]quinolin-8-ol (36)

Compound 26 (0.13 g, 0.69 mmol) was dissolved in 1 mL MeOH. The solution was chilled in an ice bath, then was treated with HCl (2 M, 10 mL). After 15 mins, p-nitrobenzenediazonium tetrafluoroborate (0.18 g, 0.76 mmol) was added to the solution in 5 portions over 15 mins, then stirred at 0° C. for additional 1 h. During which time, the color of the reaction mixture changed from orange to dark red. After which, the solution was carefully basified with solid K₂CO₃ until pH value of the solution rose above 8. The deep red precipitate was collected via vacuum filtration and washed with small portions of DI water. The product was left in the funnel and air dried overnight to afford compound 36 (186 mg, 80%) as a dark red solid, which was used for the next step without further purification.

2,3,6,7,12,13,16,17-octahydro-1H,5H,11H,15H-diquinolizino[1,9-bc:1',9'-hi]phenoxazin-4-ium (LGW-02-87)

Compound 26 (50 mg, 0.26 mmol) was dissolved in a solution of i-PrOH/H₂O (9/1, 3 mL) at 80° C. for 30 min. Compound 36 (89 mg, 0.33 mmol) was added to the solution above in 5 portions over 15 mins. Then the reaction mixture was treated with HClO₄ (70%, 25 μL). The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-02-87 (37 mg, 34%) as a dark blue solid.

Scheme 18

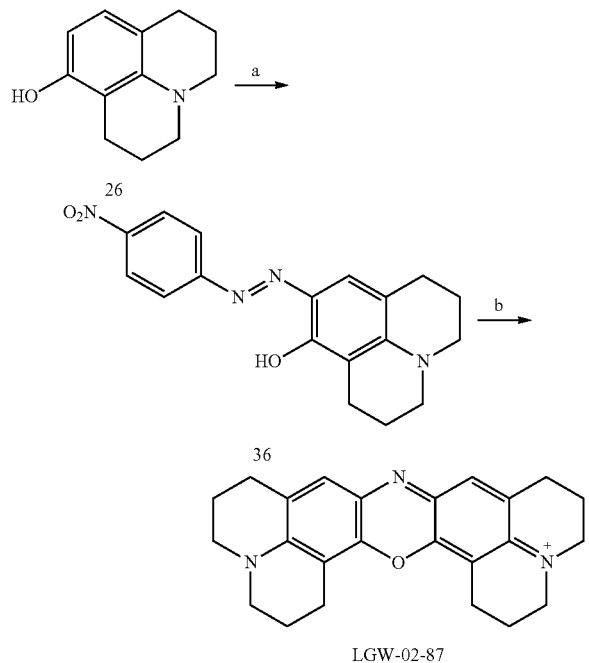

Reagents and conditions:
a) i) 2M HCl, p-nitrobenzenediazonium tetrafluoroborate, 0° C.;
ii) K₂CO₃, 0° C.;
b) Compound 26, HClO₄, 90% i-PrOH, 80° C.

Scheme 19

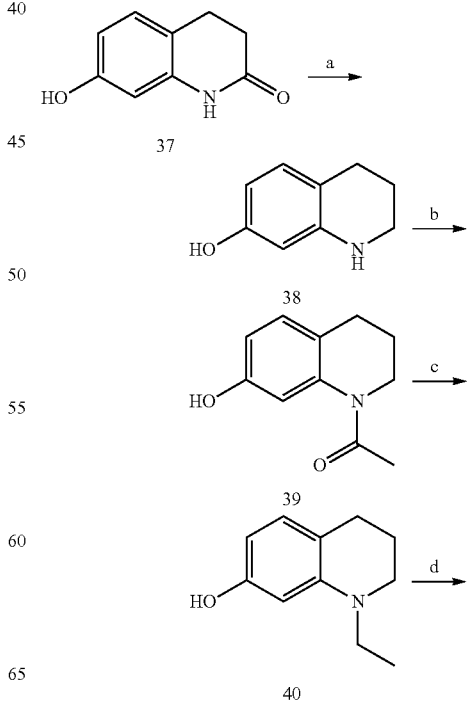

-continued

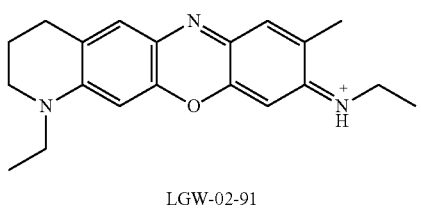

LGW-02-91

Reagents and conditions:
a) BH₃—THF, THF, 0° C. to rt;
b) Ac₂O, H₂O, 50° C. to rt;
c) BH₃—THF, THF, 0° C. to rt;
d) Compound 7, HClO₄, 90% i-PrOH, 80° C.

1,2,3,4-tetrahydroquinolin-7-ol (38)

A solution of 37 (2 g, 12.87 mmol) in anhydrous THF (38 mL) was stirred in an ice bath under N2 for 30 mins. Borane tetrahydrofuran complex solution (1 M, 38 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel (50 g), using EtOAc/Hexane as eluent to give 38 (1.83 g, 95%) as a yellow solid.

1-(7-hydroxy-3,4-dihydroquinolin-1(2H)-yl)ethan-1-one (39)

Compound 38 (1 g, 6.7 mmol) was suspended in 10 mL DI water, to which Acetic anhydride (1.9 mL, 20.11 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 39 (1.13 g, 88%) as a white solid, which was used for the next step without further purification.

1-ethyl-1,2,3,4-tetrahydroquinolin-7-ol (40)

A solution of 39 (1.13 g, 5.91 mmol) in anhydrous THF (18 mL) was stirred in an ice bath under N2 for 30 mins. Borane tetrahydrofuran complex solution (1 M, 18 mL) was added to the solution above using a syringe pump over 30 mins, while maintaining the temperature of the solution below 5° C. The resulting reaction mixture was left in the ice bath and slowly warmed to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel (25 g), using EtOAc/Hexane as eluent to obtain 40 (0.96 g, 92%) as dark oil.

(Z)—N-(1-ethyl-8-methyl-1,2,3,4-tetrahydro-9H-pyrido[3,2-b]phenoxazin-9-ylidene)ethanaminium (LGW-02-91)

Compound 40 (50 mg, 0.28 mmol) was dissolved in a solution of i-PrOH/H₂O (9/1, 1 mL) at 80° C. for 30 min. A suspended solution of 35 (54 mg, 0.30 mmol) and HClO₄ (70%, 30 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-02-91 (39 mg, 38%) as a dark blue solid.

Scheme 20 Synthesis of LGW-02-92.

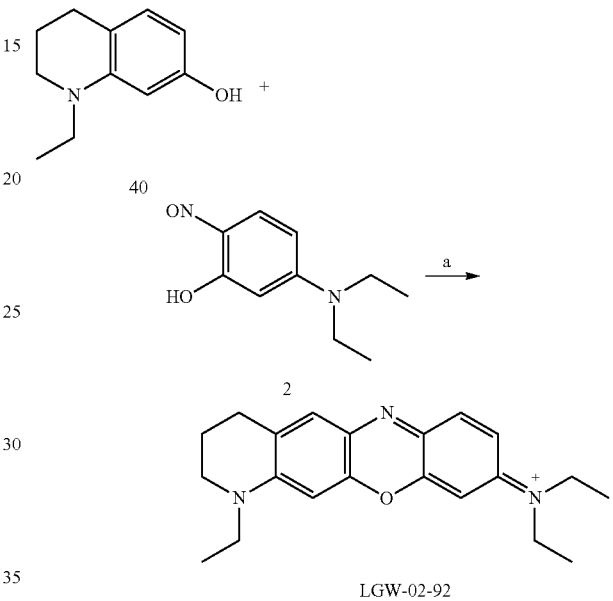

LGW-02-92

Reagents and conditions:
a) HClO₄, 90% i-PrOH, 80° C.

N-ethyl-N-(1-ethyl-1,2,3,4-tetrahydro-9H-pyrido[3,2-b]phenoxazin-9-ylidene)ethanaminium (LGW-02-92)

Compound 40 (50 mg, 0.28 mmol) was dissolved in a solution of i-PrOH/H₂O (9/1, 1 mL) at 80° C. for 30 min. A suspended solution of 2 (58 mg, 0.30 mmol) and HClO₄ (70%, 30 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-02-92 (43 mg, 40%) as a dark blue solid.

Scheme 21 Synthetic route to LGW-02-95.

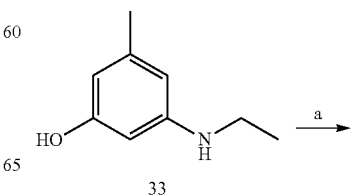

33

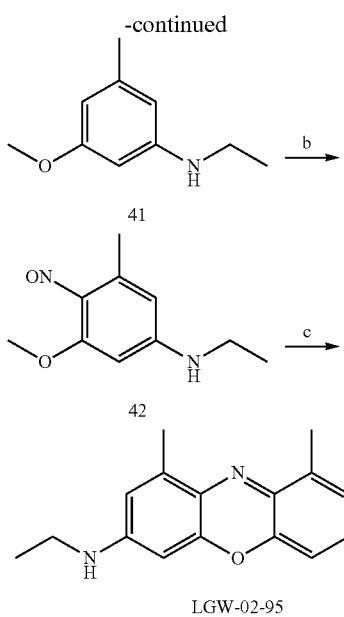

LGW-02-95

Reagents and conditions:
a) MeI, NaH, THF, 0° C. to rt;
b) 2M HCl, NaNO$_2$, 0° C.;
ii) K$_2$CO$_3$, 0° C.;
c) Compound 33, HClO$_4$, 90% i-PrOH, 80° C.

N-ethyl-3-methoxy-5-methylaniline (41)

Compound 33 (0.5 g, 3.31 mmol) was dissolved in anhydrous THF (10 mL) under N$_2$, and chilled in an ice bath for 30 mins. NaH (60%, 139 mg, 3.47 mmol) was added to the solution in 3 portions over 10 mins while the temperature was maintained below 5° C. After 10 mins, MeI (0.216 mL, 3.47 mmol) was added into the reaction mixture in one portion. The resulting suspension was slowly warmed up to rt and stirred overnight. Upon completion of the reaction, DI water was added to the reaction mixture to destroy excess NaH. Organic solvent was removed under reduced pressure, and the residue was extracted with DCM (3×25 mL). The combined organic layers were rinsed with brine and dried over anhydrous Na$_2$SO$_4$. The solvent was removed using a rotary evaporator and the residue was purified by flash column chromatography with silica gel (100 g), using DCM/Hexane as eluent to give compound 41 (0.37 g, 68%).

N-ethyl-3-methoxy-5-methyl-4-nitrosoaniline (42)

Compound 41 (200 mg, 1.21 mmol) was dissolved in an ice-cold 2 M HCl solution (5 mL). NaNO$_2$ (92 mg, 1.33 mmol) was added portion wise over 1 h while maintaining the temperature of the solution below 5° C., such that no brown NOx vapors were observed. The reaction mixture was stirred for additional 2 h. The solution was carefully basified with solid K$_2$CO$_3$ until pH value of the above solution rose above 8. After which, the aqueous solution was extracted with DCM (3×25 mL). The combined organic layers were rinsed with brine and dried over anhydrous Na$_2$SO$_4$. The solvent was removed using a rotary evaporator to give 42 (109 mg, 46%) as a light green oil, which was used for the next step without further purification.

(E)-N-(7-(ethylamino)-1,9-dimethyl-3H-phenoxazin-3-ylidene)ethanaminium (LGW-02-95)

Compound 33 (50 mg, 0.33 mmol) was dissolved in a solution of i-PrOH/H$_2$O (9/1, 1 mL) at 80° C. for 30 min. A suspended solution of 42 (68 mg, 0.35 mmol) and HClO$_4$ (70%, 30 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-02-95 (9 mg, 7%) as a dark blue solid.

Scheme 22 Synthetic route to LGW-02-99.

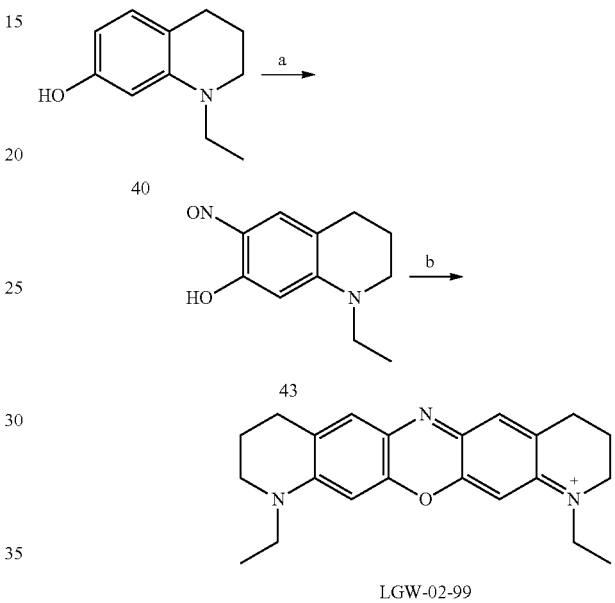

LGW-02-99

Reagents and conditions:
a) 6M HCl, NaNO$_2$, 0° C.;
b) Compound 40, HClO$_4$, 90% i-PrOH, 80° C.

1-ethyl-6-nitroso-1,2,3,4-tetrahydroquinolin-7-ol (43)

Compound 40 (450 mg, 2.54 mmol) was dissolved in an ice-cold 6 M HCl solution (8 mL). NaNO$_2$ (184 mg, 2.67 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 43 (392 mg, 75%), which was used for the next step without further purification.

1,11-diethyl-3,4,8,9,10,11-hexahydro-2H-dipyrido[3,2-b:2',3'-i]phenoxazin-1-ium (LGW-02-99)

Compound 40 (33 mg, 0.19 mmol) was dissolved in a solution of i-PrOH/H$_2$O (9/1, 1 mL) at 80° C. for 30 min. A suspended solution of 43 (40 mg, 0.2 mmol) and HClO$_4$ (70%, 20 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-02-99 (12 mg, 19%) as a dark blue solid.

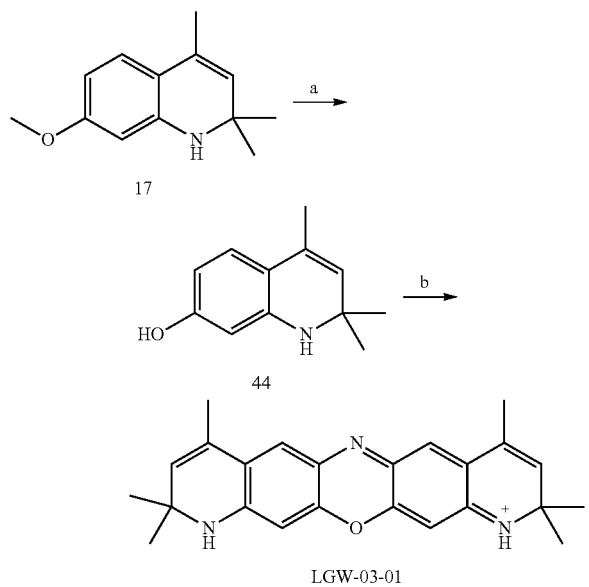

Scheme 23 Synthetic route to LGW-03-01.

Reagents and conditions:
a) 48% HBr, AcOH, reflux;
b) Compound 18, HClO₄, 90% i-PrOH, 80° C.

2,2,4-trimethyl-1,2-dihydroquinolin-7-ol (44)

Compound 17 (1 g, 4.92 mmol) was dissolved in glacial AcOH (4 mL) at rt and aqueous HBr (48%, 4 mL) was added. The resulting solution was heated at 110° C. for 5 h before cooling. After which the reaction mixture was diluted with 50 mL DI water, and the pH of the solution was adjusted to 5-6 with 2 M NaOH solution. The aqueous solution was extracted with DCM (3×50 mL). The combined organic layers were rinsed with brine and dried over anhydrous Na₂SO₄. The solvent was removed using a rotary evaporator and the residue was purified by flash column chromatography with silica gel (30 g), using EtOAc/Hexane as eluent to give compound 44 (619 mg, 67%) as a brown solid.

2,2,4,8,10,10-hexamethyl-10,11-dihydro-2H-dipyrido[3,2-b:2',3'-i]phenoxazin-1-ium (LGW-03-01)

Compound 44 (55 mg, 0.29 mmol) was dissolved in a solution of i-PrOH/H₂O (9/1, 1 mL) at 80° C. for 30 min. A suspended solution of 18 (71 mg, 0.31 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-03-01 (17 mg, 16%) as a dark blue solid.

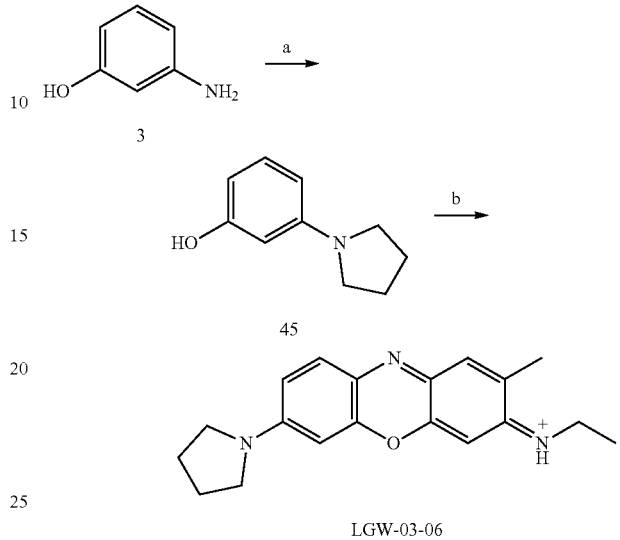

Scheme 24 Synthetic route to LGW-03-06.

Reagents and conditions: a) i) 14-dichlorobutane, Toluene, reflux; ii) Et₃N, Na₂CO₃, reflux; b) Compound 7, HClO₄, 90% i-PrOH, 80° C.

3-(pyrrolidin-1-yl)phenol (45)

To a suspension of compound 3 (5 g, 45.82 mmol) in anhydrous toluene, was added 1,4-dichlorobutane (5.52 mL, 50.40 mmol). The reaction mixture was refluxed for 24 h then cooled down to rt. After which, Et₃N (9.58 mL, 68.73 mmol) and Na₂CO₃ (4.86 g, 45.82 mmol) in 10 mL DI water was added to the reaction flask. The resulting reaction mixture was refluxed for an additional 24 h. Upon completion of the reaction, organic solvent was removed under reduced pressure. The aqueous phase was extracted with DCM (3×100 mL). The combined organic layers were rinsed with brine and dried over anhydrous Na₂SO₄. The solvent was removed using a rotary evaporator and the residue was purified by flash column chromatography with silica gel (100 g), using DCM/Hexane as eluent to give compound 45 (5.37 g, 72%) as a light gray solid.

(Z)—N-(2-methyl-7-(pyrrolidin-1-yl)-3H-phenoxazin-3-ylidene)ethanaminium (LGW-03-06)

Compound 45 (50 mg, 0.31 mmol) was dissolved in a solution of i-PrOH/H₂O (9/1, 1 mL) at 80° C. for 30 min. A suspended solution of 7 (58 mg, 0.32 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-03-06 (64 mg, 59%) as a dark blue solid.

53

Scheme 25 Synthesis of LGW-03-07.

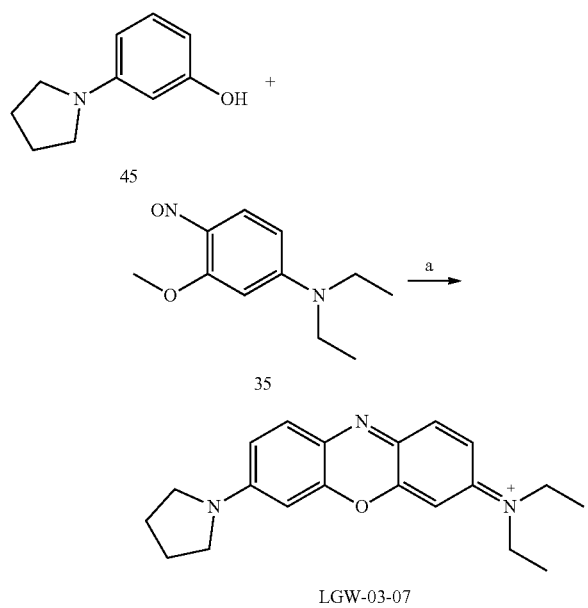

Reagents and conditions: a) HClO$_4$, 90% i-PrOH, 80° C.

N-ethyl-N-(7-(pyrrolidin-1-yl)-3H-phenoxazin-3-ylidene)ethanaminium (LGW-03-07)

Compound 45 (50 mg, 0.31 mmol) was dissolved in a solution of i-PrOH/H$_2$O (9/1, 1 mL) at 80° C. for 30 min. A suspended solution of 35 (67 mg, 0.32 mmol) and HClO$_4$ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-03-07 (13 mg, 12%) as a dark blue solid.

Scheme 26 Synthesis of LGW-03-12.

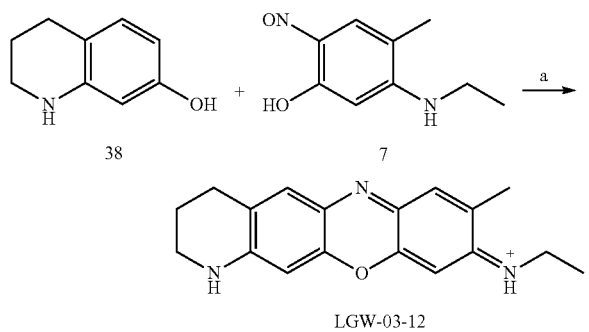

Reagents and conditions:
a) HClO$_4$, 90% i-PrOH, 80° C.

54

(Z)—N-(8-methyl-1,2,3,4-tetrahydro-9H-pyrido[3,2-b]phenoxazin-9-ylidene)ethanaminium (LGW-03-12)

Compound 38 (50 mg, 0.34 mmol) was dissolved in a solution of i-PrOH/H$_2$O (9/1, 1 mL) at 80° C. for 30 min. A suspended solution of 7 (63 mg, 0.35 mmol) and HClO$_4$ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-03-12 (57 mg, 50%) as a dark blue solid.

Scheme 27 Synthesis of LGW-03-13.

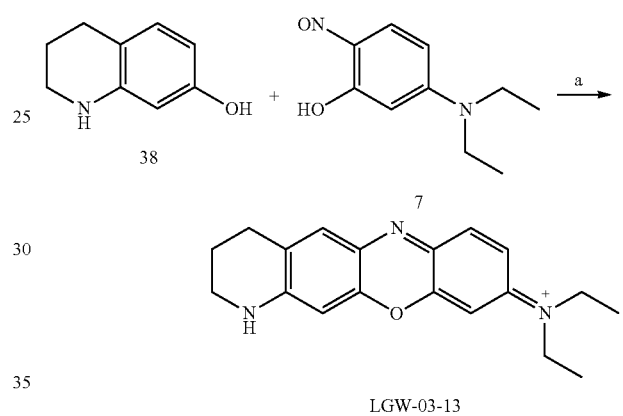

Reagents and conditions:
a) HClO$_4$, 90% i-PrOH, 80° C.

N-ethyl-N-(1,2,3,4-tetrahydro-9H-pyrido[3,2-b]phenoxazin-9-ylidene)ethanaminium (LGW-03-13)

Compound 38 (50 mg, 0.34 mmol) was dissolved in a solution of i-PrOH/H$_2$O (9/1, 1 mL) at 80° C. for 30 min. A suspended solution of 2 (68 mg, 0.35 mmol) and HClO$_4$ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-03-13 (23 mg, 20%) as a dark blue solid.

Scheme 28 Synthetic route to LGW-03-18.

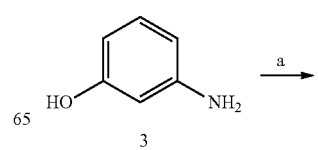

-continued

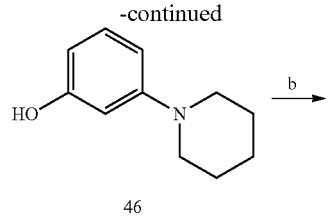

46

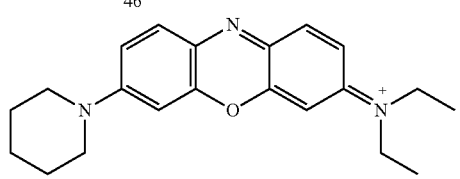

LGW-03-18

Reagents and conditions:
a) i) 15-dichloropoantane, Toluene, reflux;
ii) Et₃N, Na₂CO₃, reflux;
b) Compound 35, HClO₄, 90% i-PrOH, 80° C.

3-(piperidin-1-yl)phenol (46)

To a suspension of compound 3 (5 g, 45.82 mmol) in anhydrous toluene, was added 1,4-dichloropantane (6.64 mL, 50.40 mmol). The reaction mixture was refluxed for 24 h then cooled down to rt. After which, Et₃N (9.58 mL, 68.73 mmol) and Na₂CO₃ (4.86 g, 45.82 mmol) in 10 mL DI water was added to the reaction flask. The resulting reaction mixture was refluxed for an additional 24 h. Upon completion of the reaction, organic solvent was removed under reduced pressure. The aqueous phase was extracted with DCM (3×100 mL). The combined organic layers were rinsed with brine and dried over anhydrous Na₂SO₄. The solvent was removed using a rotary evaporator and the residue was purified by flash column chromatography with silica gel (100 g), using DCM/Hexane as eluent to give compound 46 (5.71 g, 70%).

N-ethyl-N-(7-(piperidin-1-yl)-3H-phenoxazin-3-ylidene)ethanaminium (LGW-03-18)

Compound 46 (50 mg, 0.28 mmol) was dissolved in a solution of i-PrOH/H₂O (9/1, 1 mL) at 80° C. for 30 min. A suspended solution of 35 (62 mg, 0.30 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-03-18 (49 mg, 46%) as a dark blue solid.

-continued

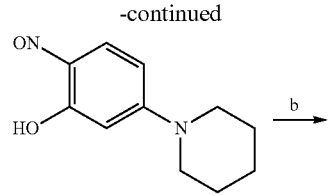

47

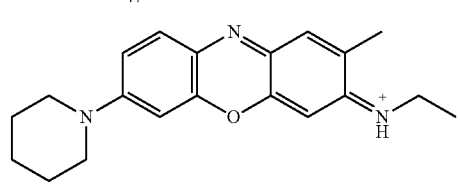

LGW-03-21

Reagents and conditions:
a) 6M HCl, NaNO₂, 0° C.;
b) Compound 6, HClO₄, 90% i-PrOH, 80° C.

2-nitroso-5-(piperidin-1-yl)phenol (47)

Compound 46 (0.5 g, 2.82 mmol) was dissolved in an ice-cold 6 M HCl solution (5 mL). To the solution, NaNO₂ (0.214 g, 3.10 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 47 (0.514 g, 88%) as a brown solid, which was used for the next step without further purification.

(Z)—N-(2-methyl-7-(piperidin-1-yl)-3H-phenoxazin-3-ylidene)ethanaminium (LGW-03-21)

Compound 6 (30 mg, 0.2 mmol) was dissolved in a solution of i-PrOH/H₂O (9/1, 1 mL) at 80° C. for 30 min. A suspended solution of 47 (43 mg, 0.35 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-03-21 (12 mg, 17%) as a dark blue solid.

Scheme 29 Synthetic route to LGW-03-21.

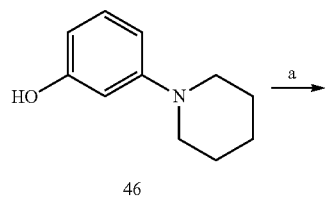

46

Scheme 30 Synthesis of LGW-03-23.

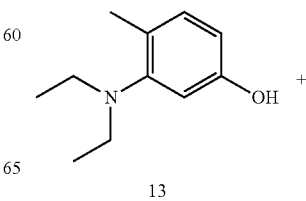

13

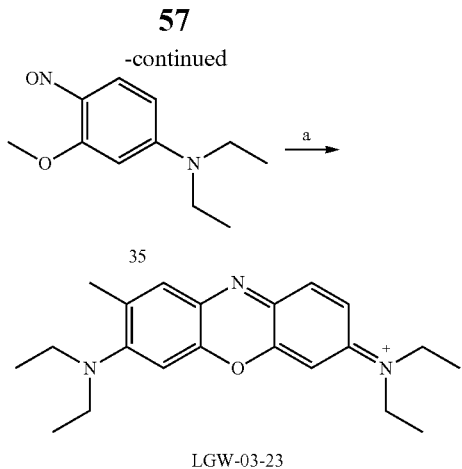

LGW-03-23

Reagents and conditions:
a) HClO₄, 90% i-PrOH, 80° C.

N-(7-(diethylamino)-8-methyl-3H-phenoxazin-3-ylidene)-N-ethylethanaminium (LGW-03-23)

Compound 13 (50 mg, 0.28 mmol) was dissolved in a solution of i-PrOH/H₂O (9/1, 1 mL) at 80° C. for 30 min. A suspended solution of 35 (61 mg, 0.29 mmol) and HClO₄ (70%, 30 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-03-23 (60 mg, 56%) as a dark blue solid.

Scheme 31 Synthetic route to LGW-03-31.

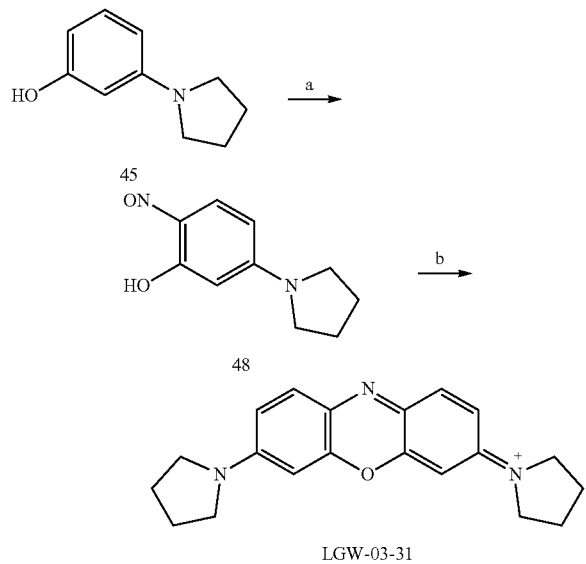

LGW-03-31

Reagents and conditions: (a) 6M HCl, NaNO₂, 0° C.;
(b) Compound 45, HClO₄, 90° i-PrOH, 80° C.

2-nitroso-5-(pyrrolidin-1-yl)phenol (48)

Compound 45 (0.4 g, 2.45 mmol) was dissolved in an ice-cold 6 M HCl solution (4 mL). To the solution, NaNO₂ (0.178 g, 2.57 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 48 (0.403 g, 86%) as a bright yellow solid, which was used for the next step without further purification.

1-(7-(pyrrolidin-1-yl)-3H-phenoxazin-3-ylidene) pyrrolidin-1-ium (LGW-03-31)

Compound 45 (40 mg, 0.25 mmol) was dissolved in a solution of i-PrOH/H₂O (9/1, 1 mL) at 80° C. for 30 min. A suspended solution of 48 (50 mg, 0.26 mmol) and HClO₄ (70%, 25 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-03-31 (37 mg, 41%) as a dark blue solid.

Scheme 32 Synthetic route to LGW-03-32.

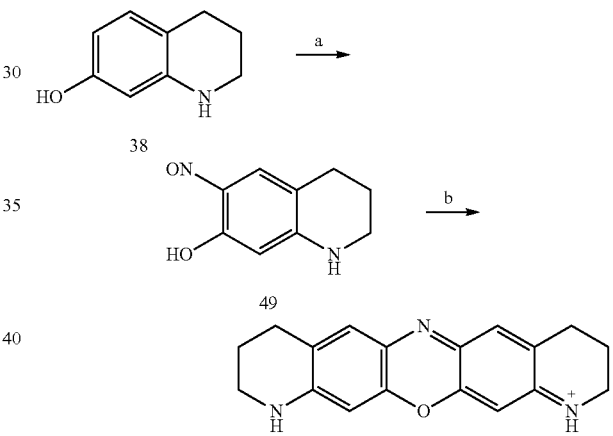

LGW-03-32

Reagents and conditions: a) 6M HCl, NaNO₂, 0° C.;
(b) Compound 38, HClO₄, 90% i-PrOH, 80° C.

6-nitroso-1,2,3,4-tetrahydroquinolin-7-ol (49)

Compound 38 (0.4 g, 2.68 mmol) was dissolved in an ice-cold 6 M HCl solution (4 mL). To the solution, NaNO₂ (0.2 g, 2.95 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 49 (0.418 g, 89%) as a light green solid, which was used for the next step without further purification.

3,4,8,9,10,11-hexahydro-2H-dipyrido[3,2-b:2',3'-i] phenoxazin-1-ium (LGW-03-32)

Compound 38 (40 mg, 0.27 mmol) was dissolved in a solution of i-PrOH/H₂O (9/1, 1 mL) at 80° C. for 30 min. A suspended solution of 49 (50 mg, 0.28 mmol) and HClO$_4$ (70%, 25 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-03-32 (31 mg, 40%) as a dark blue solid.

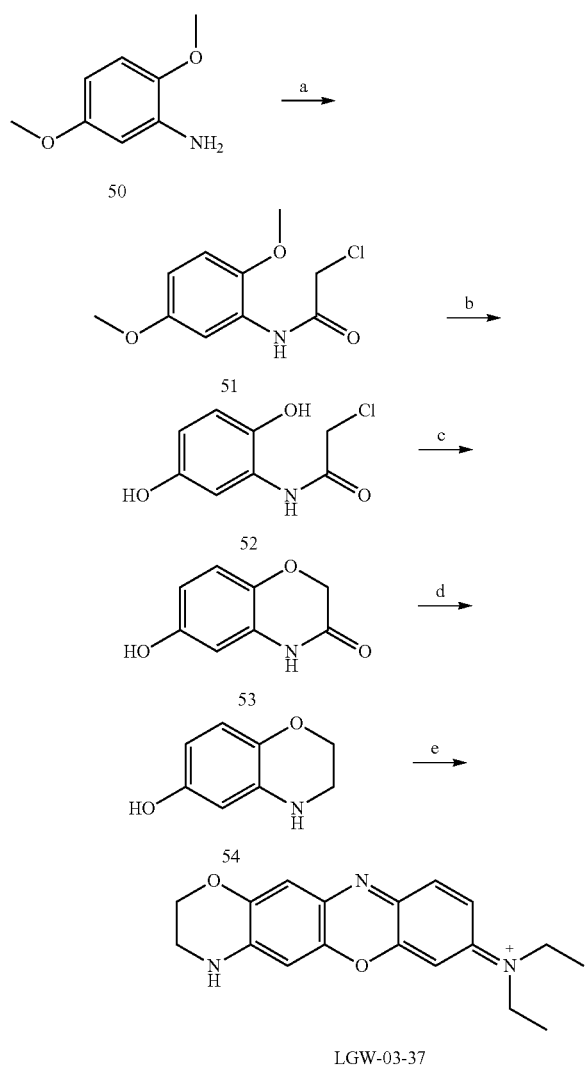

Scheme 33 Synthetic route to LGW-03-37.

LGW-03-37

Reagents and conditions: a) Chloroacetic chloride, TBAB, NaHCO$_3$, H$_2$O, 0° C.; b) 1M BBr3, DCM, 0° C. to rt; c) NaH, THF, 0° C. to rt; d) BH$_3$-THF, THF, 0° C. to rt; e) Compound 35, HClO$_4$, 90% i-PrOH, 80° C.

2-chloro-N-(2,5-dimethoxyphenyl)acetamide (51)

Compound 50 (20 g, 130 mmol) was dissolved in anhydrous MeCN (60 mL) under N2, and chilled in an ice bath. To the solution, Et$_3$N (40 mL, 287 mmol) and Chloroacetic chloride (12.68 mL, 159 mmol) were carefully added. The reaction mixture was stirred for 1 h, then diluted with 500 mL DI water. The solid suspension was filtered off to yield compound 51 (21 g, 70%) as a light brown solid, which was used for the next step without further purification.

2-chloro-N-(2,5-dihydroxyphenyl)acetamide (52)

Compound 51 (10 g, 43.54 mmol) was dissolved in anhydrous DCM (20 mL) under N2, and chilled in an ice bath. To the solution above, was added BBr$_3$ (1 M in DCM, 130 mL, 130 mmol) dropwise over 1 h using a syringe pump. The reaction mixture was slowly warmed up to rt and stirred overnight. The reaction flask was placed in an ice bath, after sufficient amount of time for cooling, water was carefully added to the reaction mixture to destroy excess BBr$_3$. The resulting precipitate was collected via vacuum filtration and washed with small portions of DI water. The product was left in the funnel and air dried overnight to afford compound 52 (7.96 g, 91%), which was used for the next step without further purification.

6-hydroxy-2H-benzo[b][1,4]oxazin-3(4H)-one (53)

Compound 52 (6 g, 29.76 mmol) was dissolved in anhydrous THE (50 mL) under N2, and chilled in an ice bath. After sufficient time for cooling, NaH (60%, 4.17 g, 104 mmol) was added to the solution in 4 portions over 10 mins. The reaction mixture was slowly warmed to rt and stirred overnight. Upon the completion of the reaction, ice-cold water was carefully added to the reaction flask to destroy excess NaH. The reaction mixture was acidified with 2 M HCl, followed by extraction with EtOAc (5×100 mL). The combined organic layers were rinsed with brine and dried over anhydrous Na$_2$SO$_4$. The solvent was removed using a rotary evaporator and the residue was purified by flash column chromatography with silica gel (100 g), using EtOAc/DCM/Hexane as eluent to give compound 53 (3.12 g, 63%) as a light brown solid.

3,4-dihydro-2H-benzo[b][1,4]oxazin-6-ol (54)

A solution of 53 (2.2 g, 13.32 mmol) in anhydrous THE (40 mL) was stirred in an ice bath under N2 for 30 mins. Borane tetrahydrofuran complex solution (1 M, 40 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel (50 g), using ErOAc/Hexane as eluent to obtain 54 (1.914 g, 95%).

N-(3,4-dihydro-[1,4]oxazino[2,3-b]phenoxazin-8 (2H)-ylidene)-N-ethylethanaminium (LGW-03-37)

Compound 54 (36 mg, 0.24 mmol) was dissolved in a solution of i-PrOH/H$_2$O (9/1, 1 mL) at 80° C. for 30 min. A suspended solution of 35 (52 mg, 0.25 mmol) and HClO$_4$ (70%, 25 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-03-37 (27 mg, 32%) as a dark blue solid.

Scheme 34 Synthesis of o LGW-03-07.

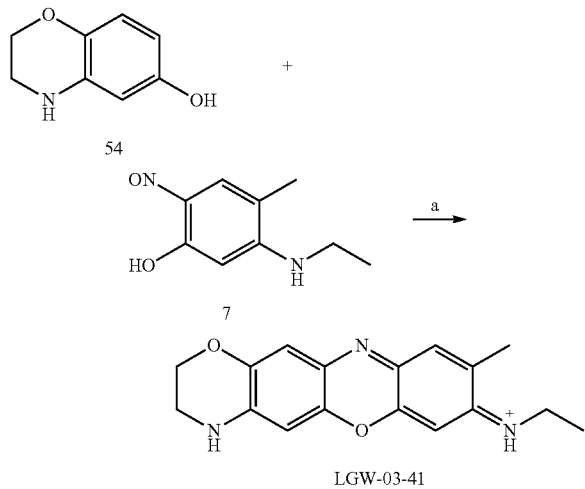

Reagents and conditions: a) HClO₄, 90% i-PrOH, 80° C.

(Z)—N-(9-methyl-3,4-dihydro-[1,4]oxazino[2,3-b] phenoxazin-8(2H)-ylidene)ethanaminium (LGW-03-41)

Compound 54 (50 mg, 0.33 mmol) was dissolved in a solution of i-PrOH/H₂O (9/1, 1 mL) at 80° C. for 30 min. A suspended solution of 7 (63 mg, 0.35 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-03-41 (50 mg, 44%) as a dark blue solid.

Scheme 35 Synthetic route to LGW-03-52.

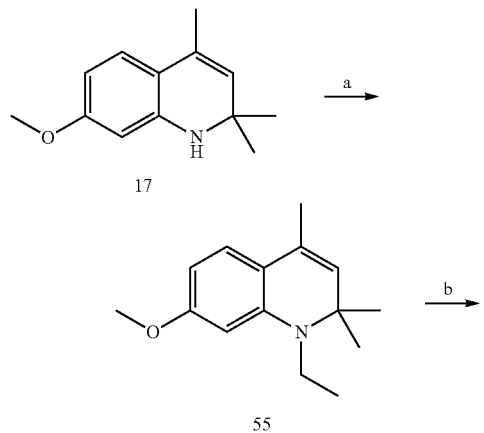

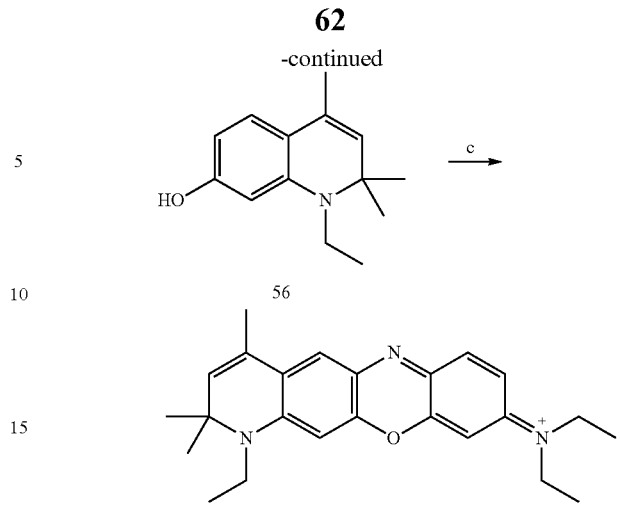

Reagents and conditions: a) EtI, K₂CO₃, DMF, 100° C.; b) 48% HBr, AcOH, reflux; c) Compound 35, HClO₄, 90% i-PrOH, 80° C.

1-ethyl-7-methoxy-2,2,4-trimethyl-1,2-dihydroquinoline (55)

To a suspension of compound 17 (4 g, 19.68 mmol) and K₂CO₃ (2.72 g, 19.68 mmol) in anhydrous DMF (20 mL) under N2, was added EtI (4.75 mL, 59.03 mmol) at rt. The reaction mixture was then heated up to 90° C. and stirred overnight. The solution was cooled down to rt and concentrated under reduced pressure. The crude product was diluted with 100 mL DI water, and the aqueous phase was extracted with EtOAc (4×100 mL). The combined organic layers were rinsed with brine and dried over anhydrous Na₂SO₄. The solvent was removed using a rotary evaporator and the residue was purified by flash column chromatography with silica gel (200 g), using DCM/Hexane as eluent to give compound 55 (3.95 g, 87%) as clear oil.

1-ethyl-2,2,4-trimethyl-1,2-dihydroquinolin-7-ol (56)

Compound 55 (0.5 g, 2.16 mmol) was dissolved in glacial AcOH (2 mL) at rt, aqueous HBr (48%, 2 mL) was added to the solution above. The resulting solution was heated at 110° C. for 5 h before cooling. After which the reaction mixture was diluted with 50 mL DI water, and the pH of the solution was adjusted to 5-6 with 2 M NaOH solution. The aqueous solution was extracted with DCM (3×25 mL). The combined organic layers were rinsed with brine and dried over anhydrous Na₂SO₄. The solvent was removed using a rotary evaporator and the residue was purified by flash column chromatography with silica gel (25 g), using EtOAc/Hexane as eluent to give compound 56 (292 mg, 62%).

N-ethyl-N-(1-ethyl-2,2,4-trimethyl-1,2-dihydro-9H-pyrido[3,2-b]phenoxazin-9-ylidene)ethanaminium (LGW-03-52)

Compound 56 (40 mg, 0.18 mmol) was dissolved in a solution of i-PrOH/H₂O (9/1, 1 mL) at 80° C. for 30 min. A suspended solution of 35 (40 mg, 0.19 mmol) and HClO₄ (70%, 20 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-03-52 (18 mg, 24%) as a dark blue solid.

Scheme 36 Synthesis of LGW-03-57.

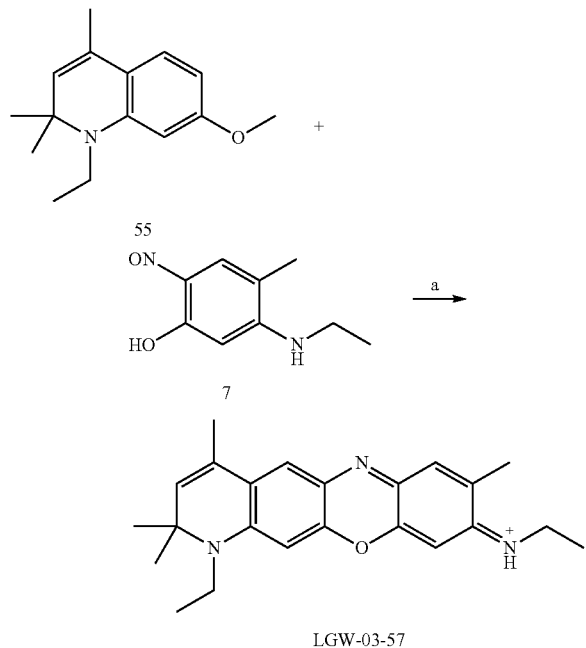

LGW-03-57

Reagents and conditions: a) HClO₄, 90% i-PrOH, 80° C.

(Z)—N-(1-ethyl-2,2,4,8-tetramethyl-1,2-dihydro-9H-pyrido[3,2-b]phenoxazin-9-ylidene)ethanaminium (LGW-03-57)

Compound 55 (50 mg, 0.22 mmol) was dissolved in a solution of i-PrOH/H₂O (9/1, 1 mL) at 80° C. for 30 min. A suspended solution of 7 (41 mg, 0.23 mmol) and HClO₄ (70%, 25 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-03-57 (67 mg, 76%) as a dark blue solid.

Scheme 37 Synthetic route to LGW-03-65.

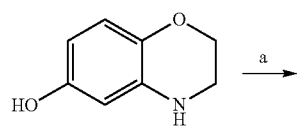

54

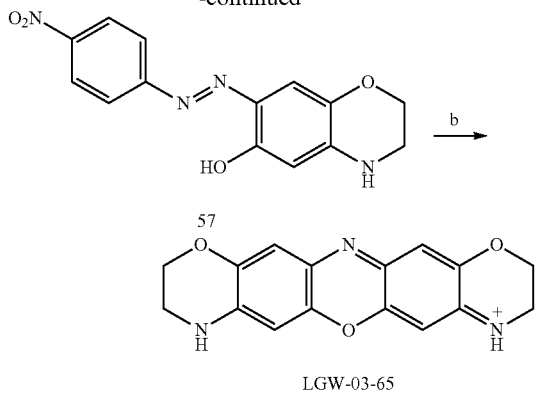

LGW-03-65

Reagents and conditions: a) i) 2M HCl, p-nitrobenzenediazonium tetrafluoroborate, 0° C.; ii) K₂CO₃, 0° C.; b) Compound 54, HClO₄, 90% i-PrOH, 80° C.

(E)-7-((4-nitrophenyl)diazenyl)-3,4-dihydro-2H-benzo[b][1,4]oxazin-6-ol (57)

Compound 54 (0.2 g, 1.32 mmol) was dissolved in 0.6 mL MeOH. The solution was chilled in an ice bath, then was treated with HCl (2 M, 6 mL). After 15 mins, p-nitrobenzenediazonium tetrafluoroborate (345 mg, 1.46 mmol) was added to the solution in 5 portions over 15 mins, then stirred at 0° C. for additional 1 h. During which time, the color of the reaction mixture changed from orange to dark red. After which, the solution was carefully basified with solid K₂CO₃ until pH value of the solution rose above 8. The deep red precipitate was collected via vacuum filtration and washed with small portions of DI water. The product was left in the funnel and air dried overnight to afford compound 57 (344 mg, 87%), which was used for the next step without further purification.

3,8,9,10-tetrahydro-2H-bis([1,4]oxazino)[2,3-b:3',2'-i]phenoxazin-4-ium (LGW-03-65)

Compound 54 (50 mg, 0.33 mmol) was dissolved in a solution of i-PrOH/H₂O (9/1, 3 mL) at 80° C. for 30 min. Compound 57 (99 mg, 0.33 mmol) was added to the solution above in 5 portions over 15 mins. Then the reaction mixture was treated with HClO₄ (70%, 30 µL). The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-03-65 (62 mg, 55%) as a dark blue solid.

Scheme 38 Synthesis of LGW-03-76.

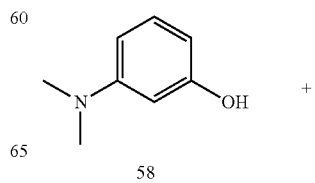

58

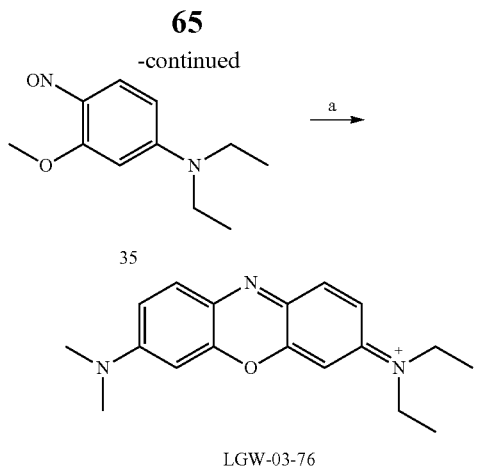

LGW-03-76

Reagents and conditions: a) HClO₄, 90% i-PrOH, 80° C.

N-(7-(dimethylamino)-3H-phenoxazin-3-ylidene)-N-ethylethanaminium (LGW-03-76)

Compound 58 (50 mg, 0.36 mmol) was dissolved in a solution of i-PrOH/H$_2$O (9/1, 1 mL) at 80° C. for 30 min. A suspended solution of 35 (80 mg, 0.38 mmol) and HClO$_4$ (70%, 35 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-03-52 (19 mg, 15%) as a dark blue solid.

Scheme 39 Synthetic route to LGW-03-88.

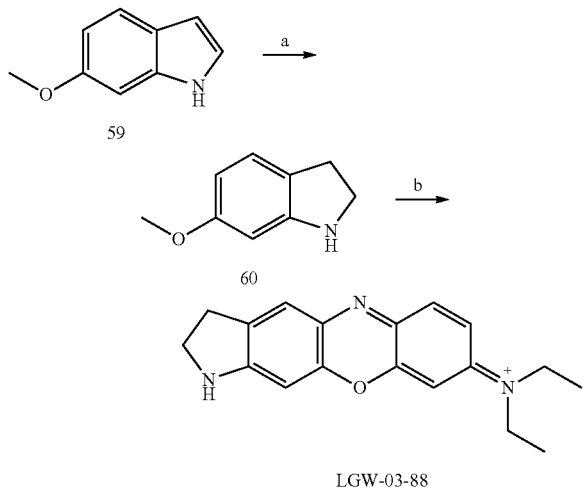

LGW-03-88

Reagents and conditions: a) NaBH₃CN, AcOH, 0° C.;
b) Compound 2, HClO₄, 90% i-PrOH, 80° C.

6-methoxyindoline (60)

Compound 39 (4 g, 27.18 mmol) was dissolved in acetic acid (10 mL). NaBH$_3$CN (6.83 g, 108.71 mmol) was added into the reaction flask portion-wise while maintaining the temperature below 10° C. The resulting solution was stirred for 1 h. After which, the solution was diluted with ice-cold water and basified with 2 M NaOH until the pH of the solution rose above 8. The reaction mixture was extracted with EtOAc (4×100 mL). The combined organic layers were rinsed with brine and dried over anhydrous Na$_2$SO$_4$. The solvent was removed using a rotary evaporator and the residue was purified by flash column chromatography with silica gel (100 g), using DCM/Hexane as eluent to give compound 60 (3.52 g, 87%) as light brown oil.

N-(2,3-dihydropyrrolo[3,2-b]phenoxazin-8(1H)-ylidene)-N-ethylethanaminium (LGW-03-88)

Compound 60 (50 mg, 0.34 mmol) was dissolved in a solution of i-PrOH/H$_2$O (9/1, 1 mL) at 80° C. for 30 min. A suspended solution of 2 (68 mg, 0.35 mmol) and HClO$_4$ (70%, 35 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-03-88 (59 mg, 52%) as a dark blue solid.

Scheme 40 Synthesis of LGW-04-31.

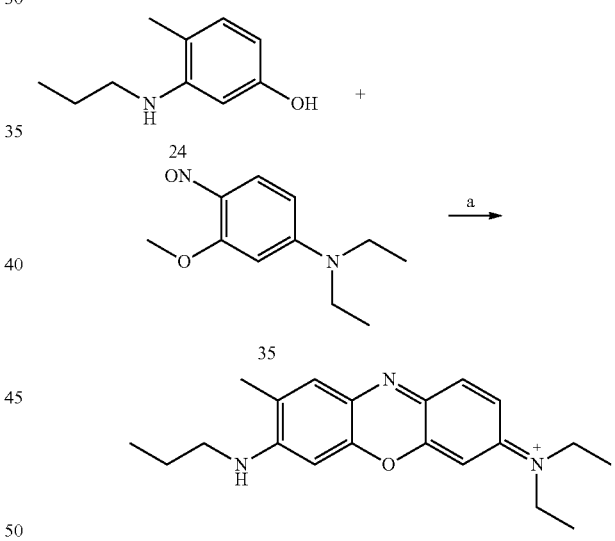

LGW-04-31

Reagents and conditions: a) HClO₄, 90% i-PrOH, 80° C.

N-ethyl-N-(8-methyl-7-(propylamino)-3H-phenoxazin-3-ylidene)ethanaminium (LGW-04-31)

Compound 24 (40 mg, 0.24 mmol) was dissolved in a solution of i-PrOH/H$_2$O (9/1, 1 mL) at 80° C. for 30 min. A suspended solution of 35 (53 mg, 0.25 mmol) and HClO$_4$ (70%, 25 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-04-31 (53 mg, 59%) as a dark blue solid.

Scheme 41 Synthesis of LGW-04-32.

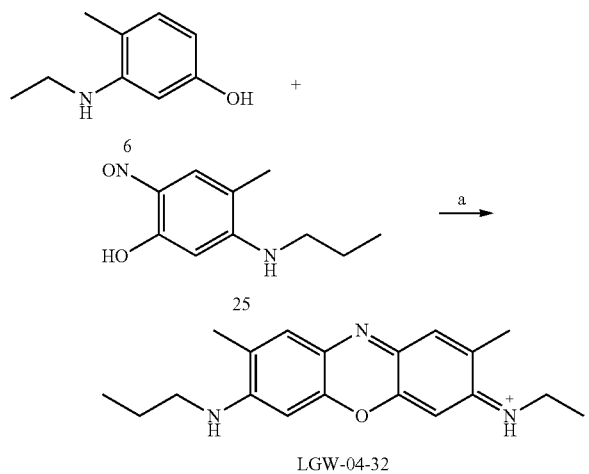

Reagents and conditions: a) HClO$_4$, 90% i-PrOH, 80° C.

(Z)—N-(2,8-dimethyl-7-(propylamino)-3H-phenoxazin-3-ylidene)ethanaminium (LGW-04-32)

Compound 6 (50 mg, 0.33 mmol) was dissolved in a solution of i-PrOH/H$_2$O (9/1, 1 mL) at 80° C. for 30 min. A suspended solution of 25 (67 mg, 0.35 mmol) and HClO$_4$ (70%, 35 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-04-32 (76 mg, 65%) as a dark blue solid.

Scheme 42 Synthesis of LGW-04-36.

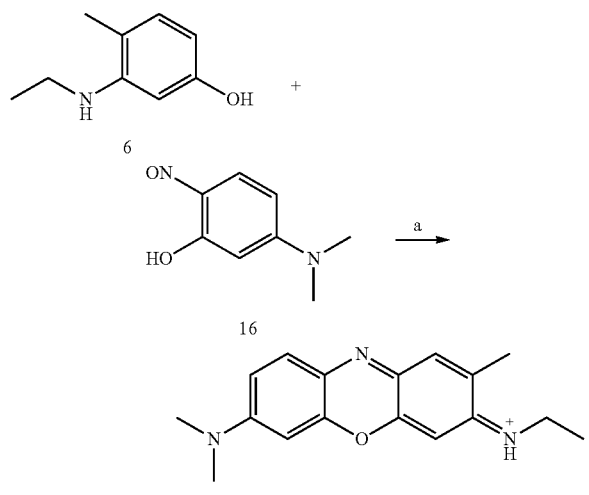

Reagents and conditions: a) HClO$_4$, 90% i-PrOH, 80° C.

(Z)—N-(7-(dimethylamino)-2-methyl-3H-phenoxazin-3-ylidene)ethanaminium (LGW-04-36)

Compound 6 (50 mg, 0.33 mmol) was dissolved in a solution of i-PrOH/H$_2$O (9/1, 1 mL) at 80° C. for 30 min. A suspended solution of 16 (58 mg, 0.35 mmol) and HClO$_4$ (70%, 35 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-04-36 (52 mg, 48%) as a dark blue solid.

Scheme 43 Synthetic route to LGW-04-81.

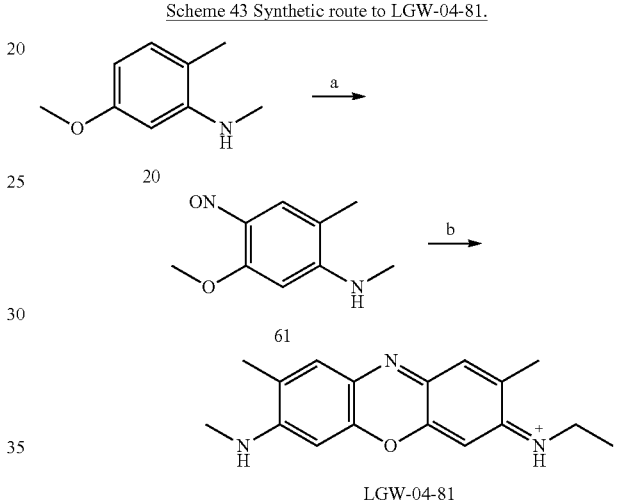

Reagents and conditions: a) i) 2M HCl, NaNO$_2$, 0° C.;
ii) K$_2$CO$_3$, 0° C.; b) Compound 6, HClO$_4$, 90% i-PrOH, 80° C.

5-methoxy-N,2-dimethyl-4-nitrosoaniline (61)

Compound 20 (0.4 g, 2.65 mmol) was dissolved in an ice-cold 2 M HCl solution (5 mL). To the solution above, NaNO$_2$ (0.2 g, 2.91 mmol) was added portion wise over 1 h while maintaining the temperature of the solution below 5° C., such that no brown NOx vapors were observed. The reaction mixture was stirred for additional 2 h. The solution was carefully basified with solid K$_2$CO$_3$ until the pH value of the solution rose above 8. After which, the precipitate was filtered through a Buchner funnel and washed with small portions of DI water. The product was left in the funnel and air dried overnight to afford compound 61 (407 mg, 85%) as a green solid, which was used for the next step without further purification.

(Z)—N-(2,8-dimethyl-7-(methylamino)-3H-phenoxazin-3-ylidene)ethanaminium (LGW-04-81)

Compound 6 (50 mg, 0.33 mmol) was dissolved in a solution of i-PrOH/H$_2$O (9/1, 1 mL) at 80° C. for 30 min. A suspended solution of 61 (63 mg, 0.35 mmol) and HClO$_4$ (70%, 35 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-04-81 (21 mg, 23%) as a dark blue solid.

Scheme 44 Syntthesis of LGW-04-84.

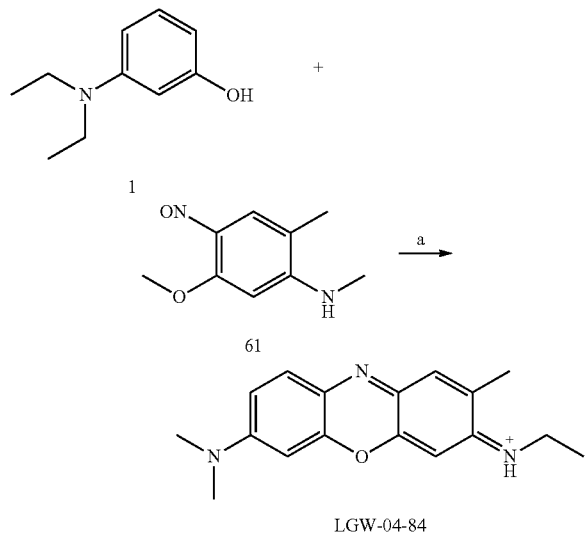

LGW-04-84

Reagents and conditions: a) HClO₄, 90% i-PrOH, 80° C.

(Z)—N-(7-(dimethylamino)-2-methyl-3H-phenoxazin-3-ylidene)ethanaminium (LGW-04-84)

Compound 1 (50 mg, 0.3 mmol) was dissolved in a solution of i-PrOH/H₂O (9/1, 1 mL) at 80° C. for 30 min. A suspended solution of 61 (57 mg, 0.32 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-04-84 (36 mg, 35%) as a dark blue solid.

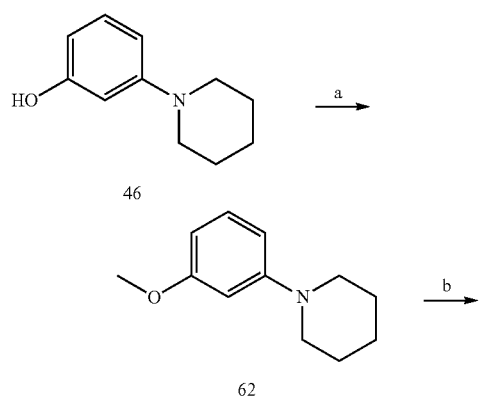

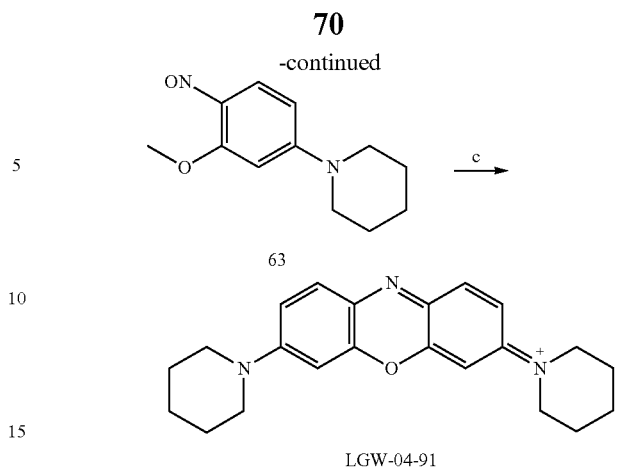

LGW-04-91

Reagents and conditions: a) MeI, NaH, THF, 0° C. to rt; b) 2M HCl, NaNO₂, 0° C.; ii) K₂CO₃, 0° C.; c) Compound 46, HClO₄, 90% iPrOH, 80° C.

1-(3-methoxyphenyl)piperidine (62)

Compound 46 (0.5 g, 2.82 mmol) was dissolved in anhydrous THF (5 mL) under N2, and chilled in an ice bath for 30 mins. NaH (60%, 0.136 g, 3.39 mmol) was added to the solution in 3 portions over 10 mins while the temperature maintained below 5° C. After 10 mins, MeI (0.211 mL, 3.39 mmol) was added into the reaction mixture. The resulting suspension was slowly warmed up to rt and stirred overnight. Upon completion of the reaction, ice-cold DI water was added to the reaction mixture to destroy excess NaH. Organic solvent was removed under reduced pressure, and the residue was extracted with DCM (3×25 mL). The combined organic layers were rinsed with brine and dried over anhydrous Na₂SO₄. The solvent was removed using a rotary evaporator and the residue was purified by flash column chromatography with silica gel (25 g), using DCM/Hexane as eluent to give compound 62 (0.447 g, 83%).

1-(3-methoxy-4-nitrosophenyl)piperidine (63)

Compound 62 (0.1 g, 0.52 mmol) was dissolved in an ice-cold 2 M HCl solution (2 mL). To the solution above, NaNO₂ (0.04 g, 0.58 mmol) was added portion wise over 1 h while maintaining the temperature of the solution below 5° C., such that no brown NOx vapors were observed. The reaction mixture was stirred for additional 2 h. The solution was carefully basified with solid K₂CO₃ until pH value of the solution rose above 8. After which, the aqueous solution was extracted with DCM (3×25 mL). The combined organic layers were rinsed with brine and dried over anhydrous Na₂SO₄. The solvent was removed using a rotary evaporator to give 63 (102 mg, 89%) as a light green oil, which was used for the next step without further purification.

1-(7-(piperidin-1-yl)-3H-phenoxazin-3-ylidene)piperidin-1-ium (LGW-04-91)

Compound 46 (50 mg, 0.28 mmol) was dissolved in a solution of i-PrOH/H₂O (9/1, 1 mL) at 80° C. for 30 min. A suspended solution of 63 (65 mg, 0.30 mmol) and HClO₄ (70%, 30 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-04-91 (28 mg, 26%) as a dark blue solid.

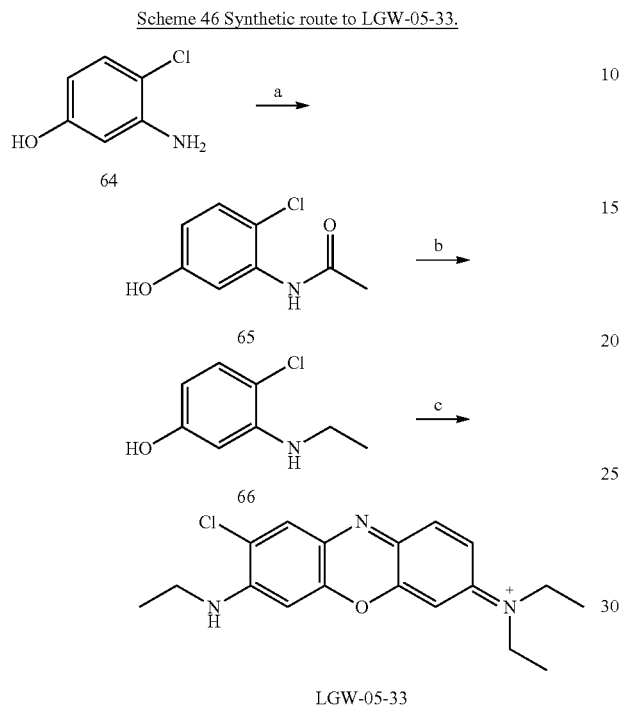

Scheme 46 Synthetic route to LGW-05-33.

LGW-05-33

Reagents and conditions: a) Ac₂O, H₂O, 50° C. to rt;
b) BH₃—THF, THF, 0° C. to rt; c) Compound 35, HClO₄, 90% i-PrOH, 80° C.

N-(2-chloro-5-hydroxyphenyl)acetamide (65)

Compound 64 (1 g, 6.97 mmol) was suspended in 10 mL DI water, to which Acetic anhydride (2.6 mL, 27.86 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 65 (1.03 g, 80%) as a white solid, which was used for the next step without further purification.

4-chloro-3-(ethylamino)phenol (66)

A solution of 65 (1 g, 5.39 mmol) in anhydrous THF (16 mL) was stirred in an ice bath under N2 for 30 mins. Borane tetrahydrofuran complex solution (1 M, 16 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, and the residue was purified by flash column chromatography with silica gel (25 g), using DCM/Hexane as eluent to obtain 66 (0.82 g, 89%) as a white solid.

N-(8-chloro-7-(ethylamino)-3H-phenoxazin-3-ylidene)-N-ethylethanaminium (LGW-05-33)

Compound 66 (40 mg, 0.23 mmol) was dissolved in a solution of i-PrOH/H₂O (9/1, 1 mL) at 80° C. for 30 min. A suspended solution of 35 (51 mg, 0.24 mmol) and HClO₄ (70%, 25 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-05-33 (13 mg, 15%) as a dark blue solid.

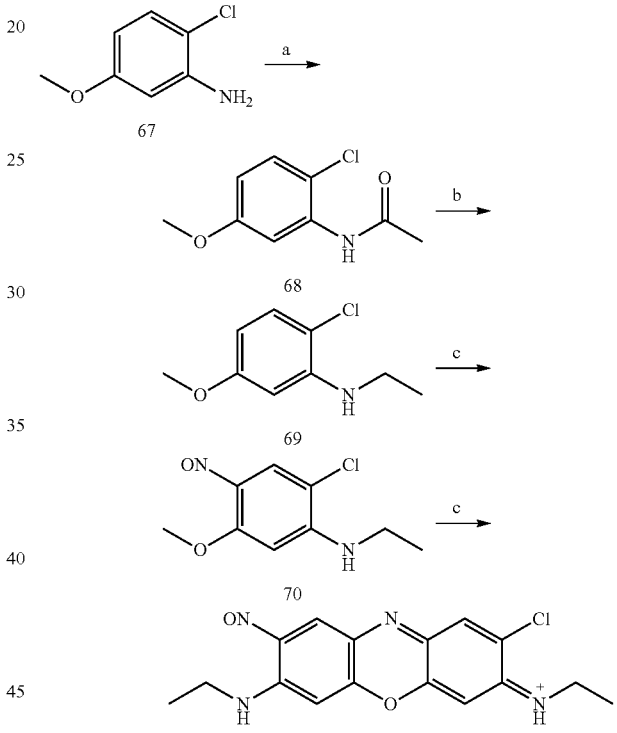

Scheme 47 Synthetic route to LGW-05-39.

LGW-05-39

Reagents and conditions:
a) Ac₂O, H₂O, 50° C. to rt;
b) BH₃-THF, THF, 0° C. to rt;
c) i) 2M HCl, NaNO₂, 0° C.; ii) K₂CO₃, 0° C.;
d) Compound 66, HClO₄, 90% i-PrOH, 80° C.

N-(2-chloro-5-methoxyphenyl)acetamide (68)

Compound 67 (4 g, 25.38 mmol) was suspended in 40 mL DI water, to which Acetic anhydride (9.6 mL, 102 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 68 (4.91 g, 97%) as a white solid, which was used for the next step without further purification.

2-chloro-N-ethyl-5-methoxyaniline (69)

A solution of 68 (2 g, 10 mmol) in anhydrous THF (30 mL) was stirred in an ice bath under N2 for 30 mins. Borane tetrahydrofuran complex solution (1 M, 30 mL) was added to the solution using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel (25 g), using DCM/Hexane as eluent to obtain 69 (1.43 g, 77%) as a white solid.

2-chloro-N-ethyl-5-methoxy-4-nitrosoaniline (70)

Compound 69 (0.5 g, 2.69 mmol) was dissolved in an ice-cold 2 M HCl solution (10 mL). NaNO$_2$ (0.2 g, 2.96 mmol) was added portion wise over 1 h while maintaining the temperature of the solution below 5° C., such that no brown NOx vapors were observed. The reaction mixture was stirred for additional 2 h. The solution was carefully basified with solid K$_2$CO$_3$ until pH value of the solution rose above 8. After which, the aqueous solution was extracted with DCM (3×25 mL). The combined organic layers were rinsed with brine and dried over anhydrous Na$_2$SO$_4$. The solvent was removed using a rotary evaporator to give 63 (469 mg, 81%) as dark green oil, which was used for the next step without further purification.

(Z)—N-(2,8-dichloro-7-(ethylamino)-3H-phenoxazin-3-ylidene)ethanaminium (LGW-05-39)

Compound 66 (60 mg, 0.35 mmol) was dissolved in a solution of i-PrOH/H$_2$O (9/1, 1 mL) at 80° C. for 30 min. A suspended solution of 70 (79 mg, 0.37 mmol) and HClO$_4$ (70%, 35 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-05-39 (99 mg, 74%) as a dark blue solid.

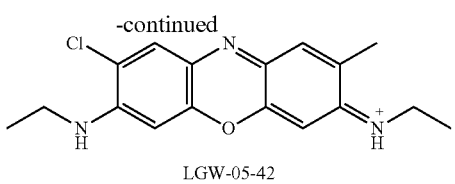

LGW-05-42

Reagents and conditions:
a) i) 2M HCl, p-nitrobenzenediazonium tetrafluoroborate, 0° C.; ii) K$_2$CO$_3$, 0° C.;
b) Compound 6, HClO$_4$, 90% i-PrOH, 80° C.

(E)-2-chloro-N-ethyl-5-methoxy-4-((4-nitrophenyl)diazenyl)aniline (71)

Compound 69 (0.5 g, 2.69 mmol) was dissolved in 1.5 mL MeOH. The solution was chilled in an ice bath, then was treated with HCl (2 M, 13 mL). After 15 mins, p-nitrobenzenediazonium tetrafluoroborate (702 mg, 2.96 mmol) was added in 5 portions over 15 mins, then stirred at 0° C. for additional 1 h. During which time, the color of the reaction mixture changed from orange to dark red. After which, the solution was carefully basified with solid K$_2$CO$_3$ until pH value of the solution rose above 8. The deep red precipitate was collected via vacuum filtration and washed with small portions of DI water. The product was left in the funnel and air dried overnight to afford compound 71 (812 mg, 90%) as a red solid, which was used for the next step without further purification.

(Z)—N-(8-chloro-7-(ethylamino)-2-methyl-3H-phenoxazin-3-ylidene)ethanaminium (LGW-05-42)

Compound 6 (45 mg, 0.3 mmol) was dissolved in a solution of i-PrOH/H$_2$O (9/1, 3 mL) at 80° C. for 30 min. Compound 71 (100 mg, 0.3 mmol) was added to the solution in 5 portions over 15 mins. Then the reaction mixture was treated with HClO$_4$ (70%, 30 µL). The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-05-42 (22 mg, 21%) as a dark blue solid.

Scheme 48

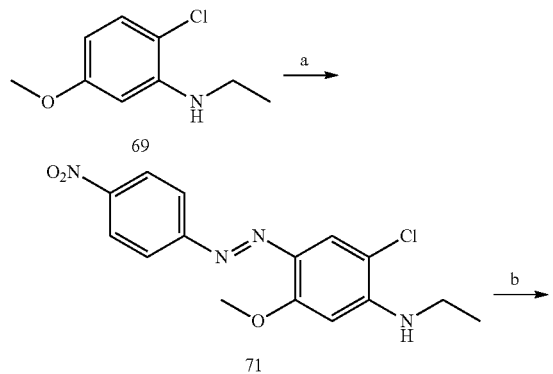

Scheme 49 Synthetic route to LGW-05-65.

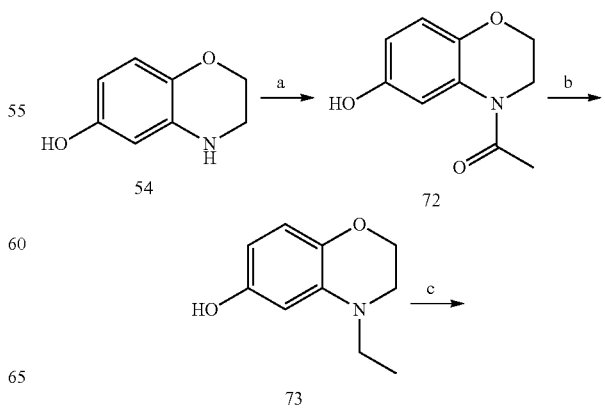

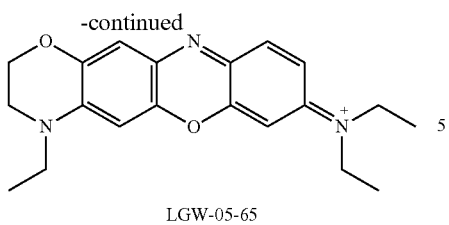

LGW-05-65

Reagents and conditions:
a) Ac₂O, H₂O, 50° C. to rt;
b) BH₃-THF, THF, 0° C. to rt;
c) Compound 35, HClO₄, 90% i-PrOH, 80° C.

1-(6-hydroxy-2,3-dihydro-4H-benzo[b][1,4]oxazin-4-yl)ethan-1-one (72)

Compound 54 (1 g, 6.62 mmol) was suspended in 10 mL DI water, to which Acetic anhydride (2.5 mL, 26.46 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 72 (1.21 g, 95%) as a white solid, which was used for the next step without further purification.

4-ethyl-3,4-dihydro-2H-benzo[b][1,4]oxazin-6-ol (73)

A solution of 72 (0.9 g, 10 mmol) in anhydrous THE (14 mL) was stirred in an ice bath under N2 for 30 mins. Borane tetrahydrofuran complex solution (1 M, 14 mL) was added to the solution using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel (25 g), using DCM/Hexane as eluent to give 73 (756 mg, 91%) as brown oil.

N-ethyl-N-(4-ethyl-3,4-dihydro-[1,4]oxazino[2,3-b]phenoxazin-8(2H)-ylidene)ethanaminium (LGW-05-65)

Compound 73 (50 mg, 0.28 mmol) was dissolved in a solution of i-PrOH/H₂O (9/1, 1 mL) at 80° C. for 30 min. A suspended solution of 35 (61 mg, 0.29 mmol) and HClO₄ (70%, 30 µL) in 90% i-PrOH (2 mL) was in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-05-65 (81 mg, 76%) as a dark blue solid.

Scheme 50

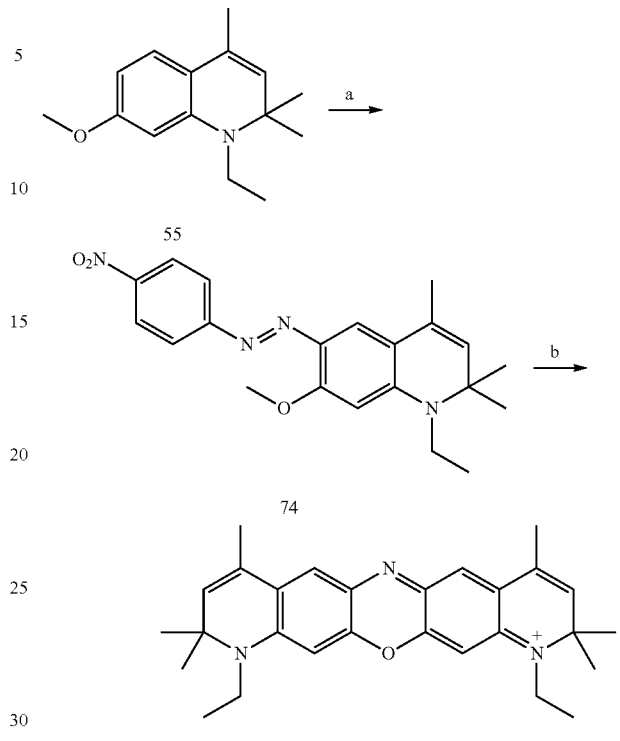

LGW-05-66

Reagents and conditions: a) i) 2M HCl, p-nitrobenzenediazonium tetrafluoroborate, 0° C.; ii) K₂CO₃, 0° C.; b) Compound 56, HClO₄, 90% i-PrOH, 80° C.

(E)-1-ethyl-7-methoxy-2,2,4-trimethyl-6-((4-nitrophenyl)diazenyl)-1,2-dihydroquinoline (74)

Compound 55 (0.2 g, 0.86 mmol) was dissolved in 1 mL MeOH. The solution was chilled in an ice bath, then treated with HCl (2 M, 5 mL). After 15 mins, p-nitrobenzenediazonium tetrafluoroborate (215 mg, 0.91 mmol) was added to the solution in 5 portions over 15 mins, then stirred at 0° C. for additional 1 h. During which time, the color of the reaction mixture changed from orange to dark red. After which, the solution was carefully basified with solid K₂CO₃ until the pH value of the solution rose above 8. The deep red precipitate was collected via vacuum filtration and washed with small portions of DI water. The product was left in the funnel and air dried overnight to afford compound 74 (305 mg, 93%) as a deep red solid, which was used for the next step without further purification.

1,11-diethyl-2,2,4,8,10,10-hexamethyl-10,11-dihydro-2H-dipyrido[3,2-b:2',3'-i]phenoxazin-1-ium (LGW-05-66)

Compound 56 (40 mg, 0.18 mmol) was dissolved in a solution of i-PrOH/H₂O (9/1, 3 mL) at 80° C. for 30 min. Compound 74 (70 mg, 0.18 mmol) was added to the solution in 5 portions over 15 mins. Then the reaction mixture was treated with HClO₄ (70%, 20 µL). The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl$_3$). The fractions containing product were pooled and evaporated, affording LGW-05-66 (11 mg, 13%) as a dark blue solid.

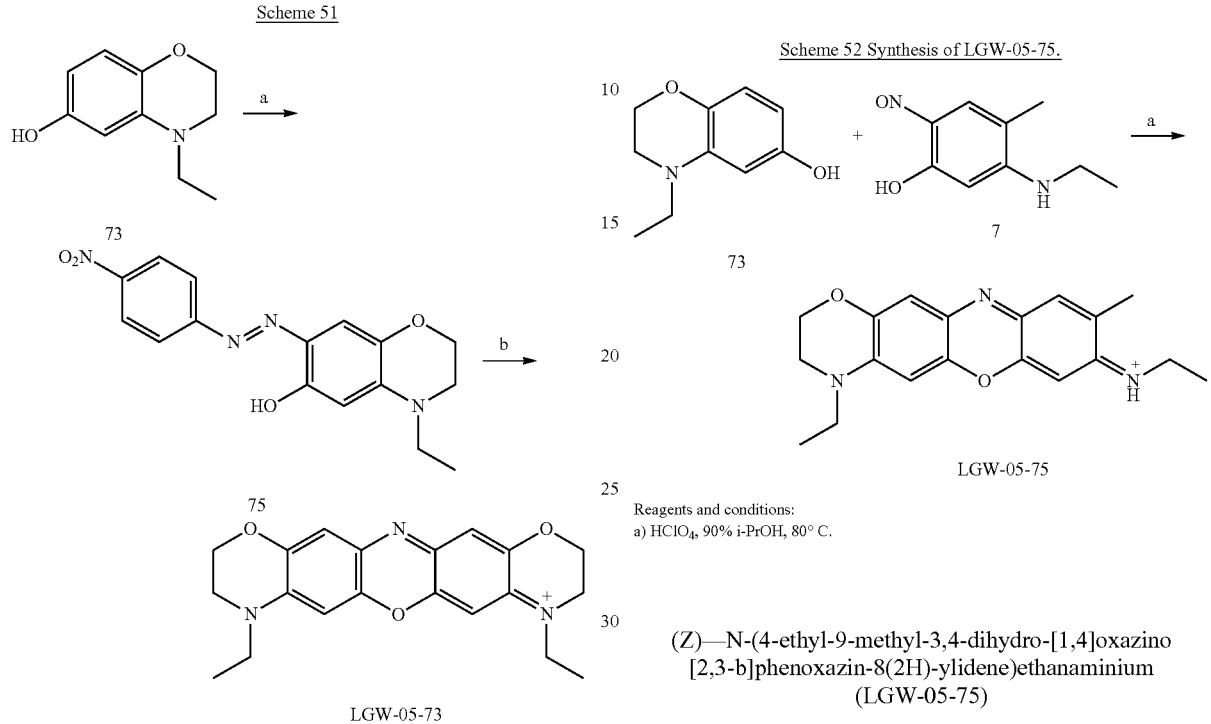

Scheme 51

Reagents and conditions: a) i) 2M HCl, p-nitrobenzenediazonium tetrafluoroborate, 0° C.; ii) K$_2$CO$_3$, 0° C.; b) Compound 73, HClO$_4$, 90% i-PrOH, 80° C.

(E)-4-ethyl-7-((4-nitrophenyl)diazenyl)-3,4-dihydro-2H-benzo[b][1,4]oxazin-6-ol (75)

Compound 73 (0.2 g, 1.12 mmol) was dissolved in 1 mL MeOH. The solution was chilled in an ice bath, then was treated with HCl (2 M, 5 mL). After 15 mins, p-nitrobenzenediazonium tetrafluoroborate (290 mg, 1.23 mmol) was added to the solution in 5 portions over 15 mins, then stirred at 0° C. for an additional 1 h. During which time, the color of the reaction mixture changed from orange to dark red. After which, the solution was carefully basified with solid K$_2$CO$_3$ until pH value of the solution rose above 8. The deep red precipitate was collected via vacuum filtration and washed with small portions of DI water. The product was left in the funnel and air dried overnight to afford compound 75 (319 mg, 87%), which was used for the next step without further purification.

4,8-diethyl-3,8,9,10-tetrahydro-2H-bis([1,4]oxazino)[2,3-b:3',2'-i]phenoxazin-4-ium (LGW-05-73)

Compound 73 (40 mg, 0.22 mmol) was dissolved in a solution of i-PrOH/H$_2$O (9/1, 3 mL) at 80° C. for 30 min. Compound 75 (73 mg, 0.22 mmol) was added to the solution in 5 portions over 15 mins. Then the reaction mixture was treated with HClO$_4$ (70%, 20 µL). The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-05-72 (12 mg, 14%) as a dark blue solid.

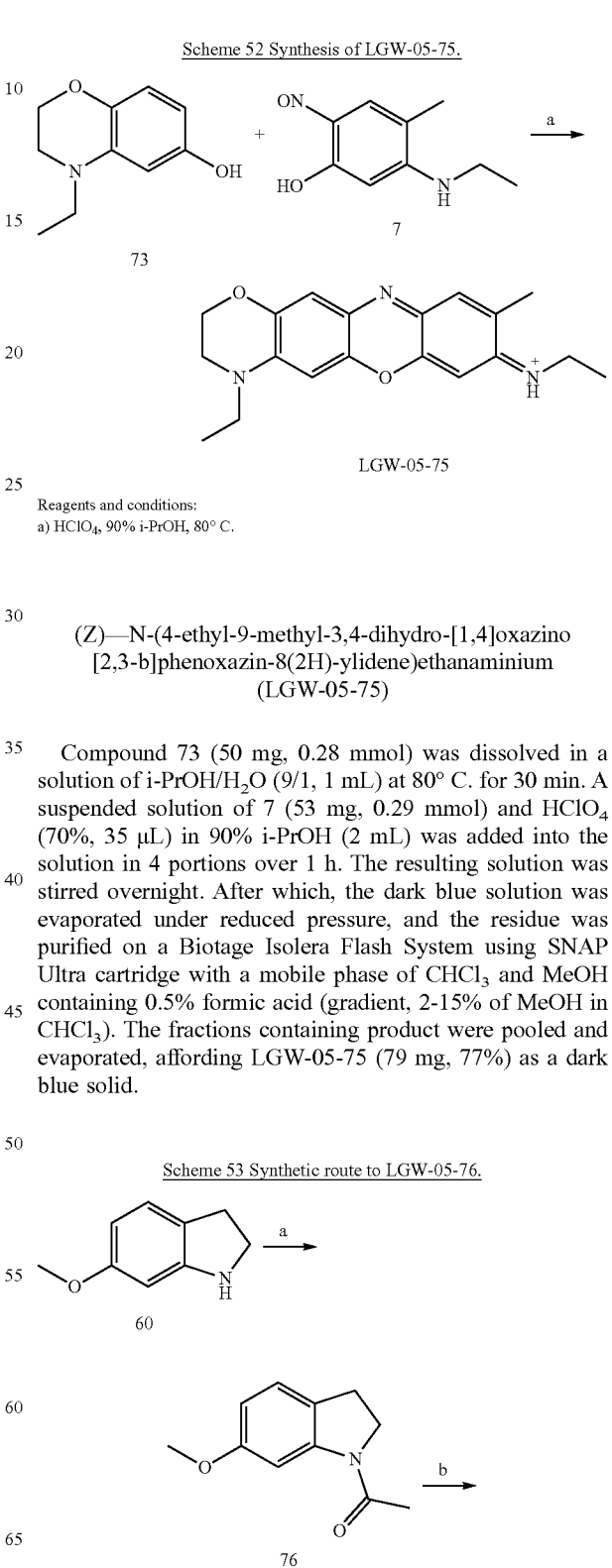

Scheme 52 Synthesis of LGW-05-75.

Reagents and conditions:
a) HClO$_4$, 90% i-PrOH, 80° C.

(Z)—N-(4-ethyl-9-methyl-3,4-dihydro-[1,4]oxazino[2,3-b]phenoxazin-8(2H)-ylidene)ethanaminium (LGW-05-75)

Compound 73 (50 mg, 0.28 mmol) was dissolved in a solution of i-PrOH/H$_2$O (9/1, 1 mL) at 80° C. for 30 min. A suspended solution of 7 (53 mg, 0.29 mmol) and HClO$_4$ (70%, 35 µL) in 90% i-PrOH (2 mL) was added into the solution in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-05-75 (79 mg, 77%) as a dark blue solid.

Scheme 53 Synthetic route to LGW-05-76.

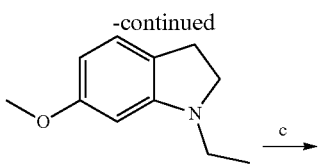

Reagents and conditions:
a) Ac₂O, H₂O, 50° C. to rt;
b) BH₃-THF, THF, 0° C. to rt;
c) Compound 7, HClO₄, 90% i-PrOH, 80° C.

1-(6-methoxyindolin-1-yl)ethan-1-one (76)

Compound 60 (1 g, 6.7 mmol) was suspended in 10 mL DI water, to which Acetic anhydride (2.53 mL, 26.81 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 76 (1.12 g, 87%) as a white solid, which was used for the next step without further purification.

1-ethyl-6-methoxyindoline (77)

A solution of 76 (1 g, 5.23 mmol) in anhydrous THF (16 mL) was stirred in an ice bath under N2 for 30 mins. Borane tetrahydrofuran complex solution (1 M, 16 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel (25 g), using DCM/Hexane as eluent to give 77 (861 mg, 93%).

(Z)—N-(1-ethyl-7-methyl-2,3-dihydropyrrolo[3,2-b]phenoxazin-8(1H)-ylidene)ethanaminium (LGW-05-76)

Compound 77 (40 mg, 0.23 mmol) was dissolved in a solution of i-PrOH/H₂O (9/1, 1 mL) at 80° C. for 30 min. A suspended solution of 7 (43 mg, 0.24 mmol) and HClO₄ (70%, 25 µL) in 90% i-PrOH (2 mL) was added into the solution in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl₃ and MeOH containing 0.5% formic acid (gradient, 2-15% of MeOH in CHCl₃). The fractions containing product were pooled and evaporated, affording LGW-05-76 (20 mg, 25%) as a dark blue solid.

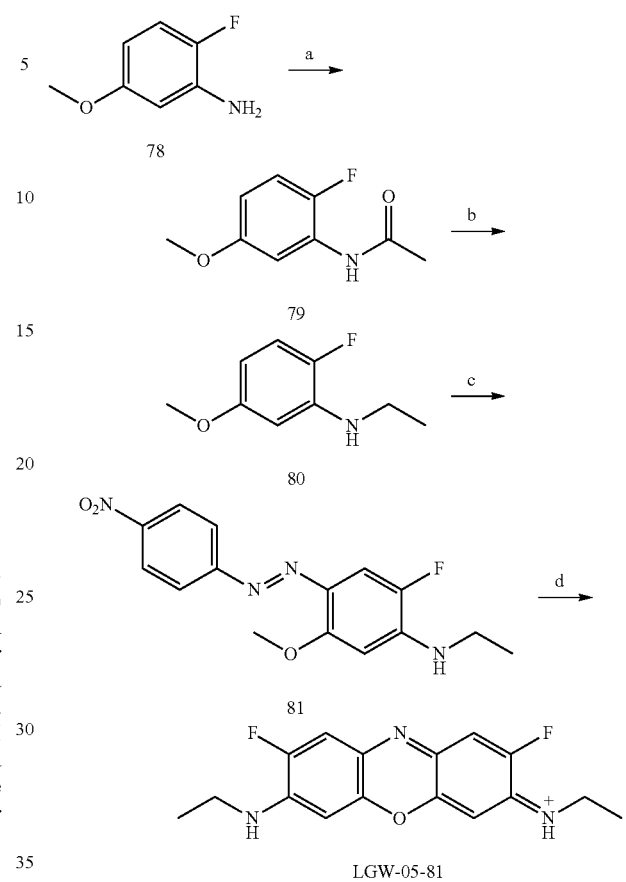

Scheme 54 Synthetic route to LGW-05-81.

Reagents and conditions: a) Ac₂O, H₂O, 50° C. to rt; b) BH₃—THF, THF, 0° C. to rt; c) i) 2M HCl, p-nitrobenzenediazonium tetrafluoroborate, 0° C.; ii) K₂CO₃, 0° C.; d) Compound 6, HClO₄, 90% i-PrOH, 80° C.

N-(2-fluoro-5-methoxyphenyl)acetamide (79)

Compound 78 (4 g, 28.34 mmol) was suspended in 40 mL DI water, to which Acetic anhydride (10.72 mL, 113.4 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 79 (4.71 g, 91%) as a brown solid, which was used for the next step without further purification.

N-ethyl-2-fluoro-5-methoxyaniline (80)

A solution of 79 (2 g, 10.92 mmol) in anhydrous THF (33 mL) was stirred in an ice bath under N2 for 30 mins. Borane tetrahydrofuran complex solution (1 M, 33 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel (25 g), using DCM/Hexane as eluent to give 80 (1.69 g, 92%) as brown oil.

(E)-N-ethyl-2-fluoro-5-methoxy-4-((4-nitrophenyl)diazenyl)aniline (81)

Compound 80 (0.2 g, 1.18 mmol) was dissolved in 1 mL MeOH. The solution was chilled in an ice bath, then was treated with HCl (2 M, 6 mL). After 15 mins, p-nitrobenzenediazonium tetrafluoroborate (308 mg, 1.3 mmol) was added to the solution in 5 portions over 15 mins, then stirred at 0° C. for additional 1 h. During which time, the color of the reaction mixture changed from orange to dark red. After which, the solution was carefully basified with solid $K_2CO_3$ until the pH value of the solution rose above 8. The deep red precipitate was collected via vacuum filtration and washed with small portions of DI water. The product was left in the funnel and air dried overnight to afford compound 81 (325 mg, 86%) as a dark red solid, which was used for the next step without further purification.

(Z)—N-(7-(ethylamino)-8-fluoro-2-methyl-3H-phenoxazin-3-ylidene)ethanaminium (LGW-05-81)

Compound 6 (40 mg, 0.26 mmol) was dissolved in a solution of i-PrOH/$H_2O$ (9/1, 3 mL) at 80° C. for 30 min. Compound 81 (84 mg, 0.26 mmol) was added to the solution in 5 portions over 15 mins. Then the reaction mixture was treated with $HClO_4$ (70%, 25 μL). The resulting solution was stirred overnight. After which, the dark blue solution was evaporated under reduced pressure, and the residue was purified on a Biotage Isolera Flash System using SNAP Ultra cartridge with a mobile phase of $CHCl_3$ and MeOH containing 0.5% formic acid (gradient, 2-15% of MeOH in $CHCl_3$). The fractions containing product were pooled and evaporated, affording LGW-05-81 (60 mg, 66%) as a dark blue solid.

Scheme 55 Synthesis of LGW-05-82.

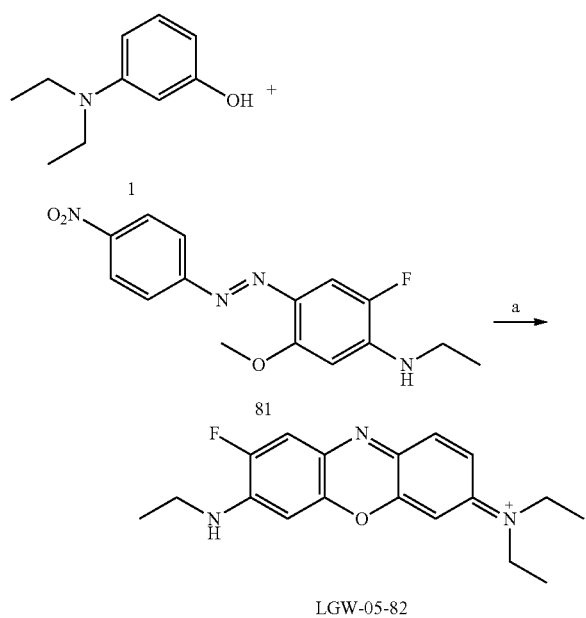

Reagents and conditions:
a) $HClO_4$, 90% i-ProH, 80° C.

N-ethyl-N-(7-(ethylamino)-8-fluoro-3H-phenoxazin-3-ylidene)ethanaminium (LGW-05-82)

Compound 1 (40 mg, 0.24 mmol) was dissolved in a solution of i-PrOH/$H_2O$ (9/1, 3 mL) at 80° C. for 30 min. Compound 81 (77 mg, 0.24 mmol) was added to the solution in 5 portions over 15 mins. Then the reaction mixture was treated with $HClO_4$ (70%, 25 μL). The resulting solution was stirred overnight. After which, the dark blue solution was evaporated under reduced pressure, and the residue was purified on a Biotage Isolera Flash System using SNAP Ultra cartridge with a mobile phase of $CHCl_3$ and MeOH containing 0.5% formic acid (gradient, 2-15% of MeOH in $CHCl_3$). The fractions containing product were pooled and evaporated, affording LGW-05-82 (17 mg, 20%) as a dark blue solid.

Scheme 56 Synthesis of LGW-05-84.

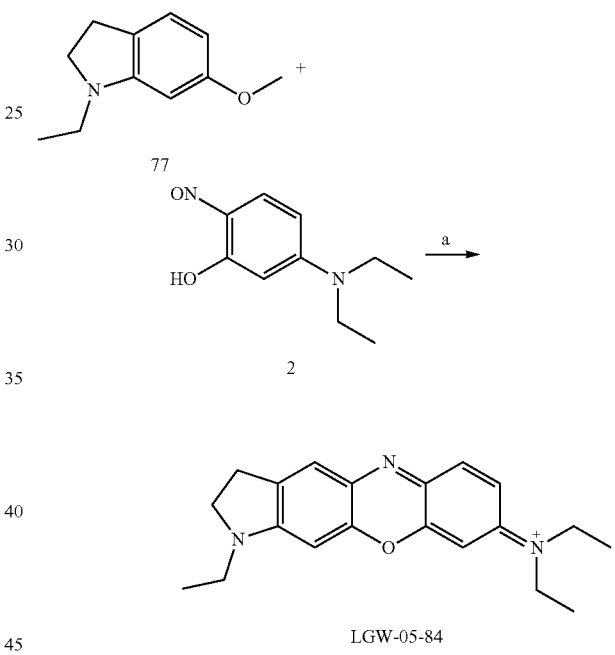

Reagents and conditions:
a) $HClO_4$, 90% i-ProH, 80° C.

N-ethyl-N-(1-ethyl-2,3-dihydropyrrolo[3,2-b]phenoxazin-8(1H)-ylidene)ethanaminium (LGW05-84)

Compound 77 (100 mg, 0.56 mmol) was dissolved in a solution of i-PrOH/$H_2O$ (9/1, 2 mL) at 80° C. for 30 min. A suspended solution of 2 (115 mg, 0.24 mmol) and $HClO_4$ (70%, 55 μL) in 90% i-PrOH (2 mL) was added into the solution above in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of $CHCl_3$ and MeOH containing 0.5% formic acid (gradient, 2-15% of MeOH in $CHCl_3$). The fractions containing product were pooled and evaporated, affording LGW-05-84 (103 mg, 50%) as a dark blue solid.

Scheme 57 Synthesis of LGW-05-85.

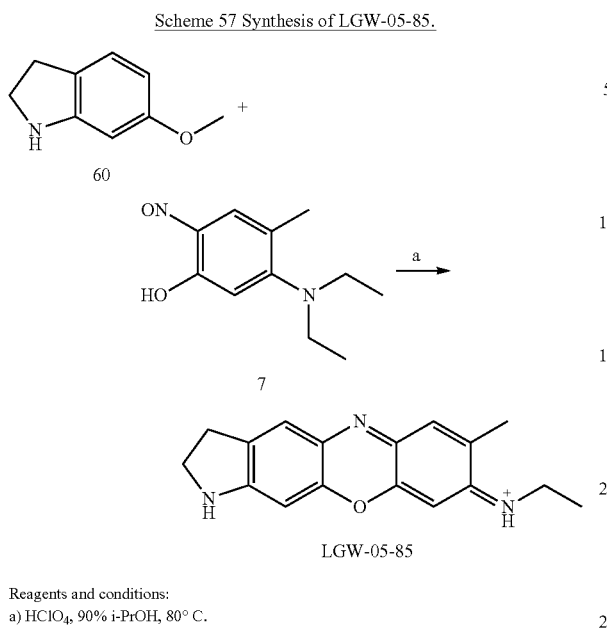

LGW-05-85

Reagents and conditions:
a) HClO₄, 90% i-PrOH, 80° C.

(Z)—N-(7-methyl-2,3-dihydropyrrolo[3,2-b]phenoxazin-8(1H)-ylidene)ethanaminium (LGW-05-85)

Compound 60 (40 mg, 0.27 mmol) was dissolved in a solution of i-PrOH/H$_2$O (9/1, 1 mL) at 80° C. for 30 min. A suspended solution of 7 (51 mg, 0.28 mmol) and HClO$_4$ (70%, 55 μL) in 90% i-PrOH (2 mL) was added into the solution in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-05-85 (12 mg, 13%) as a dark blue solid.

Scheme 58 Synthesis of LGW-05-91.

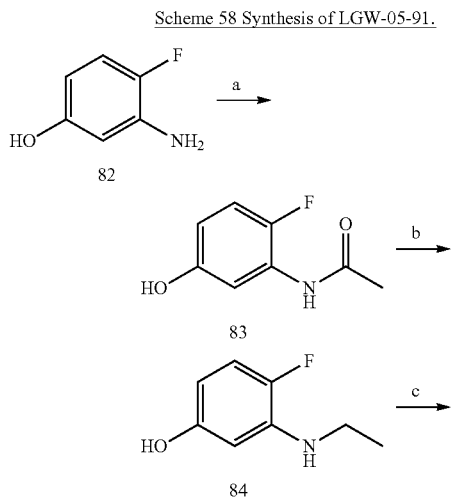

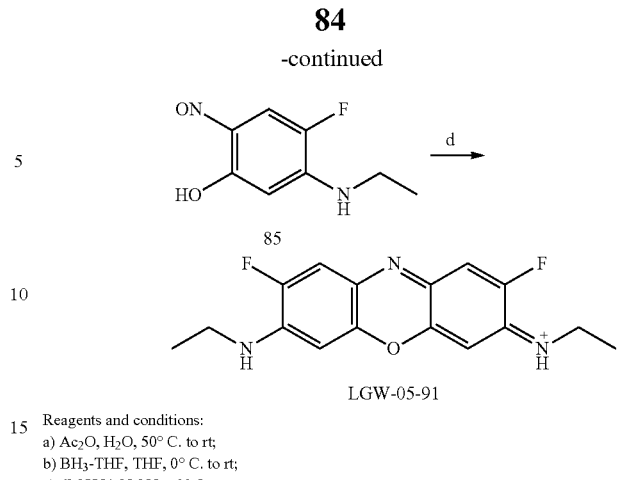

LGW-05-91

Reagents and conditions:
a) Ac$_2$O, H$_2$O, 50° C. to rt;
b) BH$_3$-THF, THF, 0° C. to rt;
c) 6M HCl, NaNO$_2$, 0° C.;
d) Compound 80, HClO$_4$, 90% i-PrOH, 80° C.

N-(2-fluoro-5-hydroxyphenyl)acetamide (83)

Compound 82 (4 g, 31.47 mmol) was suspended in 40 mL DI water, to which Acetic anhydride (11.9 mL, 125.87 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 83 (4.89 g, 92%) as a light gray solid, which was used for the next step without further purification.

3-(ethylamino)-4-fluorophenol (84)

A solution of 83 (2 g, 11.82 mmol) in anhydrous THF (36 mL) was stirred in an ice bath under N2 for 30 mins. Borane tetrahydrofuran complex solution (1 M, 36 mL) was added to the solution using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel (25 g), using DCM/Hexane as eluent to obtain 84 (1.61 g, 88%) as a brown solid.

5-(ethylamino)-4-fluoro-2-nitrosophenol (85)

Compound 84 (0.5 g, 3.22 mmol) was dissolved in an ice-cold 6 M HCl solution (5 mL). NaNO$_2$ (233 mg, 3.38 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 85 (419 mg, 71%) as a brown solid, which was used for the next step without further purification.

(Z)—N-(7-(ethylamino)-2,8-difluoro-3H-phenoxazin-3-ylidene)ethanaminium (LGW-05-91)

Compound 80 (30 mg, 0.18 mmol) was dissolved in a solution of i-PrOH/H$_2$O (9/1, 1 mL) at 80° C. for 30 min. A suspended solution of 85 (34 mg, 0.19 mmol) and HClO$_4$ (70%, 55 μL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-05-91 (3.5 mg, 6%) as a dark blue solid.

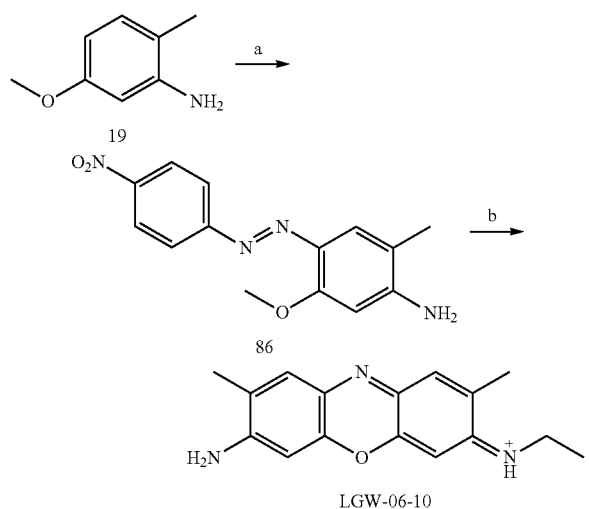

Scheme 59 LGW-06-10.

LGW-06-10

Reagents and conditions:
a) i) 2M HCl, p-nitrobenzenediazonium tetrafluoroborate, 0° C.; ii) K$_2$CO$_3$, 0° C.;
b) Compound 6, HClO$_4$, 90% i-PrOH, 80° C.

(E)-5-methoxy-2-methyl-4-((4-nitrophenyl)diazenyl)aniline (86)

Compound 19 (0.2 g, 1.46 mmol) was dissolved in 1 mL MeOH. The solution was chilled in an ice bath, then was treated with HCl (2 M, 7 mL). After 15 mins, p-nitrobenzenediazonium tetrafluoroborate (380 mg, 1.6 mmol) was added to the solution in 5 portions over 15 mins, then stirred at 0° C. for an additional 1 h. During which time, the color of the reaction mixture changed from orange to dark red. After which, the solution was carefully basified with solid K$_2$CO$_3$ until pH value of the solution rose above 8. The deep red precipitate was collected via vacuum filtration and washed with small portions of DI water. The product was left in the funnel and air dried overnight to afford compound 86 (316 mg, 76%) as a dark red solid, which was used for the next step without further purification.

(Z)—N-(7-amino-2,8-dimethyl-3H-phenoxazin-3-ylidene)ethanaminium (LGW-06-10)

Compound 6 (50 mg, 0.33 mmol) was dissolved in a solution of i-PrOH/H$_2$O (9/1, 2 mL) at 80° C. for 30 min. Compound 86 (95 mg, 0.33 mmol) was added to the solution in 5 portions over 15 mins. Then the reaction mixture was treated with HClO$_4$ (70%, 30 μL). The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-06-10 (50 mg, 49%) as a dark blue solid.

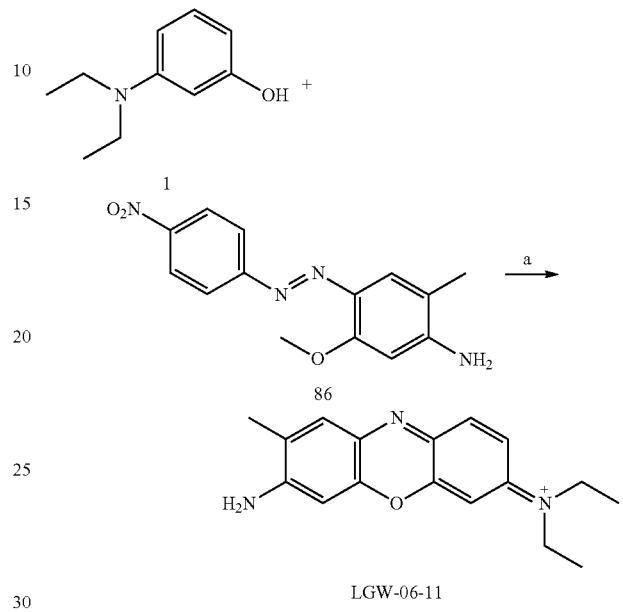

Scheme 60 Synthesis of LGW-06-11.

LGW-06-11

Reagents and conditions:
a) HClO$_4$, 90% i-PrOH, 80° C.

N-(7-amino-8-methyl-3H-phenoxazin-3-ylidene)-N-ethylethanaminium (LGW-06-11)

Compound 1 (40 mg, 0.24 mmol) was dissolved in a solution of i-PrOH/H$_2$O (9/1, 2 mL) at 80° C. for 30 min. Compound 86 (69 mg, 0.24 mmol) was added to the solution in 5 portions over 15 mins. Then the reaction mixture was treated with HClO$_4$ (70%, 25 μL). The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-06-11 (12 mg, 15%) as a dark blue solid.

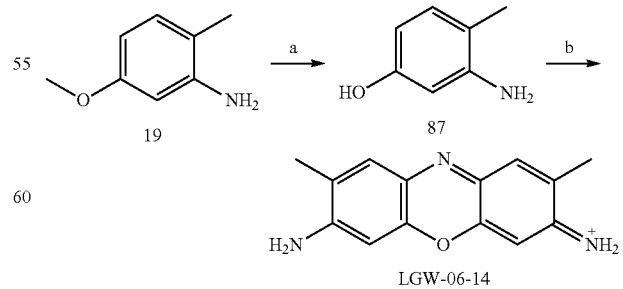

Scheme 61 Synthetic route to LGW-06-14.

LGW-06-14

Reagents and conditions:
a) 48% HBr, AcOH, reflux;
b) Compound 86, HClO$_4$, 90% i-PrOH, 80° C.

3-amino-4-methylphenol (87)

Compound 61 (0.5 g, 3.64 mmol) was dissolved in glacial AcOH (3 mL) at rt and aqueous HBr (48%, 3 mL) was added to the solution. The resulting solution was heated at 110° C. for 5 h before cooling. After which, the reaction mixture was diluted with 20 mL DI water, and the pH of the solution was adjusted to 5-6 with 2 M NaOH solution. The aqueous solution was extracted with DCM (3×25 mL). The combined organic layers were rinsed with brine and dried over anhydrous $Na_2SO_4$. The solvent was removed using a rotary evaporator and the residue was purified by flash column chromatography with silica gel (25 g), using EtOAc/Hexane as eluent to give compound 87 (288 mg, 64%) as a dark red solid.

7-amino-2,8-dimethyl-3H-phenoxazin-3-iminium (LGW-06-14)

Compound 87 (40 mg, 0.32 mmol) was dissolved in a solution of i-PrOH/$H_2O$ (9/1, 2 mL) at 80° C. for 30 min. Compound 86 (93 mg, 0.32 mmol) was added to the solution in 5 portions over 15 mins. Then the reaction mixture was treated with $HClO_4$ (70%, 30 µL). The resulting solution was stirred overnight. After which, the dark blue solution was evaporated under reduced pressure, and the residue was purified on a Biotage Isolera Flash System using SNAP Ultra cartridge with a mobile phase of $CHCl_3$ and MeOH containing 0.5% formic acid (gradient, 2-15% of MeOH in $CHCl_3$). The fractions containing product were pooled and evaporated, affording LGW-06-14 (13 mg, 14%) as a dark blue solid.

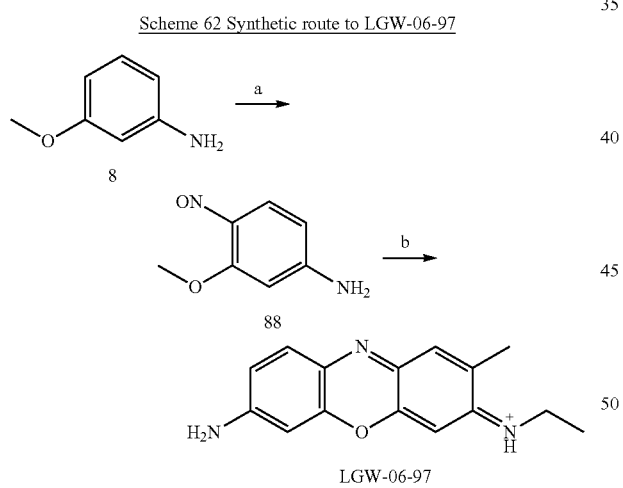

Scheme 62 Synthetic route to LGW-06-97

Reagents and conditions:
a) i) 2M HCl, NaNO$_2$, 0° C.; ii) K$_2$CO$_3$, 0° C.;
b) Compound 6, HClO$_4$, 90% i-PrOH, 80° C.

3-methoxy-4-nitrosoaniline (88)

Compound 8 (0.909 mL, 7.88 mmol) was dissolved in an ice-cold 2 M HCl solution (25 mL). To the solution above, NaNO$_2$ (598 mg, 8.66 mmol) was added portion wise over 1 h while maintaining the temperature of the solution below 5° C., such that no brown NOx vapors were observed. The reaction mixture was stirred for an additional 2 h. The solution was carefully basified with solid $K_2CO_3$ until the pH value of the solution rose above 8. After which, the precipitate was filtered through a Buchner funnel and washed with small portions of DI water. The product was left in the funnel and air dried overnight to afford compound 88 (937 mg, 78%) as a brown solid, which was used for the next step without further purification.

(Z)—N-(7-amino-2-methyl-3H-phenoxazin-3-ylidene)ethanaminium (LGW-06-97)

Compound 6 (50 mg, 0.33 mmol) was dissolved in a solution of i-PrOH/$H_2O$ (9/1, 2 mL) at 80° C. for 30 min. A suspended solution of 88 (53 mg, 0.35 mmol) and $HClO_4$ (70%, 35 µL) in 90% i-PrOH (2 mL) was added into the solution in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of $CHCl_3$ and MeOH containing 0.5% formic acid (gradient, 2-15% of MeOH in $CHCl_3$). The fractions containing product were pooled and evaporated, affording LGW-06-97 (13 mg, 15%) as a dark blue solid.

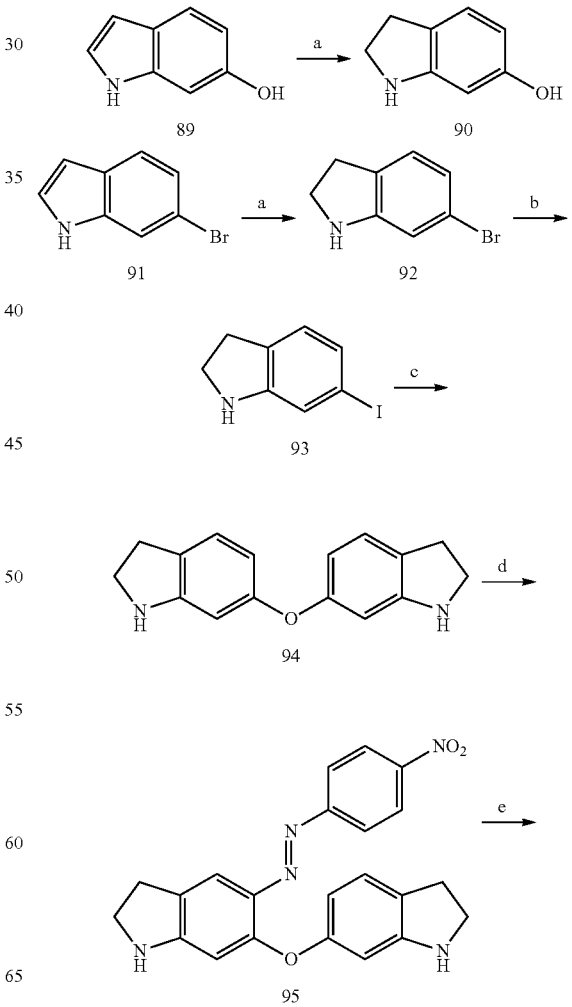

Scheme 63 Synthetic route to LGW-07-55.

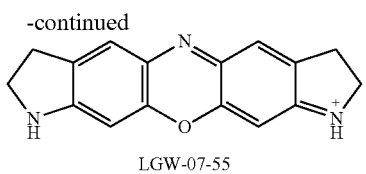

LGW-07-55

Reagents and conditions:
a) NaBH$_3$CN, AcOH, 0° C.;
b) NaI, CuI, N,N'-Dimethylethylenediamine, 1,4-dioxane, 110° C.;
c) Compound 90, CuI, 2-picolinic acid, K$_3$PO$_4$, DMSO, 85° C.;
d) i) 2M HCl, p-nitrobenediazonium tetrafluoroborate, 0° C.; ii) K$_2$CO$_3$, 0° C.;
ii) K$_2$CO$_3$, 0° C.;
e) HClO$_4$, 90% i-PrOH, 80° C.

Indolin-6-ol (90)

Compound 89 (2 g, 15.02 mmol) was dissolved in acetic acid (5 mL). NaBH$_3$CN (2.83 g, 45.06 mmol) was added into the reaction flask portion-wise while maintaining the temperature below 10° C. The resulting solution was stirred for 1 h. After which, the solution was diluted with ice-cold water and neutralized with 2 M NaOH until the pH of the solution rose between 5-6. The reaction mixture was extracted with EtOAc (4×75 mL). The combined organic layers were rinsed with brine and dried over anhydrous Na$_2$SO$_4$. The solvent was removed using a rotary evaporator and the residue was purified by flash column chromatography with silica gel (50 g), using DCM/Hexane as eluent to give compound 90 (1.54 g, 76%).

6-bromoindoline (92)

Compound 91 (2 g, 10.2 mmol) was dissolved in acetic acid (5 mL). NaBH$_3$CN (1.92 g, 45.06 mmol) was added into the reaction flask portion-wise while maintaining the temperature below 10° C. The resulting solution was stirred for 1 h. After which, the solution was diluted with ice-cold water and neutralized with 2 M NaOH until the pH of the solution rose above 7. The reaction mixture was extracted with EtOAc (4×50 mL). The combined organic layers were rinsed with brine and dried over anhydrous Na$_2$SO$_4$. The solvent was removed using a rotary evaporator and the residue was purified by flash column chromatography with silica gel (50 g), using DCM/Hexane as eluent to give compound 92 (1.60 g, 79%) as light brown oil.

6-iodoindoline (93)

Compound 93 was synthesized using a slightly modified protocol published by Klapars and Buchwald.[3] An oven or flame dried, microwave glass tube was charged with a magnetic stir bar, compound 92 (1 g, 5.05 mmol), CuI (106 mg, 0.56 mmol), and NaI (1.66 g, 11.11 mmol). The glass tube was evacuated under vacuum and backfilled with N$_2$ 5 times. N,N'-dimethylethylenediamine (0.12 mL, 1.11 mmol) was added into the reaction vessel very quickly just before the tube was sealed with a Teflon cap. Anhydrous 1,4-dioxane (4.0 mL) was delivered via a syringe. The reaction was then heated to 110° C. and stirred for 24 h. After cooling to rt, the reaction mixture was diluted with 10 mL of saturated NH$_4$Cl and extracted with DCM (4×25 mL). The combined organic layers were washed with brine and dried over anhydrous Na$_2$SO$_4$, then concentrated in vacuo. The residue was purified by flash column chromatography with silica gel (25 g), using DCM/Hexane as eluent to give compound 93 (1.01 g, 82%) as a light brown solid.

6,6'-oxydiindoline (94)

Compound 94 was synthesized using a slightly modified protocol published by Maiti and Buchwald.[4] An oven or flame dried, microwave glass tube was charged with a magnetic stir bar, compound 90 (150 mg, 1.11 mmol), 93 (272 mg, 1.11 mmol), CuI (21 mg, 0.11 mmol), 2-picolinic acid (27 mg, 0.22 mmol), and anhydrous K$_3$PO$_4$ (427 mg, 2.22 mmol). The glass tube was evacuated under vacuum and backfilled with N$_2$ 5 times before the tube was immediately sealed with a Teflon cap. Anhydrous DMSO (2 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous Na$_2$SO$_4$, then concentrated in vacuo. The residue was purified by flash column chromatography with silica gel (25 g), using DCM/Hexane as eluent to give compound 94 (227 mg, 81%) as a colorless oil.

(E)-6-(indolin-6-yloxy)-5-((4-nitrophenyl)diazenyl)indoline (95)

Compound 94 (90 mg, 0.36 mmol) was dissolved in 1 mL MeOH. The solution was chilled in an ice bath, then was treated with HCl (2 M, 5 mL). After 15 mins, p-nitrobenzenediazonium tetrafluoroborate (89 mg, 0.37 mmol) was added to the solution in 3 portions over 15 mins, then stirred at 0° C. for additional 1 h. During which time, the color of the reaction mixture changed from orange to dark red. After which, the solution was carefully basified with solid K$_2$CO$_3$ until pH value of the solution rose above 8. The deep red precipitate was collected via vacuum filtration and washed with small portions of DI water. The product was left in the funnel and air dried overnight to afford compound 95 (112 mg, 78%) as a red solid, which was used for the next step without further purification.

2,3,7,8-tetrahydro-1H-dipyrrolo[3,2-b:2',3'-i]phenoxazin-9-ium (LGW-07-55)

Compound 95 (40 mg, 0.1 mmol) was dissolved in a solution of i-PrOH/H$_2$O (9/1, 2 mL) at 80° C. for 30 min, then the reaction mixture was treated with HClO$_4$ (70%, 10 µL). The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-07-55 (4.6 mg, 15%) as a dark blue solid.

Scheme 64 Synthetic route to LGW-07-59.

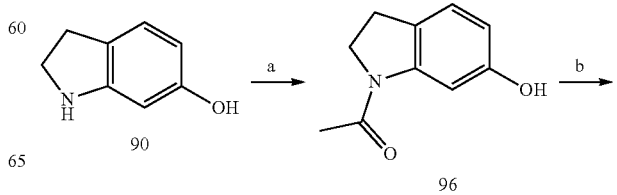

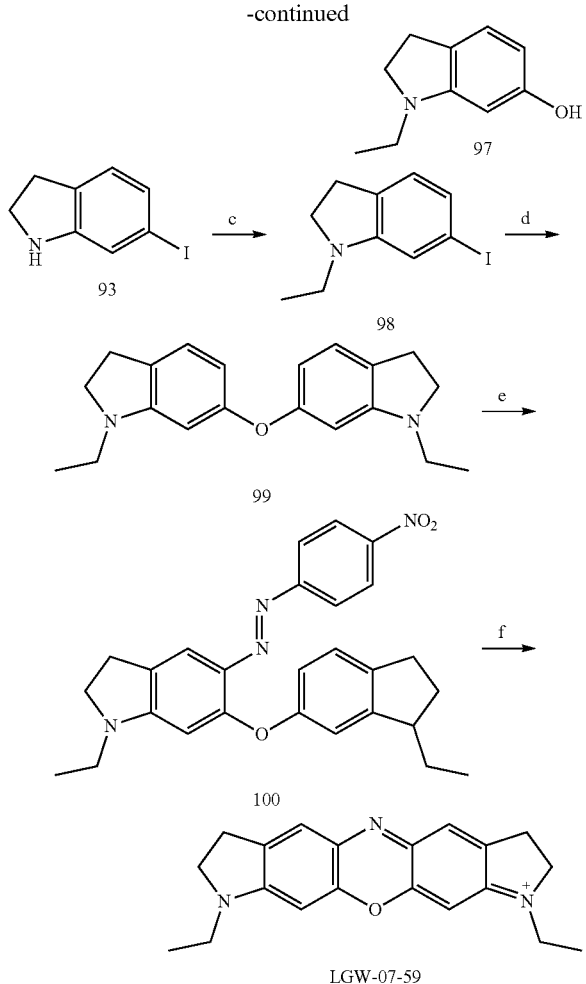

Reagents and conditions:
a) Ac₂O, H₂O, 50° C. to rt;
b) BH₃-THF, 0° C. to rt;
c) EtI, K₂CO₃, MeCN, reflux;
d) Compound 97, CuI, 2-picolinic acid, K₃PO₄, DMSO, 85° C.;
e) i) 2M HCl, p-nitrobenzenediazonium tetrafluoroborate, 0° C.; ii) K₂CO₃, 0° C.;
f) HClO₄, 90% i-PrOH, 80° C.

1-(6-hydroxyindolin-1-yl)ethan-1-one (96)

Compound 90 (0.8 g, 5.92 mmol) was suspended in 10 mL DI water, to which Acetic anhydride (2.24 mL, 23.67 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 96 (929 mg, 89%) as a light gray solid, which was used for the next step without further purification.

1-ethylindolin-6-ol (97)

A solution of 96 (0.9 g, 5.08 mmol) in anhydrous THF (15 mL) was stirred in an ice bath under N2 for 30 mins. Borane tetrahydrofuran complex solution (1 M, 15 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel (25 g), using DCM/Hexane as eluent to give 97 (706 mg, 85%) as brown oil.

1-ethyl-6-iodoindoline (98)

To a suspension of compound 93 (0.4 g, 1.63 mmol) and K₂CO₃ (751 mg, 3.26 mmol) in anhydrous MeCN (10 mL) under N2, was added EtI (0.16 mL, 1.96 mmol) at rt. The reaction mixture was then heated to reflux and stirred overnight. The solution was cooled down to rt and concentrated under reduced pressure. The crude product was diluted with DI water, and the resulting suspension was extracted with DCM (3×50 mL). The combined organic layers were rinsed with brine and dried over anhydrous Na₂SO₄. The solvent was removed using a rotary evaporator. The resulting residue was purified by flash column chromatography with silica gel (25 g), using DCM/Hexane as eluent to give compound 98 (369 mg, 83%) as clear oil.

6,6'-oxybis(1-ethylindoline) (99)

Compound 99 was synthesized using a slightly modified protocol published by Maiti and Buchwald.[4] An oven or flame dried, microwave glass tube was charged with a magnetic stir bar, compound 97 (96 mg, 0.59 mmol), 98 (160 mg, 0.59 mmol), CuI (11 mg, 0.06 mmol), 2-picolinic acid (15 mg, 0.12 mmol), and anhydrous K₃PO₄ (249 mg, 1.17 mmol). The glass tube was evacuated under vacuum and backfilled with N₂ 5 times before the tube was immediately sealed with a Teflon cap. Anhydrous DMSO (1.5 mL) was delivered via a syringe. The reaction was then heated to 85° C. and stirred for 18 h. After cooling to rt, the reaction mixture was diluted with 10 mL DI water and extracted with DCM (4×25 mL). The combined organic layers were washed with brine and dried over anhydrous Na₂SO₄, then concentrated in vacuo. The residue was purified by flash column chromatography with silica gel (25 g), using DCM/Hexane as eluent to give compound 99 (151 mg, 84%) as a colorless oil.

(E)-1-ethyl-6-((1-ethylindolin-6-yl)oxy)-5-((4-nitrophenyl)diazenyl)indoline (100)

Compound 99 (90 mg, 0.29 mmol) was dissolved in 1 mL MeOH. The solution was chilled in an ice bath, then was treated with HCl (2 M, 5 mL). After 15 mins, p-nitrobenzenediazonium tetrafluoroborate (73 mg, 0.31 mmol) was added to the solution in 3 portions over 15 mins, then stirred at 0° C. for an additional 1 h. During which time, the color of the reaction mixture changed from orange to dark red. After which, the solution was carefully basified with solid K₂CO₃ until the pH value of the solution rose above 8. The deep red precipitate was collected via vacuum filtration and washed with small portions of DI water. The product was left in the funnel and air dried overnight to afford compound 100 (109 mg, 82%), which was used for the next step without further purification.

1,9-diethyl-2,3,7,8-tetrahydro-1H-dipyrrolo[3,2-b:2',3'-i]phenoxazin-9-ium (LGW-07-59)

Compound 100 (40 mg, 0.087 mmol) was dissolved in a solution of i-PrOH/H₂O (9/1, 2 mL) at 80° C. for 30 min, then the reaction mixture was treated with HClO$_4$ (70%, 10 µL). The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-07-59 (17 mg, 60%) as a dark blue solid.

Scheme 65: Route to LGW-04-84.

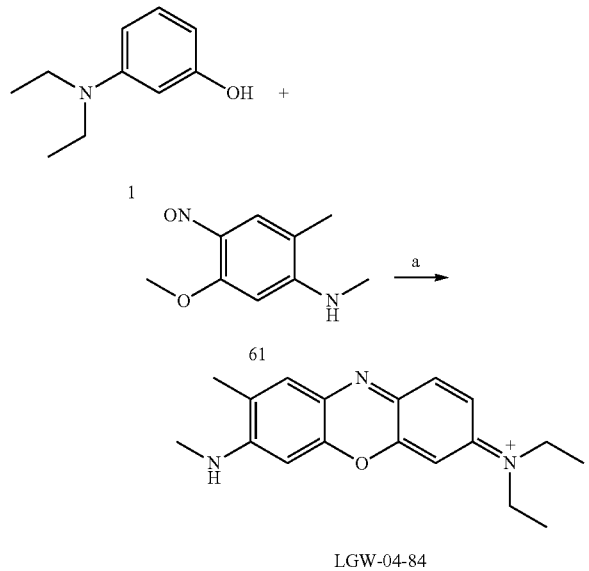

LGW-04-84

Reagents and conditions: a) HClO$_4$, 90% i-PrOH, 80° C. N-ethyl-N-(8-methyl-7-(methylamino)-3H-phenoxazin-3-ylidene)ethanaminium (LGW-04-84) Compound 1 (50 mg, 0.3 mmol) was dissolved in a solution of i-PrOH/H$_2$O (9/1, 1 mL) at 80° C. for 30 min. A suspended solution of 61 (57 mg, 0.32 mmol) and HClO$_4$ (70%, 30 µL) in 90% i-PrOH (2 mL) was added in 4 portions over 1 h. The resulting solution was stirred overnight. After which, the dark blue solution was evaporated under reduced pressure, and the residue was purified on a Biotage Isolera Flash System using SNAP Ultra cartridge with a mobile phase of CHCl$_3$ and MeOH containing 0.5% formic acid (gradient, 2-15% of MeOH in CHCl$_3$). The fractions containing product were pooled and evaporated, affording LGW-04-84 (36 mg, 35%) as a dark blue solid.

Bio Testing

Oxazine derivative library optical and physicochemical property characterization. The 64 Oxazine derivatives, as well as Oxazines 1 and 4, underwent characterization for their optical and physicochemical properties. The maximum absorbance and emission values of the library ranged from 590 to 701 nm and 606 to 718 nm, respectively, resulting in 42 compounds with NIR emission. The Oxazine derivatives yielded a wide range of extinction coefficients (16,934-128,790 M$^{-1}$cm$^{-1}$) and quantum yields (0.21-44%), which were used to calculate overall brightness (0.05-39.28). The molecular and physicochemical properties of each Oxazine derivative were calculated including molecular weight (MW), partition coefficient (Log D), number of hydrogen bond donors and acceptors, polar surface area (PSA), and number of rotatable bonds to facilitate assessment of the drug-like properties of each Oxazine derivative. The MW of the Oxazine library varied from 240.3 to 428.6 g/mol, with all compounds below the MW threshold (500 g/mol) thought to be required for BNB penetration (Gibbs-Strauss, S. L., et al., *Molecular imaging* 10, 91-101 (2011); Pajouhesh, H. & Lenz, G. R., *NeuroRx* 2, 541-553 (2005); Fagerholm, *Drug Discov Today* 12, 1076-1082 (2007); and Waterhouse, *Molecular imaging and biology: MIB: the official publication of the Academy of Molecular Imaging* 5, 376-389 (2003)). The majority of the calculated physicochemical properties of the Oxazine derivative library demonstrated that the novel compounds fell within the requirements for tissue targeting as well as for nerve uptake and binding (Pajouhesh et al., *NeuroRx* 2, 541-553 (2005); Lipinski et al., *Advanced drug delivery reviews* 46, 3-26 (2001); and Veber et al., *J Med Chem*, 45, 2615-2623 (2002)). The Log D values varied from 2.59 to 7.21, with 47 compounds falling within the desired range for nerve uptake and binding (Log D<5). Additionally, all 64 compounds had hydrogen bond donor (0-2) and acceptors (3-5) within the desired range for nerve specificity.

Oxazine derivative library nerve-specificity screening. All 64 Oxazine derivatives were screened for nerve specificity using a previously described ex vivo tissue staining assay (Gibbs, S. L., et al., *PloS one* 8, e73493 (2013)). Ex vivo nerve and muscle tissue fluorescence intensities varied, with many compounds showing minimal nerve or muscle tissue fluorescence above control autofluorescence following Oxazine derivative staining. Nerve and muscle tissue fluorescence intensity values were used to calculate N/M SBRs, where only two of the 64 Oxazine derivatives displayed significantly higher N/M SBR compared to the unstained control group (*=p<0.05, Fig. S3C). Interestingly, these two Oxazines, LGW01-39 and LGW01-44, showed similar ex vivo nerve fluorescence staining patterns. All Oxazine derivatives were further screened for nerve-specificity in vivo using both direct and systemic administration strategies. The direct administration strategy enabled quantification of nerve-specificity and contrast following fluorophore contact with the nerves and surrounding tissues without the requirement of BNB penetration, providing the most similar comparison to ex vivo nerve-specificity screening. The systemic administration screening studies required not only nerve specificity, but also adequate biodistribution and BNB penetration to generate SBR for visualization.

Following direct and systemic administration routes, brachial plexus and sciatic nerve imaging facilitated quantification of nerve, muscle, and adipose tissue fluorescence intensities. Nerve fluorescence intensity varied widely across the library, with brighter overall signal following direct compared to systemic administration. Muscle and adipose tissue fluorescence intensities varied similarly following direct administration, but less so following systemic administration, with more compounds yielding muscle and adipose endogenous autofluorescent levels. Measurements of tissue fluorescence intensities enabled N/M and N/A SBR quantification. N/M ratios varied widely between library compounds with mean values ranging from 0.73 to 5.29 for direct administration and from 0.69 to 3.43 for systemic administration. N/A ratios were also widely variable between library compounds with mean values ranging from 0.69 to 4.97 following direct administration and from 0.81 to 2.94 following systemic administration. All Oxazine derivatives with a significantly higher N/M ratio compared to the control group (*=p<0.05, =p<0.01, *=p<0.001, ****=p<0.0001) were considered to have nerve specificity and provide positive nerve contrast. Thus, following direct administration, 51 Oxazine derivatives yielded positive N/M contrast. The direct administration nerve-specificity screening results translated well to systemic administration nerve specificity screening, where 38 Oxazine derivatives had significantly higher N/M contrast than the control group. N/A contrast levels were additionally high overall, where 47 and 43 Oxazine derivatives had significantly higher N/A levels compared to the control group following direct and systemic administration, respectively. As expected, some compounds displayed positive nerve specificity via direct administration but were negative for nerve contrast following systemic administration including LGW06-97, LGW06-10, LGW05-91, LGW02-95, LGW01-21, LGW07-55, LGW01-23, LGW01-64, LGW05-85, LGW06-11, LGW01-44, LGW03-37, LGW03-57, LGW03-23 and LGW03-01. Two compounds (LGW01-64 and LGW01-99) were toxic upon systemic administration and therefore have no quantified tissue intensities or SBRs. Surprisingly, two compounds (LGW03-07 and LGW05-84) displayed negative nerve specificity via direct administration but were positive following systemic administration. Four novel Oxazine derivatives (LGW01-08, LGW05-75, LGW04-31 and LGW03-76) were selected for additional study based on their NIR spectral properties, high nerve specificity following both direct and systemic administration and structural diversity.

NIR LGW01-08 increases nerve visualization depths. Nerve-specific fluorescence images were collected of the exposed murine brachial plexus nerves and under 1 and 2 mm of murine muscle tissue following either direct or systemic administration of Oxazine 4 or NIR LGW01-08. Image acquisition occurred using excitation and emission filters analogous to the 700 nm fluorescence channel in clinical FGS systems (Tummers, et al., *Eur J Surg Oncol* 40, 850-858 (2014); Troyan et al., *Ann Surg Oncol* 16, 2943-2952 (2009); Ashitate et al., *The Journal of surgical research* 176, 7-13 (2012); Hillary et al., *Langenbecks Arch Surg* 403, 111-118 (2018); and Mery et al, *Oncotarget* 8, 109559-109574 (2017)). Following both systemic and direct administration, LGW01-08 provided the ability to identify nerve tissue buried under up to 2 mm of muscle tissue, while Oxazine 4 only allowed coarse nerve identification beneath 1 mm of muscle tissue. Fluorescence cross-sectional line profiles across the large nerve branches following systemic administration showed the improved nerve signal intensity and SBR in buried nerves provided by LGW01-08 compared to visibly-emissive Oxazine 4. Quantitative analysis across small nerve branches following direct administration demonstrated the ability of LGW01-08 to highlight detailed nerve structures under 1 mm of muscle tissue, which was not feasible using the hypsochromically shifted Oxazine 4. Nerve branches as small as ~200 µm in width were easily distinguished via LGW01-08 under muscle tissue, while Oxazine 4 did not possess the ability to resolve smaller branches due to increased visible photon absorbance and scattering.

NIR fluorescent nerve imaging in minimally invasive robotic surgery. The NIR Oxazine derivatives LGW01-08, LGW05-75, LGW04-31 and LGW03-76 showed high nerve-to-background tissue contrast following direct or systemic administration. While tissue-specific fluorescence was variable across the selected Oxazine derivatives, all four NIR Oxazines displayed significantly higher N/M and N/A ratios than unstained control animals following either direct or systemic administration. LGW01-08 and LGW05-75 selection for swine studies stemmed from their high absolute nerve fluorescence levels and nerve SBR following direct and systemic administration in murine models. Systemic Oxazine derivative administration in swine fluorescently highlighted peripheral nerves in the pelvic region during a simulated minimally invasive surgery on a da Vinci Si Surgical robot. Only 20 minutes post-injection, LGW01-08 revealed bright lumbar nerve signal against the lateral and anterior body wall. Buried nerve tissues that were largely invisible using conventional white light were unambiguously delineated underlying peritoneal tissue and several millimeters of mixed adipose and muscle tissues (SBR ~1.5) using the nerve-specific fluorescence generated from LGW01-08 or LGW05-75. Nerve contrast was readily visible against varied, clinically relevant tissue backgrounds including adipose, muscle, fascia and vasculature tissues. Although nerves on all tissue types generated positive contrast, varied underlying tissue background levels resulted in a broad range of semi-quantitative (See Methods section) SBRs from ~1.5 in lumbar nerves running between fascia and muscle up to ~25 in exposed iliac nerves running along the iliac bifurcation.

Dissection of the highlighted buried nerve structures occurred at study completion under fluorescence guidance, where white light endoscopy positively identified exposed nerve tissue and provided nerve depth assessments. Gold standard histopathological H&E staining confirmed all linear, fluorescent structures as nerves. Interestingly, LGW01-08 and LGW05-75 demonstrated disparate pharmacokinetic profiles with LGW01-08 yielding nerve contrast starting just minutes post-injection where LGW05-75 required ~1.5 hours for sufficient background tissue clearance. However, LGW05-75 provided strong nerve SBR >4.5 hours after administration while LGW01-08 approached background levels ~4 hours post-injection. Both NIR fluorophores generated significant in vivo signal above endogenous autofluorescent levels, with unstained tissue providing little to no quantifiable fluorescence signal.

LGW05-75 facilitated a mock fluorescence-guided dissection in the presence of nerve tissue highlighting the benefit of NIR nerve imaging integration into minimally invasive surgery. In the first surgical case, the buried nerve had little risk of damage during the incision. Nerve depth assessment using conventional white light endoscopy proved challenging, demonstrating the difficulty in evaluating the nerve depth in relation to the surgical instrument. Additionally, a white linear, potential nerve structure appeared near the instrument blades, adding visual confusion in the white light image. However, fluorescent imaging provided clear identification of the true nerve below the fascial layer, putting it out of risk from accidental transection by the monopolar scissors where the white superficial structure showed no fluorescent signal. In the second surgical case, a small sub-1-mm nerve was invisible between the blades of the surgical tool in the white light image. When the surgeon switched to fluorescence imaging, the small, fluorescent nerve clearly appeared. This case demonstrated nerve tissue preservation in a high-risk situation that would have likely ended in nerve damage if relying solely on white-light endoscopy.

Discussion

Iatrogenic nerve injury, a common surgical complication, results in lasting morbidity as injured nerves show little functional improvement. FGS has the potential to revolutionize surgery, where targeted contrast could facilitate identification and real-time visualization of diseased tissues for resection and normal tissues, such as nerves, for sparing. While there are a variety of NIR imaging agents in the clinical pipeline for cancer delineation, a NIR nerve-specific contrast agent suitable for clinical use has yet to be developed. In an effort to fill this need, a focused library of 64 Oxazine derivates was designed and synthesized. Careful consideration of fluorophore photochemical and structural properties maximized library diversity and yielded nerve-targeting molecules in the NIR range. The resulting library led to 42 of the 64 compounds possessing NIR emission wavelengths, representing an extensive NIR fluorophore set for subsequent structure-activity relationship mapping. Furthermore, the physicochemical properties of the majority of the Oxazine library compounds were within the criteria for tissue targeting according to the Lipinski (Lipinski, et al., *Advanced drug delivery reviews* 46, 3-26 (2001)) and Veber (Veber et al., *Journal of medicinal chemistry* 45, 2615-2623 (2002)) rules and the requirements for nerve uptake and binding according to the Pajouhesh and Lenz rules (Pajouhesh & Lenz, *NeuroRx* 2, 541-553 (2005)). Importantly, only a handful of the NIR nerve-specific fluorophores were suitable for future clinical translation (FIGS. 7 and 8).

Oxazine library screening for tissue-specific accumulation and contrast focused on nerve specificity using three assays. Ex vivo screening had previously demonstrated predictive power for in vivo nerve-specificity in a library of distyrylbenzene derivatives (Gibbs et al., *PloS one* 8, e73493 (2013)). However, ex vivo screening of the Oxazine library had little to no predictive power for in vivo nerve-specificity. Only two of the 64 Oxazine derivatives had significantly higher N/M SBR compared to the unstained control group and the base nerve-specific compound, Oxazine 4, lacked nerve-specificity ex vivo. This confounding result has been examined, where nerve-specific Oxazine 4 staining following systemic administration can be maintained after resection, but cannot be generated ex vivo on resected nerves (Barth & Gibbs, *SPIE Photonics West—BiOS*, Vol. 9696 (2016)). Full characterization of tissue-specific staining patterns and nerve SBRs of the 64 Oxazine derivatives involved two routes of in vivo administration: direct and systemic. Following screening using both administration routes, large diversity in fluorescence staining intensity and the degree of nerve specificity occurred, where variations in nerve intensity values did not necessarily correlate with fluorophore brightness. This potentially resulted from differences in the nerve uptake characteristics of each compound, which were highly variable as evidenced by the broad range of nerve SBRs.

Direct administration yielded higher nerve intensity and SBRs compared to the systemic route. Nerve-specificity of the library was high with 51 and 38 of the Oxazine derivatives showing positive nerve contrast above the control group following direct or systemic administration, respectively. While direct administration nerve-specificity screening largely correlated with nerve-specificity following systemic administration, 15 Oxazine derivatives showed statistically significant N/M SBRs following direct administration, but not following systemic administration. This demonstrates the increased stringency required to obtain positive nerve specificity via systemic versus direct administration as intravenously injected agents must cross the BNB and clear from the surrounding tissues to create nerve contrast. Additionally, systemically administered nerve contrast agents will distribute to and accumulate in all nerve tissues within the body, which causes an overall decrease in the local contrast agent dose per nerve structure compared to direct administration, resulting in dimmer fluorescence intensity. This difference in brightness is especially apparent when imaging small nerve branches, which can be easily distinguished in the higher intensity fluorescence signal resulting from direct administration, but not visible following systemic administration. Therefore, Oxazine derivatives with unfavorable biodistribution or low BNB penetration may not reach nerve tissue and those with low brightness could remain undetected over background autofluorescence levels. Surprisingly, two Oxazine derivatives that had significant N/M SBR over the control group following systemic administration did not have positive N/M SBR following direct administration, demonstrating that the direct administration strategy does not have perfect predictive power for nerve specificity following systemic administration. Importantly, few derivates showed high adipose uptake, a problem often suffered by nerve specific compounds due to their required degree of lipophilicity for nerve partitioning (Gibbs et al, *PloS one* 8, e73493 (2013) and Lipinski et al., *Advanced drug delivery reviews* 46, 3-26 (2001)). Overall N/A SBR levels were high, with 47 and 43 of the Oxazine derivatives having significantly higher N/A SBRs compared to the control group following direct and systemic administration, respectively.

Four NIR Oxazine derivatives (i.e., LGW01-08, LGW03-76, LGW04-31 and LGW05-75) showed promising spectroscopic, pharmacokinetic and nerve imaging characteristics for future clinical translation (FIGS. 7 and 8). Tissue optical properties diverge sharply near the visible/NIR wavelength transition, enabling the "700 nm" NIR nerve-specific Oxazine fluorescence photon propagation to occur with less absorption and scattering events compared to visible-emissive Oxazine 4 (Keereweer et al., *Clinical cancer research: an official journal of the American Association for Cancer Research* 19, 3745-3754 (2013) and Zhang et al., *Clinical oncology* 14, 347-364 (2017)). Oxyhemoglobin and deoxyhemoglobin show 3.4-fold and 2.6-fold lower average molar extinction coefficients, respectively, in the 650-700 nm NIR region versus the 600-650 nm visible range (Dayer et al., *Protein Pept Lett* 17, 473-479 (2010)). The lead NIR nerve-specific Oxazines' maximum absorbance ($\lambda_{ex}$=640-655 nm) either borders or enters the NIR range, enabling ~2-3-fold higher excitation photon flux than Oxazine 4 ($\lambda_{ex}$=620 nm) solely from reduced hemoglobin attenuation, resulting in improved nerve detection at depth. The pharmacokinetic profile of LGW01-08 exhibited strong nerve contrast on unexpectedly short time-scales (~20 minutes) after systemic administration, a 2-6-fold faster time to positive N/A and N/M fluorescence compared to current visible-emissive agents (Park et al., *Theranostics* 4, 823-833 (2014); Hingorani et al., *Theranostics* 8, 4226-4237 (2018); Whitney et al., *Nature biotechnology* 29, 352-356 (2011); and Lipinski et al., *Advanced drug delivery reviews* 46, 3-26 (2001)). Since planning for surgical site complexity and aberrant anatomy prior to a procedure is not always feasible, a fast-acting nerve contrast agent that enables intraoperative use has a significant advantage over agents requiring 2-4 hours to achieve contrast with complex preoperative injection protocols. Additionally advantageous, LGW01-08 and LGW05-75 provided positive nerve contrast against key surgical tissue classes (e.g., adipose, muscle, vasculature and peritoneal tissues) encountered in laparoscopic surgery. Interestingly, LGW01-08 showed higher N/A values compared to N/M in swine, but the opposite trend in murine models. However, with positive SBRs ranging from ~1.5 (subperitoneal nerves beneath muscle) to ~25 (exposed iliac nerves above vasculature) in swine, NIR Oxazines exhibited excellent cross-species contrast. Finally, NIR fluorescent nerve imaging integration with minimally invasive FGS systems demonstrated the potential to redefine surgical navigation through nerve delineation abilities not achievable using conventional white-light endoscopy as well as enhanced nerve depth assessment within surrounding tissues.

In summary, the synthetic design, development and preclinical characterization of a focused Oxazine derivative library identified strong NIR fluorophore candidates for clinical translation. The generated library possessed diverse physicochemical properties and nerve binding characteristics, resulting in the first NIR nerve-specific fluorophores with superior optical, pharmacokinetic, and pharmacodynamics properties. Swine imaging of LGW01-08 and LGW05-75 demonstrated the power of these NTR probes, where buried nerves completely invisible under conventional white light illumination proved readily identifiable using a clinical laparoscopic FGS system. Based on their spectral properties, in vivo fluorescence intensities, and resulting nerve SBRs, LGW01-08 and 05-75 are strong candidates for future clinical translation, offering high nerve specificity and NIR emission for nerve visualization at depth within the native tissue environment using FDA-approved FGS systems.

In vivo nerve-specificity screening of the Oxazine derivative library. Each compound was screened for its tissue-specificity using two in vivo methods including a direct (Barth & Gibbs, *Theranostics* 7, 573-593 (2017)) and systemic administration strategy where nerve contrast was examined in murine brachial plexus and sciatic nerves. The Oxazine derivatives were solubilized for in vivo use in the previously described co-solvent formulation (Gibbs-Strauss et al., *Molecular imaging* 10, 91-101 (2011)). For direct administration, the previously optimized staining procedure was utilized (Gibbs et al., *PloS one* 8, e73493 (2013)), which is described briefly as follows. The brachial plexus and sciatic nerves were surgically exposed by removal of overlaying adipose and muscle tissues. The Oxazine compound was formulated at 125 µM in the co-solvent formulation and 100 µL was incubated on the exposed brachial plexus or sciatic nerve for 5 minutes. The fluorophore containing solution was removed and the area was irrigated with saline nine times, followed by a five-minute incubation with blank formulation and then irrigation with saline nine more times to remove any unbound fluorophore. Images were acquired 30 minutes following completion of staining. Unstained nerve sites were used for all control images to quantify autofluorescence. Each Oxazine derivative was screened in n=3 mice or 6 nerve sites/fluorophore.

The optimal dose and pharmacokinetics of Oxazine 4 ((Barth & Gibbs, *Theranostics* 7, 573-593 (2017)) and Park et al., *Theranostics* 4, 823-833 (2014)) were used to screen the Oxazine derivatives by systemic administration where 200 nmol of each compound in 100 µL of co-solvent formulation were administered intravenously (IV) 4 hours prior to imaging. This fluorophore administration to imaging window had been previously shown to provide the highest nerve to background tissue fluorescence for Oxazine 4 and several other nerve specific fluorophores (Gibbs-Strauss, S. L., et al., *Molecular imaging* 10, 91-101 (2011); Gibbs et al., *PloS one* 8, e73493 (2013); and Park et al., *Theranostics* 4, 823-833 (2014)). Uninjected animals were used for all control images to quantify autofluorescence. Each Oxazine derivative was screened in n=3 mice or 6 nerve sites/fluorophore with the two brachial plexus and two sciatic nerve sites being averaged together for a total of two replicates per animal, one of each nerve type.

Intraoperative fluorescence imaging systems. A custom-built small animal imaging system capable of real-time color and fluorescence imaging was used to acquire in vivo rodent images (Hackman et al., *Molecular pharmaceutics* (2015)). Briefly, the imaging system consisted of a QImaging EXi Blue monochrome camera (Surrey, British Columbia, Calif.) for fluorescence detection with a removable Bayer filter for collection of co-registered color and fluorescence images. A PhotoFluor II light source was focused onto the surgical field through a liquid light guide and used unfiltered for white light illumination. For fluorescence excitation, the Photo-Fluor II was filtered with a 620±30 nm bandpass excitation filter. The resulting fluorescence was collected with a 700±37.5 nm bandpass emission filter. All filters were obtained from Chroma Technology (Bellows Falls, Vt.). Camera and light source positions did not vary throughout the course of all imaging studies, allowing quantitative comparison of in vivo fluorescence intensities. Camera exposure times ranged from 5-2000 ms for fluorescence image collection.

A custom-built laparoscopic imaging system also capable of real-time color and fluorescence imaging was used to acquire in vivo swine images and videos. The imaging system was integrated into the da Vinci Si surgical system (Intuitive Surgical, Sunnyvale, Calif.) and consisted of a Necsel Neon 5 W 640 nm laser (Necsel, Milpitas, Calif.) coupled to the da Vinci Si endoscope with a 642 nm StopLine single-notch blocking filter (Semrock, Rochester, N.Y.). The single-notch blocking filter was placed in the Si camera sterile adaptor between the rod lens endoscope and the Si camera head. Fluorescent signal acquisition occurred in the Si white light mode with the blocking filter removing the excitation light and the fluorescent signal detected primarily on the red, green, blue (RGB) red-Bayer elements of a modified Si endoscope camera head. Laser power at the endoscope tip measured 800 mW with the optical power loses occurring primarily at the laser fiber/light guide and the Si camera head/rod lens interfaces. Fluorescence and color videos were captured using the Si Vision side cart at an exposure time of 2 ms. Videos were recorded on a Panasonic HD-SDI recorder connected to the TilePro video out connections on the da Vinci Si Vision side cart. Video clips were edited in iMovie to crop their length and include text overlays. Screen captures of the in vivo video clips were collected and are presented as figures. Da Vinci Si imaging display algorithms apply non-linear gamma and color corrections to the collected video, and thus, while image quantification is possible to report what would be visible to surgeons intraoperatively, these values are only semi-quantitative and could vary from what is observed in a more controlled system.

Nerve imaging at depth studies using a model Oxazine derivative. Oxazine 4 and LGW01-08 were used to stain mouse brachial plexus nerves using both direct and systemic administration methods using the same dose and administration methods previously described. The ability to image the brachial plexus nerve at depth was assessed under varying thicknesses of mouse muscle tissue. Muscle tissue was resected from the peritoneal muscle layer and measured for thickness. One and two layers of resected peritoneal muscle tissue was placed over the stained nerves, providing one and two mm thick homogenous tissue through which the stained nerve tissue was imaged. The same muscle tissue was used to cover the stained nerves from both fluorophores with care taken to orient the muscle in the same way to ensure equivalent comparison. The imaging system configuration was changed to reflect the 700 nm channel in clinically relevant FGS systems (Tummers et al., *Eur J Surg Oncol* 40, 850-858 (2014); Troyan et al., *Ann Surg Oncol* 16, 2943-2952 (2009); Ashitate et al., *The Journal of surgical research* 176, 7-13 (2012); Verbeek et al., *The Journal of urology* 190, 574-579 (2013); Hillary et al., *Langenbecks Arch Surg* 403, 111-118 (2018); and Mery et al., *Oncotarget* 8, 109559-109574 (2017). For fluorescence excitation, the PhotoFluor II was filtered with a 650±22.5 nm bandpass excitation filter. The resulting fluorescence was collected with a 720±30 nm bandpass emission filter for image collection. Camera exposure times ranged from 0.025-4 s for fluorescence image collection.

Swine nerve imaging studies of Oxazine derivatives. LGW01-08 and LGW05-75 were administered via IV injection at a body surface area scaled dose from mice for swine nerve imaging studies (0.34 mg/kg) (Nair & Jacob, *J Basic Clin Pharm* 7, 27-31 (2016) and Sharma & McNeill, *Br J Pharmacol* 157, 907-921 (2009)). Nerves running along the body wall in the peritoneal cavity buried beneath 1-3 mm of fascia and adipose tissue were imaged using the previously described fluorescence enabled laparoscopic imaging system docked to the da Vinci Si Surgical System. Nerve contrast was monitored immediately following injection and up to 6 hours after systemic administration. Dissection and resection of the identified nerve structures was performed using the da Vinci system, where the resected tissues were fixed in formalin. The fixed tissues were sent to the OHSU Histopathology Shared Resource for paraffin embedding, sectioning and subsequent gold standard H&E staining.

Image analysis of intraoperative nerve contrast. Custom written MatLab code was used to analyze the tissue specific fluorescence where regions of interest (ROIs) were selected on the nerve, muscle and adipose tissue using the white light images, but blinded to the fluorescence images. These ROIs were then analyzed on the co-registered, matched fluorescence images permitting assessment of the mean tissue intensities as well as the nerve to muscle (N/M) and nerve to adipose (N/A) ratios. Fluorescence intensity measurements were divided by the exposure time to obtain normalized intensity per second measurements. Mean nerve to background tissue ratios (N/M and N/A) were calculated for each Oxazine derivative. For nerve imaging at depth image analysis, fluorescent line profiles and 3-D intensity topographical plots were generated in ImageJ using the plot profile and surface plot functions, respectively. The line profiles were background and exposure time corrected by dividing by the exposure time of each image and subtracting the average intensity of background pixels from the entire line profile. Line profiles and SBRs quantified from large animal laparoscopic studies quantify the RGB image displayed on the da Vinci Surgical System. The tissue-level SBR may differ slightly than the displayed-level SBR as image-signal processing pipelines contain non-linear elements including gamma and color corrections that take place prior to video capture in the da Vinci Si endoscope system, and thus SBRs are reported as semi-quantitative. In addition, non-uniform tissue surfaces, variable endoscope-tissue positioning, and vignetting add further complications to resolving tissue-level SBRs. The reported SBRs represent the nerve signal displayed to a surgeon on the da Vinci High Resolution Stereo Viewer (HRSV) and thus are representative of clinical integration.

Statistical analysis. Significant differences between nerve signal to background (SBR) means were evaluated using a one-way analysis of variance (ANOVA) followed by a Fisher's LSD multiple comparison test with no assumption of sphericity using the Geisser-Greenhouse correction to compare all mean nerve to background tissue ratios. The a value was set to 0.05 for all analyses. Results are presented as mean±standard deviation (S.D.). All statistical analysis was performed using Prism (GraphPad, La Jolla, Calif.).

REFERENCES

1 Barth, C. W. & Gibbs, S. L. Direct Administration of Nerve-Specific Contrast to Improve Nerve Sparing Radical Prostatectomy. *Theranostics* 7, 573-593, doi:10.7150/thno.17433 (2017).

2 Belov Vladimir, N., Bossi Mariano, L., Folling, J., Boyarskiy Vadim, P. & Hell Stefan, W. Rhodamine Spiroamides for Multicolor Single-Molecule Switching Fluorescent Nanoscopy. *Chemistry—A European Journal* 15, 10762-10776, doi:10.1002/chem.200901333 (2009).

3 Klapars, A. & Buchwald, S. L. Copper-Catalyzed Halogen Exchange in Aryl Halides: An Aromatic Finkelstein Reaction. *Journal of the American Chemical Society* 124, 14844-14845, doi:10.1021/ja028865v (2002).

4 Maiti, D. & Buchwald, S. L. Orthogonal Cu- and Pd-based catalyst systems for the O- and N-arylation of aminophenols. *J Am Chem Soc* 131, 17423-17429, doi:10.1021/ja9081815 (2009).

What is claimed:
1. A compound of
(a) Formula I(a)

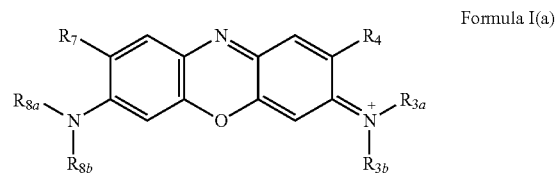

Formula I(a)

wherein $R_4$ and $R_7$ are independently selected from $CH_3$ and halogen; and each of $R_{3a}$, $R_{3b}$, $R_{8a}$, and $R_{8b}$ are independently selected from hydrogen and $C_1$-$C_4$ alkyl;

(b) Formula I(b)

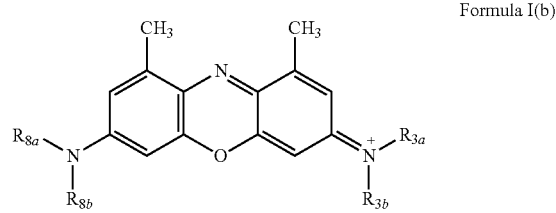

Formula I(b)

wherein
$R_{3a}$ and $R_{3b}$ in each instance are independently selected from hydrogen and $C_1$-$C_4$ alkyl, with the proviso that at least one of $R_{3a}$ and $R_{3b}$ is not hydrogen; or $R_{3a}$ and $R_{3b}$ together with the nitrogen atom to which they are bound form a 5- or 6-membered nitrogen-containing ring; and
$R_{8a}$ and $R_{8b}$ in each instance are independently selected from hydrogen and $C_1$-$C_4$ alkyl, with the proviso that at least one of $R_{8a}$ and $R_{8b}$ is not hydrogen; or $R_{8a}$ and $R_{8b}$ together with the nitrogen to which they are bound form a 5- or 6-membered nitrogen-containing ring optionally substituted by 1, 2, 3, or 4 $C_1$-$C_4$ alkyl substituents;

(c) Formula I(c)

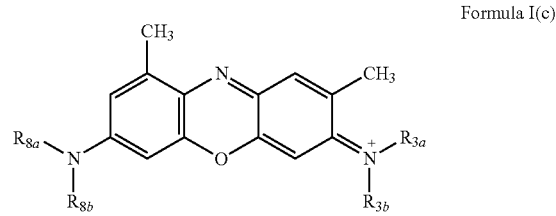

Formula I(c)

wherein
- $R_{3a}$ and $R_{3b}$ in each instance are independently selected from hydrogen and $C_1$-$C_4$ alkyl, with the proviso that at least one of $R_{3a}$ and $R_{3b}$ is not hydrogen; or $R_{3a}$ and $R_{3b}$ together with the nitrogen atom to which they are bound form a 5- or 6-membered nitrogen-containing ring; and
- $R_{8a}$ and $R_{8b}$ in each instance are independently selected from hydrogen and $C_1$-$C_4$ alkyl, with the proviso that at least one of $R_{8a}$ and $R_{8b}$ is not hydrogen; or $R_{8a}$ and $R_{8b}$ together with the nitrogen to which they are bound form a 5- or 6-membered nitrogen-containing ring optionally substituted by 1, 2, 3, or 4 $C_1$-$C_4$ alkyl substituents;

(d) Formula I(d)

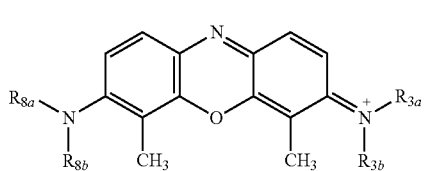

Formula I(d)

wherein
- $R_{3a}$ and $R_{3b}$ in each instance are independently selected from hydrogen and $C_1$-$C_4$ alkyl, with the proviso that at least one of $R_{3a}$ and $R_{3b}$ is not hydrogen; or $R_{3a}$ and $R_{3b}$ together with the nitrogen atom to which they are bound form a 5- or 6-membered nitrogen-containing ring; and
- $R_{8a}$ and $R_{8b}$ in each instance are independently selected from hydrogen and $C_1$-$C_4$ alkyl, with the proviso that at least one of $R_{8a}$ and $R_{8b}$ is not hydrogen; or $R_{8a}$ and $R_{8b}$ together with the nitrogen to which they are bound form a 5- or 6-membered nitrogen-containing ring optionally substituted by 1, 2, 3, or 4 $C_1$-$C_4$ alkyl substituents;

(e) Formula I(e)

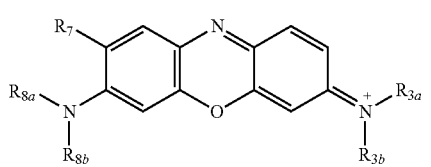

Formula I(e)

wherein
- $R_{3a}$ and $R_{3b}$ are independently selected from the group of hydrogen and $C_1$-$C_4$ alkyl, with the proviso that at least one of $R_{3a}$ and $R_{3b}$ is not hydrogen; or $R_{3a}$ and $R_{3b}$ together with the nitrogen atom to which they are bound form a 5- or 6-membered nitrogen-containing ring;
- $R_7$ is selected from the group of hydrogen, halogen, oxygen, or $C_1$-$C_4$ alkyl; and
- $R_{8a}$ and $R_{8b}$ are independently selected from the group of hydrogen and $C_1$-$C_4$ alkyl, with the proviso that at least one of $R_{8a}$ and $R_{8b}$ is not hydrogen; or $R_{8a}$ and $R_{8b}$ together with the nitrogen to which they are bound form a 5- or 6-membered nitrogen-containing ring optionally substituted by 1, 2, 3, or 4 $C_1$-$C_4$ alkyl substituents;

or $R_{8b}$ is selected from the group of hydrogen and $C_1$-$C_4$ alkyl, and $R_{8a}$ together with the nitrogen to which it is bound and $R_7$ forms a fused 6-membered ring having one nitrogen heteroatom and one oxygen heteroatom, wherein each nitrogen heteroatom is optionally substituted by 1, 2, 3, or 4 $C_1$-$C_4$ alkyl substituents;

with the proviso that the compounds of Formula I do not include N3,N3,N7,N7-tetraethyl-10H-phenoxazine-3,7-diamine; N3,N7-diethyl-10H-phenoxazine-3,7-diamine; N3,N3,N7,N7-tetramethyl-10H-phenoxazine-3,7-diamine; and N7,N7-diethyl-N3,N3,2-trimethyl-10H-phenoxazine-3,7-diamine; or (f) Formula I(f)

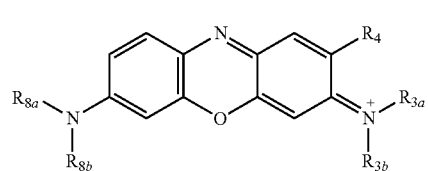

Formula I(f)

wherein
- $R_{3a}$ and $R_{3b}$ are independently selected from the group of hydrogen and $C_1$-$C_4$ alkyl, with the proviso that at least one of $R_{8a}$ and $R_{3b}$ is not hydrogen; or $R_{8a}$ and $R_{3b}$ together with the nitrogen to which they are bound form a 5- or 6-membered nitrogen-containing ring optionally substituted by 1, 2, 3, or 4 $C_1$-$C_4$ alkyl substituents;
- or $R_{3b}$ is selected from the group of hydrogen and $C_1$-$C_4$ alkyl, and $R_{3a}$ together with the nitrogen to which it is bound and $R_4$ forms a fused 6-membered ring having one nitrogen heteroatom and one oxygen heteroatom, wherein each nitrogen heteroatom is optionally substituted by 1, 2, 3, or 4 $C_1$-$C_4$ alkyl substituents;
- $R_4$ is selected from the group of hydrogen, halogen, oxygen, or $C_1$-$C_4$ alkyl; and
- $R_{8a}$ and $R_{8b}$ are independently selected from the group of hydrogen and $C_1$-$C_4$ alkyl, with the proviso that at least one of $R_{3a}$ and $R_{3b}$ is not hydrogen; or $R_{3a}$ and $R_{3b}$ together with the nitrogen atom to which they are bound form a 5- or 6-membered nitrogen-containing ring;
- with the proviso that the compounds of Formula I do not include N3,N3,N7,N7-tetraethyl-10H-phenoxazine-3,7-diamine; N3,N7-diethyl-10H-phenoxazine-3,7-diamine; N3,N3,N7,N7-tetramethyl-10H-phenoxazine-3,7-diamine; and N7,N7-diethyl-N3,N3,2-trimethyl-10H-phenoxazine-3,7-diamine.

2. A compound selected from the group consisting of:

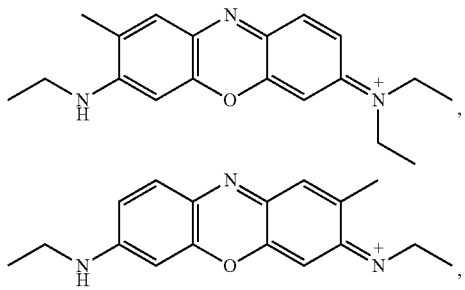

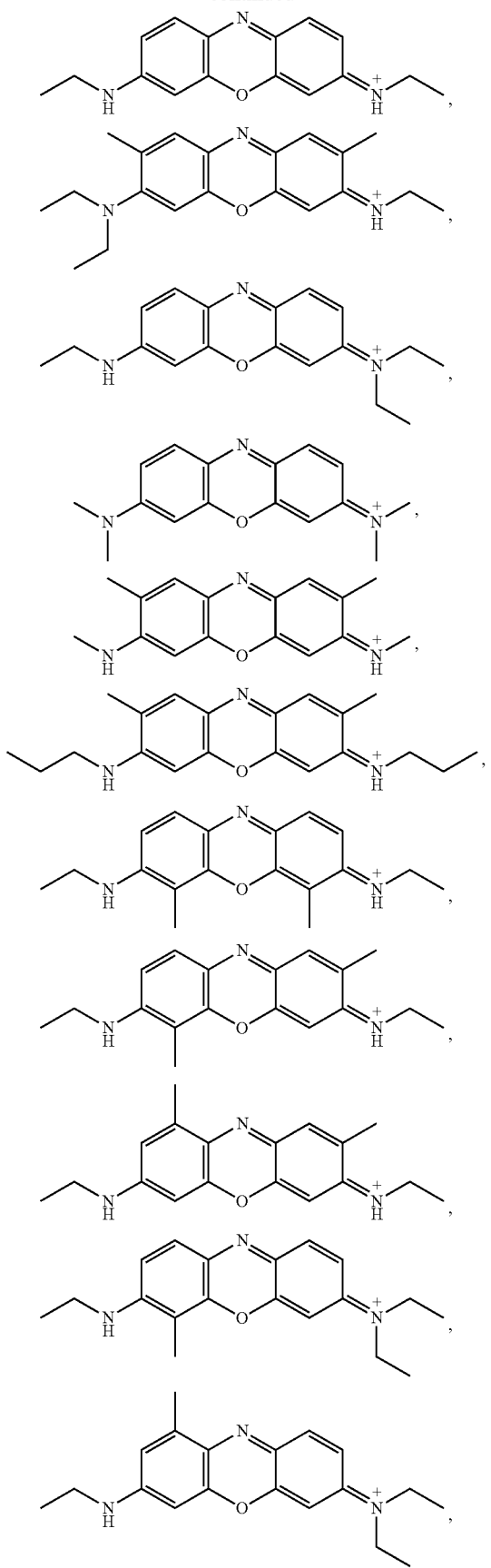
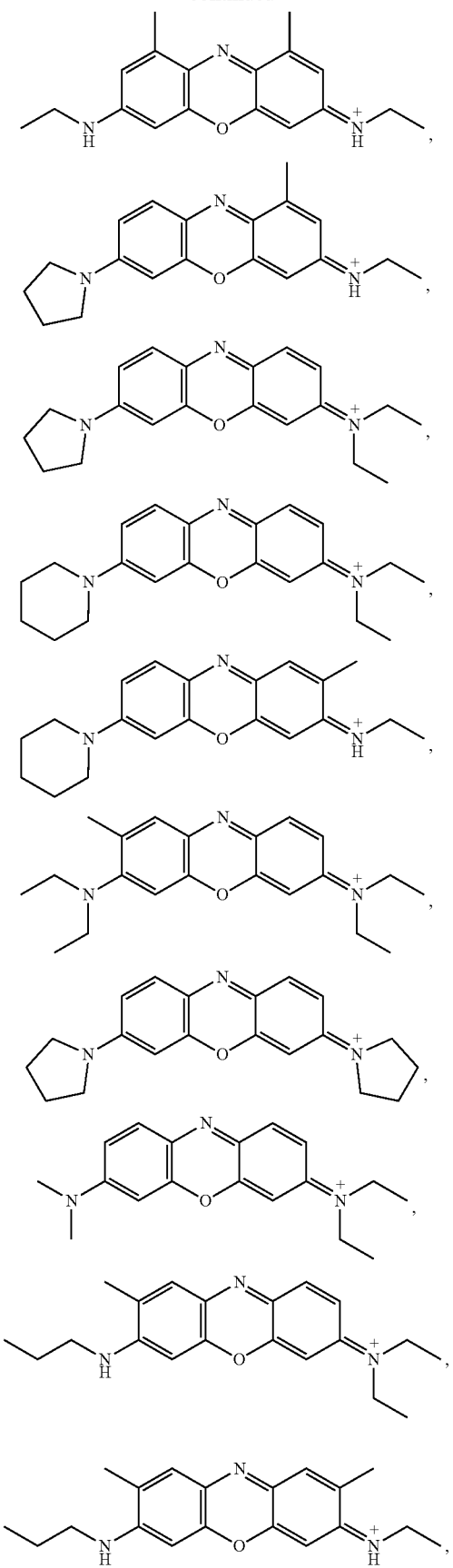

107
-continued
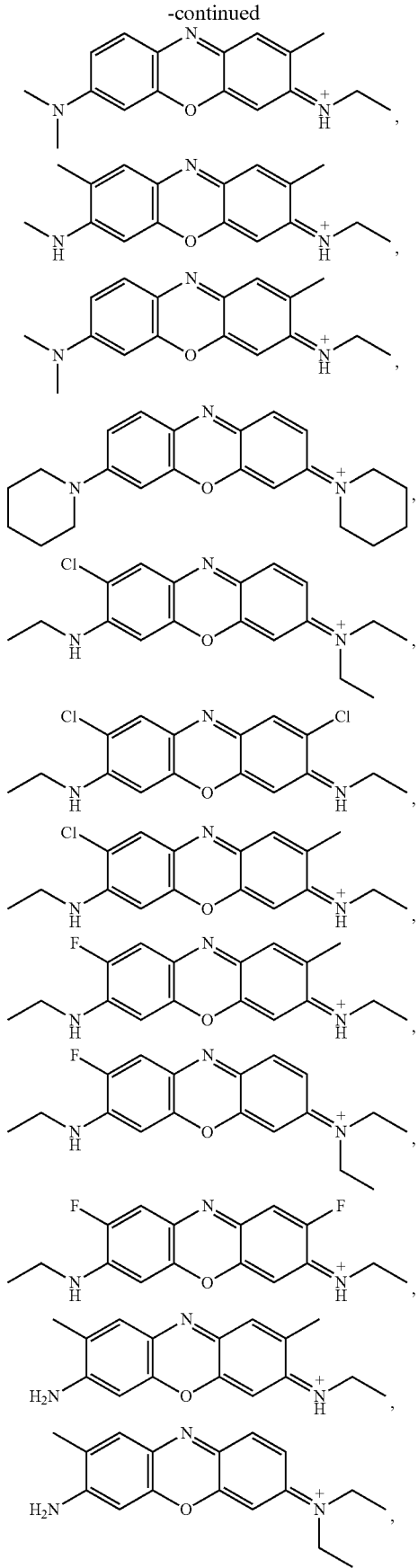
108
-continued
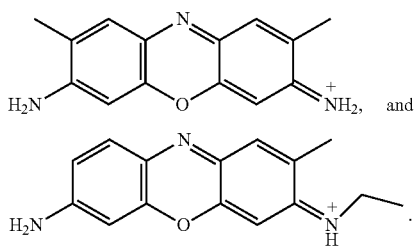
3. A compound selected from the group consisting of:
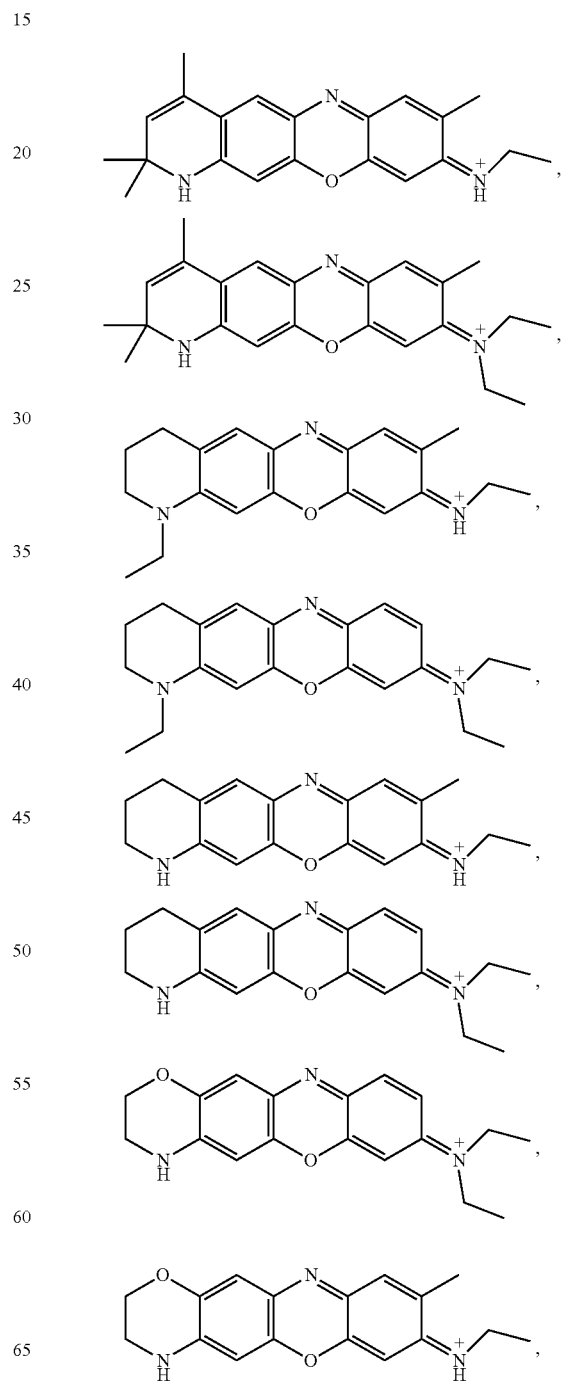

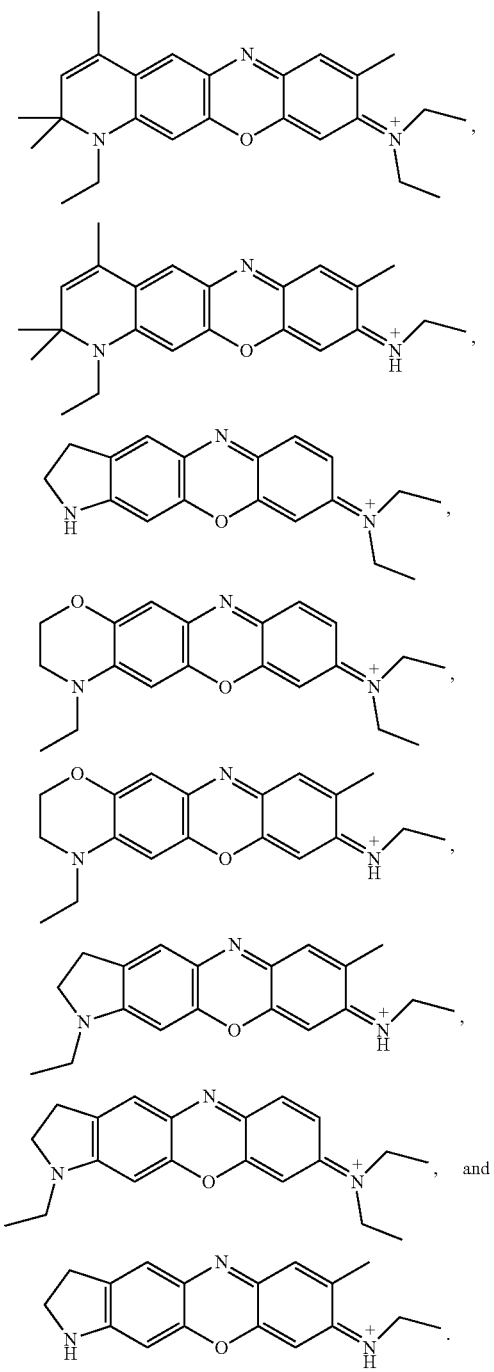
4. A compound selected from the group consisting of:
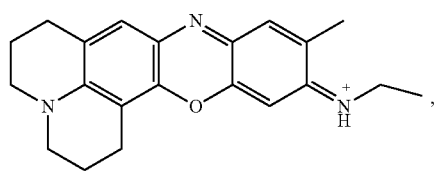
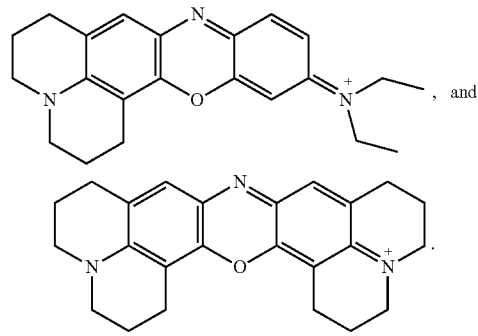
5. A compound selected from the group consisting of:
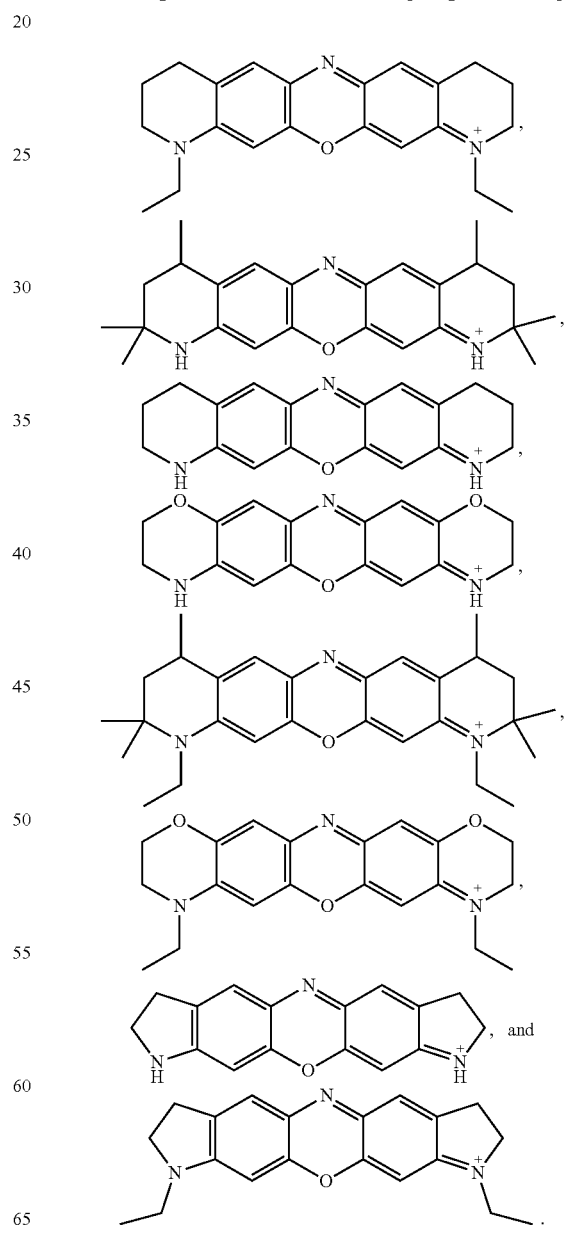

6. A method of imaging a target area in a subject, the method comprising contacting the target area in the subject with a compound of claim 1 and detecting the compound in the target area.

7. A method of imaging one or more nerves in a target area in a subject, the method comprising contacting the target area in the subject with a compound of claim 2 and detecting the compound in the target area using fluorescence or near-infrared imaging.

8. The method of claim 7, wherein the target area in the subject is contacted with the compound by direct administration.

9. The method of claim 7, wherein the target area in the subject is contacted with the compound by systemic administration.

10. A method of imaging one or more nerves in a target area in a subject, the method comprising contacting the target area in the subject with a compound of claim 3 and detecting the compound in the target area using fluorescence or near-infrared imaging.

11. A method of imaging one or more nerves in a target area in a subject, the method comprising contacting the target area in the subject with a compound of claim 4 and detecting the compound in the target area using fluorescence or near-infrared imaging.

12. A method of imaging one or more nerves in a target area in a subject, the method comprising contacting the target area in the subject with a compound of claim 5 and detecting the compound in the target area using fluorescence or near-infrared imaging.

13. A compound of Formula II:

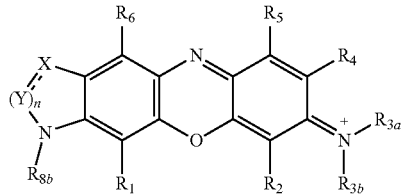

Formula II wherein:
$R_1$, $R_2$, $R_4$, $R_5$, and $R_6$ are each independently selected from the group of hydrogen or $C_1$-$C_4$ alkyl;
X is selected from the group of —C(H)—, —CH$_2$—, —CH($C_1$-$C_4$ alkyl)-, —C($C_1$-$C_4$ alkyl)-, —N(H)—, —N($C_1$-$C_4$ alkyl)-, and —O—;
Y is selected from the group of —CH$_2$—, —CH$_2$—CH$_2$—, —CH$_2$—CH—, —CH($C_1$-$C_4$ alkyl)-CH$_2$—, —C($C_1$-$C_4$ alkyl)$_2$-CH$_2$—, —CH($C_1$-$C_4$ alkyl)-CH—, and —C($C_1$-$C_4$ alkyl)$_2$-CH—;
the dashed line (----) represents an optional double bond that exists when X is selected from —C(H)— or —C($C_1$-$C_4$ alkyl)- and Y is selected from —CH$_2$—CH—, —CH($C_1$-$C_4$ alkyl)-CH—, and —C($C_1$-$C_4$ alkyl)$_2$-CH—;
$R_{3a}$ and $R_{3b}$ are each independently selected from the group of hydrogen or $C_1$-$C_4$ alkyl, with the proviso that at least one of $R_{3a}$ and $R_{3b}$ is not hydrogen, or $R_{3a}$ and $R_{3b}$ together with the nitrogen atom to which they are bound form a 5- or 6-membered nitrogen containing ring; and
$R_{8b}$ is selected from the group of hydrogen and $C_1$-$C_4$ alkyl.

14. A method of imaging one or more nerves in a target area in a subject, the method comprising contacting the target area in the subject with a compound of claim 13 and detecting the compound in the target area using fluorescence or near-infrared imaging.

15. A compound of Formula IV:

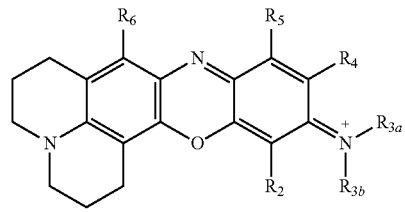

Formula IV wherein:
$R_2$, $R_4$, $R_5$, and $R_6$ are each independently selected from hydrogen and $C_1$-$C_4$ alkyl; and
$R_{3a}$ and $R_{3b}$ are each independently hydrogen or $C_1$-$C_4$ alkyl, with the proviso that at least one of $R_{3a}$ and $R_{3b}$ is not hydrogen, or $R_{3a}$ and $R_{3b}$ together with the nitrogen atom to which they are bound form a 5- or 6-membered nitrogen containing ring.

16. A method of imaging one or more nerves in a target area in a subject, the method comprising contacting the target area in the subject with a compound of claim 15 and detecting the compound in the target area using fluorescence or near-infrared imaging.

* * * * *